United States Patent
Durrant et al.

(10) Patent No.: US 8,742,088 B2
(45) Date of Patent: Jun. 3, 2014

(54) NUCLEIC ACIDS ENCODING ANTIBODIES OR PORTIONS THEREOF COMPRISING A HETEROLOGOUS T CELL EPITOPE AND THEIR USE IN MODULATING T CELL RESPONSES

(75) Inventors: Linda Gillian Durrant, Nottingham (GB); Rachael Louise Metheringham, Nottingham (GB); Victoria Anne Pudney, Nottingham (GB)

(73) Assignee: Scancell Limited, Nottingham (GB)

( * ) Notice: Subject to any disclaimer, the term of this patent is extended or adjusted under 35 U.S.C. 154(b) by 1065 days.

(21) Appl. No.: 12/566,465

(22) Filed: Sep. 24, 2009

(65) Prior Publication Data

US 2010/0260806 A1  Oct. 14, 2010

Related U.S. Application Data

(63) Continuation of application No. PCT/EP2008/053761, filed on Mar. 28, 2008.

(30) Foreign Application Priority Data

Mar. 28, 2007 (GB) .................................. 0706070.0

(51) Int. Cl.
*C07H 21/04* (2006.01)
*C07K 19/00* (2006.01)

(52) U.S. Cl.
CPC ............... *C07H 21/04* (2013.01); *C07K 19/00* (2013.01); *C07K 2319/00* (2013.01)
USPC ................... 536/23.53; 514/44 R; 530/387.3; 424/133.1; 424/184.1; 424/185.1

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,698,679 A * | 12/1997 | Nemazee | 530/387.3 |
| 7,067,110 B1 | 6/2006 | Gillies et al. | |
| 2004/0146505 A1 * | 7/2004 | Durrant et al. | 424/132.1 |

FOREIGN PATENT DOCUMENTS

| | | | |
|---|---|---|---|
| WO | 9531483 A1 | 11/1995 | |
| WO | 9619584 A1 | 6/1996 | |
| WO | 9925379 A1 | 5/1999 | |
| WO | 0064488 A2 | 11/2000 | |
| WO | 02058728 A2 | 8/2002 | |
| WO | 02092126 A1 | 11/2002 | |
| WO | 2008116937 A3 | 10/2008 | |

OTHER PUBLICATIONS

Sweetser et al., Nature 342, 180-182 (Nov. 9, 1989); doi:10.1038/342180a0.*
Kim et al., Proc Natl Acad Sci U S A. May 11, 2010;107(19):8742-7. doi: 10.1073/pnas.0911756107. Epub Apr. 26, 2010.*
Taylor et al., J Transplant. 2011;2011:246856. doi: 10.1155/2011/246856. Epub Sep. 15, 2011.*
Masteller et al., Semin Immunol. Apr. 2006;18(2):103-10. Epub Feb. 3, 2006.*
Hammond et al., J Cell Biol. Jul. 1994;126(1):41-52.*
Middleton, J. E., "An Anti-Tumour DNA Vaccine Targeting the Endothelial Antigen Tie-2," Thesis submitted to the University of Nottingham, pp. i-xv and 1-294, Nov. 2007.
Rosenberg, S. A., et al., "Vitiligo in Patients with Melanoma: Normal Tissue Antigens Can Be Targets for Cancer Immunotherapy," Journal of Immunotherapy, 19(1): 81-84 (1996).
Cho, J. H., et al., Cross-Priming as a Predominant Mechanism for Inducing CD8+ T Cell Responses in Gene Gun DNA Immunization, Journal of Immunology, 167: 5549-5557 (2001).
Li, S., et al., "Defining target antigens for CD25+FOXP3+IFN-γ regulatory T cells in chronic hepatitis C virus infection," Immunology and Cell Biology, 85: 197-204 (2007).
Akbar, et al., "The dynamic co-evolution of memory and regulatory CD4+ T Cells in the periphery," Nature Reviews/Immunology, 7:231-237, 2007.
Alexander-Miller, et al., "Selective expansion of high- or low-avidity cytotoxic T lymphocytes and efficacy for adoptive immunotherapy," Proc. Natl. Acad. Sci., 93:4102-4107, 1996.
Alvaro, et al., "Outcome in Hodgkin's Lymphoma Can Be Predicated from the Presence of Accompanying Cytotoxic and Regulatory T Cells," Clinical Cancer Research, 11:1467-1473, 2005.
Annacker, et al., "CD25+ CD4+ T Cells Regulate the Expansion of Peripheral T Cells Through the Production of IL-101," The Journal of Immunology, 166:3008-3018, 2001.
Bloom, et al., "Identification of Tyrosinase-related Protein 2 as a Tumor Rejection Antigen for the B16 Melanoma," The Journal of Experimental Medicine, 185(3):453-459, 1997.
Chapiro, et al., "Destructive Cleavage of Antigenic Peptides Either by the Immunoproteasome or by the Standard Proteasome Results in Differential Antigen Presentation," The Journal of Immunoloogy, 176:1053-1061, 2006.
Coleman, et al., "T regulatory cells: aid or hindrance in the clearance of disease?," J. Cell. Mol. Med., 11(6):1291-1325, 2007.
Curiel, et al., "Specific recruitment of regulatory T cells in ovarian carcinoma fosters immune privilege and predicts reduced survival," Nature Medicine, 10(9):942-949, 2004.
Dannull, et al., "Enhancement of vaccine-mediated antitumor immunity in cancer patients after depletion of regulatory T cells," The Journal of Clinical Investigation, 115(12):3623-3633, 2005.
Dudley, et al., "Adoptive Transfer of Cloned Melanoma-Reactive T Lymphocytes for the Treatment of Patients with Metastatic Melanoma," Journal of Immunotherapy, 24(4):363-373, 2001.

(Continued)

*Primary Examiner* — Michael Szperka
(74) *Attorney, Agent, or Firm* — Darlene A. Vanstone, Esq.; Carolyn S. Elmore, Esq.; Elmore Patent Law Group, P.C.

(57) ABSTRACT

The present invention provides a nucleic acid which comprises a non-specific promoter and at least one sequence that encodes a polypeptide that has at least one heterologous T cell epitope therein but does not have any regulatory T cell epitopes. The polypeptide may be one chain of a heterodimer such as the heavy or light chain of an antibody molecule, the heterologous T cell epitope causing disruption of the heterodimer chain such that it cannot bind with the other chain of the heterodimer. The nucleic acid can be used to raise a T cell response against the at least one heterologous T cell epitope.

51 Claims, 73 Drawing Sheets

(56) References Cited

OTHER PUBLICATIONS

Harada, et al., "Evidence of the extrathymic development of tyrosinase-related protein-2-recognizing CD8+ T cells with low avidity," Immunology, 104:67-74, 2001.
Hodge, et al., "Multiple Costimulatory Modalities Enhance CTL Activity", The Journal of Immunology, 174:5994-6004, 2005.
Ichihara, et al., "Increased Populations of Regulatory T Cells in Peripheral Blood and Tumor-Infiltrating Lymphocytes in Patients with Gastric and Esophageal Cancers," Clinical Cancer Research, 9:4404-4408, 2003.
Jordan, et al., "Thymic selection of CD4+CD25+ regulatory T cells induced by an agonist self-peptide," Nature Immunology, 2(4):301-306, 2001.
Lane, et al., "Vaccination-Induced Autoimmune Vitiligo is a Consequence of Secondary Trauma to the Skin," Cancer Research, 64:1509-1514, 2004.
Lim, et al., "Cutting Edge: Direct Suppression of B Cells by CD4+CD25+ Regulatory T Cells1," The Journal Immunology, 175:4180-4183, 2005.
Liyanage, et al., "Prevalence of Regulatory T Cells is Increased in Peripheral Blood and Tumor Microenvironment of Patients with Pancreas or Breast Adenocarcinoma1," The Journal of Immunology, 169:2756-2761, 2002.
MacAgno, et al., "Pronounced up-regulation of the PA28α/β proteasome regulatory but little increase in the steady-state content of immunoproteasome during dendritic cell maturation," Eur. J. Immunol., 31:3271-3280, 2001.
Matsuura, et al., "Maturation of Dendritic Cells and T-Cell Responses in Sentinel Lymph Nodes from Patients with Breast Carcinoma," Cancer, 106(6):1227-1236, 2006.
Mempel, et al., "Regulatory T Cells Reversibly Suppress Cytotoxic T Cell Function Independent of Effector Differentiation," Immunology, 25:129-141, 2006.
Morgan, et al., "High Efficiency TCR Gene Transfer into Primary Human Lymphocytes Affords Avid Recognition of Melanoma Tumor Antigen Glycoprotein 100 and Does Not Altar the Recognition of Autologous Melanoma Antigens," The Journal of Immunology, 171:3287-3295, 2003.
Nishikawa, et al., "CD4+ CD25+ regulatory T cells control the induction of antigen-specific CD4 + helper T cell responses in cancer patients," Blood, 106(3):1008-1011, 2005.
Oh, et al., "Selective Induction of High Avidity CTL by Altering the Balance of Signals from APC," The Journal of Immunology, 170:2523-2530, 2003.
Onizuka, et al., "Tumor Rejection by in Vivo Administration of Anti-CD26 (Interleukin-2 Receptor α) Monoclonal Antibody1," Cancer Research, 59:3128-3133, 1999.
Overwijk, et al., "Vaccination with a recombbinant vaccinia virus encoding a "self" antigen induces autoimmune vitiligo and tumor cell destruction in mice: Requirement for CD4+ T lymphocytes," Proc. Natl. Acad. Sci., 96:2982-2987, 1999.
Picca, et al., "The role of self-peptides in the development of CD4+ CD25+ regulatory T cells," Current Opinion in Immunology, 17:131-136, 2005.
Picca, et al., "Role of TCR specificity in CD4+ CD25+ regulatory T-cell selection," Immunology Reviews, 212:74-85, 2006.
Piccirillo, et al., "Cutting Edge: Control of CD8+ T Cell Activation by CD4+ CD25+ Immunoregulatory Cells," Journal of Immunology, 167:1137-1140, 2001.
Ramage, et al., "Identification of an HLA-A*0201 Cytotoxic T Lymphocyte Epitope Specific to the Endothelial Antigen Tie-2," Int. J. Cancer, 110:245-250, 2004.
Romagnani, et al., "Activation of human NK cells by plasmacytoid dendritic cells and its modulation by CD4+ T helper cells and CD4+ CD25hi T regulatory cells," Eur. J. Immunol., 35:2452-2458, 2005.
Rosenberg, et al., "Cancer immunotherapy: moving beyond current vaccines," Nature Medicine, 10(9):909-915, 2004.
Rosenberg, et al., "Tumor Progression Can Occur despite the Induction of Very High Levels of Self/Tumor Antigen-Specific CD8+ T Cells in Patients with Melanoma," The Journal of Immunology, 175:6169-6176, 2005.
Rosenberg, et al., "Cancer regression in patients with metastatic melanoma after the transfer of autologous antitumor lymphocytes," PNAS, 101(2):14639-14645, 2004.
Sakaguchi, et al., "Immunologic Self-Tolerance Maintained by Activated T Cells Expressing IL-2 Receptor α-Chains (CD25)," Journal of Immunology, 155:1151-1164, 1995.
Sakaguchi, "Naturally arising Foxp3-expressing CD25+ CD4+ regulatory T cells in immunological tolerance to self and non-self," Nature Immunology, 6(4):345-352, 2005.
Sanger, et al., "DNA sequencing with chain-terminating inhibitors," Proc. Natl. Acad. Sci., 74(12):5463-5467, 1977.
Sasada, et al., "CD4+CD25+ Regulatory T Cells in Patients with Gastrointestinal Malignancies," Cancer, 98:1089-1099, 2003.
Shevach, et al., "From Vanilla to 28 Flavors: Multiple Varieties of T Regulatory Cells," Immunity, 25:195-201, 2006.
Shimizu, et al., "Induction of Tumor Immunity by Removing CD25+CD4+ T Cells: A Common Basis Between Tumor Immunity and Autoimmunity," Journal of Immunology, 163:5211-5218, 1999.
Steitz, et al., "Effective induction of anti-melanoma immunity following genetic vaccination with synthetic mRNA coding for the fusion protein EGFP.TRP2," Cancer Immunol Immunother, 55:246-253, 2006.
Sutmuller, et al., "Synergism of Cytotoxic T Lymphocyte-associated Antigen 4 Blockade and Depletion of CD25+ Regulatory T Cells in Antitumor Therapy Reveals Alternative Pathways for Suppression of Autoreactive Cytotoxic T Lymphocyte Responses," J. Exp. Med., 194(6):823-832, 2001.
Tanaka, et al., "Depletion of CD4+CD25+ Regulatory Cells Augments the Generation of Specific Immune T Cells in Tumor-Draining Lymph Nodes," Journal of Immunotherapy, 25(3):207-217, 2002.
Thornton, et al., "Suppressor Effector Funtion of CD4+CD25+ Immunoregulatory T Cells Is Antigen Nonspecific," The Journal of Immunology, 164:183-190, 2000.
Valmori, et al., "Vaccination with a Melan-A Peptide Selects an Oligoclonal T Cell Population with Increased Functional Avidity and Tumor Reactivity1," Journal of Immunology, 168:4231-4240, 2002.
Vence, et al., "Circulating tumor antigen-specific regulatory T cells in patients with metastatic melanoma," PNAS, 104(52):20884-20889, 2007.
Von Boehmer, "Mechanisms of suppression by suppressor T cells," Nature Immunology, 6(4):338-344, 2005.
Wang, et al., "Tumor-Specific Human CD4+ Regulatory T Cells and Their Ligands: Implications for Immunotherapy," Immunity, 20:107-118, 2004.
Wolf, et al., "Increase of Regulatory T Cells in the Peripheral Blood of Cancer Patients1," Clinical Cancer Research, 9:606-612, 2003.
Woo, et al., "Regulatory CD4+CD25+ T Cells in Tumors from Patients with Early-Stage Non-Small Cell Lung Cancer and Late-Stage Ovarian Cancer," Cancer Research, 61:4766-4772, 2001.
Woo, et al., "Cutting Edge: Regulatory T Cells from Lung Cancer Patients Directly Inhibit Autologous T Cell Proliferation," Journal of Immunology, 168:4272-4276, 2002.
Yang, et al., "Intratumoral CD4+CD25+ regulatory T-cell-mediated suppression of infiltrating CD4+ T cells in B-cell in B-cell non-Hodgkin lymphoma," Blood, 107:3639-3646, 2006.
Zeh, et al., "High Avidity CTLs for Two-Self-Antigens Demonstrate Superior In Vitro and In Vivo Antitumor Efficacy," Journal of Immunology, 162:989-994, 1999.
Alexander-Miller, "High-Avidity CD8+ T Cells," Immunologic Research, 31(1):13-24, 2005.
Ralainirina, et al., "Control of NK cell functions by CD4+ CD25+ regulatoryTcells," Journal of Leukocyte Biology, 81:144-153, 2007.
Vignard, et al., "Adoptive Transfer of Tumor-Reactive Melan-A-Specific CTL Clones in Melanoma Patients Is Followed by Increased Frequencies of Additional Melan-A-Specific T Cells1," The Journal of Immunology, 175:4797-4805, 2005.
Zaghouani, et al., "Engineered Immunoglobulin Molecules as Vehicles for T Cell Epitopes," International Reviews of Immunology, 10(2-3):265-278, 1993.
Chakraborty, et al., "Regulatory T-Cell Response and Tumor Vaccine-induced Cytotoxic T Lymphocytes in Human Melanoma," Human Immunology, 65:794-802, 2004.

* cited by examiner a
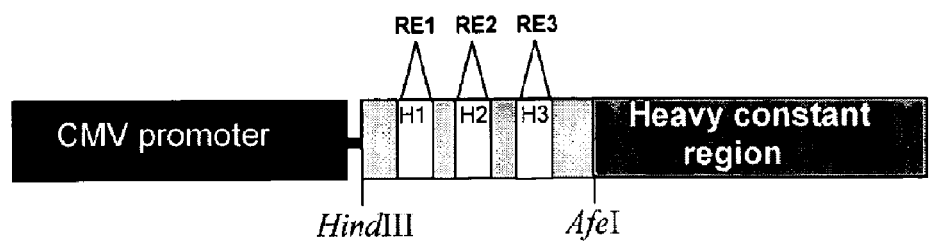
b
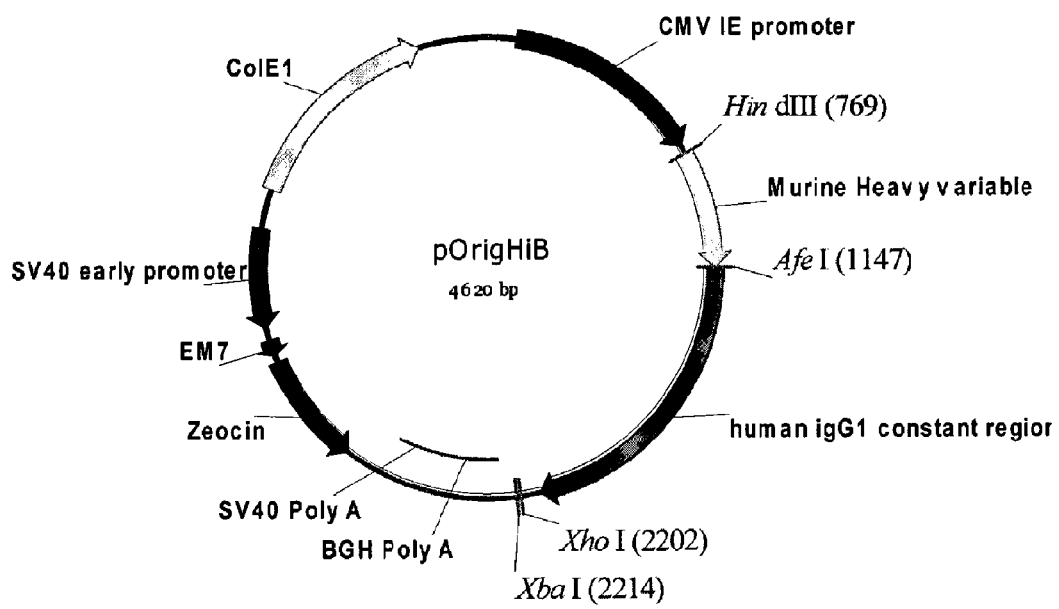
FIG. 1

```
HindIII   M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1   ---------!---------!---------!---------!---------!---------!---------!---------!---------!  90
          G  G  L  I  Q  P  G  G  S  L  R  M  S  C  A  A  S  G  F  A  F  N   CDR1
                                                                           T  Y  D  M  S  W  V  R
GGAGGCTTAATCCAGCCTGGAGGGTCCCTGAGAATGTCCTGTGCAGCCTCTGGATTCGCTTTCAATACCTATGACATGTCTTGGGTTCGC
91  ---------!---------!---------!---------!---------!---------!---------!---------!---------! 180
                                            CDR2
     Q  A  P  G  K  G  L  E  W  I  A   Y  I  G  S  G  G  D  R  T  Y  Y  P  D  T  V  K  G  R  F
CAGGCTCCGGGGAAGGGGCTGGAGTGGATCGCATACATTGGTAGTGGTGGTGATAGAACCTACTATCCAGACACTGTGAAGGGCCGATTC
181 ---------!---------!---------!---------!---------!---------!---------!---------!---------! 270

T  I  S  R  D  N  S  K  N  T  L  Y  L  Q  L  N  S  L  R  A  E  D  T  A  V  Y  Y  C  A  R
ACCATTTCCAGAGACAATAGCAAGAACACCCTGTATTTGCAATTGAACAGTCTGAGGGCTGAGGACACAGCCGTGTATTACTGTGCAAGA
271 ---------!---------!---------!---------!---------!---------!---------!---------!---------! 360
         CDR3                                               AfeI
     H  Y  G  H  Y  V  D  Y  A  V  D  Y   W  G  Q  G  I  T  V  T  V  S  S  A  S  T  K  G  P  S
CATTATGGTCACTACGTGGACTATGCTGTGGACTACTGGGGTCAAGGAACCACGGTCACCGTCTCCAGCGCTTCCACCAAGGGCCCATCG
361 ---------!---------!---------!---------!---------!---------!---------!---------!---------! 450

V  F  P  L  A  P  S  S  K  S  T  S  G  G  T  A  A  L  G  C  L  V  K  D  Y  F  P  E  P  V
GTCTTCCCCCTGGCACCCTCCTCCAAGAGCACCTCTGGGGGCACAGCGGCCCTGGGCTGCCTGGTCAAGGACTACTTCCCCGAACCGGTG
451 ---------!---------!---------!---------!---------!---------!---------!---------!---------! 540

T  V  S  W  N  S  G  A  L  T  S  G  V  H  T  F  P  A  V  L  Q  S  S  G  L  Y  S  L  S  S
ACGGTGTCGTGGAACTCAGGCGCCCTGACCAGCGGCGTGCACACCTTCCCGGCTGTCCTACAGTCCTCAGGACTCTACTCCCTCAGCAGC
541 ---------!---------!---------!---------!---------!---------!---------!---------!---------! 630

V  V  T  V  P  S  S  S  L  G  T  Q  T  Y  I  C  N  V  N  H  K  P  S  N  T  K  V  D  K  K
GTGGTGACCGTGCCCTCCAGCAGCTTGGGCACCCAGACCTACATCTGCAACGTGAATCACAAGCCCAGCAACACCAAGGTGGACAAGAAA
631 ---------!---------!---------!---------!---------!---------!---------!---------!---------! 720

V  E  P  K  S  C  D  K  T  H  T  C  P  P  C  P  A  P  E  L  L  G  G  P  S  V  F  L  F  P
GTTGAGCCCAAATCTTGTGACAAAACTCACACATGCCCACCGTGCCCAGCACCTGAACTCCTGGGGGGACCGTCAGTCTTCCTCTTCCCC
721 ---------!---------!---------!---------!---------!---------!---------!---------!---------! 810

P  K  P  K  D  T  L  M  I  S  R  T  P  E  V  T  C  V  V  V  D  V  S  H  E  D  P  E  V  K
CCAAAACCCAAGGACACCCTCATGATCTCCCGGACCCCTGAGGTCACATGCGTGGTGGTGGACGTGAGCCACGAAGACCCTGAGGTCAAG
811 ---------!---------!---------!---------!---------!---------!---------!---------!---------! 900

F  N  W  Y  V  D  G  V  E  V  H  N  A  K  T  K  P  R  E  E  Q  Y  N  S  T  Y  R  V  V  S
TTCAACTGGTACGTGGACGGCGTGGAGGTGCATAATGCCAAGACAAAGCCGCGGGAGGAGCAGTACAACAGCACGTACCGTGTGGTCAGC
901 ---------!---------!---------!---------!---------!---------!---------!---------!---------! 990

V  L  T  V  L  H  Q  D  W  L  N  G  K  E  Y  K  C  K  V  S  N  K  A  L  P  A  P  I  E  K
GTCCTCACCGTCCTGCACCAGGACTGGCTGAATGGCAAGGAGTACAAGTGCAAGGTCTCCAACAAAGCCCTCCCAGCCCCCATCGAGAAA
991 ---------!---------!---------!---------!---------!---------!---------!---------!---------! 1080

T  I  S  K  A  K  G  Q  P  R  E  P  Q  V  Y  T  L  P  P  S  R  D  E  L  T  K  N  Q  V  S
ACCATCTCCAAAGCCAAAGGGCAGCCCCGAGAACCACAGGTGTACACCCTGCCCCCATCCCGGGATGAGCTGACCAAGAACCAGGTCAGC
1081 ---------!---------!---------!---------!---------!---------!---------!---------!---------! 1170

L  T  C  L  V  K  G  F  Y  P  S  D  I  A  V  E  W  E  S  N  G  Q  P  E  N  N  Y  K  T  T
CTCACCTGCCTGGTCAAAGGCTTCTATCCCAGCGACATCGCCGTGGAGTGGGAGAGCAATGGGCAGCCGGAGAACAACTACAAGACCACG
1171 ---------!---------!---------!---------!---------!---------!---------!---------!---------! 1260

P  P  V  L  D  S  D  G  S  F  F  L  Y  S  K  L  T  V  D  K  S  R  W  Q  Q  G  N  V  F  S
CCTCCCGTGCTGGACTCCGACGGCTCCTTCTTCCTCTACAGCAAGCTCACCGTGGACAAGAGCAGGTGGCAGCAGGGGAACGTCTTCTCA
1261 ---------!---------!---------!---------!---------!---------!---------!---------!---------! 1350

C  S  V  M  H  E  A  L  H  N  H  Y  T  Q  K  S  L  S  L  S  P  G  K    (SEQ ID NO: 99)
TGCTCCGTGATGCATGAGGCTCTGCACAACCACTACACGCAGAAGAGCCTCTCCCTGTCTCCGGGTAAATGATCTAAAGGGCGAATTCGC
1351 ---------!---------!---------!---------!---------!---------!---------!---------!---------! 1440
                                                     XhoI   (SEQ ID NO: 98)
CCTTAAGGGCGAATTTTGCAGATATCCATCACACTGGCGGCCGCCTCGAG
1441 ---------!---------!---------!---------!--------- 1489
```

FIG. 3

```
         BamHI    M  G  W  S  C  I  I  L  F  L  V  A  T  A  T  G  V  H  S  D  V  L  M  T  Q  S  P
              GGATCCACCATGGGATGGAGCTGTATCATCCTCTTCTTGGTAGCAACAGCTACCGGAGTCCACTCCGATGTGTTGATGACCCAATCTCCA
    1    ---------!---------!---------!---------!---------!---------!---------!---------!---------!  90
                                                                               CDR1
         L  S  L  P  V  T  P  G  E  P  A  S  I  S  C  R  S  S  Q  S  L  V  H  S  N  G  N  T  Y  L
              CTCTCCCTGCCTGTCACTCCTGGGGAGCCAGCCTCCATCTCTTGCAGATCTAGTCAGAGCCTGGTACATAGTAATGGAAACACCTATTTA
   91    ---------!---------!---------!---------!---------!---------!---------!---------!---------! 180
                                              CDR2
         E  W  Y  L  Q  K  P  G  Q  S  P  Q  L  L  I  Y  K  V  S  N  R  F  S  G  V  P  D  R  F  S
              GAATGGTACCTGCAGAAACCAGGCCAGTCTCCACAGCTCCTGATCTACAAAGTTTCCAACCGATTTTCTGGGGTCCCAGACAGATTCAGT
  181    ---------!---------!---------!---------!---------!---------!---------!---------!---------! 270
                                                                                        CDR3
         G  S  G  S  G  T  D  F  T  L  K  I  S  R  V  E  A  E  D  T  G  V  Y  Y  C  F  Q  G  S  H
              GGCAGTGGATCAGGGACAGATTTCACACTCAAGATCAGCAGAGTGGAGGCTGAGGATACCGGAGTGTATTACTGCTTTCAAGGTTCACAT
  271    ---------!---------!---------!---------!---------!---------!---------!---------!---------! 360
                                              BsiWI
         V  P  W  T  F  G  G  G  T  K  V  E  I  K  R  T  V  A  A  P  S  V  F  I  F  P  P  S  D  E
              GTTCCGTGGACGTTCGGTGGAGGCACCAAGGTGGAAATCAAGCGTACGGTAGCGGCCCCATCTGTCTTCATCTTCCCGCCATCTGATGAG
  361    ---------!---------!---------!---------!---------!---------!---------!---------!---------! 450

Q  L  K  S  G  T  A  S  V  V  C  L  L  N  N  F  Y  P  R  E  A  K  V  Q  W  K  V  D  N  A
              CAGTTGAAATCTGGAACTGCCTCTGTTGTGTGCCTGCTGAATAACTTCTATCCCAGAGAGGCCAAAGTACAGTGGAAGGTGGATAACGCC
  451    ---------!---------!---------!---------!---------!---------!---------!---------!---------! 540

L  Q  S  G  N  S  Q  E  S  V  T  E  Q  D  S  K  D  S  T  Y  S  L  S  S  T  L  T  L  S  K
              CTCCAATCGGGTAACTCCCAGGAGAGTGTCACAGAGCAGGACAGCAAGGACAGCACCTACAGCCTCAGCAGCACCCTGACGCTGAGCAAA
  541             !         !         !         !         !         !         !         !         ! 630

A  D  Y  E  K  H  K  V  Y  A  C  E  V  T  H  Q  G  L  S  S  P  V  T  K  S  F  N  R  G  E
              GCAGACTACGAGAAACACAAAGTCTACGCCTGCGAAGTCACCCACCAGGGCCTGAGCTCGCCCGTCACAAAGAGCTTCAACAGGGGAGAG
  631    ---------!---------!---------!---------!---------!---------!---------!---------!---------! 720

C  *  XhoI      (SEQ ID NO: 101)
              TGTTGACTCGAG  (SEQ ID NO: 100)
  721    ---------!-732
```

```
  M   G   W   S   C   I   I   L   F   L   V   A   T   A   T   G   V   H   S   Q   V   Q   L   V   E   T
ATGGGATGGAGCTGTATCATCCTCTTCTTGGTAGCAACAGCTACCGGAGTCCACTCCCAGGTGCAGCTGGTGGAGACT
                                                                 FspI
  G   G   G   L   I   Q   P   G   G   S   L   R   M   S   C   Q   A   P   G   K   G   L   E   W   I   A
GGGGGAGGCTTAATCCAGCCTGGAGGGTCCCTGAGAATGTCCTGCGCAGGCTCCGGGGAAGGGGCTGGAGTGGATCGCA

Y   I   G   S   G   G   D   R   T   Y   Y   P   D   T   V   K   G   R   F   T   I   S   R   D   N   S
TACATTGGTAGTGGTGGTGATAGAACCTACTATCCAGACACTGTGAAGGGCCGATTCACCATTTCCAGAGACAATAGC

K   N   T   L   Y   L   Q   L   N   S   L   R   A   E   D   T   A   V   Y   Y   C   A   R   H   Y   G
AAGAACACCCTGTATTTGCAATTGAACAGTCTGAGGGCTGAGGACACAGCCGTGTATTACTGTGCAAGACATTATGGT

H   Y   V   D   Y   A   V   D   Y   W   G   Q   G   T   T   V   T   V   S   S   A           (SEQ ID NO: 103)
CACTACGTGGACTATGCTGTGGACTACTGGGGTCAAGGTACCACGGTCACCGTCTCCAGCGCT                  (SEQ ID NO: 102)
```

H2

```
  M   G   W   S   C   I   I   L   F   L   V   A   T   A   T   G   V   H   S   Q   V   Q   L   V   E   T
ATGGGATGGAGCTGTATCATCCTCTTCTTGGTAGCAACAGCTACCGGAGTCCACTCCCAGGTGCAGCTGGTGGAGACT

G   G   G   L   I   Q   P   G   G   S   L   R   M   S   C   A   A   S   G   F   A   F   N   T   Y   D
GGGGGAGGCTTAATCCAGCCTGGAGGGTCCCTGAGAATGTCCTGTGCAGCCTCTGGATTCGCTTTCAATACCTATGAC
                                                                                    MscI
  M   S   W   V   R   Q   A   P   G   K   G   L   E   W   I   A   Y   I   G   S   G           I   S   R   D
ATGTCTTGGGTTCGCCAGGCTCCGGGGAAGGGGCTGGAGTGGATCGCATACATTGGTAGTGGTGGCCATTTCCAGAGAC

N   S   K   N   T   L   Y   L   Q   L   N   S   L   R   A   E   D   T   A   V   Y   Y   C   A   R   H
AATAGCAAGAACACCCTGTATTTGCAATTGAACAGTCTGAGGGCTGAGGACACAGCCGTGTATTACTGTGCAAGACAT

Y   G   H   Y   V   D   Y   A   V   D   Y   W   G   Q   G   T   T   V   T   V   S   S   A   (SEQ ID NO: 105)
TATGGTCACTACGTGGACTATGCTGTGGACTACTGGGGTCAAGGTACCACGGTCACCGTCTCCAGCGCT           (SEQ ID NO: 104)
```

H3

```
  M   G   W   S   C   I   I   L   F   L   V   A   T   A   T   G   V   H   S   Q   V   Q   L   V   E   T
ATGGGATGGAGCTGTATCATCCTCTTCTTGGTAGCAACAGCTACCGGAGTCCACTCCCAGGTGCAGCTGGTGGAGACT

G   G   G   L   I   Q   P   G   G   S   L   R   M   S   C   A   A   S   G   F   A   F   N   T   Y   D
GGGGGAGGCTTAATCCAGCCTGGAGGGTCCCTGAGAATGTCCTGTGCAGCCTCTGGATTCGCTTTCAATACCTATGAC

M   S   W   V   R   Q   A   P   G   K   G   L   E   W   I   A   Y   I   G   S   G   G   D   R   T   Y
ATGTCTTGGGTTCGCCAGGCTCCGGGGAAGGGGCTGGAGTGGATCGCATACATTGGTAGTGGTGGTGATAGAACCTAC

Y   P   D   T   V   K   G   R   F   T   I   S   R   D   N   S   K   N   T   L   Y   L   Q   L   N   S
TATCCAGACACTGTGAAGGGCCGATTCACCATTTCCAGAGACAATAGCAAGAACACCCTGTATTTGCAATTGAACAGT

SrfI
  L   R   A   E   D   T   A   V   Y   Y   C   A           G   Q   G   T   T   V   T   V   S   S   A   (SEQ ID NO: 107)
CTGAGGGCTGAGGACACAGCCGTGTATTACTGTGCCCGGGCCAAGGTACCACGGTCACCGTCTCCAGCGCT         (SEQ ID NO: 106)
```

```
          M   G   W   S   C   I   I   L   F   L   V   A   T   A   T   G   V   H   S   Q   V   Q   L   V   E   T
          ATGGGATGGAGCTGTATCATCCTCTTCTTGGTAGCAACAGCTACCGGAGTCCACTCCCAGGTGCAGCTGGTGGAGACT

FspI
          G   G   G   L   I   Q   P   G   G   S   L   R   M   S   C   Q   A   P   G   K   G   L   E   W   I   A
          GGGGGAGGCTTAATCCAGCCTGGAGGGTCCCTGAGAATGTCCTGCGCAGGCTCCGGGGAAGGGGCTGGAGTGGATCGCA

MscI
          Y   I   G   S   G               I   S   R   D   N   S   K   N   T   L   Y   L   Q   L   N   S   L   R   A   E
          TACATTGGTAGTGGTGGCCATTTCCAGAGACAATAGCAAGAACACCCTGTATTTGCAATTGAACAGTCTGAGGGCTGAG

D   T   A   V   Y   Y   C   A   R   H   Y   G   H   Y   V   D   Y   A   V   D   Y   W   G   Q   G   T
          GACACAGCCGTGTATTACTGTGCAAGACATTATGGTCACTACGTGGACTATGCTGTGGACTACTGGGGTCAAGGTACC

T   V   T   V   S   S   A         (SEQ ID NO: 109)
          ACGGTCACCGTCTCCAGCGCT              (SEQ ID NO: 108)
```

H1/H3

```
          M   G   W   S   C   I   I   L   F   L   V   A   T   A   T   G   V   H   S   Q   V   Q   L   V   E   T
          ATGGGATGGAGCTGTATCATCCTCTTCTTGGTAGCAACAGCTACCGGAGTCCACTCCCAGGTGCAGCTGGTGGAGACT

FspI
          G   G   G   L   I   Q   P   G   G   S   L   R   M   S   C   Q   A   P   G   K   G   L   E   W   I   A
          GGGGGAGGCTTAATCCAGCCTGGAGGGTCCCTGAGAATGTCCTGCGCAGGCTCCGGGGAAGGGGCTGGAGTGGATCGCA

Y   I   G   S   G   G   D   R   T   Y   Y   P   D   T   V   K   G   R   F   T   I   S   R   D   N   S
          TACATTGGTAGTGGTGGTGATAGAACCTACTATCCAGACACTGTGAAGGGCCGATTCACCATTTCCAGAGACAATAGC

SrfI
          K   N   T   L   Y   L   Q   L   N   S   L   R   A   E   D   T   A   V   Y   Y   C   A       G   Q   G
          AAGAACACCCTGTATTTGCAATTGAACAGTCTGAGGGCTGAGGACACAGCCGTGTATTACTGTGCCCGGGCCAAGGT

T   T   V   T   V   S   S   A          (SEQ ID NO: 111)
          ACCACGGTCACCGTCTCCAGCGCT               (SEQ ID NO: 110)
```

H2/H3

```
          M   G   W   S   C   I   I   L   F   L   V   A   T   A   T   G   V   H   S   Q   V   Q   L   V   E   T
          ATGGGATGGAGCTGTATCATCCTCTTCTTGGTAGCAACAGCTACCGGAGTCCACTCCCAGGTGCAGCTGGTGGAGACT

G   G   G   L   I   Q   P   G   G   S   L   R   M   S   C   A   A   S   G   F   A   F   N   T   Y   D
          GGGGGAGGCTTAATCCAGCCTGGAGGGTCCCTGAGAATGTCCTGTGCAGCCTCTGGATTCGCTTTCAATACCTATGAC

MscI
          M   S   W   V   R   Q   A   P   G   K   G   L   E   W   I   A   Y   I   G   S   G           I   S   R   D
          ATGTCTTGGGTTCGCCAGGCTCCGGGGAAGGGGCTGGAGTGGATCGCATACATTGGTAGTGGTGGCCATTCCAGAGAC

SrfI
          N   S   K   N   T   L   Y   L   Q   L   N   S   L   R   A   E   D   T   A   V   Y   Y   C   A       G
          AATAGCAAGAACACCCTGTATTTGCAATTGAACAGTCTGAGGGCTGAGGACACAGCCGTGTATTACTGTGCCCGGGC

Q   G   T   T   V   T   V   S   S   A      (SEQ ID NO: 113)
          CAAGGTACCACGGTCACCGTCTCCAGCGCT              (SEQ ID NO: 112)
```

```
  M   G   W   S   C   I   I   L   F   L   V   A   T   A   T   G   V   H   S   Q   V   Q   L   V   E   T
ATGGGATGGAGCTGTATCATCCTCTTCTTGGTAGCAACAGCTACCGGAGTCCACTCCCAGGTGCAGCTGGTGGAGACT
                                                         FspI
  G   G   G   L   I   Q   P   G   G   S   L   R   M   S   C   Q   A   P   G   K   G   L   E   W   I   A
GGGGGAGGCTTAATCCAGCCTGGAGGGTCCCTGAGAATGTCCTGCGCAGGCTCCGGGGAAGGGGCTGGAGTGGATCGCA
              MscI
  Y   I   G   S   G       I   S   R   D   N   S   K   N   T   L   Y   L   Q   L   N   S   L   R   A   E
TACATTGGTAGTGGTGGCCATTTCCAGAGACAATAGCAAGAACACCCTGTATTTGCAATTGAACAGTCTGAGGGCTGAG
                      SrfI
  D   T   A   V   Y   Y   C   A       G   Q   G   T   T   V   T   V   S   S   A            (SEQ ID NO: 115)
GACACAGCCGTGTATTACTGTGCCCGGGCCAAGGTACCACGGTCACCGTCTCCAGCGCT                              (SEQ ID NO: 114)
```

```
M  G  W  S  C  I  I  L  F  L  V  A  T  A  T  G  V  H  S  D  V  L  M  T  Q  S  P  L
ATGGGATGGAGCTGTATCATCCTCTTCTTGTAGCAACAGCTACCGGAGTCCACTCCGATGTGTTGATGACCCAATCTCCACTC

S  L  P  V  T  P  G  E  P  A  S          L  Q  K  P  G  Q  S  P  Q  L  L  I  Y  K  V  S
                                EcoRV
TCCCTGCCTGTCACTCCTGGGGAGCCAGCCTGCAGAAACCAGGCCAGTCTCCACAGCTCCTGATCTACAAAGTTTCC

N  R  F  S  G  V  P  D  R  F  S  G  S  G  S  G  T  D  F  T  L  K  I  S  R  V  E  A
AACCGATTTTCTGGGGTCCCAGACAGATTCAGTGGCAGTGGATCAGGGACAGATTTCACACTCAAGATCAGCAGAGTGGAGGCT

E  D  T  G  V  Y  Y  C  F  Q  G  S  H  V  P  W  T  F  G  G  G  T  K  V  E  I  K
GAGGATACCGGAGTGTATTACTGCTTTCAAGGTTCACATGTTCCGTGGACGTTCGGTGGAGGCACCAAGGTGGAAATCAAGCGTACG  (SEQ ID NO: 117)
                                                                                        (SEQ ID NO: 116)
```

L2

```
M  G  W  S  C  I  I  L  F  L  V  A  T  A  T  G  V  H  S  D  V  L  M  T  Q  S  P  L
ATGGGATGGAGCTGTATCATCCTCTTCTTGTAGCAACAGCTACCGGAGTCCACTCCGATGTGTTGATGACCCAATCTCCACTC

S  L  P  V  T  P  G  E  P  A  S  I  S  C  R  S  S  Q  S  L  V  H  S  N  G  N  T  Y
TCCCTGCCTGTCACTCCTGGGGAGCCAGCCTCCATCTCTTGCAGATCTAGTCAGAGCCTTGGTACACATAGTAATGGAAACACCTAT

L  E  W  Y  L  Q  K  P  G  Q  S  P  Q  L  L           F  S  G  S  G  S  G  T  D  F  T  L
                                                SspI
TTAGAATGGTACCTGCAGAAACCAGGCCAGTCTCCTCACAGCTCCTAATATTCAGTGGCAGTGGATCAGGGACAGATTTCACACTC

K  I  S  R  V  E  A  E  D  T  G  V  Y  Y  C  F  Q  G  S  H  V  P  W  T  F  G  G  G
AAGATCAGCAGAGTGGAGGCTGAGGATACCGGAGTGTATTACTGCTTTCAAGGTTCACATGTTCCGTGGACGTTCGGTGGAGGC

T  K  V  E  I  K
ACCAAGGTGGAAATCAAGCGTACG  (SEQ ID NO: 119)
                          (SEQ ID NO: 118)
```

```
  M   G   W   S   C   I   I   L   F   L   V   A   T   A   T   G   V   H   S   D   V   L   M   T   Q   S   P   L
ATGGGATGGAGCTGTATCATCCTCTTCTTGGTAGCAACAGCTACCGGAGTCCACTCCGATGTGTTGATGACCCAATCTCCACTC

S   L   P   V   T   P   G   E   P   A   S   I   S   C   R   S   S   Q   S   L   V   H   S   N   G   N   T   Y
TCCCTGCCTGTCACTCCTGGGGAGCCAGCCTCCATCTCTTGCAGATCTAGTCAGAGCCTGGTACATAGTAATGGAAACACCTAT

L   E   W   Y   L   Q   K   P   G   Q   S   P   Q   L   L   I   Y   K   V   S   N   R   F   S   G   V   P   D
TTAGAATGGTACCTGCAGAAACCAGGCCAGTCTCCACAGCTCCTGATCTACAAAGTTTCCAACCGATTTTCTGGGGTCCCAGAC

HpaI
  R   F   S   G   S   G   S   G   T   D   F   T   L   K   I   S   R   V   E   A   E   D   T   G   V   T   K   V
AGATTCAGTGGCAGTGGATCAGGGACAGATTTCACACTCAAGATCAGCAGAGTGGAGGCTGAGGATACCGGAGTTAACCAAGGTG

E   I   K            (SEQ ID NO: 121)
GAAATCAAGCGTACG        (SEQ ID NO: 120)
```

L1/L2

```
  M   G   W   S   C   I   I   L   F   L   V   A   T   A   T   G   V   H   S   D   V   L   M   T   Q   S   P   L
ATGGGATGGAGCTGTATCATCCTCTTCTTGGTAGCAACAGCTACCGGAGTCCACTCCGATGTGTTGATGACCCAATCTCCACTC

EcoRV                                   SspI
  S   L   P   V   T   P   G   E   P   A   S       L   Q   K   P   G   Q   S   P   Q   L   L       F   S   G   S
TCCCTGCCTGTCACTCCTGGGGAGCCAGCCTCGATATCTGCAGAAACCAGGCCAGTCTCCACAGCTCCTAATATTCAGTGGCAGT

G   S   G   T   D   F   T   L   K   I   S   R   V   E   A   E   D   T   G   V   Y   Y   C   F   Q   G   S   H
GGATCAGGGACAGATTTCACACTCAAGATCAGCAGAGTGGAGGCTGAGGATACCGGAGTGTATTACTGCTTTCAAGGTTCACAT

V   P   W   T   F   G   G   G   T   K   V   E   I   K       (SEQ ID NO: 123)
GTTCCGTGGACGTTCGGTGGAGGCACCAAGGTGGAAATCAAGCGTACG             (SEQ ID NO: 122)
```

L1/L3

```
  M   G   W   S   C   I   I   L   F   L   V   A   T   A   T   G   V   H   S   D   V   L   M   T   Q   S   P   L
ATGGGATGGAGCTGTATCATCCTCTTCTTGGTAGCAACAGCTACCGGAGTCCACTCCGATGTGTTGATGACCCAATCTCCACTC

EcoRV
  S   L   P   V   T   P   G   E   P   A   S       L   Q   K   P   G   Q   S   P   Q   L   L   I   Y   K   V   S
TCCCTGCCTGTCACTCCTGGGGAGCCAGCCTCGATATCTGCAGAAACCAGGCCAGTCTCCACAGCTCCTGATCTACAAAGTTTCC

N   R   F   S   G   V   P   D   R   F   S   G   S   G   S   G   T   D   F   T   L   K   I   S   R   V   E   A
AACCGATTTTCTGGGGTCCCAGACAGATTCAGTGGCAGTGGATCAGGGACAGATTTCACACTCAAGATCAGCAGAGTGGAGGCT

HpaI
  E   D   T   G   V   I   K   V   E   I   K           (SEQ ID NO: 125)
GAGGATACCGGAGTTAACCAAGGTGGAAATCAAGCGTACG             (SEQ ID NO: 124)
```

```
  M  G  W  S  C  I  I  L  F  L  V  A  T  A  T  G  V  H  S  D  V  L  M  T  Q  S  P  L
ATGGGATGGAGCTGTATCATCCTCTTCTTGTAGCAACAGCTACCGGAGTCCACTCCGATGTGTTGATGACCCAATCTCCACTC

S  L  P  V  T  P  G  E  P  A  S  I  S  C  R  S  S  Q  S  L  V  H  S  N  G  N  T  Y
TCCCTGCCCTGTCACTCCTGGGGAGCCAGCCTCCATCTCTTGCAGATCTAGTCAGAGCCTGGTACATAGTAATGGAAACACCTAT

L  E  W  Y  L  Q  K  P  G  Q  S  P  Q  L  L  F  S  G  S  G  S  G  T  D  F  T  L
TTAGAATGGTACCTGCAGAAACCAGGCCAGTCTCCACAGCTCCTCCACAGTCTCCACAGCTCCTCCAGTGGCAGTCAGGGACAGATTTCACACTC
                                                                     SspI
  K  I  S  R  V  E  A  E  D  T  G  V         T  K  V  E  I  K                   (SEQ ID NO: 127)
AAGATCAGCAGAGTGGAGGCTGAGGATACCGGAGTAATATTCAGTGGCAGT    (SEQ ID NO: 126)
                                HpaI                                       CGTACG
                             GTTAACCAAGGTGAAATCAAGCGTACG

```

L1/L2/L3

```
  M  G  W  S  C  I  I  L  F  L  V  A  T  A  T  G  V  H  S  D  V  L  M  T  Q  S  P  L
ATGGGATGGAGCTGTATCATCCTCTTCTTGTAGCAACAGCTACCGGAGTCCACTCCGATGTGTTGATGACCCAATCTCCACTC

S  L  P  V  T  P  G  E  P  A  S         L  Q  K  P  G  Q  S  P  Q  L  L  F  S  G  S
TCCCTGCCCTGTCACTCCTGGGGAGCCAGCCTCGATATCTGCAGAAACCAGGCCAGTCTCCACAGCTCCTCCACAGCTCCTCCAGTCTCCACAGCTCCTCCAGTCTCCACAGCTCCTCCACAGCTCCTC
                            EcoRV                                          SspI
  G  S  G  T  D  F  T  L  K  I  S  R  V  E  A  E  D  T  G  V        T  K  V  E  I  K    (SEQ ID NO: 129)
GGATCAGGGACAGATTTCACACTCAAGATCAGCAGAGTGGAGGCTGAGGATACCGGAGTAATATTCAGTGGCAGT (SEQ ID NO: 128)
                                             HpaI                                CGTACG
                                          GTTAACCAAGGTGAAATCAAGCGTACG
```

FIG. 7 continued

Heavy chain

```
         HindIII      M   G   W   S   C   I   I   L   F   L   V   A   T   G   V   H   S   Q   V   Q   L   V   E   T   G
         AAGCTTACCATGGAGCTGTATCATCCTCTTCTTGGTAGCAACAGCTACCGAGTCCACTCCCAGGTGCAGCTGGTGGAGACTGGG
    1    ----+----|----+----|----+----|----+----|----+----|----+----|----+----|----+----|----+----|  90

G   G   L   I   Q   P   G   G   S   L   R   M   S   C   |   I   M   D   Q   V   P   F   S   V |  W   V   R   Q   A   P
         GGAGGCTTAATCCAGCCTGGAGGGTCCCTGAGAATGTCCTGA|ATGGACCAGGTGCCTTCTCCGTG|GGGTTCGGCAGGCTCCG
   91    ----+----|----+----|----+----|----+----|----+----|----+----|----+----|----+----|----+----| 180

G   K   G   L   E   W   I   A   Y   I   G   S   G   G | S   V   Y   D   F   F   V   W   L | R   F   T   I   S   R   D
         GGGAAGGGGCTGGAGTGGATCGCATACATTGGTAGTGGTGGT|AGTGTTTATGATTTTTTTGTGTGGCTC|CGATTCACCATTTCCAGAGAC
  181    ----+----|----+----|----+----|----+----|----+----|----+----|----+----|----+----|----+----| 270

N   S   K   N   T   L   Y   L   Q   L   N   S   L   R   A   E   D   T   A   V   Y   Y   C   A   R   H   Y   G   H   Y
         AATAGCAAGAACACCCTGTATTTGCAATTGAACAGTCTGAGGGCTGAGGACACAGCCGTGTATTACTGTGCGAGACATTATGGTCACTAC
  271    ----+----|----+----|----+----|----+----|----+----|----+----|----+----|----+----|----+----| 360

AfeI
           V   D   Y   A   V   D   Y   W   G   Q   G   T   T   V   T   V   S   S   A   S   T   K   G   P   S   V   F   P   L   A
         GTGGACTATGCTGTGGACTACTGGGGTCAAGGCACCACGGTCACCGTCTCCAGCGCTTCCACCAAGGGCCCATCGGTCTTCCCCCTGGCA
  361    ----+----|----+----|----+----|----+----|----+----|----+----|----+----|----+----|----+----| 450

P   S   S   K   S   T   S   G   G   T   A   A   L   G   C   L   V   K   D   Y   F   P   E   P   V   T   V   S   W   N
         CCCTCCTCCAAGAGCACCTCTGGGGGCACAGCGGCCCTGGGCTGCCTGGTCAAGGACTACTTCCCCGAACCGGTGACGGTGTCGTGGAAC
  451    ----+----|----+----|----+----|----+----|----+----|----+----|----+----|----+----|----+----| 540

S   G   A   L   T   S   G   V   H   T   F   P   A   V   L   Q   S   S   G   L   Y   S   L   S   S   V   V   T   V   P
         TCAGGCGCCCTGACCAGCGGCGTGCACACCTTCCCGGCTGTCCTACAGTCCTCAGGACTCTACTCCCTCAGCAGCGTGGTGACCGTGCCC
  541    ----+----|----+----|----+----|----+----|----+----|----+----|----+----|----+----|----+----| 630

S   S   S   L   G   T   Q   T   Y   I   C   N   V   N   H   K   P   S   N   T   K   V   D   K   K   V   *   P   K   S       (SEQ ID NO: 131)
         TCCAGCAGCTTGGGCACCCAGACCTACATCTGCAACGTGAATCACAAGCCCAGCAACACCAAGGTGGACAAGAAAGTTTGACCCAAATCT     (SEQ ID NO: 130)
  631    ----+----|----+----|----+----|----+----|----+----|----+----|----+----|----+----|----+----| 720
```

FIG. 9

Heavy Chain

```
        M   Q   V   Q   L   V   E   T   G   G   G   L   I   Q   P   G   G   S   L   R   M   S   C   T   I   M   D
HindIII
AAGCTTACCATGCAGGTGCAGCTGGTGGAGACTGGGGGAGGCTTAATCCAGCCTGGAGGGTCCCTGAGAATGTCCTGCACCATTATGGAC
1      -----|----|----|----|----|----|----|----|----|: 90

Q   V   P   F   S   V       W   V   R   Q   A   P   G   K   G   L   E   W   I   A   Y   I   G   S   G   G       S   V   Y   D
CAGGTGCCTTTCTCCGTGTGGGTCCGTGGGGTTCGGCAGGCTCCGGGAAGGGGCTCGAGTGGATCGCATACATTGGTAGTGGTGGTAGTGTTTATGAT
91     -----|----|----|----|----|----|----|----|----|: 180

F   F   V   W   L   R   F   T   I   S   R   D   N   S   K   N   T   L   Y   L   Q   L   N   S   L   R   A   E   D   T
TTTTTTGTGTGGCTCCGGATTCACCATTTCCAGAGACAATAGCAAGAACACCCTGTATTTGCAATTGAACAGTCTGAGGGCTGAGGACACA
181    -----|----|----|----|----|----|----|----|----|: 270

A   V   Y   Y   C   A   R   H   Y   G   H   Y   V   D   Y   A   V   D   Y   W   G   Q   G   T   T   V   T   V   S   S
                                                                                                                    AfeI
GCCGTGTATTACTGTGCGAGACATTATGGTCACTACGTGGACTACGCTGTGGACTACTGGGGTCAAGGTACCACGGTCACCGTCTCCAGC        (SEQ ID NO: 133)
271    -----|----|----|----|----|----|----|----|----|: 360

A
GCT
361 --- 363   (SEQ ID NO: 132)
```

FIG. 10

Light Chain

```
BamHI     M  D  V  L  M  T  Q  S  P  L  S  L  P  V  T  P  G  E  P  A  S  I  S  C  T  P  P
       GGATCCACCATGGATGTTGATGTTGATGACCCAATCTCCACTCTCCCTGCCTGTCACTCCTGGGGAGCCAGCCTCCATCTCTTGCACTCCTCCA
    1  ----:----|----:----|----:----|----:----|----:----|----:----|----:----|----:----|----:----|    90

A  Y  R  P  P  N  A  P  I  L  W  Y  L  Q  K  P  G  Q  S  P  Q  L  L  I  Y  K  V  S  N  R
       GCTTATAGACCACCAAATGCCCCTATCCTATGGTATCTGCAGAAACCAGGCCAGTCTCCACAGCTCCTGATCTACAAAGTTTCCAACCGA
   91  ----:----|----:----|----:----|----:----|----:----|----:----|----:----|----:----|----:----|   180

F  S  G  V  P  D  R  F  S  G  S  G  S  G  T  D  F  T  L  K  I  S  R  V  E  A  E  D  T  G
       TTTTCTGGGGTCCCAGACAGATTCAGTGGCAGTGGATCAGGGACAGATTTCACACTCAAGATCAGCAGAGTGGAGGCTGAGGATACCGGA
  181  ----:----|----:----|----:----|----:----|----:----|----:----|----:----|----:----|----:----|   270

V  Y  Y  C  F  Q  G  S  H  V  P  W  T  F  G  G  G  T  K  V  E  I  K       BsiWI      (SEQ ID NO: 134)
       GTGTATTACTGCTTTCAAGGTTCACATGTTCCGTGGACGTTCGGTGGAGGCACCAAGGTGGAAATCAAGCGTACG              (SEQ ID NO: 135)
  271  ----:----|----:----|----:----|----:----|----:----|----:----|----:----|                       345
```

FIG. 11

```
     AfeI
       S  A  S  T  K  G  P  S  V  F  P  L  A  P  C  S  R  S  T  S  E  S  T  A  A  L  G  C  L  V
     AGCGCTTCCACCAAGGGCCCATCGGTCTTCCCCCTGGCGCCCTGCTCCAGGAGCACCTCCGAGAGCACAGCGGCCCTGGGCTGCCTGGTC
  1  ---------!---------!---------!---------!---------!---------!---------!---------!---------! 90

K  D  Y  F  P  E  P  V  T  V  S  W  N  S  G  A  L  T  S  G  V  H  T  F  P  A  V  L  Q  S
     AAGGACTACTTCCCCGAACCCGTGACGGTGTCGTGGAACTCAGGCGCTCTGACCAGCGGCGTGCACACCTTCCCGGCTGTCCTACAGTCC
 91  ---------!---------!---------!---------!---------!---------!---------!---------!---------! 180

S  G  L  Y  S  L  S  S  V  V  T  V  P  S  S  N  F  G  T  Q  T  Y  T  C  N  V  D  H  K  P
     TCAGGACTCTACTCCCTCAGCAGCGTGGTGACCGTGCCCTCCAGCAACTTCGGCACCCAGACCTACACCTGCAACGTAGATCACAAGCCC
181  ---------!---------!---------!---------!---------!---------!---------!---------!---------! 270

S  N  T  K  V  D  K  T  V  E  R  K  C  C  V  E  C  P  P  C  P  A  P  P  V  A  G  P  S  V
     AGCAACACCAAGGTGGACAAGACAGTTGAGCGCAAATGTTGTGTCGAGTGCCCACCGTGCCCAGCACCACCTGTGGCAGGACCGTCAGTC
271  ---------!---------!---------!---------!---------!---------!---------!---------!---------! 360

F  L  F  P  P  K  P  K  D  T  L  M  I  S  R  T  P  E  V  T  C  V  V  V  D  V  S  H  E  D
     TTCCTCTTCCCCCCAAAACCCAAGGACACCCTCATGATCTCCCGGACCCCTGAGGTCACGTGCGTGGTGGTGGACGTGAGCCACGAAGAC
361  ---------!---------!---------!---------!---------!---------!---------!---------!---------! 450

P  E  V  Q  F  N  W  Y  V  D  G  V  E  V  H  N  A  K  T  K  P  R  E  E  Q  F  N  S  T  F
     CCCGAGGTCCAGTTCAACTGGTACGTGGACGGCGTGGAGGTGCATAATGCCAAGACAAAGCCACGGGAGGAGCAGTTCAACAGCACGTTC
451  ---------!---------!---------!---------!---------!---------!---------!---------!---------! 540

R  V  V  S  V  L  T  V  V  H  Q  D  W  L  N  G  K  E  Y  K  C  K  V  S  N  K  G  L  P  A
     CGTGTGGTCAGCGTCCTCACCGTCGTGCACCAGGACTGGCTGAACGGCAAGGAGTACAAGTGCAAGGTCTCCAACAAAGGCCTCCCAGCC
541  ---------!---------!---------!---------!---------!---------!---------!---------!---------! 630

P  I  E  K  T  I  S  K  T  K  G  Q  P  R  E  P  Q  V  Y  T  L  P  P  S  R  E  E  M  T  K
     CCCATCGAGAAAACCATCTCCAAAACCAAAGGGCAGCCCCGAGAACCACAGGTGTACACCCTGCCCCCATCCCGGGAGGAGATGACCAAG
631  ---------!---------!---------!---------!---------!---------!---------!---------!---------! 720

N  Q  V  S  L  T  C  L  V  K  G  F  Y  P  S  D  I  A  V  E  W  E  S  N  G  Q  P  E  N  N
     AACCAGGTCAGCCTGACCTGCCTGGTCAAAGGCTTCTACCCCAGCGACATCGCCGTGGAGTGGGAGAGCAATGGGCAGCCGGAGAACAAC
721  ---------!---------!---------!---------!---------!---------!---------!---------!---------! 810

Y  K  T  T  P  P  M  L  D  S  D  G  S  F  F  L  Y  S  K  L  T  V  D  K  S  R  W  Q  Q  G
     TACAAGACCACACCTCCCATGCTGGACTCCGACGGCTCCTTCTTCCTCTACAGCAAGCTCACCGTGGACAAGAGCAGGTGGCAGCAGGGG
811  ---------!---------!---------!---------!---------!---------!---------!---------!---------! 900

SapI
       N  V  F  S  C  S  V  M  H  E  A  L  H  N  H  Y  T  Q  K  S  L  S  L  S  P  G  K  *     (SEQ ID NO: 137)
     AACGTCTTCTCATGCTCCGTGATGCATGAGGCTCTGCACAACCACTACACGCAGAAGAGCCTCTCCCTGTCTCCGGGTAAATGATATCCA
901  ---------!---------!---------!---------!---------!---------!---------!---------!---------! 990

CTAAGGGCGAATTCTGCAGATATCCAGCACAGTGGCGGCCGCTCGAG  (SEQ ID NO: 136)
991  ---------!---------!---------!---------!-------  1037
```

FIG. 12

```
        AfeI
        S  A  S  T  K  G  P  S  V  F  P  L  A  P  C  S  R  S  T  S  G  G  T  A  A  L  G  C  L  V
        AGCGCTTCCACCAAGGGCCCATCGGTCTTCCCCCTGGCGCCCTGCTCCAGGAGCACCTCTGGGGGCACAGCGGCCCTGGGCTGCCTGGTC
     1  ---------!---------!---------!---------!---------!---------!---------!---------!---------!  90

K  D  Y  F  P  E  P  V  T  V  S  W  N  S  G  A  L  T  S  G  V  H  T  F  P  A  V  L  Q  S
        AAGGACTACTTCCCCGAACCGGTGACGGTGTCGTGGAACTCAGGCGCCCTGACCAGCGGCGTGCACACCTTCCCGGCTGTCCTACAGTCC
    91  ---------!---------!---------!---------!---------!---------!---------!---------!---------! 180

S  G  L  Y  S  L  S  S  V  V  T  V  P  S  S  S  L  G  T  Q  T  Y  T  C  N  V  K  H  K  P
        TCAGGACTCTACTCCCTCAGCAGCGTGGTGACCGTGCCCTCCAGCAGCTTGGGCACCCAGACCTACACCTGCAACGTGAATCACAAGCCC
   181  ---------!---------!---------!---------!---------!---------!---------!---------!---------! 270

S  N  T  K  V  D  K  R  V  E  L  K  T  P  L  G  D  T  T  H  T  C  P  R  C  P  E  P  K  S
        AGCAACACCAAGGTGGACAAGAGAGTTGAGCTCAAAACCCCACTTGGTCACACAACTCACACATGCCCACGGTGCCCAGAGCCCAAATCT
   271  ---------!---------!---------!---------!---------!---------!---------!---------!---------! 360

C  D  T  P  P  P  C  P  R  C  P  E  P  K  S  C  D  T  P  P  P  C  P  R  C  P  E  P  K  S
        TGTGACACACCTCCCCCGTGCCCACGGTGCCCAGAGCCCAAATCTTGTGACACACCTCCCCCATGCCCACGGTGCCCAGAGCCCAAATCT
   361  ---------!---------!---------!---------!---------!---------!---------!---------!---------! 450

C  D  T  P  P  P  C  P  R  C  P  A  P  E  L  L  G  G  P  S  V  F  L  F  P  P  K  P  K  D
        TGTGACACACCTCCCCCATGCCCACGGTGCCCAGCACCTGAACTCCTGGGAGGACCGTCAGTCTTCCTCTTCCCCCCAAAACCCAAGGAT
   451  ---------!---------!---------!---------!---------!---------!---------!---------!---------! 540

T  L  M  I  S  R  T  P  E  V  T  C  V  V  V  D  V  S  H  E  D  P  E  V  Q  F  K  W  Y  V
        ACCCTTATGATTTCCCGGACCCCTGAGGTCACGTGCGTGGTGGTGGACGTGAGCCACGAAGACCCCGAGGTCCAGTTCAAGTGGTACGTG
   541  ---------!---------!---------!---------!---------!---------!---------!---------!---------! 630

D  G  V  E  V  H  N  A  K  T  K  P  R  E  E  Q  F  N  S  T  F  R  V  V  S  V  L  T  V  L
        GACGGCGTGGAGGTGCATAATGCCAAGACAAAGCCGCGGGAGGAGCAGTTCAACAGCACGTTCCGTGTGGTCAGCGTCCTCACCGTCCTG
   631  ---------!---------!---------!---------!---------!---------!---------!---------!---------! 720

H  Q  D  W  L  N  G  K  E  Y  K  C  K  V  S  N  K  A  L  P  A  P  I  E  K  T  I  S  K  T
        CACCAGGACTGGCTGAACGGCAAGGACTACAACTGCAAGGTCTCCAACAAAGCCCTCCCAGCCCCCATCGAGAAAACCATCTCCAAAACC
   721  ---------!---------!---------!---------!---------!---------!---------!---------!---------! 810

K  G  Q  P  R  E  P  Q  V  Y  T  L  P  P  S  R  E  E  M  T  K  N  Q  V  S  L  T  C  L  V
        AAAGGACAGCCCCGAGAACCACAGGTGTACACCCTGCCCCCATCCCGGGAGGAGATGACCAAGAACCAGGTCAGCCTGACCTGCCTGGTC
   811  ---------!---------!---------!---------!---------!---------!---------!---------!---------! 900

K  G  F  Y  P  S  D  I  A  V  E  W  E  S  S  G  Q  P  E  N  N  Y  N  T  T  P  P  M  L  D
        AAAGGCTTCTACCCCAGCGACATCGCCGTGGAGTGGGAGAGCAGCGGGCAGCCGGAGAACAACTACAACACCACGCCTCCCATGCTGGAC
   901  ---------!---------!---------!---------!---------!---------!---------!---------!---------! 990

S  D  G  S  F  F  L  Y  S  K  L  T  V  D  K  S  R  W  Q  Q  G  N  I  F  S  C  S  V  M  H
        TCCGACGGCTCCTTCTTCCTCTACAGCAAGCTCACCGTGGACAAGAGCAGGTGGCAGCAGGGGAACATCTTCTCATGCTCCGTGATGCAT
   991  ---------!---------!---------!---------!---------!---------!---------!---------!---------! 1080
                                              SapI              (SEQ ID NO: 139)
        E  A  L  H  N  R  F  T  Q  K  S  L  S  L  S  P  G  K  *                      (SEQ ID NO: 138)
        CAGGCTCTGCACAACCCCTTCACGCAGAAGAGCCTCTCCCTGTCTCCCGGTAAATGATATCCATCACACTGGCGCCCGCTCGAG
  1081  ---------!---------!---------!---------!---------!---------!---------!---------!---- 1164
```

FIG. 13

Heavy chain

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1    ---------!---------!---------!---------!---------!---------!---------!---------!---------! 90

G  G  L  I  Q  P  G  G  S  L  R  M  S  C │T  I  M  D  Q  V  P  F  S  V│ W  V  R  Q  A  P
GGAGGCTTAATCCAGCCTGGAGGGTCCCTGAGAATGTCCTGCACCATTATGGACCAGTGCCTTTCTCCGTGTGGGTTCGGCAGGCTCCG
91   ---------!---------!---------!---------!---------!---------!---------!---------!---------! 180

G  K  G  L  E  W  I  A  Y  I  G  S  G  G │S  V  Y  D  F  F  V  W  L│ R  F  T  I  S  R  D
GGGAAGGGGCTGGAGTGGATCGCATACATTGGTAGTGGTGGTAGTGTTTATGATTTTTTTGTGTGGCTCCGATTCACCATTTCCAGAGAC
181  ---------!---------!---------!---------!---------!---------!---------!---------!---------! 270

N  S  K  N  T  L  Y  L  Q  L  N  S  L  R  A  E  D  T  A  V  Y  Y  C  A  R  H  Y  G  H  Y
AATAGCAAGAACACCCTGTATTTGCAATTGAACAGTCTGAGGGCTGAGGACACAGCCGTGTATTACTGTGCGAGACATTATGGTCACTAC
271  ---------!---------!---------!---------!---------!---------!---------!---------!---------! 360
                                                              AfeI
           V  D  Y  A  V  D  Y  W  G  Q  G  T  T  V  T  V  S  S  A  S  T  K  G  P  S  V  F  P  L  A
GTGGACTATGCTGTGGACTACTGGGGTCAAGGTACCACGGTCACCGTCTCCAGCGCTTCCACCAAGGGCCCATCGGTCTTCCCCCTGGCA
361  ---------!---------!---------!---------!---------!---------!---------!---------!---------! 450
                                                                        AgeI
           P  S  S  K  S  T  S  G  G  T  A  A  L  G  C  L  V  K  D  Y  F  P  E  P  V  T  V  S  W  N
CCCTCCTCCAAGAGCACCTCTGGGGGCACAGCGGCCCTGGGCTGCCTGGTCAAGGACTACTTCCCCGAACCGGTGACGGTGTCGTGGAAC
451  ---------!---------!---------!---------!---------!---------!---------!---------!---------! 540

S  G  A  L  T  S  G  V  H  T  F  P  A  V  L  Q  S  S  G  L  Y  S  L  S  S  V  V  T  V  P
TCAGGCGCCCTGACCAGCGGCGTGCACACCTTCCCGGCTGTCCTACAGTCCTCAGGACTCTACTCCCTCAGCAGCGTGGTGACCGTGCCC
541  ---------!---------!---------!---------!---------!---------!---------!---------!---------! 630

S  S  S  L  G  T  Q  T  Y  I  C  N  V  N  H  K  P  S  N  T  K  V  D  K  K  V  E  P  K  S
TCCAGCAGCTTGGGCACCCAGACCTACATCTGCAACGTGAATCACAAGCCCAGCAACACCAAGGTGGACAAGAAAGTTGAGCCCAAATCT
631  ---------!---------!---------!---------!---------!---------!---------!---------!---------! 720
                                                  AhdI
           C  D  K  T  H  T  C  P  P  C  P  A  P │P  V  A│ G  G  P  S  V  F  L  F  P  P  K  P  K  D
TGTGACAAAACTCACACATGCCCACCGTGCCCAGCACCTCCAGTCGCGGGGGACCGTCAGTCTTCCTCTTCCCCCCAAAACCCAAGGAC
721  ---------!---------!---------!---------!---------!---------!---------!---------!---------! 810

T  L  M  I  S  R  T  P  E  V  T  C  V  V  V  D  V  S  H  E  D  P  E  V  K  F  N  W  Y  V
ACCCTCATGATCTCCCGGACCCCTGAGGTCACATGCGTGGTGGTGGACGTGAGCCACGAAGACCCTGAGGTCAAGTTCAACTGGTACGTG
811  ---------!---------!---------!---------!---------!---------!---------!---------!---------! 900

D  G  V  E  V  H  N  A  K  T  K  P  R  E  E  Q  Y  N  S  T  Y  R  V  V  S  V  L  T  V  L
GACGGCGTGGAGGTGCATAATGCCAAGACAAAGCCGCGGGAGGAGCAGTACAACAGCACGTACCGTGTGGTCAGCGTCCTCACCGTCCTG
901  ---------!---------!---------!---------!---------!---------!---------!---------!---------! 990

H  Q  D  W  L  N  G  K  E  Y  K  C  K  V  S  N  K  A  L  P  A  P  I  E  K  T  I  S  K  A
CACCAGGACTGGCTGAATGGCAAGGAGTACAAGTGCAAGGTCTCCAACAAAGCCCTCCCAGCCCCCATCGAGAAAACCATCTCCAAAGCC
991  ---------!---------!---------!---------!---------!---------!---------!---------!---------! 1080

K  G  Q  P  R  E  P  Q  V  Y  T  L  P  P  S  R  D  E  L  T  K  N  Q  V  S  L  T  C  L  V
AAAGGGCAGCCCCGAGAACCACAGGTGTACACCCTGCCCCCATCCCGGGATGAGCTGACCAAGAACCAGGTCAGCCTGACCTGCCTGGTC
1081 ---------!---------!---------!---------!---------!---------!---------!---------!---------! 1170

K  G  F  Y  P  S  D  I  A  V  E  W  E  S  N  G  Q  P  E  N  N  Y  K  T  T  P  P  V  L  D
AAAGGCTTCTATCCCAGCGACATCGCCGTGGAGTGGGAGAGCAATGGGCAGCCGGAGAACAACTACAAGACCACGCCTCCCGTGCTGGAC
1171 ---------!---------!---------!---------!---------!---------!---------!---------!---------! 1260

S  D  G  S  F  F  L  Y  S  K  L  T  V  D  K  S  R  W  Q  Q  G  N  V  F  S  C  S  V  M  H
TCCGACGGCTCCTTCTTCCTCTACAGCAAGCTCACCGTGGACAAGAGCAGGTGGCAGCAGGGGAACGTCTTCTCATGCTCCGTGATGCAT
1261 ---------!---------!---------!---------!---------!---------!---------!---------!---------! 1350

E  A  L  H  N  H  Y  T  Q  K  S  L  S  L  S  P  G  K  *       (SEQ ID NO: 141)
GAGGCTCTGCACAACCACTACACGCAGAAGAGCCTCTCCCTGTCTCCGGGTAAATGATCTAAAGGGCGAATTCGCCCTTAAGGGCGAATT            (SEQ ID NO: 140)
1351 ---------!---------!---------!---------!---------!---------!---------!---------!---------! 1440
```

FIG. 15

Heavy chain

```
  HindIII    M  G  W  S  C  I  I  L  F  L  V  A  T  A  T  G  V  H  S  Q  V  Q  L  V  E  T  G
  AAGCTTACCATGGGATGGAGCTGTATCATCCTCTTCTTGGTAGCAACAGCTACCGGAGTCCACTCCCAGGTGCAGCTGGTGGAGACTGGG
 1 ---------!---------!---------!---------!---------!---------!---------!---------!---------! 90

G  G  L  I  Q  P  G  G  S  L  R  M  S  C │ T  I  M  D  Q  V  P  F  S  V │ W  V  R  Q  A  P
     GGACGCTTAATCCAGCCTGGAGGGTCCCTGAGAATGTCTCTGC ACCATTATGGACCAGGTGCCTTTCTCCCTG TGGGTTCGGCACGCTCCC
 91 ---------!---------!---------!---------!---------!---------!---------!---------!---------! 180

G  K  G  L  E  W  I  A  Y  I  G  S  G  G │ S  V  Y  D  F  F  V  W  L │ R  F  T  I  S  R  D
     GGGAAGGGGCTGGAGTGGATCGCATACATTGGTAGTGGTGGT AGTGTTTATGATTTTTTTGTGTGGCTC CGATTCACCATTTCCAGAGAC
181 ---------!---------!---------!---------!---------!---------!---------!---------!---------! 270

N  S  K  N  T  L  Y  L  Q  L  N  S  L  R  A  E  D  T  A  V  Y  Y  C  A  R  H  Y  G  H  Y
     AATAGCAAGAACACCCTGTATTTGCAATTGAACAGTCTGAGGGCTGAGGACACAGCCGTGTATTACTGTGCGAGACATTATGGTCACTAC
271 ---------!---------!---------!---------!---------!---------!---------!---------!---------! 360
                                                                      AfeI
        V  D  Y  A  V  D  Y  W  G  Q  G  T  T  V  T  V  S  S  A  S  T  K  G  P  S  V  F  P  L  A
     GTGGACTATGCTGTGGACTACTGGGGTCAAGGTACCACGGTCACCGTCTCCAGCGCTTCCACCAAGGGCCCATCGGTCTTCCCCCTGGCG
361 ---------!---------!---------!---------!---------!---------!---------!---------!---------! 450
                                                                      AgeI
        P  C  S  R  S  T  S  E  S  T  A  A  L  G  C  L  V  K  D  Y  F  P  E  P  V  T  V  S  W  N
     CCCTGCTCCAGGAGCACCTCCGAGAGCACAGCGGCCCTGGGCTGCCTGGTCAAGGACTACTTCCCCGAACCGGTGACGGTGTCGTGGAAC
451 ---------!---------!---------!---------!---------!---------!---------!---------!---------! 540

S  G  A  L  T  S  G  V  H  T  F  P  A  V  L  Q  S  S  G  L  Y  S  L  S  S  V  V  T  V  P
     TCAGGCGCTCTGACCAGCGGCGTGCACACCTTCCCGGCTGTCCTACAGTCCTCAGGACTCTACTCCCTCAGCAGCGTGGTGACCGTGCCC
541 ---------!---------!---------!---------!---------!---------!---------!---------!---------! 630

S  S  N  F  G  T  Q  T  Y  T  C  N  V  D  H  K  P  S  N  T  K  V  D  K  T  V  E  R  K  C
     TCCAGCAACTTCGGCACCCAGACCTACACCTGCAACGTAGATCACAAGCCCAGCAACACCAAGGTGGACAAGACAGTTGAGCGCAAATGT
631 ---------!---------!---------!---------!---------!---------!---------!---------!---------! 720
                                         AhdI
        C  V  E  C  P  P  C  P  A  P │ E  L  L  G │ G  P  S  V  F  L  F  P  P  K  P  K  D  T  L  M
     TGTGTCGAGTGCCCACCGTGCCCAGCACCA GAACTGTTAGGA GACCGTCAGTCTTCCTCTTCCCCCCAAAACCCAAGGACACCCTCATG
721 ---------!---------!---------!---------!---------!---------!---------!---------!---------! 810

T  S  R  T  P  E  V  T  C  V  V  V  D  V  S  H  E  D  P  E  V  Q  F  N  W  Y  V  D  G  V
     ATCTCCCGGACCCCTGAGGTCACGTGCGTGGTGGTGGACGTGAGCCACGAAGACCCCGAGGTCCAGTTCAACTGGTACGTGGACGGCGTG
811 ---------!---------!---------!---------!---------!---------!---------!---------!---------! 900

E  V  H  N  A  K  T  K  P  R  E  E  Q  F  N  S  T  F  R  V  V  S  V  L  T  V  V  H  Q  D
     GAGGTGCATAATGCCAAGACAAAGCCACGGGAGGAGCAGTTCAACAGCACGTTCCGTGTGGTCAGCGTCCTCACCGTCGTGCACCAGGAC
901 ---------!---------!---------!---------!---------!---------!---------!---------!---------! 990

W  L  N  G  K  E  Y  K  C  K  V  S  N  K  G  L  P  A  P  I  E  K  T  I  S  K  T  K  G  Q
     TGGCTGAACGGCAAGGAGTACAAGTGCAAGGTCTCCAACAAAGGCCTCCCAGCCCCCATCGAGAAAACCATCTCCAAAACCAAAGGGCAG
991 ---------!---------!---------!---------!---------!---------!---------!---------!---------! 1080

P  R  E  P  Q  V  Y  T  L  P  P  S  R  E  E  M  T  K  N  Q  V  S  L  T  C  L  V  K  G  F
      CCCCGAGAACCACAGGTGTACACCCTGCCCCCATCCCGGGAGGAGATGACCAAGAACCAGGTCAGCCTGACCTGCCTGGTCAAAGGCTTC
1081 ---------!---------!---------!---------!---------!---------!---------!---------!---------! 1170

Y  P  S  D  I  A  V  E  W  E  S  N  G  Q  P  E  N  N  Y  K  T  T  P  P  M  L  D  S  D  G
      TACCCCAGCGACATCGCCGTGGAGTGGGAGAGCAATGGGCAGCCGGAGAACAACTACAAGACCACACCTCCCATGCTGGACTCCGACGGC
1171 ---------!---------!---------!---------!---------!---------!---------!---------!---------! 1260

S  F  F  L  Y  S  K  L  T  V  D  K  S  R  W  Q  Q  G  N  V  F  S  C  S  V  M  H  E  A  L
      TCCTTCTTCCTCTACAGCAAGCTCACCGTGGACAAGAGCAGGTGGCAGCAGGGGAACGTCTTCTCATGCTCCGTGATGCATGAGGCTCTG
1261 ---------!---------!---------!---------!---------!---------!---------!---------!---------! 1350
                                              (SEQ ID NO: 143)
        H  N  H  Y  T  Q  K  S  L  S  L  S  P  G  K  *
      CACAACCACTACACGCAGAAGAGCCTCTCCCTGTCTCCGGGTAAATGATATCCACTAAGGGCGAATTCTGCAGATATCCAGCACAGTGGC             (SEQ ID NO: 142)
1351 ---------!---------!---------!---------!---------!---------!---------!---------!---------! 1440
```

FIG. 16

Heavy Variable

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C  T  I  M  D  Q  V  P  F  S  V  W  V  R  Q  A  P
GGAGGCTTAATCCAGCCTGGAGGGTCCCTGAGAATGTCCTGCACCATTATGGACCAGGTGCCTTTCTCCGTGTGGGTTCGGCAGGCTCCG
 91 ---------!---------!---------!---------!---------!---------!---------!---------!---------! 180

G  K  G  L  E  W  I  A  Y  I  G  S  G  G  S  V  Y  D  F  F  V  W  L  R  F  T  I  S  R  D
GGGAAGGGGCTGGAGTGGATCGCATACATTGGTAGTGGTGGTAGTGTTTATGATTTTTTTGTGTGGCTCCGATTCACCATTTCCAGAGAC
181 ---------!---------!---------!---------!---------!---------!---------!---------!---------! 270

N  S  K  N  T  L  Y  L  Q  L  N  S  L  R  A  E  D  T  A  V  Y  Y  C  A  R  H  Y  G  H  Y
AATAGCAAGAACACCCTGTATTTGCAATTGAACAGTCTGAGGGCTGAGGACACAGCCGTGTATTACTGTGCGAGACATTATGGTCACTAC
271 ---------!---------!---------!---------!---------!---------!---------!---------!---------! 360
                                                                          AfeI
           V  D  Y  A  V  D  Y  W  G  Q  G  T  T  V  T  V  S  S              (SEQ ID NO: 145)
GTGGACTATGCTGTGGACTACTGGGGTCAAGGTACCACGGTCACCGTCTCCAGCGCT                    (SEQ ID NO: 144)
361 ---------!---------!---------!---------!---------!------- 417
```

Light Variable

```
BamH1     M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C  T  P  P  A  Y  R  P  P  N  A  P  I  L  W  Y
CTCTCCCTGCCTGTCACTCCTGGGGAGCCAGCCTCGATCTCTTGCACTCCTCCAGCTTATAGACCACCAAATGCCCCTATCCTATGGTAT
 91 ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
CTGCAGAAACCAGGCCAGTCTCCACAGCTCCTGATCTACAAAGTTTCCAACCGATTTTCTGGGGTCCCAGACAGATTCAGTGGCAGTGGA
181 ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

T  F  G  G  G  T  K  V  E  I  K  BsiWI     (SEQ ID NO: 147)
ACGTTCGGTGGAGGCACCAAGGTGGAAATCAAGCGTACG             (SEQ ID NO: 146)
361 ---------!---------!---------!--------- 399
```

FIG. 19 a.
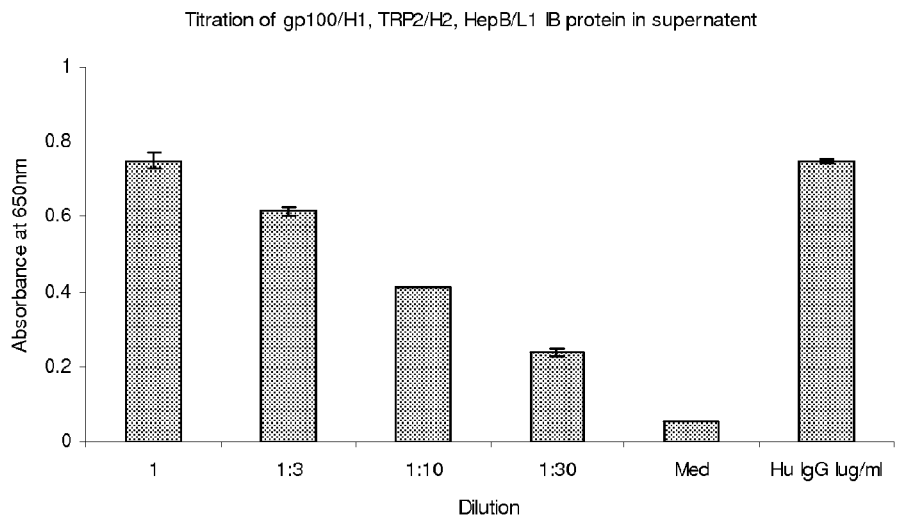
b.
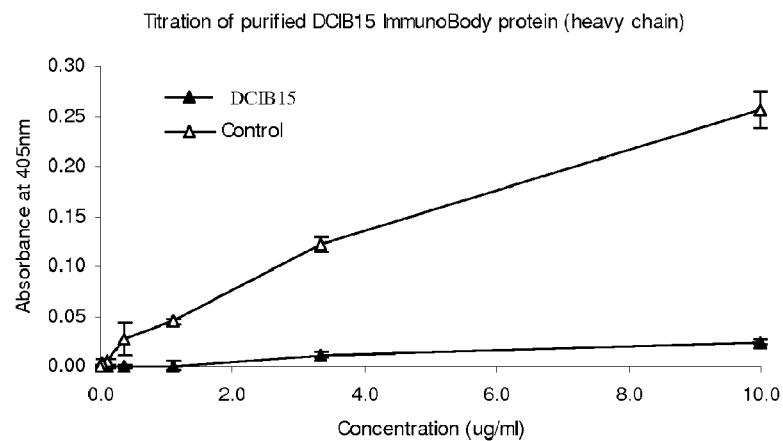
c.
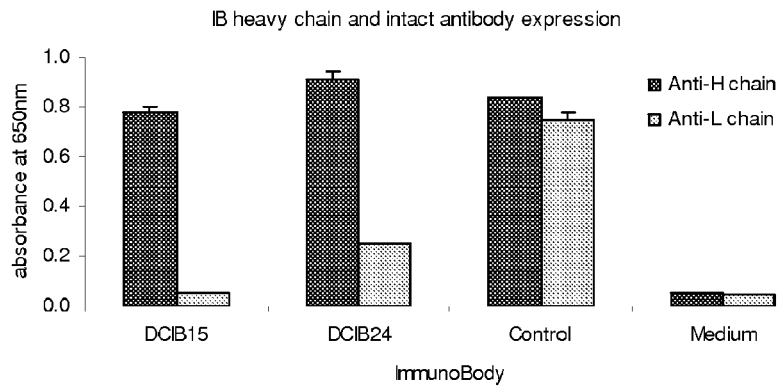
FIG. 20

Heavy Variable

```
HindIII   M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1    ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
        GGAGGCTTAATCCAGCCTGGAGGGTCCCTGAGAATGTCCTGTGCAGCCTCTGGATTCGCTTTCAATACCTATGACATGTCTTGGGTTCGC
91   ---------!---------!---------!---------!---------!---------!---------!---------!---------! 180

Q  A  P  G  K  G  L  E  W  I  A  Y  I  G  S  G  G |S  I  I  N  F  E  K  L| R  F  T  I  S
        CAGGCTCCGGGAAGGGGCTGGAGTGGATCGCATACATTGGTAGTGGTGGTAGTATAATCAACTTTGAAAAACTGCGATTCACCATTTCC
181  ---------!---------!---------!---------!---------!---------!---------!---------!---------! 270

R  D  N  S  K  N  T  L  Y  L  Q  L  N  S  L  R  A  E  D  T  A  V  Y  Y  C  A  R  H  Y  G
        AGAGACAATAGCAAGAACACCCTGTATTTGCAATTGAACAGTCTGAGGGCTGAGGACACAGCCGTGTATTACTGTGCAAGACATTATGGT
271  ---------!---------!---------!---------!---------!---------!---------!---------!---------! 360

AfeI
          H  Y  V  D  Y  A  V  D  Y  W  G  Q  G  T  T  V  T  V  S  S              (SEQ ID NO: 149)
        CACTACGTGGACTATGCTGTGGACTACTGGGGTCAAGGAACCACGGTCACCGTCTCCAGCGCT              (SEQ ID NO: 148)
361  ---------!---------!---------!---------!---------!---------!---  423
```

Light Variable

```
BamH1     M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1    ---------!---------!---------!---------!---------!---------!---------!---------!---------! 90

L  S  L  P  V  T  P  G  E  P  A  S  I  S  C |T  P  P  A  Y  R  P  P  N  A  P  I  L| W  Y
        CTCTCCCTGCCTGTCACTCCTGGGGAGCCAGCCTCGATCTCTTGCACTCCTCCAGCTTATAGACCACCAAATGCCCCTATCCTATGGTAT
91   ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
        CTGCAGAAACCAGGCCAGTCTCCACAGCTCCTGATCTACAAAGTTTCCAACCGATTTTCTGGGGTCCCAGACAGATTCAGTGGCAGTGGA
181  ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
        TCAGGGACAGATTTCACACTCAAGATCAGCAGAGTGGAGGCTGAGGATACCGGAGTGTATTACTGCTTTCAAGGTTCACATGTTCCGTGG
271  ---------!---------!---------!---------!---------!---------!---------!---------!---------! 360

T  F  G  G  G  T  K  V  E  I  K  BsiWI       (SEQ ID NO: 151)
        ACGTTCGGTGGAGGCACCAAGGTGGAAATCAAGCGTACG          (SEQ ID NO: 150)
361  ---------!---------!---------!---------  399
```

FIG. 21

Heavy Variable

```
HindIII   M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C │ T  I  M  D  Q  V  P  F  S  V │ W  V  R  Q  A  P
GGAGGCTTAATCCAGCCTGGAGGGTCCCTGAGAATGTCCTGCACCATTATGGACCAGGTGCCTTTCTCCGTGTGGGTTCGGCAGGCTCCG
 91 ---------!---------!---------!---------!---------!---------!---------!---------!---------! 180

G  K  G  L  E  W  I  A  Y  I  G  S  G  G │ S  V  Y  D  F  F  V  W  L │ R  F  T  I  S  R  D
GGGAAGGGGCTGGAGTGGATCGCATACATTGGTAGTGGTGGTAGTGTTTATGATTTTTTTGTGTGGCTCCGATTCACCATTTCCAGAGAC
181 ---------!---------!---------!---------!---------!---------!---------!---------!---------! 270

N  S  K  N  T  L  Y  L  Q  L  N  S  L  R  A  E  D  T  A  V  Y  Y  C  A  R  H  Y  G  H  Y
AATAGCAAGAACACCCTGTATTTGCAATTGAACAGTCTGAGGGCTGAGGACACAGCCGTGTATTACTGTGCGAGACATTATGGTCACTAC
271 ---------!---------!---------!---------!---------!---------!---------!---------!---------! 360

AfeI
          V  D  Y  A  V  D  Y  W  G  Q  G  T  T  V  T  V  S  S
GTGGACTATGCTGTGGACTACTGGGGTCAAGGTACCACGGTCACCGTCTCCAGCGCT         (SEQ ID NO: 155)
361 ---------!---------!---------!---------!---------!------- 417   (SEQ ID NO: 152)
```

Light Variable

```
BamHI     M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
CTCTCCCTGCCTGTCACTCCTGGGGAGCCAGCCTCCATCTCTTGCAGATCTAGTCAGAGCCTGGTACATAGTAATGGAAACACCTATTTA
 91 ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
GAATGGTACCTGCAGAAACCAGGCCAGTCTCCACAGCTCCTGATCTACAAAGTTTCCAACCGATTTTCTGGGGTCCCAGACAGATTCAGT
181 ---------!---------!---------!---------!---------!---------!---------!---------!---------! 270

G  S  G  S  G  T  D  F  T  L  K  I  S  R  V  E  A  E  D  T  G  V  Y  Y  C │ T  P  P  A  Y
GGCAGTGGATCAGGGACAGATTTCACACTCAAGATCAGCAGAGTGGAGGCTGAGGATACCGGAGTGTATTACTGCACTCCTCCAGCTTAT
271 ---------!---------!---------!---------!---------!---------!---------!---------!---------! 360

│ R  P  P  N  A  P  I  L │ F  G  G  G  T  K  V  E  I  K  BsiW1      (SEQ ID NO: 154)
AGACCACCAAATGCCCCTATCCTATTCGGTGGAGGCACCAAGGTGGAAATCAAGCGTACG              (SEQ ID NO: 153)
361 ---------!---------!---------!---------!---------!---------! 420
```

FIG. 22

Heavy Variable

```
HindIII    M  G  W  S  C  I  I  L  F  L  V  A  T  A  T  G  V  H  S  Q  V  Q  L  V  E  T  G
       AAGCTTACCATGGGATGGAGCTGTATCATCCTCTTCTTGGTAGCAACAGCTACCGGAGTCCACTCCCAGGTGCAGCTGGTGGAGACTGGG
     1 ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
       GGAGGCTTAATCCAGCCTGGAGGGTCCCTGAGAATGTCCTGTGCAGCCTCTGGATTCGCTTTCAATACCTATGACATGTCTTGGGTTCGC
    91 ---------!---------!---------!---------!---------!---------!---------!---------!---------! 180

Q  A  P  G  K  G  L  E  W  I  A  Y  I  G  S  G  G  D  R  T  Y  Y  P  D  T  V  K  G  R  F
       CAGGCTCCGGGGAAGGGGCTGGAGTGGATCGCATACATTGGTAGTGGTGGTGATAGAACCTACTATCCAGACACTGTGAAGGGCCGATTC
   181 ---------!---------!---------!---------!---------!---------!---------!---------!---------! 270

T  I  S  R  D  N  S  K  N  T  L  Y  L  Q  L  N  S  L  R  A  E  D  T  A  V  Y  Y  C  A  R
       ACCATTTCCAGAGACAATAGCAAGAACACCCTGTATTTGCAATTGAACAGTCTGAGGGCTGAGGACACAGCCGTGTATTACTGTGCCCGA
   271 ---------!---------!---------!---------!---------!---------!---------!---------!---------! 360

AfeI
           S  V  Y  D  F  F  V  W  L   W  G  Q  G  T  T  V  T  V  S  S                    (SEQ ID NO: 157)
       AGTGTTTATGATTTTTTTGTGTGGCTCTGGGGCCAAGGAACCACGGTCACCGTCTCCAGCGCT                    (SEQ ID NO: 156)
   361 ---------!---------!-------!---------!---------!---------!--- 423
```

Light Variable

```
BamHI     M  G  W  S  C  I  I  L  F  L  V  A  T  A  T  G  V  H  S  D  V  L  M  T  Q  S  P
      GGATCCACCATGGATGGAGCTGTATCATCCTCTTCTTGGTAGCAACAGCTACCGGAGTCCACTCCGATGTGTTGATGACCCAATCTCCA
    1 ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
      CTCTCCCTGCCTGTCACTCCTGGGGAGCCAGCCTCCATCTCTTGCAGATCTAGTCAGAGCCTGGTACATAGTAATGGAAACACCTATTTA
   91 ---------!---------!---------!---------!---------!---------!---------!---------!---------! 180

E  W  Y  L  Q  K  P  C  Q  S  P  Q  L  L  I  Y  K  V  S  N  R  F  S  G  V  P  D  R  F  S
      GAATGGTACCTGCAGAAACCAGGCCAGTCTCCACAGCTCCTGATCTACAAAGTTTCCAACCGATTTTCTGGGGTCCCAGACAGATTCAGT
  181 ---------!---------!---------!---------!---------!---------!---------!---------!---------! 270

G  S  G  S  G  T  D  F  T  L  K  I  S  R  V  E  A  E  D  T  G  V  Y  Y  C  F  Q  G  S  H
      GGCAGTGGATCAGGGACAGATTTCACACTCAAGATCAGCAGAGTGGAGGCTGAGGATACCGGAGTGTATTACTGCTTTCAAGGTTCACAT
  271 ---------!---------!---------!---------!---------!---------!---------!---------!---------! 360

BsiWI
          V  P  W  T  F  G  G  G  T  K  V  E  I  K              (SEQ ID NO: 159)
      GTTCCGTGGACGTTCGGTGGAGGCACCAAGGTGGAAATCAAGCGTACG            (SEQ ID NO: 158)
  361 ---------!---------!---------!---------!-------- 408
```

FIG. 23

Heavy Variable

```
HindIII   M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1   ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
GGAGGCTTAATCCAGCCTGGAGGGTCCCTGAGAATGTCCTGTGCAGCCTCTGGATTCGCTTTCAATACCTATGACATGTCTTGGGTTCGC
91  ---------!---------!---------!---------!---------!---------!---------!---------!---------! 180

Q  A  P  G  K  G  L  E  W  I  A  Y  I  G  S  G  G  D  R  T  Y  Y  P  D  T  V  K  G  R  F
CAGGCTCCGGGGAAGGGGCTGGAGTGGATCGCATACATTGGTAGTGGTGGTGATAGAACCTACTATCCAGACACTGTGAAGGGCCGATTC
181 ---------!---------!---------!---------!---------!---------!---------!---------!---------! 270

T  I  S  R  D  N  S  K  N  T  L  Y  L  Q  L  N  S  L  R  A  E  D  T  A  V  Y  Y  C  A  R
ACCATTTCCAGAGACAATAGCAAGAACACCCTGTATTTGCAATTGAACAGTCTGAGGGCTGAGGACACAGCCGTGTATTACTGTGCCCGA
271 ---------!---------!---------!---------!---------!---------!---------!---------!---------! 360
                                                                         AfeI
          ┌─S  V  Y  D  F  F  V  W  L─┐ W  G  Q  G  T  T  V  T  V  S  S
          │AGTGTTTATGATTTTTTTGTGTGGCTC│TGGGGCCAAGGAACCACGGTCACCGTCTCCAGCGCT       (SEQ ID NO: 161)
361       └───────────────────────────┘--!---------!---------!---------!--- 423   (SEQ ID NO: 160)
```

Light Variable

```
BamHI     M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1   ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
CTCTCCCTGCCTGTCACTCCTGGGGAGCCAGCCTCCATCTCTTGCAGATCTAGTCAGAGCCTGGTACATAGTAATGGAAACACCTATTTA
91  ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
GAATGGTACCTGCAGAAACCAGGCCAGTCTCCACAGCTCCTGATCTACAAAGTTTCCAACCGATTTTCTGGGGTCCCAGACAGATTCAGT
181 ---------!---------!---------!---------!---------!---------!---------!---------!---------! 270

G  S  G  S  G  T  D  F  T  L  K  I  S  R  V  E  A  E  D  T  G  V  Y  Y  C ┌T  P  P  A  Y┐
GGCAGTGGATCAGGGACAGATTTCACACTCAAGATCAGCAGAGTGGAGGCTGAGGATACCGGAGTGTATTACTGC│ACTCCTCCAGCTTAT│
271 ---------!---------!---------!---------!---------!---------!---------!----└─────!─────────┘ 360

┌R  P  P  N  A  P  I  L┐ F  G  G  G  T  K  V  E  I  K  BsiW1                (SEQ ID NO: 185)
          │AGACCACCAAATGCCCCTATCCTA│TCGGTGGAGGCACCAAGGTGGAAATCAAGCGTACG                (SEQ ID NO: 162)
361       └───────────────────────┘---!---------!---------!---! 420
```

FIG. 24

Heavy Variable

```
     HindIII  M  G  W  S  C  I  I  L  F  L  V  A  T  A  T  G  V  H  S  Q  V  Q  L  V  E  T  G
     AAGCTTACCATGGGATGGAGCTGTATCATCCTCTTCTTGGTAGCAACAGCTACCGGAGTCCACTCCCAGGTGCAGCTGGTGGAGACTGGG
  1  ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
        GGAGGCTTAATCCAGCCTGGAGGGTCCCTGAGAATGTCCTGTGCAGCCTCTGGATTCGCTTTCAATACCTATGACATGTCTTGGGTTCGC
  91 ---------!---------!---------!---------!---------!---------!---------!---------!---------! 180

Q  A  P  G  K  G  L  E  W  I  A  Y  I  G  S  G  G  D  R  T  Y  Y  P  D  T  V  K  G  R  F
        CAGGCTCCGGGGAAGGGGCTGGAGTGGATCGCATACATTGGTAGTGGTGGTGATAGAACCTACTATCCAGACACTGTGAAGGGCCGATTC
 181 ---------!---------!---------!---------!---------!---------!---------!---------!---------! 270

T  I  S  R  D  N  S  K  N  T  L  Y  L  Q  L  N  S  L  R  A  E  D  T  A  V  Y  Y  C  A  R
        ACCATTTCCAGAGACAATAGCAAGAACACCCTGTATTTGCAATTGAACAGTCTGAGGGCTGAGGACACAGCCGTGTATTACTGTGCAAGA
 271 ---------!---------!---------!---------!---------!---------!---------!---------!---------! 360
                                                                            AfeI    (SEQ ID NO: 164)
     H  Y  G  H  Y  V  D  Y  A  V  D  Y  W  G  Q  G  T  T  V  T  V  S  S                (SEQ ID NO: 163)
     CATTATGGTCACTACGTGGACTATGCTGTGGACTACTGGGGTCAAGGAACCACGGTCACCGTCTCCAGCGCT
 361 ---------!---------!---------!---------!---------!---------!---------!-- 432
```

Light Variable

```
     BamHI    M  G  W  S  C  I  I  L  F  L  V  A  T  A  T  G  V  H  S  D  V  L  M  T  Q  S  P
     GGATCCACCATGGGATGGAGCTGTATCATCCTCTTCTTGGTAGCAACAGCTACCGGAGTCCACTCCGATGTGTTGATGACCCAATCTCCA
  1  ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
        CTCTCCCTGCCTGTCACTCCTGGGGAGCCAGCCTCCATCTCTTGCAGATCTAGTCAGAGCCTGGTACATAGTAATGGAAACACCTATTTA
  91 ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
        GAATGGTACCTGCAGAAACCAGGCCAGTCTCCACAGCTCCTGATCTACAAAGTTTCCAACCGATTTTCTGGGGTCCCAGACAGATTCAGT
 181 ---------!---------!---------!---------!---------!---------!---------!---------!---------! 270

G  S  G  S  G  T  D  F  T  L  K  I  S  R  V  E  A  E  D  T  G  V  Y  Y  C  S  V  Y  D  F
        GGCAGTGGATCAGGGACAGATTTCACACTCAAGATCAGCAGAGTGGAGGCTGAGGATACCGGAGTGTATTACTGCAGTGTTTATGATTTT
 271 ---------!---------!---------!---------!---------!---------!---------!---------!---------! 360

F  V  W  L  F  G  G  G  T  K  V  E  I  K  BsiW1  (SEQ ID NO: 166)
     TTTGTGTGGCTTTTCGGTGGAGGCACCAAGGTGGAAATCAAGCGTACG   (SEQ ID NO: 165)
 361 ---------!---------!---------!---------!---------! 420
```

FIG. 25

Heavy Variable

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1   ---------!---------!---------!---------!---------!---------!---------!---------!---------! 90

G  G  L  I  Q  P  G  G  S  L  R  M  S  C  A  A  S  G  F  A  F  N  I  Y  D  M  S  W  V  R
GGAGGCTTAATCCAGCCTGGAGGGTCCCTGAGAATGTCCTGTGCAGCCTCTGGATTCGCTTTCAATACCTATGACATGTCTTGGGTTCGC
91  ---------!---------!---------!---------!---------!---------!---------!---------!---------! 180

Q  A  P  G  K  G  L  E  W  I  A  Y  I  G  S  G  G  S  V  Y  D  F  F  V  W  L  R  F  T  I
CAGGCTCCGGGGAAGGGGCTGGAGTGGATCGCATACATTGGTAGTGGTGGTAGTGTTTATGATTTTTTTGTGTGGCTCCGATTCACCATT
181 ---------!---------!---------!---------!---------!---------!---------!---------!---------! 270

S  R  D  N  S  K  N  T  L  Y  L  Q  L  N  S  L  R  A  E  D  T  A  V  Y  Y  C  A  R  W  N
TCCAGAGACAATAGCAAGAACACCCTGTATTTGCAATTGAACAGTCTGAGGGCTGAGGACACAGCCGTGTATTACTGTGCCCGATGGAAC
271 ---------!---------!---------!---------!---------!---------!---------!---------!---------! 360
                                                                           AfeI
     R  Q  L  Y  P  E  W  T  E  A  Q  R  L  D  W  G  Q  G  T  T  V  T  V  S  S
AGGCAGCTGTATCCAGAGTGGACAGAAGCCCAGAGACTTGACTGGGGCCAAGGAACCACGGTCACCGTCTCCAGCGCT        (SEQ ID NO: 168)
361 ---------!---------!---------!---------!---------!---------!---------!-------- 438    (SEQ ID NO: 167)
```

Light Variable

```
BamHI      M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1   ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
CTCTCCCTCCCTGTCACTCCTGGGGAGCCAGCCTCCATCTCTTGCAGATCTAGTCAGAGCCTGGTACATACTAATGGAAACACCTATTTA
91  ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
GAATGGTACCTGCAGAAACCAGGCCAGTCTCCACAGCTCCTGATCTACAAAGTTTCCAACCGATTTTCTGGGGTCCCAGACAGATTCAGT
181 ---------!---------!---------!---------!---------!---------!---------!---------!---------! 270

G  S  G  S  G  T  D  F  T  L  K  I  S  R  V  E  A  E  D  T  G  V  Y  Y  C  F  Q  G  S  H
GGCAGTGGATCAGGGACAGATTTCACACTCAAGATCAGCAGAGTGGAGGCTGAGGATACCGGAGTGTATTACTGCTTTCAAGGTTCACAT
271 ---------!---------!---------!---------!---------!---------!---------!---------!---------! 360
                                        BsiWI
     V  P  W  T  F  G  G  G  T  K  V  E  I  K                (SEQ ID NO: 186)
GTTCCGTGGACGTTCGGTGGAGGCACCAAGGTGGAAATCAAGCGTACG            (SEQ ID NO: 169)
361 ---------!---------!---------!---------!-------- 408
```

FIG. 26

Heavy Variable

```
    HindIII   M  G  W  S  C  I  I  L  F  L  V  A  T  A  T  G  V  H  S  Q  V  Q  L  V  E  T  G
    AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
    GGAGGCTTAATCCAGCCTGGAGGGTCCCTGAGAATGTCCTGTGCAGCCTCTGGATTCGCTTTCAATACCTATGACATGTCTTGGGTTCGC
 91 ---------!---------!---------!---------!---------!---------!---------!---------!---------! 180

Q  A  P  G  K  G  L  E  W  I  A  Y  I  G  S  G  G  D  R  T  Y  Y  P  D  T  V  K  G  R  F
    CAGGCTCCGGGGAAGGGGCTGGAGTGGATCGCATACATTGGTAGTGGTGGTGATAGAACCTACTATCCAGACACTGTGAAGGGCCGATTC
181 ---------!---------!---------!---------!---------!---------!---------!---------!---------! 270

T  I  S  R  D  N  S  K  N  T  L  Y  L  Q  L  N  S  L  R  A  E  D  T  A  V  Y  Y  C  A  R
    ACCATTTCCAGAGACAATAGCAAGAACACCCTGTATTTGCAATTGAACAGTCTGAGGGCTGAGGACACAGCCGTGTATTACTGTGCCCGA
271 ---------!---------!---------!---------!---------!---------!---------!---------!---------! 360

AfeI
      T  P  P  A  Y  R  P  P  N  A  P  I  L  W  G  Q  G  T  T  V  T  V  S  S                      (SEQ ID NO: 171)
    ACTCCTCCAGCTTATAGACCACCAAATGCCCCTATCCTATGGGGCCAAGGAACCACGGTCACCGTCTCCAGCGCT                   (SEQ ID NO: 170)
361 ---------!---------!---------!---------!---------!---------!---------!----- 435
```

Light Variable

```
    BamHI     M  G  W  S  C  I  I  L  F  L  V  A  T  A  T  G  V  H  S  D  V  L  M  T  Q  S  P
    GGATCCACCATGGGATGGAGCTGTATCATCCTCTTCTTGGTAGCAACAGCTACCGGAGTCCACTCCGATGTGTTGATGACCCAATCTCCA
  1         !         !         !         !         !         !         !         !         ! 90

L  S  L  P  V  T  P  G  E  P  A  S  I  S  C  R  S  S  Q  S  L  V  H  S  N  G  N  T  Y  L
    CTCTCCCTGCCTGTCACTCCTGGGGAGCCAGCCTCCATCTCTTGCAGATCTAGTCAGAGCCTGGTACATAGTAATGGAAACACCTATTTA
 91 ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
    GAATGGTACCTGCAGAAACCAGGCCAGTCTCCACAGCTCCTGATCTACAAAGTTTCCAACCGATTTTCTGGGGTCCCAGACAGATTCAGT
181 ---------!---------!---------!---------!---------!---------!---------!---------!---------! 270

G  S  G  S  G  T  D  F  T  L  K  I  S  R  V  E  A  E  D  T  G  V  Y  Y  C  F  Q  G  S  H
    GGCAGTGGATCAGGGACAGATTTCACACTCAAGATCAGCAGAGTGGAGGCTGAGGATACCGGAGTGTATTACTGCTTTCAAGGTTCACAT
271 ---------!---------!---------!---------!---------!---------!---------!---------!---------! 360

BsiWI
      V  P  W  T  F  G  G  G  T  K  V  E  I  K            (SEQ ID NO: 187)
    GTTCCGTGGACGTTCGGTGGAGGCACCAAGGTGGAAATCAAGCGTACG      (SEQ ID NO: 172)
361             :         !         !         !    408
```

FIG. 27

Heavy Variable

```
    HindIII   M  G  W  S  C  I  I  L  F  L  V  A  T  A  T  G  V  H  S  Q  V  Q  L  V  E  T  G
    AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
    GGAGGCTTAATCCAGCCTGGAGGGTCCCTGAGAATGTCCTGTGCAGCCTCTGGATTCGCTTTCAATACCTATGACATGTCTTGGGTTCGC
 91 ---------!---------!---------!---------!---------!---------!---------!---------!---------! 180

Q  A  P  G  K  G  L  E  W  I  A  Y  I  G  S  C  G  S  Y  Y  D  F  F  V  W  L  R  F  T  I
    CAGGCTCCGGGGAAGGGGCTGGAGTGGATCGCATACATTGGTAGTGGTGGTAGTGTTTATGATTTTTTTGTGTGGCTCCGATTCACCATT
181 ---------!---------!---------!---------!---------!---------!---------!---------!---------! 270

S  R  D  N  S  K  N  T  L  Y  L  Q  L  N  S  L  R  A  E  D  T  A  V  Y  Y  C  A  R  T  P
    TCCAGAGACAATAGCAAGAACACCCTGTATTTGCAATTGAACAGTCTGAGGGCTGAGGACACAGCCGTGTATTACTGTGCCCGAACTCCT
271 ---------!---------!---------!---------!---------!---------!---------!---------!---------! 360

AfeI   (SEQ ID NO: 174)
      P  A  Y  R  P  P  N  A  P  I  L  W  G  Q  G  T  T  V  T  V  S  S             (SEQ ID NO: 173)
    CCAGCTTATAGACCACCAAATGCCCCTATCCTATGGGGCCAAGGAACCACGGTCACCGTCTCCAGCGCT
361 ---------!---------!---------!---------!---------!---------!--------- 429
```

Light Variable

```
    BamHI    M  G  W  S  C  I  I  L  F  L  V  A  T  A  T  G  V  H  S  D  V  L  M  T  Q  S  P
    GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
    CTCTCCCTGCCTGTCACTCCTGGGGAGCCAGCCTCCATCTCTTGCAGATCTAGTCAGAGCCTGGTACATAGTAATGGAAACACCTATTTA
 91 ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
    GAATGGTACCTGCAGAAACCAGGCCAGTCTCCACAGCTCCTGATCTACAAAGTTTCCAACCGATTTTCTGGGGTCCCAGACAGATTCAGT
181 ---------!---------!---------!---------!---------!---------!---------!---------!---------! 270

G  S  G  S  G  T  D  F  T  L  K  I  S  R  V  E  A  E  D  T  G  V  Y  Y  C  F  Q  G  S  H
    GGCAGTGGATCAGGGACAGATTTCACACTCAAGATCAGCAGAGTGGAGGCTGAGGATACCGGAGTGTATTACTGCTTTCAAGGTTCACAT
271 ---------!---------!---------!---------!---------!---------!---------!---------!---------! 360

BsiWI
      V  P  W  T  F  G  G  G  T  K  V  E  I  K          (SEQ ID NO: 178)
    GTTCCGTGGACGTTCGGTGGAGGCACCAAGGTGGAAATCAAGCGTACG    (SEQ ID NO: 175)
361 ---------!---------!---------!---------!-------- 408
```

FIG. 28

Heavy Variable

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C │G  T  G  R  A  M  L  G  T  H  T  M  E  V  T  V
GGAGGCTTAATCCAGCCTGCAGCCTCCCTGAGAATGTCCTGC│GGGACACCCAGCGCAATGCTGGGCACACACACCATGGAACTAACTGTC
 91 ---------!---------!---------!---------!---------!---------!---------!---------!---------! 180

Y  H │ W  V  R  Q  A  P  G  K  G  L  E  W  I  A  Y  I  G  S  G  G │S  V  Y  D  F  F  V  W
TACCAT│TGGGTTCGGCAGGCTCCGGGGAAGGGGCTGGAGTGGATCGCATACATTGGTAGTGGTGGT│AGTGTTTATGATTTTTTTGTGTGG
181 ---│------!---------!---------!---------!---------!---------!---│------!---------!---------! 270

L│ R  F  T  I  S  R  D  N  S  K  N  T  L  Y  L  Q  L  N  S  L  R  A  E  D  T  A  V  Y  Y
CT C│CGATTCACCATTTCCAGAGACAATAGCAAGAACACCCTGTATTTGCAATTGAACAGTCTGAGGGCTGAGGACACAGCCGTGTATTAC
271 ─┴┴-------!---------!---------!---------!---------!---------!---------!---------!---------!360
                                                                                           AfeI
     C  A  R │W  N  R  Q  L  Y  P  E  W  T  E  A  Q  R  L  D │W  G  Q  G  T  T  V  T  V  S  S
TGTGCCCGA│TGGAACAGGCAGCTGTATCCAGAGTGGACAGAAGCCCAGAGACTTGAC│TGGGGCCAAGGTACCACGGTCACCGTCTCCAGC
361 ---------│!---------!---------!---------!---------!---------│!---------!---------!---------! 450
                                                     (SEQ ID NO: 177)
        GCT                                          (SEQ ID NO: 176)
451 --- 453
```

Light Variable

```
BamHI      M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
CTCTCCCTGCCTGTCACTCCTGGGGAGCCAGCCTCCATCTCTTGCAGATCTAGTCAGAGCCTGGTACATAGTAATGGAAACACCTATTTA
 91 ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
GAATGGTACCTGCAGAAACCAGGCCAGTCTCCACAGCTCCTGATCTACAAAGTTTCCAACCGATTTTCTGGGGTCCCAGACAGATTCAGT
181 ---------!---------!---------!---------!---------!---------!---------!---------!---------! 270

G  S  G  S  G  T  D  F  T  L  K  I  S  R  V  E  A  E  D  T  G  V  Y  Y  C  F  Q  G  S  H
GGCAGTGGATCAGGGACAGATTTCACACTCAAGATCAGCAGAGTGGAGGCTGAGGATACCGGAGTGTATTACTGCTTTCAAGGTTCACAT
271 ---------!---------!---------!---------!---------!---------!---------!---------!---------! 360
                                                        BsiWI
        V  P  W  T  F  G  G  G  T  K  V  E  I  K                 (SEQ ID NO: 180)
GTTCCGTGGACGTTCGGTGGAGGCACCAAGGTCGAAATCAAGCGTACG                 (SEQ ID NO: 179)
361 ---------!---------!---------!---------!-------- 408
```

FIG. 29

Heavy Variable

```
    HindIII   M  G  W  S  C  I  I  L  F  L  V  A  T  A  T  G  V  H  S  Q  V  Q  L  V  E  T  G
    AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
    GGAGGCTTAATCCAGCCTGGAGGGTCCCTGAGAATGTCCTGTGCAGCCTCTGGATTCGCTTTCAATACCTATGACATGTCTTGGGTTCGC
 91 ---------!---------!---------!---------!---------!---------!---------!---------!---------! 180

Q  A  P  G  K  G  L  E  W  I  A  Y  I  G  S  G  G  S  V  Y  D  F  F  V  W  L  R  F  T  I
    CAGGCTCCGGGAAGGGGCTGGAGTGGATCGCATACATTGGTAGTGGTGGTAGTGTTTATGATTTTTTTGTGTGGCTCCGATTCACCATT
181 ---------!---------!---------!---------!---------!---------!---------!---------!---------! 270

S  R  D  N  S  K  N  T  L  Y  L  Q  L  N  S  L  R  A  E  D  T  A  V  Y  Y  C  A  R  H  Y
    TCCAGAGACAATAGCAAGAACACCCTGTATTTGCAATTGAACAGTCTGAGGGCTGAGGACACAGCCGTGTATTACTGTGCAAGACATTAT
271 ---------!---------!---------!---------!---------!---------!---------!---------!---------! 360

AfeI
       G  H  Y  V  D  Y  A  V  D  Y  W  G  Q  G  T  T  V  T  V  S  S                (SEQ ID NO: 182)
    GGTCACTACGTGGACTATGCTGTGGACTACTGGGGTCAAGGAACCACGGTCACCGTCTCCAGCGCT                (SEQ ID NO: 181)
361 ---------!---------!---------!---------!---------!---------!------ 426
```

Light Variable

```
    BamH1     M  G  W  S  C  I  I  L  F  L  V  A  T  A  T  G  V  H  S  D  V  L  M  T  Q  S  P
    GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C  T  P  P  A  Y  R  P  P  N  A  P  I  L  W  Y
    CTCTCCCTGCCTGTCACTCCTGGGGAGCCAGCCTCGATCTCTTGCACTCCTCCAGCTTATAGACCACCAAATGCCCCTATCCTATGGTAT
 91 ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
    CTGCAGAAACCAGGCCAGTCTCCACAGCTCCTGATCTACAAAGTTTCCAACCGATTTTCTGGGGTCCCAGACAGATTCAGTGGCAGTGGA
181 ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
    TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

T  F  G  G  G  T  K  V  E  I  K   BsiWI       (SEQ ID NO: 184)
    ACCTTCGGTGGAGGCACCAAGGTGGAAATCAACCGTACG          (SEQ ID NO: 183)
361 ---------!---------!---------!--------- 399
```

FIG. 30 e.
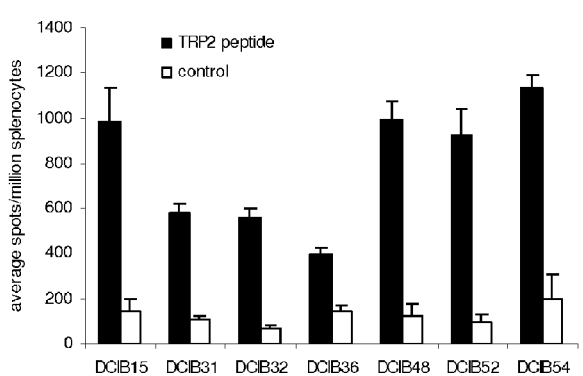
f.
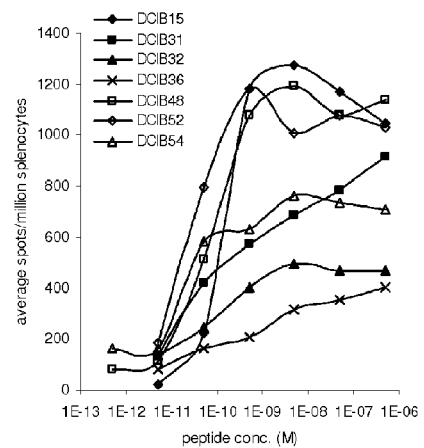
g.
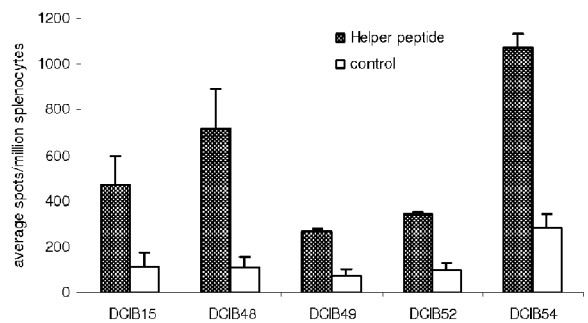
FIG. 31 continued

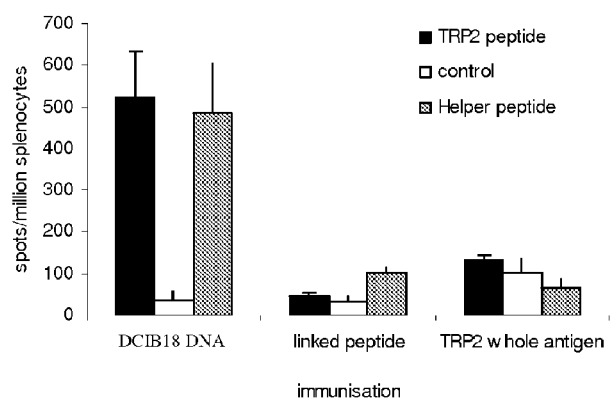
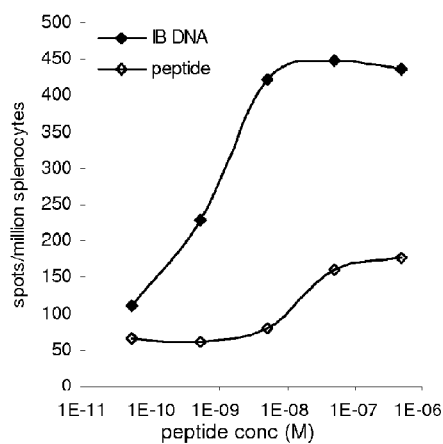
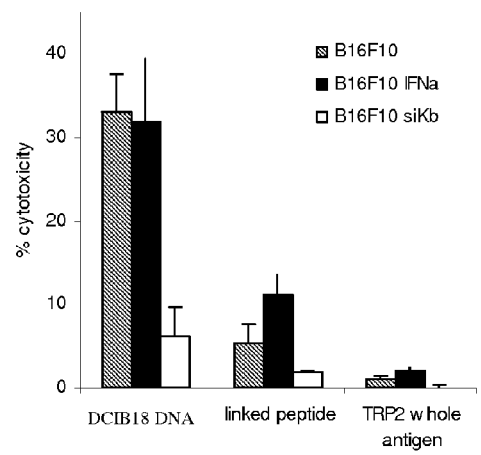
FIG. 32 d.
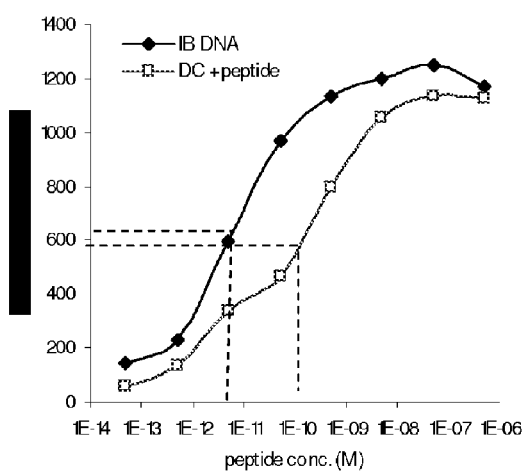
e.
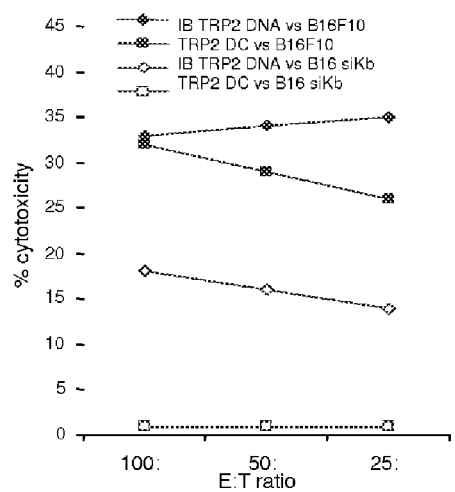
f.
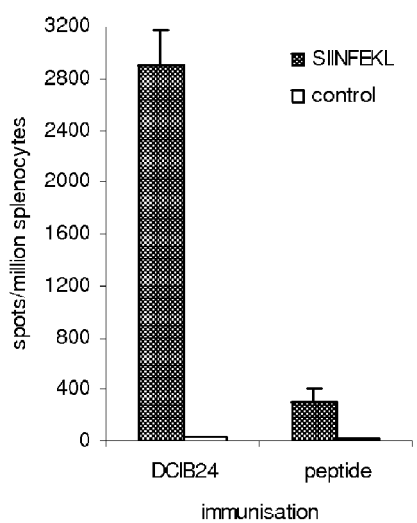
g.
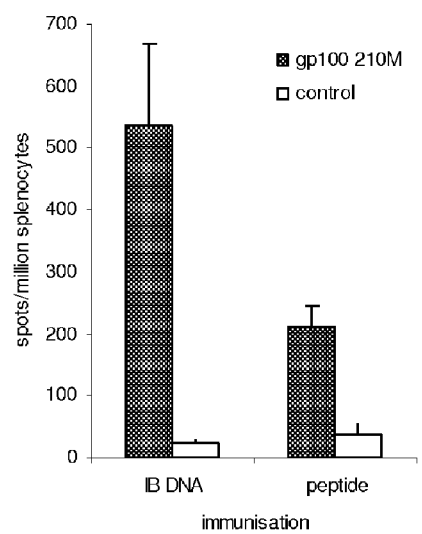
FIG. 32 continued h. 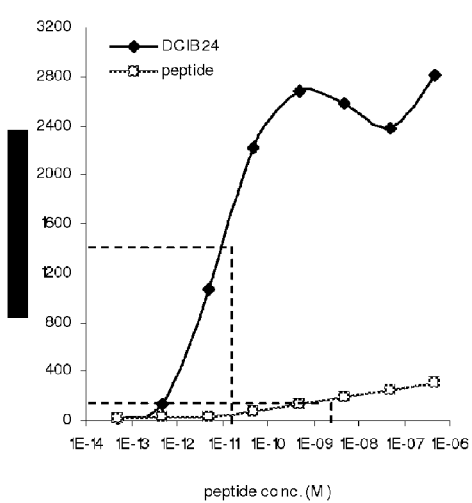
i. 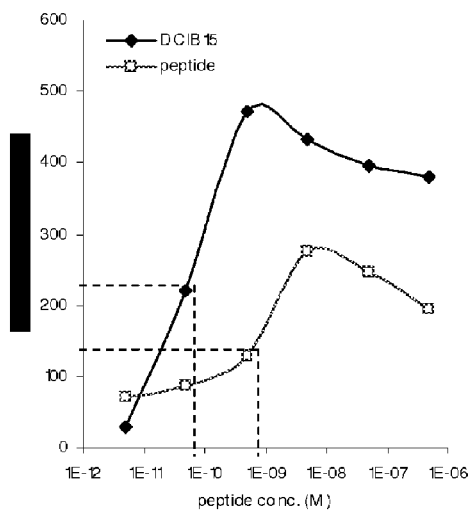
FIG. 32 continued

Heavy Variable

```
HindIII        M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1   ---------!---------!---------!---------!---------!---------!---------!---------!---------! 90

1: G  G  L  I  Q  P  G  G  S  L  R  M  S  C  A  A  S  G  F  A  F  N  T  Y  D  M  S  W  V  R
   GGAGGCTTAATCCAGCCTGGAGGGTCCCTGAGAATGTCCTGTGCAGCCTCTGGATTCGCTTTCAATACCTATGACATGTCTTGGGTTCGC
91  ---------!---------!---------!---------!---------!---------!---------!---------!---------! 180

1: Q  A  P  G  K  G  L  E  W  I  A  Y  I  G  S  G  G │I  P  Q  S  L  D  S  W  W  T  S  L│ R
   CAGGCTCCGGGGAAGGGGCTGGAGTGGATCGCATACATTGGTAGTGGTGG TATACCGCAGAGTCTAGACTCGTGGTGGACTTCTCT CCGA
181 ---------!---------!---------!---------!---------!---------!---------!---------!---------! 270

1: F  T  I  S  R  D  N  S  K  N  T  L  Y  L  Q  L  N  S  L  R  A  E  D  T  A  V  Y  Y  C  A
   TTCACCATTTCCAGAGACAATAGCAAGAACACCCTGTATTTGCAATTGAACAGTCTGAGGGCTGAGGACACAGCCGTGTATTACTGTGCA
271 ---------!---------!---------!---------!---------!---------!---------!---------!---------! 360

AfeI
1: R  H  Y  G  H  Y  V  D  Y  A  V  D  Y  W  G  Q  G  T  T  V  T  V  S  S               (SEQ ID NO: 189)
   AGACATTATGGTCACTACGTGGACTATGCTGTGGACTACTGGGGTCAAGGAACCACGGTCACCGTCTCCAGCGCT           (SEQ ID NO: 188)
361 ---------!---------!---------!---------!---------!---------!---------!----- 435
```

Light Variable

```
BamHI        M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1   ---------!---------!---------!---------!---------!---------!---------!---------!---------! 90

L  S  L  P  V  T  P  G  E  P  A  S  I  S  C │F  E  R  F  E  I  F  P  K  E│ W  Y  L  Q  K
   CTCTCCCTGCCTGTCACTCCTGGGGAGCCAGCCTCCATCTCTTGC TTTGAAAGGTTTGAGATATTCCCCAAGGAA TGGTACCTGCAGAAA
91  ---------!---------!---------!---------!---------!---------!---------!---------!---------! 180

P  G  Q  S  P  Q  L  L  I  Y  K  V  S  N  R  F  S  G  V  P  D  R  F  S  G  S  G  S  G  T
   CCAGGCCAGTCTCCACAGCTCCTGATCTACAAAGTTTCCAACCGATTTTCTGGGGTCCCAGACAGATTCAGTGGCAGTGGATCAGGGACA
181 ---------!---------!---------!---------!---------!---------!---------!---------!---------! 270

D  F  T  L  K  I  S  R  V  E  A  E  D  T  G  V  Y  Y  C  F  Q  G  S  H  V  P  W  T  F  G
   GATTTCACACTCAAGATCAGCAGAGTGGAGGCTGAGGATACCGGAGTGTATTACTGCTTTCAAGGTTCACATGTTCCGTGGACGTTCGGT
271 ---------!---------!---------!---------!---------!---------!---------!---------!---------! 360

G  G  T  K  V  E  I  K BsiWI       (SEQ ID NO: 191)
   GGAGGCACCAAGGTGGAAATCAAGCGTACG      (SEQ ID NO: 190)
361 ---------!---------!---------! 390
```

FIG. 33

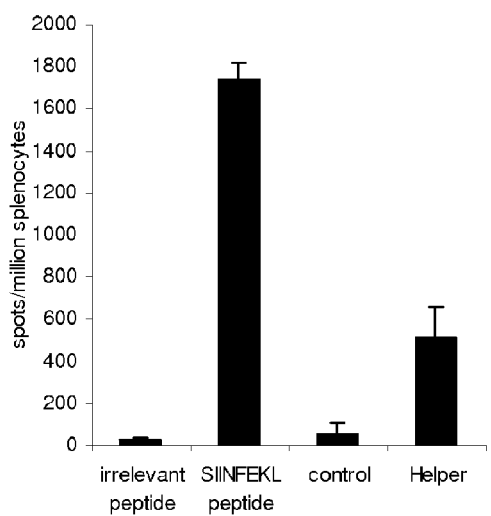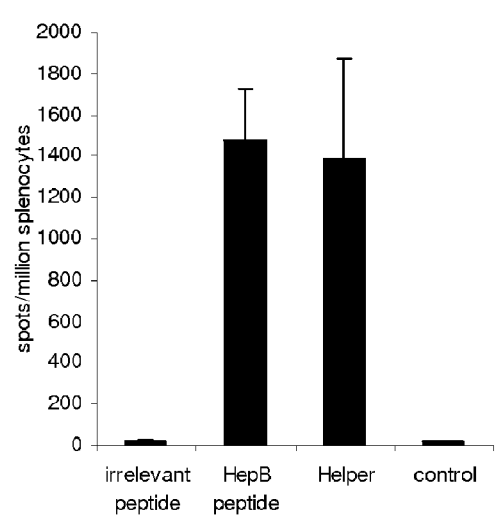
FIG. 34

Heavy Variable

```
HindIII    M  G  W  S  C  I  I  L  F  L  V  A  T  A  T  G  V  H  S  Q  V  Q  L  V  E  T  G
           AAGCTTACCATGGGATGGAGCTGTATCATCCTCTTCTTGGTAGCAACAGCTACCGGAGTCCACTCCCAGGTGCAGCTGGTGGAGACTGGG
     1     ---------!---------!---------!---------!---------!---------!---------!---------!---------! 90

G  G  L  I  Q  P  G  G  S  L  R  M  S  C │T  I  M  D  Q  V  P  F  S  V│ W  V  R  Q  A  P
           GGAGGCTTAATCCAGCCTGGAGGGTCCCTGAGAATGTCCTG ACCATTATGGACCAGGTGCCTTTCTCCGT GTGGGTTCGGCAGGCTCCG
    91     ---------!---------!---------!---------!---------!---------!---------!---------!---------! 180

G  K  G  L  E  W  I  A  Y  I  G  S  G  G  D  R  T  Y  Y  P  D  T  V  K  G  R  F  T  I  S
           GGGAAGGGGCTGGAGTGGATCGCCATACATTGGTAGTGGTGGTGATAGAACCTACTATCCAGACACTGTGAAGGGCCGATTCACCATTTCC
   181     ---------!---------!---------!---------!---------!---------!---------!---------!---------! 270

R  D  N  S  K  N  T  L  Y  L  Q  L  N  S  L  R  A  E  D  T  A  V  Y  Y  C  A  R  H  Y  G
           AGAGACAATAGCAAGAACACCCTGTATTTGCAATTGAACAGTCTGAGGGCTGAGGACACAGCCGTGTATTACTGTGCAAGACATTATGGT
   271     ---------!---------!---------!---------!---------!---------!---------!---------!---------! 360

AfeI       (SEQ ID NO: 193)
           H  Y  V  D  Y  A  V  D  Y  W  G  Q  G  T  T  V  T  V  S  S                      (SEQ ID NO: 192)
           CACTACGTGGACTATGCTGTGGACTACTGGGGTCAAGGAACCACGGTCACCGTCTCCAGCGCT
   361     ---------!---------!---------!---------!---------!---------!--- 423
```

Light Variable

```
BamH1      M  G  W  S  C  I  I  L  F  L  V  A  T  A  T  G  V  H  S  D  V  L  M  T  Q  S  P
           GGATCCACCATGGGATGGAGCTGTATCATCCTCTTCTTGGTAGCAACAGCTACCGGAGTCCACTCCGATGTGTTGATGACCCAATCTCCA
     1     ---------!---------!---------!---------!---------!---------!---------!---------!---------! 90

L  S  L  P  V  T  P  G  E  P  A  S  I  S  C │T  P  P  A  Y  R  P  P  N  A  P  I  L│ W  Y
           CTCTCCCTGCCTGTCACTCCTGGGGAGCCAGCCTCGATCTCTTGC ACTCCTCCAGCTTATAGACCACCAAATGCCCCTATCCTA TGGTAT
    91     ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
           CTGCAGAAACCAGGCCAGTCTCCACAGCTCCTGATCTACAAAGTTTCCAACCGATTTTCTGGGGTCCCAGACAGATTCAGTGGCAGTGGA
   181                !          !          !          !          !          !          !          ! 270

S  G  T  D  F  T  L  K  I  S  R  V  E  A  E  D  T  G  V  Y  Y  C  F  Q  G  S  H  V  P  W
           TCAGGGACAGATTTCACACTCAAGATCAGCAGAGTGGAGGCTGAGGATACCGGAGTGTATTACTGCTTTCAAGGTTCACATGTTCCGTGG
   271     ---------!---------!---------!---------!---------!---------!---------!---------!---------! 360

T  F  G  G  G  T  K  V  E  I  K  BsiWI       (SEQ ID NO: 195)
           ACGTTCGGTGGAGGCACCAAGCTGGAAATCAAGCGTACG         (SEQ ID NO: 194)
   361     ---------!---------!---------!---------! 399
```

FIG. 35

Heavy Variable

```
HindIII    M  G  W  S  C  I  I  L  F  L  V  A  T  A  T  G  V  H  S  Q  V  Q  L  V  E  T  G
           AAGCTTACCATGGGATGGAGCTGTATCATCCTCTTCTTGGTAGCAACAGCTACCGGAGTCCACTCCCAGGTGCAGCTGGTGGAGACTGGG
     1     ---------!---------!---------!---------!---------!---------!---------!---------!---------! 90

G  G  L  I  Q  P  G  G  S  L  R  M  S  C │F  L  P  A  T  L  T  M  V│ W  V  R  Q  A  P  G
           GGAGGCTTAATCCAGCCTGGAGGGTCCCTGAGAATGTCCTGC TTCCTACCAGCTACTTTAACTATGGTT GGGTTCGGCAGGCTCCGGGG
    91     ---------!---------!---------!---------!---------!---------!---------!---------!---------! 180

K  G  L  E  W  I  A  Y  I  G  S  G  G  D  R  T  Y  Y  P  D  T  V  K  G  R  F  T  I  S  R
           AAGGGGCTGGAGTGGATCGCATACATTGGTAGTGGTGGTGATAGAACCTACTATCCAGACACTGTGAAGGGCCGATTCACCATTTCCAGA
   181     ---------!---------!---------!---------!---------!---------!---------!---------!---------! 270

D  N  S  K  N  T  L  Y  L  Q  L  N  S  L  R  A  E  D  T  A  V  Y  Y  C  A  R  H  Y  G  H
           GACAATAGCAAGAACACCCTGTATTTGCAATTGAACAGTCTGAGGGCTGAGGACACAGCCCTGTATTACTGTGCAAGACATTATGGTCAC
   271     ---------!---------!---------!---------!---------!---------!---------!---------!---------! 360

AfeI
           Y  V  D  Y  A  V  D  Y  W  G  Q  G  T  T  V  T  V  S  S                  (SEQ ID NO: 197)
           TACGTGGACTATGCTGTGGACTACTGGGGTCAAGGAACCACGGTCACCGTCTCCAGCGCT              (SEQ ID NO: 196)
   361     ---------!---------!---------!---------!---------!---------! 420
```

Light Variable

```
BamH1      M  G  W  S  C  I  I  L  F  L  V  A  T  A  T  G  V  H  S  D  V  L  M  T  Q  S  P
           GGATCCACCATGGGATGGAGCTGTATCATCCTCTTCTTGGTAGCAACAGCTACCGGAGTCCACTCCGATGTGTTGATGACCCAATCTCCA
     1     ---------!---------!---------!---------!---------!---------!---------!---------!---------! 90

L  S  L  P  V  T  P  G  E  P  A  S  I  S  C │T  P  P  A  Y  R  P  P  N  A  P  I  L│ W  Y
           CTCTCCCTGCCTGTCACTCCTGGGGAGCCAGCCTCGATCTCTTGC ACTCCTCCAGCTTATAGACCACCAAATGCCCCTATCCTA TGGTAT
    91     ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
           CTGCAGAAACCAGGCCAGTCTCCACAGCTCCTGATCTACAAAGTTTCCAACCGATTTTCTGGGGTCCCAGACAGATTCAGTGGCAGTGGA
   181     ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
           TCAGGGACAGATTTCACACTCAAGATCAGCAGAGTGGAGGCTGAGGATACCGGAGTGTATTACTGCTTCAAGGTTCACATGTTCCGTGG
   271     ---------!---------!---------!---------!---------!---------!---------!---------!---------! 360

T  F  G  G  G  T  K  V  E  I  K  BsiWI      (SEQ ID NO: 199)
           ACGTTCGGTGGAGGCACCAAGGTGGAAATCAAGCGTACG       (SEQ ID NO: 198)
   361     ---------!---------!--------- 399
```

FIG. 36

Heavy Variable

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1   ---------!---------!---------!---------!---------!---------!---------!---------!---------! 90

G  G  L  I  Q  P  G  G  S  L  R  M  S  C │T  I  T  D  Q  V  P  L  S  V│W  V  R  Q  A  P
GGAGGCTTAATCCAGCCTGCAGGGTCCCTGAGAATGTCCTG CACCATTACTGACCAGGTGCCTTTGTCCGTG TGGGTTCGGCAGGCTCCG
91  ---------!---------!---------!---------!---------!---------!---------!---------!---------! 180

G  K  G  L  E  W  I  A  Y  I  G  S  G  G  D  R  T  Y  Y  P  D  T  V  K  G  R  F  T  I  S
GGGAAGGGGCTGGAGTGGATCGCATACATTGGTAGTGGTGGTGATAGAACCTACTATCCAGACACTGTGAAGGGCCGATTCACCATTTCC
181 ---------!---------!---------!---------!---------!---------!---------!---------!---------! 270

R  D  N  S  K  N  T  L  Y  L  Q  L  N  S  L  R  A  E  D  T  A  V  Y  Y  C  A  R  H  Y  G
AGAGACAATAGCAAGAACACCCTGTATTTGCAATTGAACAGTCTGAGGGCTGAGGACACAGCCGTGTATTACTGTGCAAGACATTATGGT
271 ---------!---------!---------!---------!---------!---------!---------!---------!---------! 360

AfeI
           H  Y  V  D  Y  A  V  D  Y  W  G  Q  G  T  T  V  T  V  S  S              (SEQ ID NO: 201)
CACTACGTGGACTATGCTGTGGACTACTGGGGTCAAGGAACCACGGTCACCGTCTCCAGCGCT                   (SEQ ID NO: 200)
361 ---------!---------!---------!---------!---------!--- 423
```

Light Variable

```
BamH1     M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1   ---------!---------!---------!---------!---------!---------!---------!---------!---------! 90

L  S  L  P  V  T  P  G  E  P  A  S  I  S  C │T  P  P  A  Y  R  P  P  N  A  P  I  L│W  Y
CTCTCCCTGCCTGTCACTCCTGGGGAGCCAGCCTCGATCTCTTGC ACTCCTCCAGCTTATAGACCACCAAATGCCCCTATCCTA TGGTAT
91  ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
CTGCAGAAACCAGGCCAGTCTCCACAGCTCCTGATCTACAAAGTTTCCAACCGATTTTCTGGGGTCCCAGACAGATTCAGTGGCAGTGGA
181     !         !         !         !         !         !         !         :         ! 270

S  G  T  D  F  T  L  K  I  S  R  V  E  A  E  D  T  G  V  Y  Y  C  F  Q  G  S  H  V  P  W
TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

T  F  G  G  G  T  K  V  E  I  K  BsiWI     (SEQ ID NO: 203)
ACGTTCGGTGGAGGCACCAAGGTGGAAATCAAGCGTACG              (SEQ ID NO: 202)
361 ---------!---------!---------!--------- 399
```

FIG. 39

Heavy Variable

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1   ---------!---------!---------!---------!---------!---------!---------!---------!---------! 90

G  G  L  I  Q  P  G  G  S  L  R  M  S  C  T  I  T  D  Q  V  P  I  S  V  W  V  R  Q  A  P
GGAGGCTTAATCCAGCCTGGAGGGTCCCTGAGAATGTCCTGCACCATTACTGACCAGGTGCCTATCTCCGTGTGGGTTCGGCAGGCTCCG
91  ---------!---------!---------!---------!---------!---------!---------!---------!---------! 180

G  K  G  L  E  W  I  A  Y  I  G  S  G  G  D  R  T  Y  Y  P  D  T  V  K  G  R  F  T  I  S
GGGAAGGGGCTGGAGTGGATCGCATACATTGGTAGTGGTGGTGATAGAACCTACTATCCAGACACTGTGAAGGGCCGATTCACCATTTCC
181 ---------!---------!---------!---------!---------!---------!---------!---------!---------! 270

R  D  N  S  K  N  T  L  Y  L  Q  L  N  S  L  R  A  E  D  T  A  V  Y  Y  C  A  R  H  Y  G
AGAGACAATAGCAAGAACACCCTGTATTTGCAATTGAACAGTCTGAGGGCTGAGGACACAGCCGTGTATTACTGTGCAAGACATTATGGT
271 ---------!---------!---------!---------!---------!---------!---------!---------!---------! 360

AfeI    (SEQ ID NO: 205)
           H  Y  V  D  Y  A  V  D  Y  W  G  Q  G  T  T  V  T  V  S  S                    (SEQ ID NO: 204)
CACTACGTGGACTATGCTGTGGACTACTGGGGTCAAGGAACCACGGTCACCGTCTCCAGCGCT
361 ---------!---------!---------!---------!---------!---------!--- 423
```

Light Variable

```
BamH1      M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1   ---------!---------!---------!---------!---------!---------!---------!---------!---------! 90

L  S  L  P  V  T  P  G  E  P  A  S  I  S  C  T  P  P  A  Y  R  P  P  N  A  P  I  L  W  Y
CTCTCCCTGCCTGTCACTCCTGGGGAGCCAGCCTCGATCTCTTGCACTCCTCCAGCTTATAGACCACCAAATGCCCCTATCCTATGGTAT
91  ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
CTGCAGAAACCAGGCCAGTCTCCACAGCTCCTGATCTACAAAGTTTCCAACCGATTTTCTGGGGTCCCAGACAGATTCAGTGGCAGTGGA
181 ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

T  F  G  G  G  T  K  V  E  I  K  BsiWI     (SEQ ID NO: 207)
ACGTTCGGTGGAGGCACCAAGGTGGAAATCAAGCGTACG              (SEQ ID NO: 206)
361 ---------!---------!---------!--------- 399
```

FIG. 40

Heavy Variable

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C │T  I  T  D  Q  V  P  F  S  V│ W  V  R  Q  A  P
         GGAGGCTTAATCCAGCCTGAGGGTCCCTGAGAATGTCCTGCACCATTACTGACCAGGTGCCTTTCTCCGTGTGGGTTCGGCAGGCTCCG
 91 ---------!---------!---------!---------!---------!---------!---------!---------!---------! 180

G  K  G  L  E  W  I  A  Y  I  G  S  G  G  D  R  T  Y  Y  P  D  T  V  K  G  R  F  T  I  S
         GGGAAGGGGCTGGAGTGGATCGCATACATTGGTAGTGGTGGTGATAGAACCTACTATCCAGACACTGTGAAGGGCCGATTCACCATTTCC
181 ---------!---------!---------!---------!---------!---------!---------!---------!---------! 270

R  D  N  S  K  N  T  L  Y  L  Q  L  N  S  L  R  A  E  D  T  A  V  Y  Y  C  A  R  H  Y  G
         AGAGACAATAGCAAGAACACCCTGTATTTGCAATTGAACAGTCTGAGGGCTGAGGACACAGCCGTGTATTACTGTGCAAGACATTATGGT
271 ---------!---------!---------!---------!---------!---------!---------!---------!---------! 360

AfeI
           H  Y  V  D  Y  A  V  D  Y  W  G  Q  G  T  T  V  T  V  S  S         (SEQ ID NO: 218)
         CACTACGTGGACTATGCTGTGGACTACTGGGGTCAAGGAACCACGGTCACCGTCTCCAGCGCT           (SEQ ID NO: 208)
361 ---------!---------!---------!---------!---------!---------!---  423
```

Light Variable

```
BamH1      M  G  W  S  C  I  I  L  F  L  V  A  T  A  T  G  V  H  S  D  V  L  M  T  Q  S  P
         GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C │T  P  P  A  Y  R  P  P  N  A  P  I  L│ W  Y
         CTCTCCCTGCCTGTCACTCCTGGGGAGCCAGCCTCGATCTCTTGCACTCCTCCAGCTTATAGACCACCAAATGCCCCTATCCTATGGTAT
 91 ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
         CTGCAGAAACCAGGCCAGTCTCCACAGCTCCTGATCTACAAAGTTTCCAACCGATTTTCTGGGGTCCCAGACAGATTCAGTGGCAGTGGA
181 ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
         TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

T  F  G  G  G  T  K  V  E  I  K  BsiWI      (SEQ ID NO: 210)
         ACGTTCGGTGGAGGCACCAAGGTGGAAATCAAGCGTACG          (SEQ ID NO: 209)
361 ---------!---------!---------!--------- 399
```

FIG. 41

Heavy Variable

```
HindIII    M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1        ---------!---------!---------!---------!---------!---------!---------!---------!---------! 90

G  G  L  I  Q  P  G  G  S  L  R  M  S  C |T  I  T  D  Q  V  P  Y  S  V| W  V  R  Q  A  P
GGAGGCTTAATCCAGCCTGGAGGGTCCCTGAGAATGTCCTGCACCATTACTGACCAGGTGCCTTACTCCGTGTGGGTTCGGCAGGCTCCG
91       ---------!---------!---------!---------!---------!---------!---------!---------!---------! 180

C  K  C  L  E  W  I  A  Y  I  C  S  C  G  D  R  T  Y  Y  P  D  T  V  K  C  R  F  T  I  S
GGGAAGGGGCTGGAGTGGATCGCATACATTGGTAGTGGTGGTGATAGAACCTACTATCCAGACACTGTGAAGGGCCGATTCACCATTTCC
181      ---------!---------!---------!---------!---------!---------!---------!---------!---------! 270

R  D  N  S  K  N  T  L  Y  L  Q  L  N  S  L  R  A  E  D  T  A  V  Y  Y  C  A  R  H  Y  G
AGAGACAATAGCAAGAACACCCTGTATTTGCAATTGAACAGTCTGAGGGCTGAGGACACAGCCGTGTATTACTGTGCAAGACATTATGGT
271      ---------!---------!---------!---------!---------!---------!---------!---------!---------! 360

AfeI
           H  Y  V  D  Y  A  V  D  Y  W  G  Q  G  T  T  V  T  V  S  S              (SEQ ID NO: 212)
CACTACGTGGACTATGCTGTGGACTACTGGGGTCAAGGAACCACGGTCACCGTCTCCAGCGCT                    (SEQ ID NO: 211)
361      ---------!---------!---------!---------!---------!---------!--- 423
```

Light Variable

```
BamH1      M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1        ---------!---------!---------!---------!---------!---------!---------!---------!---------! 90

L  S  L  P  V  T  P  G  E  P  A  S  I  S  C |T  P  P  A  Y  R  P  P  N  A  P  I  L| W  Y
CTCTCCCTGCCTGTCACTCCTGGGGAGCCAGCCTCGATCTCTTGCACTCCTCCAGCTTATAGACCACCAAATGCCCCTATCCTATGGTAT
91       ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
CTGCAGAAACCAGGCCAGTCTCCACAGCTCCTGATCTACAAAGTTTCCAACCGATTTTCTGGGGTCCCAGACAGATTCAGTGGCAGTGGA
181      ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
TCAGGGACAGATTTCACACTCAAGATCAGCAGAGTGGAGGCTGAGGATACCGGAGTGTATTACTGCTTTCAAGGTTCACATGTTCCGTGG
271      ---------!---------!---------!---------!---------!---------!---------!---------!---------! 360

I  F  G  G  G  T  K  V  E  I  K  BsiWI       (SEQ ID NO: 214)
ACGTTCGGTGGAGGCACCAAGGTGGAAATCAAGCGTACG              (SEQ ID NO: 213)
361      ---------!---------!---------!--------- 399
```

FIG. 42

Heavy Variable

```
HindIII   M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C  T  I  T  D  Q  L  P  F  S  V  W  V  R  Q  A  P
GGAGGCTTAATCCAGCCTGGAGGGTCCCTGAGAATGTCCTGCACCATTACTGACCAGCTGCCTTTCTCCGTGTGGGTTCGGCAGGCTCCG
 91 ---------!---------!---------!---------!---------!---------!---------!---------!---------! 180

G  K  G  L  E  W  I  A  Y  I  G  S  G  G  D  R  T  Y  Y  P  D  T  V  K  G  R  F  T  I  S
GGGAAGGGGCTGGAGTGGATCGCATACATTGGTAGTGGTGGTGATAGAACCTACTATCCAGACACTGTGAAGGGCCGATTCACCATTTCC
181 ---------!---------!---------!---------!---------!---------!---------!---------!---------! 270

R  D  N  S  K  N  T  L  Y  L  Q  L  N  S  L  R  A  E  D  T  A  V  Y  Y  C  A  R  H  Y  G
AGAGACAATAGCAAGAACACCCTGTATTTGCAATTGAACAGTCTGAGGGCTGAGGACACAGCCGTGTATTACTGTGCAAGACATTATGGT
271 ---------!---------!---------!---------!---------!---------!---------!---------!---------! 360

AfeI
          H  Y  V  D  Y  A  V  D  Y  W  G  Q  G  T  T  V  T  V  S  S              (SEQ ID NO: 216)
CACTACGTGGACTATGCTGTGGACTACTGGGGTCAAGGAACCACGGTCACCGTCTCCAGCGCT                   (SEQ ID NO: 215)
361 ---------!---------!---------!---------!---------!---------!---  423
```

Light Variable

```
BamH1     M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C  T  P  P  A  Y  R  P  P  N  A  P  I  L  W  Y
CTCTCCCTGCCTGTCACTCCTGGGGAGCCAGCCTCGATCTCTTGCACTCCTCCAGCTTATAGACCACCAAATGCCCCTATCCTATGGTAT
 91 ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
CTGCAGAAACCAGGCCAGTCTCCACAGCTCCTGATCTACAAAGTTTCCAACCGATTTTCTGGGGTCCCAGACAGATTCAGTGGCAGTGGA
181 ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

T  F  G  G  G  T  K  V  E  I  K   BsiWI       (SEQ ID NO: 217)
ACGTTCGGTGGAGGCACCAAGGTGGAAATCAAGCGTACG              (SEQ ID NO: 219)
361 ---------!---------!---------!---------  399
```

FIG. 43

Heavy Variable

```
 HindIII   M   G   W   S   C   I   I   L   F   L   V   A   T   A   T   G   V   H   S   Q   V   Q   L   V   E   T   G
 AAGCTTACCATGGGATGGAGCTGTATCATCCTCTTCTTGGTAGCAACAGCTACCGGAGTCCACTCCCAGGTGCAGCTGGTGGAGACTGGG
 1  ---------!---------!---------!---------!---------!---------!---------!---------!---------! 90

G   G   L   I   Q   P   G   G   S   L   R   M   S   C  |T   I   M   D   Q   V   P   F   S   V|  W   V   R   Q   A   P
 GGAGGCTTAATCCAGCCTGGAGGGTCCCTGAGAATGTCCTGCACCATTATGGACCAGGTGCCTTTCTCCGTCTGGGTTCGGCAGGCTCCG
 91 ---------!---------!---------!---------!---------!---------!---------!---------!---------! 180

G   K   G   L   E   W   I   A   Y   I   G   S   G   G  |S   V   Y   D   F   F   V   W|  L   R   F   T   I   S   R   D
 GGGAAGGGGCTGGAGTGGATCGCATACATTGGTAGTGGTGGTAGTGTTTATGATTTTTTTGTGTGGCTCCGATTCACCATTTCCAGAGAC
 181 ---------!---------!---------!---------!---------!---------!---------!---------!---------! 270

N   S   K   N   T   L   Y   L   Q   L   N   S   L   R   A   E   D   T   A   V   Y   Y   C   A   R   E   Y   G   H   Y
 AATAGCAAGAACACCCTGTATTTGCAATTGAACAGTCTGAGGGCTGAGGACACAGCCGTGTATTACTGTGCGAGACATTATGGTCACTAC
 271 ---------!---------!---------!---------!---------!---------!---------!---------!---------! 360
                                                                                AfeI
       V   D   Y   A   V   D   Y   W   G   Q   G   T   T   V   T   V   S   S
 GTGGACTATGCTGTGGACTACTGGGGTCAAGGTACCACGGTCACCGTCTCCAGCGCT          (SEQ ID NO: 221)
 361 ---------!---------!---------!---------!---------!------- 417    (SEQ ID NO: 220)
```

Light Variable

```
 BamHI    M   G   W   S   C   I   I   L   F   L   V   A   T   A   T   G   V   H   S   D   V   L   M   T   Q   S   P
 GGATCCACCATGGGATGGAGCTGTATCATCCTCTTCTTGGTAGCAACAGCTACCGGAGTCCACTCCGATGTGTTGATGACCCAATCTCCA
 1  ---------!---------!---------!---------!---------!---------!---------!---------!---------! 90

L   S   L   P   V   T   P   G   E   P   A   S   I   S   C  |W   N   R   Q   L   Y   P   E   W   T   E   A   Q   R   L
 CTCTCCCTGCCTGTCACTCCTGGGGAGCCAGCCTCGATCTCTTGCTGGAACAGGCAGCTGTATCCAGAGTGGACAGAAGCCCAGAGACTT
 91 ---------!---------!---------!---------!---------!---------!---------!---------!---------! 180

|D|  W   Y   L   Q   K   P   G   Q   S   P   Q   L   L   I   Y   K   V   S   N   R   F   S   G   V   P   D   R   F   S
 GACTGGTATCTGCAGAAACCAGGCCAGTCTCCACAGCTCCTGATCTACAAAGTTTCCAACCGATTTTCTGGGGTCCCAGACAGATTCAGT
 181 ---------!---------!---------!---------!---------!---------!---------!---------!---------! 270

G   S   G   S   G   T   D   F   T   L   K   I   S   R   V   E   A   E   D   T   G   V   Y   Y   C   F   Q   G   S   H
 GGCAGTGGATCAGGGACAGATTTCACACTCAAGATCAGCAGAGTGGAGGCTGAGGATACCGGAGTGTATTACTGCTTTCAAGGTTCACAT
 271 ---------!---------!---------!---------!---------!---------!---------!---------!---------! 360

V   P   W   T   F   G   G   G   T   K   V   E   I   K   BsiWI   (SEQ ID NO: 223)
 GTTCCGTGGACGTTCGGTGGAGGCACCAAGGTGGAAATCAAGCGTACG                   (SEQ ID NO: 222)
 361 ---------!---------!---------!---------!-------- 408
```

FIG. 45

Heavy Variable

```
HindIII   M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1       ---------!---------!---------!---------!---------!---------!---------!---------!---------! 90

G  G  L  I  Q  P  G  G  S  L  R  M  S  C │T  I  M  D  Q  V  P  F  S  V│ W  V  R  Q  A  P
        GGAGGCTTAATCCAGCCTGGAGGGTCCCTGAGAATGTCCTGCACCATTATGGACCAGGTGCCTTTCTCCGTGTGGGTTCGGCAGGCTCCG
91      ---------!---------!---------!---------!---------!---------!---------!---------!---------! 180

G  K  G  L  E  W  I  A  Y  I  G  S  G  G │S  V  Y  D  F  F  V  W  L│ R  F  T  I  S  R  D
        GGGAAGGGGCTGGAGTGGATCGCATACATTGGTAGTGGTGGTAGTGTTTATGATTTTTTTGTGTGGCTCCGATTCACCATTTCCAGAGAC
181     ---------!---------!---------!---------!---------!---------!---------!---------!---------! 270

N  S  K  N  T  L  Y  L  Q  L  N  S  L  R  A  E  D  T  A  V  Y  Y  C  A  R  H  Y  G  H  Y
        AATAGCAAGAACACCCTGTATTTGCAATTGAACAGTCTGAGGGCTGAGGACACAGCCGTGTATTACTGTGCGAGACATTATGGTCACTAC
271     ---------!---------!---------!---------!---------!---------!---------!---------!---------! 360

AfeI
          V  D  Y  A  V  D  Y  W  G  Q  G  T  T  V  T  V  S  S
        GTGGACTATGCTGTGGACTACTGGGGTCAAGGTACCACGGTCACCGTCTCCAGCGCT       (SEQ ID NO: 225)
361     ---------!---------!---------!---------!---------!------- 417  (SEQ ID NO: 224)
```

Light Variable

```
BamHI     M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1       ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
        CTCTCCCTGCCTGTCACTCCTGGGGAGCCAGCCTCCATCTCTTGCAGATCTAGTCAGAGCCTGGTACATAGTAATGGAAACACCTATTTA
91      ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
        GAATGGTACCTGCAGAAACCAGGCCAGTCTCCACAGCTCCTGATCTACAAAGTTTCCAACCGATTTTCTGGGGTCCCAGACAGATTCAGT
181     ---------!---------!---------!---------!---------!---------!---------!---------!---------! 270

G  S  G  S  G  T  D  F  T  L  K  I  S  R  V  E  A  E  D  T  G  V  Y  Y  C │W  N  R  Q  L
        GGCAGTGGATCAGGGACAGATTTCACACTCAAGATCAGCAGAGTGGAGGCTGAGGATACCGGAGTGTATTACTGCTGGAACAGGCAGCTG
271     ---------!---------!---------!---------!---------!---------!---------!---------!---------! 360

│Y  P  E  W  T  E  A  Q  R  L  D│ F  G  G  G  T  K  V  E  I  K  BsiW1      (SEQ ID NO: 227)
        TATCCAGAGTGGACAGAAGCCCAGAGACTTGACTTCGTGGAGGCACCAAGGTGGAAATCAAGCGTACG           (SEQ ID NO: 226)
361     ---------!---------!---------!---------!---------!---------! 429
```

FIG. 47

Heavy Variable

```
HindIII    M  G  W  S  C  I  I  L  F  L  V  A  T  A  T  G  V  H  S  Q  V  Q  L  V  E  T  G
           AAGCTTACCATGGGATGGAGCTGTATCATCCTCTTCTTGGTAGCAACAGCTACCGGAGTCCACTCCCAGGTGCAGCTGGTGGAGACTGGG
   1       ---------!---------!---------!---------!---------!---------!---------!---------!---------! 90

G  G  L  I  Q  P  G  G  S  L  R  M  S  C │ I  L  I  N  S  L  P  L  V │W  V  R  Q  A  P  G
           GGAGGCTTAATCCAGCCTGGAGGGTCCCTGAGAATGTCCTG│ATCTTGATCAATTCCCTACCTCTTGTA│TGGGTTCGGCAGGCTCCGGGG
  91       ---------!---------!---------!---------!---------!---------!---------!---------!---------! 180

K  G  L  E  W  I  A  Y  I  G  S  G  G  D  R  T  Y  Y  P  D  T  V  K  G  R  F  T  I  S  R
           AAGGGGCTGGAGTGGATCGCATACATTGGTAGTGGTGGTGATAGAACCTACTATCCAGACACTGTGAAGGGCCGATTCACCATTTCCAGA
 181       ---------!---------!---------!---------!---------!---------!---------!---------!---------! 270

D  N  S  K  N  T  L  Y  L  Q  L  N  S  L  R  A  E  D  T  A  V  Y  Y  C  A  R  H  Y  G  H
           GACAATAGCAAGAACACCCTGTATTTGCAATTGAACAGTCTGAGGGCTGAGGACACAGCCGTGTATTACTGTGCAAGACATTATGGTCAC
 271       ---------!---------!---------!---------!---------!---------!---------!---------!---------! 360

AfeI
           Y  V  D  Y  A  V  D  Y  W  G  Q  G  T  T  V  T  V  S  S        (SEQ ID NO: 229)
           TACGTGGACTATGCTGTGGACTACTGGGGTCAAGGAACCACGGTCACCGTCTCCAGCGCT        (SEQ ID NO: 228)
 361       ---------!---------!---------!---------!---------!---------! 420
```

Light Variable

```
BamH1      M  G  W  S  C  I  I  L  F  L  V  A  T  A  T  G  V  H  S  D  V  L  M  T  Q  S  P
           GGATCCACCATGGGATGGAGCTGTATCATCCTCTTCTTGGTAGCAACAGCTACCGGAGTCCACTCCGATGTGTTGATGACCCAATCTCCA
   1       ---------!---------!---------!---------!---------!---------!---------!---------!---------! 90

L  S  L  P  V  T  P  G  E  P  A  S  I  S  C │ T  P  P  A  Y  R  P  P  N  A  P  I  L │W  Y
           CTCTCCCTGCCTGTCACTCCTGGGGAGCCAGCCTCGATCTCTTGC│ACTCCTCAGCTTATAGACCACCAAATGCCCCTATCCTA│TGGTAT
  91       ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
           CTGCAGAAACCAGGCCAGTCTCCACAGCTCCTGATCTACAAAGTTTCCAACCGATTTTCTGGGGTCCCAGACAGATTCAGTGGCAGTGGA
 181       ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
           TCAGGGACAGATTTCACACTCAAGATCAGCAGAGTGGAGGCTGAGGATACCGGAGTGTATTACTGCTTTCAAGGTTCACATGTTCCGTGG
 271       ---------!---------!---------!---------!---------!---------!---------!---------!---------! 360

T  F  G  G  G  T  K  V  E  I  K  BsiWI       (SEQ ID NO: 231)
           ACGTTCGGTGGAGGCACCAAGGTGGAAATCAAGCGTACG         (SEQ ID NO: 230)
 361       ---------!---------!---------!---------! 399
```

FIG. 51

Heavy Variable

```
HindIII     M  G  W  S  C  I  I  L  F  L  V  A  T  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
1   ---------!---------!---------!---------!---------!---------!---------!---------!---------! 90

G  G  L  I  Q  P  G  G  S  L  R  M  S  C  A  A  S  G  F  A  F  N  T  Y  D  M  S  W  V  R
GGAGGCTTAATCCAGCCTGGAGGGTCCCTGAGAATGTCCTGTGCAGCCTCTGGATTCGCTTTCAATACCTATGACATGTCTTGGGTTCGC
91  ---------!---------!---------!---------!---------!---------!---------!---------!---------! 180

Q  A  P  G  K  G  L  E  W  I  A  Y  I  G  S  G  G │I  L  I  N  S  L  P  L  V│ R  F  T  I
CAGGCTCCGGGGAAGGGGCTGGAGTGGATCGCATACATTGGTAGTGGTGG TATCTTGATCAATTCCCTACCTCTTGTA CGATTCACCATT
181 ---------!---------!---------!---------!---------!---------!---------!---------!---------! 270

S  R  D  N  S  K  N  T  L  Y  L  Q  L  N  S  L  R  A  E  D  T  A  V  Y  Y  C  A  R  H  Y
TCCAGAGACAATAGCAAGAACACCCTGTATTTGCAATTGAACAGTCTGAGGGCTGAGGACACAGCCGTGTATTACTGTGCAAGACATTAT
271 ---------!---------!---------!---------!---------!---------!---------!---------!---------! 360

AfeI
     G  H  Y  V  D  Y  A  V  D  Y  W  G  Q  G  T  T  V  T  V  S  S          (SEQ ID NO: 233)
GGTCACTACGTGGACTATGCTGTGGACTACTGGGGTCAAGGAACCACGGTCACCGTCTCCAGCGCT          (SEQ ID NO: 232)
361 ---------!---------!---------!---------!---------!---------!------  426
```

Light Variable

```
BamH1       M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1   ---------!---------!---------!---------!---------!---------!---------!---------!---------! 90

L  S  L  P  V  T  P  G  E  P  A  S  I  S  C │T  P  P  A  Y  R  P  P  N  A  P  I  L│ W  Y
CTCTCCCTGCCTGTCACTCCTGGGGAGCCAGCCTCGATCTCTTGC ACTCCTCCAGCTTATAGACCACCAAATGCCCCTATCCTA TGGTAT
91  ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
CTGCAGAAACCAGGCCAGTCTCCACAGCTCCTGATCTACAAAGTTTCCAACCGATTTTCTGGGGTCCCAGACAGATTCAGTGGCAGTGGA
181 ---------!---------!---------!---------!---------!---------!---------!---------!---------! 270

S  G  T  D  F  T  L  K  T  S  R  V  E  A  E  D  T  G  V  Y  Y  C  F  Q  G  S  H  V  P  W
TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

T  F  G  G  G  T  K  V  E  I  K  BsiWI      (SEQ ID NO: 235)
ACGTTCGGTGGAGGCACCAAGGTGGAAATCAAGCGTACG          (SEQ ID NO: 234)
361 ---------!---------!---------!---------  399
```

FIG. 52

Heavy Chain

```
    HindIII   M  G  W  S  C  I  I  L  F  L  V  A  T  A  T  G  V  H  S  Q  V  Q  L  V  E  T  G
    AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C |T  I  M  D  Q  V  P  F  S  V| W  V  R  Q  A  P
              GGAGGCTTAATCCAGCCTGGAGGGTCCCTGAGAATGTCCTGCACCATTATGGACCAGGTGCCTTTCTCCGTGTGGGTTCGGCAGGCTCCG
 91 ---------!---------!---------!---------!---------!---------!---------!---------!---------! 180

G  K  G  L  E  W  I  A  Y  I  G  S  G  G |S  V  Y  D  F  F  V  W  L| R  F  T  I  S  R  D
              GGGAAGGGGCTGGAGTGGATCGCATACATTGGTAGTGGTGGTAGTGTTTATGATTTTTTTGTGTGGCTCCGATTCACCATTTCCAGAGAC
181 ---------!---------!---------!---------!---------!---------!---------!---------!---------! 270

N  S  K  N  T  L  Y  L  Q  L  N  S  L  R  A  E  D  T  A  V  Y  Y  C  A  R  H  Y  G  H  Y
              AATAGCAAGAACACCCTGTATTTGCAATTGAACAGTCTGAGGGCTGAGGACACAGCCGTGTATTACTGTGCGAGACATTATGGTCACTAC
271 ---------!---------!---------!---------!---------!---------!---------!---------!---------! 360
                                                                          AfeI
              V  D  Y  A  V  D  Y  W  G  Q  G  T  T  V  T  V  S  S  A  K  T  T  A  P  S  V  Y  P  L  A
              GTGGACTATGCTGTCGACTACTGGGCTCAAGGTACCACGGTCACCGTCTCCAGCGCTAAAACAACAGCCCCATCCGTCTATCCACTGGCC
361 ---------!---------!---------!---------!---------!---------!---------!---------!---------! 450

P  V  C  G  D  T  T  G  S  S  V  T  L  G  C  L  V  K  G  Y  F  P  E  P  V  T  L  T  W  N
              CCTGTGTGTGGAGATACAACTGGCTCCTCGGTGACTCTAGGATGCCTGGTCAAGGGTTATTTCCCTGAGCCAGTGACCTTGACCTGGAAC
451 ---------!---------!---------!---------!---------!---------!---------!---------!---------! 540

S  G  S  L  S  S  G  V  H  T  F  P  A  V  L  Q  S  D  L  Y  T  L  S  S  S  V  T  V  T  S
              TCTGGTTCCCTGTCCAGTGGTGTGCACACCTTCCCAGCTGTCCTGCAGTCTGACCTCTACACCCTCAGCAGCTCAGTGACTGTAACTTCG
541 ---------!---------!---------!---------!---------!---------!---------!---------!---------! 630

S  T  W  P  S  Q  S  I  T  C  N  V  A  H  P  A  S  S  T  K  V  D  K  K  I  E  P  R  G  P
              AGCACCTGGCCCAGCCAGTCCATCACCTGCAATGTGGCCCACCCGGCAAGCAGCACCAAGGTGGACAAGAAAATTGAGCCCAGAGGGCCC
631 ---------!---------!---------!---------!---------!---------!---------!---------!---------! 720

T  I  K  P  C  P  P  C  K  C  P  A  P  N  L  L  G  G  P  S  V  F  I  F  P  P  K  I  K  D
              ACAATCAAGCCCTGTCCTCCATGCAAATGCCCAGCACCTAACCTCTTGGGTGGACCATCCGTCTTCATCTTCCCTCCAAAGATCAAGGAT
721 ---------!---------!---------!---------!---------!---------!---------!---------!---------! 810

V  L  M  I  S  L  S  P  I  V  T  C  V  V  V  D  V  S  E  D  D  P  D  V  Q  I  S  W  F  V
              GTACTCATGATCTCCCTGAGCCCCATAGTCACATGTGTGGTGGTGGATGTGAGCGAGGATGACCCAGATGTCCACATCAGCTGGTTTGTG
811 ---------!---------!---------!---------!---------!---------!---------!---------!---------! 900

N  N  V  E  V  H  T  A  Q  T  Q  T  H  R  E  D  Y  N  S  T  L  R  V  V  S  A  L  P  I  Q
              AACAACGTGGAAGTACACACAGCTCAGACACAAACCCATAGAGAGGATTACAACAGTACTCTCCGGGTGGTCAGTGCCCTCCCCATCCAG
901 ---------!---------!---------!---------!---------!---------!---------!---------!---------! 990

H  Q  D  W  M  S  G  K  E  F  K  C  K  V  N  N  K  D  L  P  A  P  I  E  R  T  I  S  K  P
              CACCAGGACTGGATGAGTGGCAAGGAGTTCAAATGCAAGGTCAACAACAAAGACCTCCCAGCGCCCATCGAGAGAACCATCTCAAAACCC
991 ---------!---------!---------!---------!---------!---------!---------!---------!---------! 1080

K  G  S  V  R  A  P  Q  V  Y  V  L  P  P  P  E  E  E  M  T  K  K  Q  V  T  L  T  C  M  V
              AAAGGGTCAGTAAGAGCTCCACAGGTATATGTCTTGCCTCCACCAGAAGAAGAGATGACTAAGAAACAGGTCACTCTGACCTGCATGGTC
1081 ---------!---------!---------!---------!---------!---------!---------!---------!---------! 1170

T  D  F  M  P  E  D  I  Y  V  E  W  T  N  N  G  K  T  E  L  N  Y  K  N  T  E  P  V  L  D
              ACAGACTTCATGCCTGAAGACATTTACGTGGAGTGGACCAACAACGGGAAAACAGAGCTAAACTACAAGAACACTGAACCAGTCCTGGAC
1171 ---------!---------!---------!---------!---------!---------!---------!---------!---------! 1260

S  D  G  S  Y  F  M  Y  S  K  L  R  V  E  K  K  N  W  V  E  R  N  S  Y  S  C  S  V  V  H
              TCTGATGGTTCTTACTTCATGTACAGCAAGCTGAGAGTGGAAAAGAAGAACTGGGTGGAAAGAAATAGCTACTCCTGTTCAGTGGTCCAC
1261 ---------!---------!---------!---------!---------!---------!---------!---------!---------! 1350

E  G  L  H  N  H  H  T  T  K  S  F  S  R  T  P  G  K  *  XbaI    (SEQ ID NO: 237)
              GAGGGTCTGCACAATCACCACACGGACTAAGAGCTTCTCCCGGACTCCGGGTAAATGATCTAGA   (SEQ ID NO: 236)
1351 ---------!---------!---------!---------!---------!---------!--- 1413
```

FIG. 54

Light chain

```
BamH1      M  G  W  S  C  I  I  L  F  L  V  A  T  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
1   ---------!---------!---------!---------!---------!---------!---------!---------!---------! 90

L  S  L  P  V  T  P  G  E  P  A  S  I  S  C  T  P  P  A  Y  R  P  P  N  A  P  I  L  W  Y
    CTCTCCCTGCCTGTCACTCCTGGGGAGCCAGCCTCGATCTCTTGCACTCCTCCAGCTTATAGACCACCAAATGCCCCTATCCTATGGTAT
91  ---------!---------!---------!---------!---------!---------!---------!---------!---------! 180

L  Q  K  P  G  Q  S  P  Q  L  L  I  Y  K  V  S  N  R  F  S  G  V  P  D  R  F  S  G  S  G
    CTGCAGAAACCAGGCCAGTCTCCACAGCTCCTGATCTACAAAGTTTCCAACCGATTTTCTGGGGTCCCAGACAGATTCAGTGGCAGTGGA
181 ---------!---------!---------!---------!---------!---------!---------!---------!---------! 270

S  G  T  D  F  T  L  K  I  S  R  V  E  A  E  D  T  G  V  Y  Y  C  F  Q  G  S  H  V  P  W
    TCAGGGACAGATTTCACACTCAAGATCAGCAGAGTGGAGGCTGAGGATACCGGAGTGTATTACTGCTTTCAAGGTTCACATGTTCCGTGG
271 ---------!---------!---------!---------!---------!---------!---------!---------!---------! 360

HpaI
       T  F  G  G  G  T  K  V  E  I  K  R  A  D  A  A  P  T  V  S  I  F  P  P  S  S  E  Q  L  T
    ACGTTCGGTGGAGGCACCAAGGTGGAAATCAAGCGTGCAGATGCTGCCACCAACTGTATCGATCTTCCCACCATCCAGTGAGCAGTTAACA
361 ---------!---------!---------!---------!---------!---------!---------!---------!---------! 450

S  G  G  A  S  V  V  C  F  L  N  N  F  Y  P  K  D  I  N  V  K  W  K  I  D  G  S  E  R  Q
    TCTGGAGGTGCCTCAGTCGTGTGCTTCTTGAACAACTTCTACCCCAAAGACATCAATGTCAAGTGGAAGATTGATGGCAGTGAACGACAA
451 ---------!---------!---------!---------!---------!---------!---------!---------!---------! 540

N  G  V  L  N  S  W  T  D  Q  D  S  K  D  S  T  Y  S  M  S  S  T  L  I  L  T  K  D  E  Y
    AATGGCGTCCTGAACAGTTGGACTGATCAGGACAGCAAAGACAGCACCTACAGCATGAGCAGCACCCTCACGTTGACCAAGGACGAGTAT
541 ---------!---------!---------!---------!---------!---------!---------!---------!---------! 630

E  R  H  N  S  Y  T  C  E  A  T  H  K  T  S  T  S  P  I  V  K  S  F  N  R  N  E  C  *
    GAACGACATAACAGCTATACCTGTGAGGCCACTCACAAGACATCTACTTCACCCATTGTCAAGAGCTTCAACAGGAATGAGTGTTAGCTC
631 ---------!---------!---------!---------!---------!---------!---------!---------!---------! 720

XhoI                (SEQ ID NO: 239)
    GAGTCTAGA         (SEQ ID NO: 238)
721 ---------729
```

FIG. 54 continued

Heavy chain

```
     HindIII    M  G  W  S  C  I  I  L  F  L  V  A  T  A  T  G  V  H  S  Q  V  Q  L  V  E  T  G
              AAGCTTACCATGGGATGGAGCTGTATCATCCTCTTCTTGGTAGCAACAGCTACCGGAGTCACTCCCAGGTGCAGCTGGTGGAGACTGGGC
        1     ---------!---------!---------!---------!---------!---------!---------!---------!---------! 90

G  G  L  I  Q  P  G  G  S  L  R  M  S  C  |G  T  G  R  A  M  L  G  T  H  T  M  E  V  T  V
              GGAGGCTTAATCCAGCCTGGAGGGTCCCTGAGAATGTCCTGC|GGACAGGCAGGGCAATGCTGGGCACACACACCATGGAAGTGACTGTC
       91     ---------!---------!---------!---------!--!------!---------!---------!---------!---------! 180

|Y  H| W  V  R  Q  A  P  G  K  G  L  E  W  I  A  Y  I  G  S  G  G  |S  V  Y  D  F  F  V  W
              TACCAT|TGGGTTCGGCAGGCTCCGGGGAAGGGGCTGGAGTGGATCGCATACATTGGTAGTGGTGGT|AGTGTTTATGATTTTTTTGTGTGG
      181     ------|---!---------!---------!---------!---------!---------!------|---!---------!---------! 270

|L| R  F  T  I  S  R  D  N  S  K  N  T  L  Y  L  Q  L  N  S  L  R  A  E  D  T  A  V  Y  Y
              CT|C|CGATTCACCATTTCCAGAGACAATAGCAAGAACACCCTGTATTTGCAATTGAACAGTCTGAGGGCTGAGGACACAGCCGTGTATTAC
      271     --|-|------!---------!---------!---------!---------!---------!---------!---------!---------! 360
                                                                                                AfeI
              C  A  R  |W  N  R  Q  L  Y  P  E  W  T  E  A  Q  R  L  D|  W  G  Q  G  T  T  V  I  V  S  S
              TGTGCCCGA|TGGAACAGGCAGCTGTATCCAGAGTGGACAGAAGCCCAGAGACTGAC|TGGGGCCAAGGAACCACGGTCACCGTCTCCAGC
      361     ---------|!---------!---------!---------!---------!----|----!---------!---------!---------! 450

A  K  T  T  A  P  S  V  Y  P  L  A  P  V  C  G  D  T  T  G  S  S  V  T  L  G  C  L  V  K
              GCTAAAACAACAGCCCCATCGGTCTATCCACTGGCCCCTGTGTGTGGAGATACAACTGGCTCCTCGGTGACTCTAGGATGCCTGGTCAAG
      451     ---------!---------!---------!---------!---------!---------!---------!---------!---------! 540

G  Y  F  P  E  P  V  T  L  T  W  N  S  G  S  L  S  S  G  V  H  T  F  P  A  V  L  Q  S  D
              GGTTATTTCCCTGAGCCAGTGACCTTGACCTGGAACTCTGGTTCCCTGTCCAGTGGTGTGCACACCTTCCCAGCTGTCCTGCAGTCTGAC
      541     ---------!---------!---------!---------!---------!---------!---------!---------!---------! 630

L  Y  T  L  S  S  S  V  T  V  T  S  S  T  W  P  S  Q  S  I  T  C  N  V  A  H  P  A  S  S
              CTCTACACCCTCAGCAGCTCAGTGACTGTAACTTCGAGCACCTGGCCCAGCCAGTCCATCACCTGCAATGTGGCCCACCCGGCAAGCAGC
      631     ---------!---------!---------!---------!---------!---------!---------!---------!---------! 720

T  K  V  D  K  K  I  E  P  R  G  P  T  I  K  P  C  P  P  C  K  C  P  A  P  N  L  L  G  G
              ACCAAGGTGGACAAGAAAATTGAGCCCAGAGGGCCCACAATCAAGCCCTGTCCTCCATGCAAATGCCCAGCACCTAACCTCTTGGGTGGA
      721     ---------!---------!---------!---------!---------!---------!---------!---------!---------! 810

P  S  V  F  I  F  P  P  K  I  K  D  V  L  M  I  S  L  S  P  I  V  T  C  V  V  V  D  V  S
              CCATCCGTCTTCATCTTCCCTCCAAAGATCAAGGATGTACTCATGATCTCCCTGAGCCCCATAGTCACATGTGTGGTGGTGGATGTGAGC
      811     ---------!---------!---------!---------!---------!---------!---------!---------!---------! 900

E  D  D  P  D  V  Q  I  S  W  F  V  N  N  V  E  V  H  T  A  Q  T  Q  T  H  R  E  D  Y  N
              GAGGATGACCCAGATGTCCAGATCAGCTGGTTTGTGAACAACGTGGAAGTACACACAGCTCAGACACAAACCCATAGAGAGGATTACAAC
      901     ---------!---------!---------!---------!---------!---------!---------!---------!---------! 990

S  T  L  R  V  V  S  A  L  P  I  Q  H  Q  D  W  M  S  G  K  E  F  K  C  K  V  N  N  K  D
              AGTACTCTCCGGGTGGTCAGTGCCCTCCCCATCCAGCACCAGGACTGGATGAGTGGCAAGGAGTTCAAATGCAAGGTCAACAACAAAGAC
      991     ---------!---------!---------!---------!---------!---------!---------!---------!---------! 1080

L  P  A  P  I  E  R  T  I  S  K  P  K  G  S  V  R  A  P  Q  V  Y  V  L  P  P  P  E  E  E
              CTCCCAGCCCCCATCGAGAGAACCATCTCAAAACCCAAAGGGTCAGTAAGAGCTCCACAGGTATATGTCTTGCCTCCACCAGAAGAAGAG
     1081     ---------!---------!---------!---------!---------!---------!---------!---------!---------! 1170

M  T  K  K  Q  V  T  L  T  C  M  V  T  D  F  M  P  E  D  I  Y  V  E  W  T  N  N  G  K  T
              ATGACTAAGAAACAGGTCACTCTGACCTGCATGGTCACAGACTTCATGCCTGAAGACATTTACGTGGAGTGGACCAACAACGGGAAAACA
     1171     ---------!---------!---------!---------!---------!---------!---------!---------!---------! 1260

E  L  N  Y  K  N  T  E  P  V  L  D  S  D  G  S  Y  F  M  Y  S  K  L  R  V  E  K  K  N  W
              GAGCTAAACTACAAGAACACTGAACCAGTCCTGGACTCTGATGGTTCTTACTTCATGTACAGCAAGCTGAGAGTGGAAAAGAAGAACTGG
     1261     ---------!---------!---------!---------!---------!---------!---------!---------!---------! 1350

V  E  R  N  S  Y  S  C  S  V  V  H  E  G  L  H  N  H  H  T  T  K  S  F  S  R  T  P  G  K
              GTGGAAAGAAATAGCTACTCCTGTTCAGTGGTCCACGAGGGTCTGCACAATCACCACACGACTAAGAGCTTCTCCCGGACTCCGGGTAAA
     1351     ---------!---------!---------!---------!---------!---------!---------!---------!---------! 1440

* XbaI       (SEQ ID NO: 241)
                  TGATCTAGA    (SEQ ID NO: 240)
     1441     --------- 1449
```

FIG. 55

Light chain

```
    BamHI    M  G  W  S  C  I  I  L  F  L  V  A  T  A  T  G  V  H  S  D  V  L  M  T  Q  S  P
         GGATCCACCATGGGATGGAGCTGTATCATCCTCTTCTTGGTAGCAACAGCTACCGGAGTCCACTCCGATGTGTTGATGACCCAATCTCCA
    1    ---------!---------!---------!---------!---------!---------!---------!---------!---------! 90

L  S  L  P  V  T  P  G  E  P  A  S  I  S  C  R  S  S  Q  S  L  V  H  S  N  G  N  T  Y  L
         CTCTCCCTGCCTGTCACTCCTGGGGAGCCAGCCTCCATCTCTTGCAGATCTAGTCAGAGCCTGGTACATAGTAATGGAAACACCTATTTA
    91   ---------!---------!---------!---------!---------!---------!---------!---------!---------! 180

E  W  Y  L  Q  K  P  G  Q  S  P  Q  L  L  I  Y  K  V  S  N  R  F  S  G  V  P  D  R  F  S
         GAATGGTACCTGCAGAAACCAGGCCAGTCTCCACAGCTCCTGATCTACAAAGTTTCCAACCGATTTTCTGGGGTCCCAGACAGATTCAGT
    181  ---------!---------!---------!---------!---------!---------!---------!---------!---------! 270

G  S  G  S  G  T  D  F  T  L  K  I  S  R  V  E  A  E  D  T  G  V  Y  Y  C  F  Q  G  S  H
         GGCAGTGGATCAGGGACAGATTTCACACTCAAGATCAGCAGAGTGGAGGCTGAGGATACCGGAGTGTATTACTGCTTTCAAGGTTCACAT
    271  ---------!---------!---------!---------!---------!---------!---------!---------!---------! 360
                                                                                        ClaI
         V  P  W  T  F  G  G  G  T  K  V  E  I  K  R  A  D  A  A  P  T  V  S  I  F  P  P  S  S  E
         GTTCCGTGGACGTTCGGTGGAGGCACCAAGGTGGAAATCAAGCGTGCAGATGCTGCACCAACTGTATCGATCTTCCCACCATCCAGTGAG
    361  ---------!---------!---------!---------!---------!---------!---------!---------!---------! 450
         HpaI
         Q  L  T  S  G  G  A  S  V  V  C  F  L  N  N  F  Y  P  K  D  I  N  V  K  W  K  I  D  G  S
         CAGTTAACATCTGGAGGTGCCTCAGTCGTGTGCTTCTTGAACAACTTCTACCCCAAAGACATCAATGTCAAGTGGAAGATTGATGGCAGT
    451  ---------!---------!---------!---------!---------!---------!---------!---------!---------! 540

E  R  Q  N  G  V  L  N  S  W  T  D  Q  D  S  K  D  S  T  Y  S  M  S  S  T  L  T  L  T  K
         GAACGACAAAATGGCGTCCTGAACAGTTGGACTGATCAGGACAGCAAAGACAGCACCTACAGCATGAGCAGCACCCTCACGTTGACCAAG
    541  ---------!---------!---------!---------!---------!---------!---------!---------!---------! 630

D  E  Y  E  R  H  N  S  Y  T  C  E  A  T  H  K  T  S  T  S  P  I  V  K  S  F  N  R  N  E
         GACGAGTATGAACGACATAACAGCTATACCTGTGAGGCCACTCACAAGACATCTACTTCACCCATTGTCAAGAGCTTCAACAGGAATGAG
    631  ---------!---------!---------!---------!---------!---------!---------!---------!---------! 720

C  *  XhoI                    (SEQ ID NO: 243)
         TGTTAGCTCGAGTCTAGA            (SEQ ID NO: 242)
    721  ---------!-------- 738
```

FIG. 55 continued a.
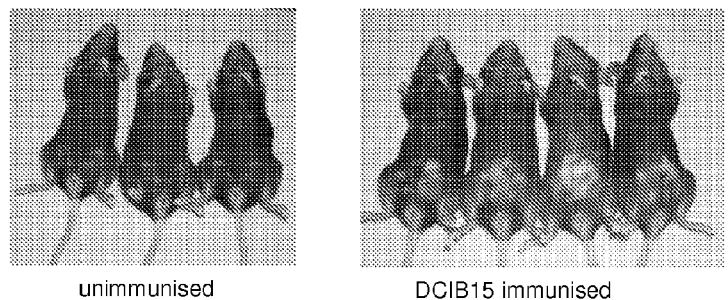
unimmunised DCIB15 immunised
b.
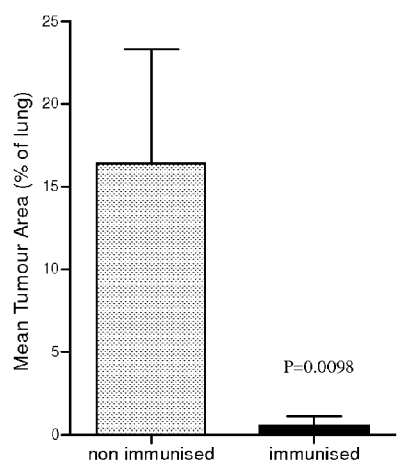
c.
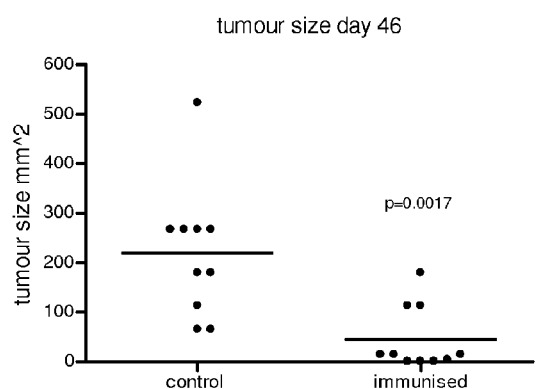
d.
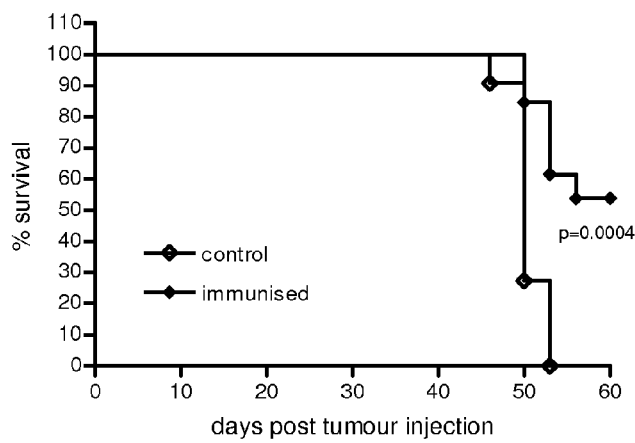
FIG. 58

Heavy Variable

```
HindIII    M  G  W  S  C  I  I  L  F  L  V  A  I  A  T  G  V  H  S  Q  V  Q  L  V  E  T  G
AAGCTTACCATGGGATGGAGCTGTATCATCCTCTTCTTGGTAGCAACAGCTACCGGAGTCCACTCCCAGGTGCAGCTGGTGGAGACTGGG
  1 ---------!---------!---------!---------!---------!---------!---------!---------!---------! 90

G  G  L  I  Q  P  G  G  S  L  R  M  S  C │ G  I  G  R  A  M  L  G  T  H  T  M  E  V  T  V
GGAGGCTTAATCCAGCCTGGAGGGTCCCTGAGAATGTCCTGC│GGGACAGGCAGGGCAATGCTGGGCACACACACCATGGAAGTAACTGTC
 91 ---------!---------!---------!---------!-│-------!---------!---------!---------!---------! 180

Y  H │ W  V  R  Q  A  P  G  K  G  L  E  W  I  A  Y  I  G  S  G  G │ S  V  Y  D  F  F  V  W
TACCAT│TGGGTTCGGCAGGCTCCGGGGAAGGGGCTGGAGTGGATCGCATACATTGGTAGTGGTGGT│AGTGTTTATGATTTTTTTGTGTGG
181 ------│---!---------!---------!---------!---------!---------!---│------!---------!--------- 270

L │ R  F  T  I  S  R  D  N  S  K  N  T  L  Y  L  Q  L  N  S  L  R  A  E  D  T  A  V  Y  Y
CTC│CGATTCACCATTTCCAGAGACAATAGCAAGAACACCCTGTATTTGCAATTGAACAGTCTGAGGGCTGAGGACACAGCCGTGTATTAC
271 ---│------!---------!---------!---------!---------!---------!---------!---------!---------!360

AfeI
    C  A  R │ W  N  R  Q  L  Y  P  E  W  T  E  A  Q  R  L  D │ W  G  Q  G  T  T  V  T  V  S  S
TGTGCCCGA│TGGAACAGGCAGCTGTATCCAGAGTGGACAGAAGCCCAGAGACTTGAC│TGGGGCCAAGGTACCACGGTCACCGTCTCCAGC
361 ---------│!---------!---------!---------!---------!--------│-!---------!---------!---------! 450
      GCT      (SEQ ID NO: 245)
451 --- 453   (SEQ ID NO: 244)
```

Light Variable

```
BamHI     M  G  W  S  C  I  I  L  F  L  V  A  I  A  T  G  V  H  S  D  V  L  M  T  Q  S  P
GGATCCACCATGGGATGGAGCTGTATCATCCTCTTCTTGGTAGCAACAGCTACCGGAGTCCACTCCGATGTGTTGATGACCCAATCTCCA
  1 ---------!---------!---------!---------!---------!---------!---------!---------!---------! 90

L  S  L  P  V  T  P  G  E  P  A  S  I  S  C │ W  N  R  Q  L  Y  P  E  W  T  E  A  Q  R  L
CTCTCCCTGCCTGTCACTCCTGGGGAGCCAGCCTCGATCTCTTGC│TGGAACAGGCAGCTGTATCCAGAGTGGACAGAAGCCCAGAGACTT
 91 ---------!---------!---------!---------!-----│----!---------!---------!---------!---------! 180

D │ W  Y  L  Q  K  P  G  Q  S  P  Q  L  L  I  Y  K  V  S  N  R  F  S  G  V  P  D  R  F  S
GAC│TGGTATCTGCAGAAACCAGGCCAGTCTCCACAGCTCCTGATCTACAAAGTTTCCAACCGATTTTCTGGGGTCCCAGACAGATTCAGT
181 ---│------!---------!---------!---------!---------!---------!---------!---------!---------! 270

G  S  G  S  G  T  D  F  T  L  K  I  S  R  V  E  A  E  D  T  G  V  Y  Y  C │ G  T  G  R  A
GGCAGTGGATCAGGGACAGATTTCACACTCAAGATCAGCAGAGTGGAGGCTGAGGATACCGGAGTGTATTACTGC│GGGACAGGCAGGGCA
271 ---------!---------!---------!---------!---------!---------!---------!----│-----!---------! 360

M  L  G  T  H  T  M  E  V  T  V  Y  H │ F  G  G  G  T  K  V  E  I  K  BsiWI    (SEQ ID NO: 247)
ATGCTGGGCACACACACCATGGAAGTGACTGTCTACCAT│TTCGGTGGAGGCACCAAGGTGGAAATCAAGCGTACG     (SEQ ID NO: 246)
361 ---------!---------!---------!--------│-!---------!---------!----- 435
```

FIG. 60

NUCLEIC ACIDS ENCODING ANTIBODIES OR PORTIONS THEREOF COMPRISING A HETEROLOGOUS T CELL EPITOPE AND THEIR USE IN MODULATING T CELL RESPONSES

RELATED APPLICATION

This application is a continuation of PCT/EP2008/053761, which designated the United States and was filed on Mar. 28, 2008, published in English, which claims priority under 35 U.S.C. §119 or 365 to United Kingdom, Application No. 0706070.0, filed on Mar. 28, 2007. The entire teachings of the above applications are incorporated herein by reference.

SUMMARY OF THE INVENTION

The present invention relates to nucleic acids and to their use as vaccines, the nucleic acids encoding T cell epitopes against which an immune response is to be raised. Such vaccines may be used in the treatment of tumours.

BRIEF DESCRIPTION OF THE DRAWINGS

FIG. 1: Map depicting features of the heavy chain vector pOrigHIB

The wild type de-immunised heavy variable region of antibody SC100 was cloned using HindIII/AfeI inframe with the human IgG1 Fc constant region. The Fc region comprises the CH1, CH2, CH3 domains and the hinge region. High-level expression in mammalian cells is driven from the human cytomegalovirus immediate early promoter. BGH polyadenylation signals downstream of the Orig HIB human IgG1 chain to ensure mRNA stability and effective termination. EM7 is a bacterial promoter that controls expression of the zeocin resistance gene allowing antibiotic selection in E. coli while the SV40 early promoter upstream of the resistance gene allows selection in mammalian cells. SV40 polyadenylation signals downstream of the resistance gene in order to direct proper processing of the 3' end of the zeo$^r$ mRNA. The vector also contains within its backbone the ColE1 origin of replication for propagation in bacteria. Complimentary determining DNA sequences were effectively removed and exchanged for restriction sites RE1, RE2 and RE3 (FspI, MscI and Srf I respectively) singly and in combination.

Figure 2:
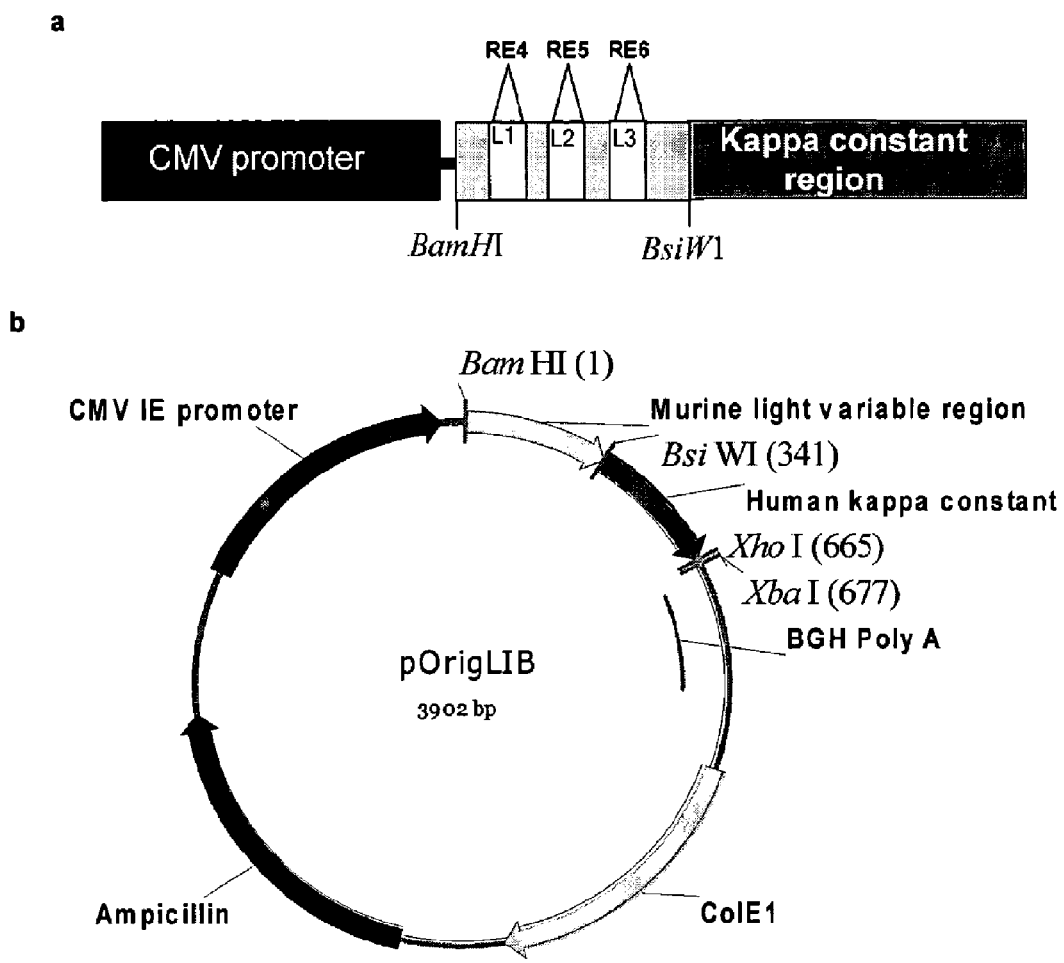

FIG. 2: Map depicting features of the heavy chain vector pOrigLIB

The wild type de-immunised light variable region of antibody SC100 was cloned using BamHI/BsiWI inframe with the human kappa constant region. High-level expression in mammalian cells is driven from the human cytomegalovirus immediate early promoter. BGH polyadenylation signals downstream of the Orig LIB chain to ensure mRNA stability and effective termination. The vector also includes the ColE1 origin of replication and the antibiotic resistance gene for ampicillin allowing propagation and selection in bacteria. Complimentary determining regions were effectively removed and exchanged for restriction sites RE4, RE5 and RE6 (EcoRV, Ssp I and Hpa I respectively) singly and in combination.

FIG. 3: Sequence of the wild type Immunobody chimeric heavy chain.

Nucleotide and on translation amino acid sequence are illustrated for the full length chimeric IgG1 heavy chain. Locations of CDR's are within boxes defined by the kabat numbering scheme. The stop codon is depicted by a red astrix. The HindIII/Afe I restriction sites are highlighted utilised in transfer of the variable heavy region.

FIG. 4: Sequence of the wild type Immunobody chimeric kappa chain

Nucleotide and on translation amino acid sequence are illustrated for the full length chimeric kappa chain. Locations of CDR's are within boxes defined by the kabat numbering scheme. The stop codon is depicted by an asterisk. The BamHI/BsiWI restriction sites utilised in transfer of the variable light region are highlighted.

Figure 5:
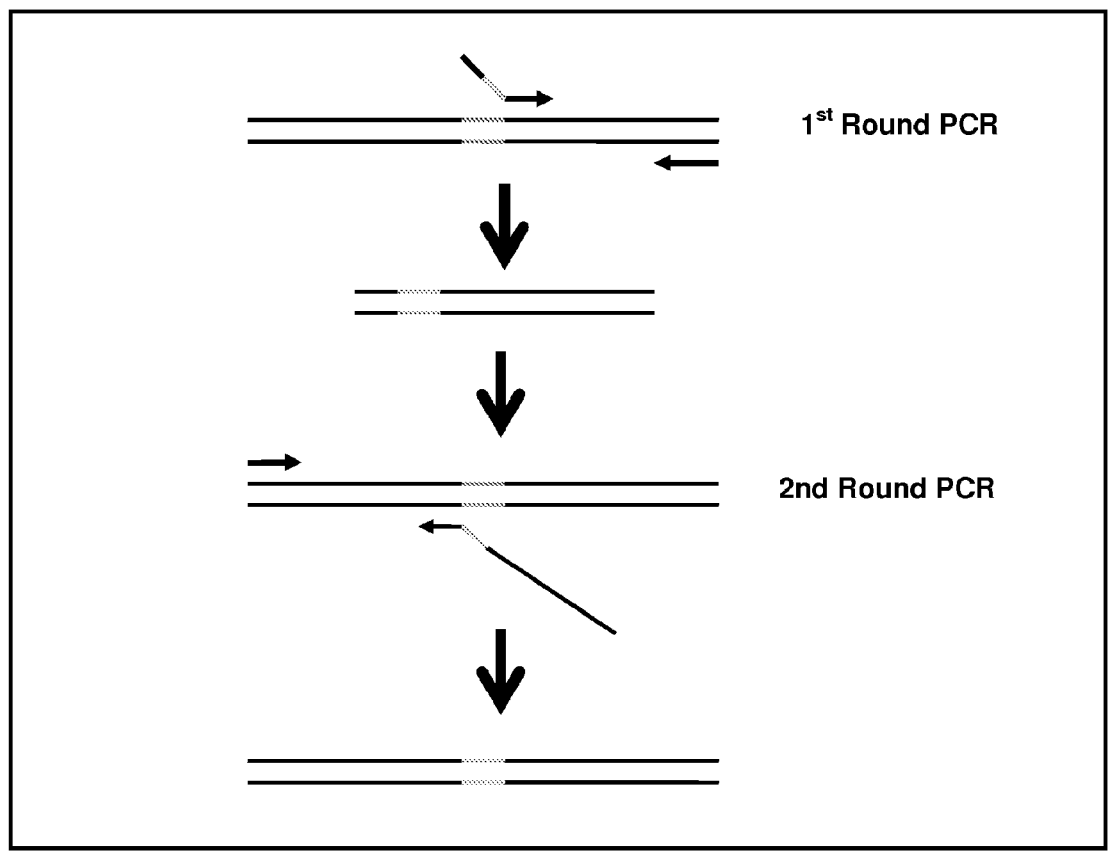

FIG. 5: Overlapping extension PCR

CDR's were removed and replaced with unique restriction sites by overlapping PCR. The forward primers H1, H2. H3, L1, L2 and L3 (Table 2) were designed to replace CDR1, 2 and 3 within the heavy and light chain variable region respectively. Each primer contained, centrally located, the chosen unique enzyme recognition sequence devoid of the CDR sequence to be removed (green section) and flanked by 10-20 bp of wild type sequence. The forward primers were used in a first round of PCR in conjunction with a general reverse primer, huHeClonR or huLiClonR (Table 2), that anneals to the human heavy and light constant domains within the wild type constructs pOrigHIB and pOrigLIB respectively. The fragment generated does not contain wild type CDR sequence (red section), but is effectively exchanged for the restriction site. In order to amplify the entire variable heavy and light region, a second round of PCR is required using the PCR product generated from the first round as a reverse primer with the general CMV forward primer that anneals to the CMV promoter within the single plasmids. Second round PCR products were subcloned into pCR2.1 (Invitrogen) and, after sequence confirmation, the heavy/light (VH and VL) variable regions containing H1, H2, H3, L1, L2 and L3 versions singly, in combination and together were inserted back into the single constructs pOrigHIB and pOrigLIB, exchanging the wild type regions using HindIII/AfeI and BamHI/BsiWI respectively.

FIG. 6: Sequence of the ImmunoBody heavy chain variable region

Nucleotide and amino acid sequence of the heavy variable region where CDR's have been replaced with their corresponding enzyme site H1, H2 and H3, singly in combination and together. The unique restriction enzyme sites are highlighted. CDR1, 2 and 3 were replaced with FspI, MscI and SrfI respectively.

FIG. 7: Sequence of the ImmunoBody kappa chain variable region

Nucleotide and amino acid sequence of the heavy variable region where CDR's have been replaced with their corresponding enzyme site L1, L2 and L3, singly in combination and together. The unique restriction enzyme sites are highlighted. CDR1, 2 and 3 were replaced with EcoRV, SspI and HpaI respectively.

Figure 8:
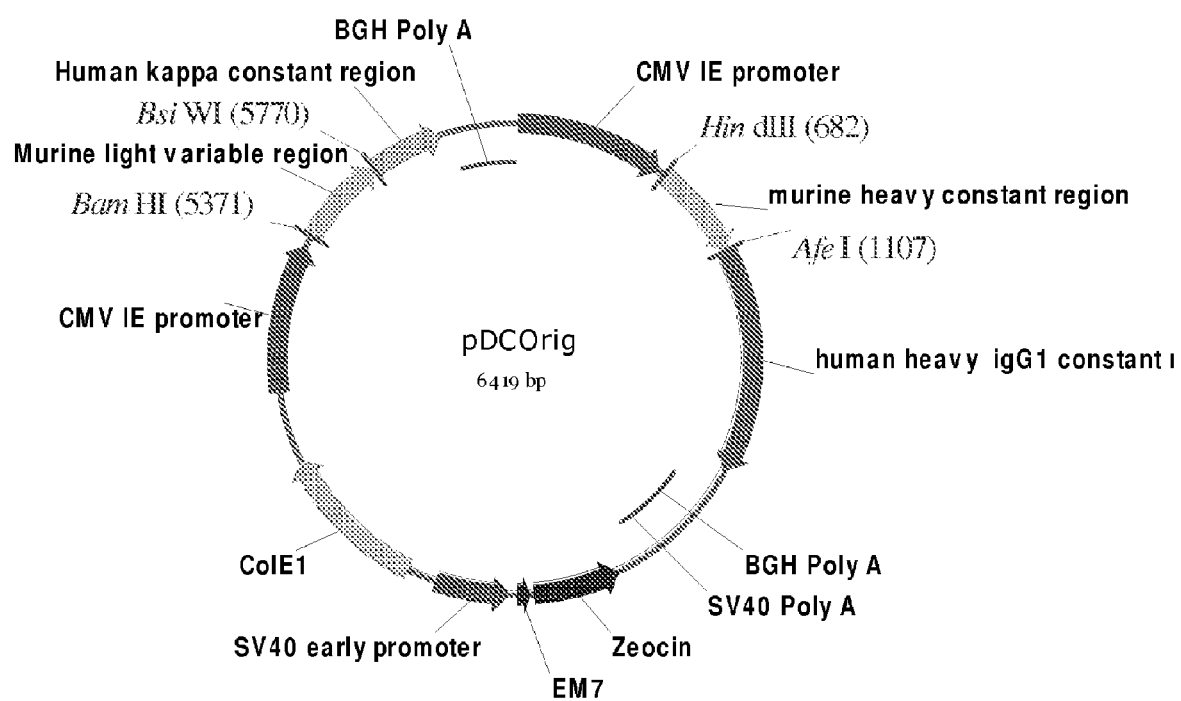

FIG. 8: Map depicting features of the double expression vector pDCOrig

Once all epitopes have been incorporated into the variable heavy and variable light sites within the single vectors, they are transferred into the double expression vector utilising as highlighted HindIII/AfeI and BamHI/BsiWI in frame with their respective human constant regions. The Fc region of the heavy chain comprises of the CH1, CH2, CH3 domains and the hinge region. High-level expression of both the heavy and light chains in mammalian cells is driven from the human cytomegalovirus immediate early promoter. BGH polyadenylation signals downstream of both chains to ensure mRNA stability and effective termination. EM7 is a bacterial promoter that controls expression of the zeocin resistance gene allowing antibiotic selection in *E. coli* while the SV40 early promoter upstream of the resistance gene allows selection in mammalian cells. SV40 polyadenylation signals downstream of the resistance gene in order to direct proper processing of the 3' end of the zeo'' mRNA. The vector also contains within its backbone the ColE1 origin of replication for propagation in bacteria.

FIG. 9: Sequence of the immunobody IB15 heavy chain containing a stop codon preventing synthesis of the FC region Nucleotide and amino acid sequence of the chimeric heavy chain, pDCOrig IB15CH1 stop. A stop codon was inserted by site directed mutagenesis after the CH1 domain of the human igG1 Fc constant region as depicted by a asterisk. Nucleotides and amino acids in bold represent the CH1 domain. Amino acids within boxes represent the GP100210M epitope in H1 (TIMDQVPFSV-SEQ ID NO: 248) and the TRP2 epitope in H2 (SVYDFFVWL-SEQ ID NO: 9). The HindIII/Afe I restriction sites are highlighted utilised in transfer of the variable heavy region from the single construct.

FIG. 10: Nucleotide and amino acid sequence of the DCIB15 heavy variable region without a leader The leader was removed by PCR using the forward primer pOrig heavy no leader with the reverse primer huHeClonR (Table 2) that binds to the human IgG1 CH1 domain effectively re amplifying the heavy variable ($V_H$) region. After sequence confirmation, the $V_H$ region minus leader was cloned back into the double expression construct DCIB15 using HindIII/AfeI inframe with the human IgG1 constant region. Amino acids within boxes represent the GP100210M epitope in H1 (TIMDQVPFSV-SEQ ID NO: 248) and the TRP2 epitope in H2 (SVYDFFVWL-SEQ ID NO: 9). The HindIII/ Afe I restriction sites utilised in transfer of the variable heavy region are highlighted.

FIG. 11: Nucleotide and amino acid sequence of the DCIB15 kappa variable region without a leader The leader was removed by PCR using the forward primer pOrig light no leader with the reverse primer huLiClonR (Table 2) re amplifying the light variable ($V_L$) region. After sequence confirmation, the $V_L$ region minus leader was cloned back into the double expression construct DCIB15 using BamHI/BsiWI in frame with the human kappa constant region. Amino acids within boxes represent the HepB CD4 epitope in L1(TPPAYRPPNAPIL-SEQ ID NO: 14). The BamHI/BsiWII restriction sites are highlighted utilised in transfer of the variable light region.

FIG. 12: Sequence of human IgG2 constant region

Nucleotide and amino acid sequence of the heavy human IgG2 constant region amplified. The AfeI and SapI restriction sites are highlighted utilised in transfer and replacement of the huigG1 constant region in the double expression vector DCIB15.

FIG. 13: Sequence of human IgG3 constant region

Nucleotide and amino acid sequence of the heavy human IgG2 constant region amplified. The AfeI and SapI restriction sites are highlighted utilised in transfer and replacement of the huigG1 constant region in the double expression vector DCIB15.

Figure 14:
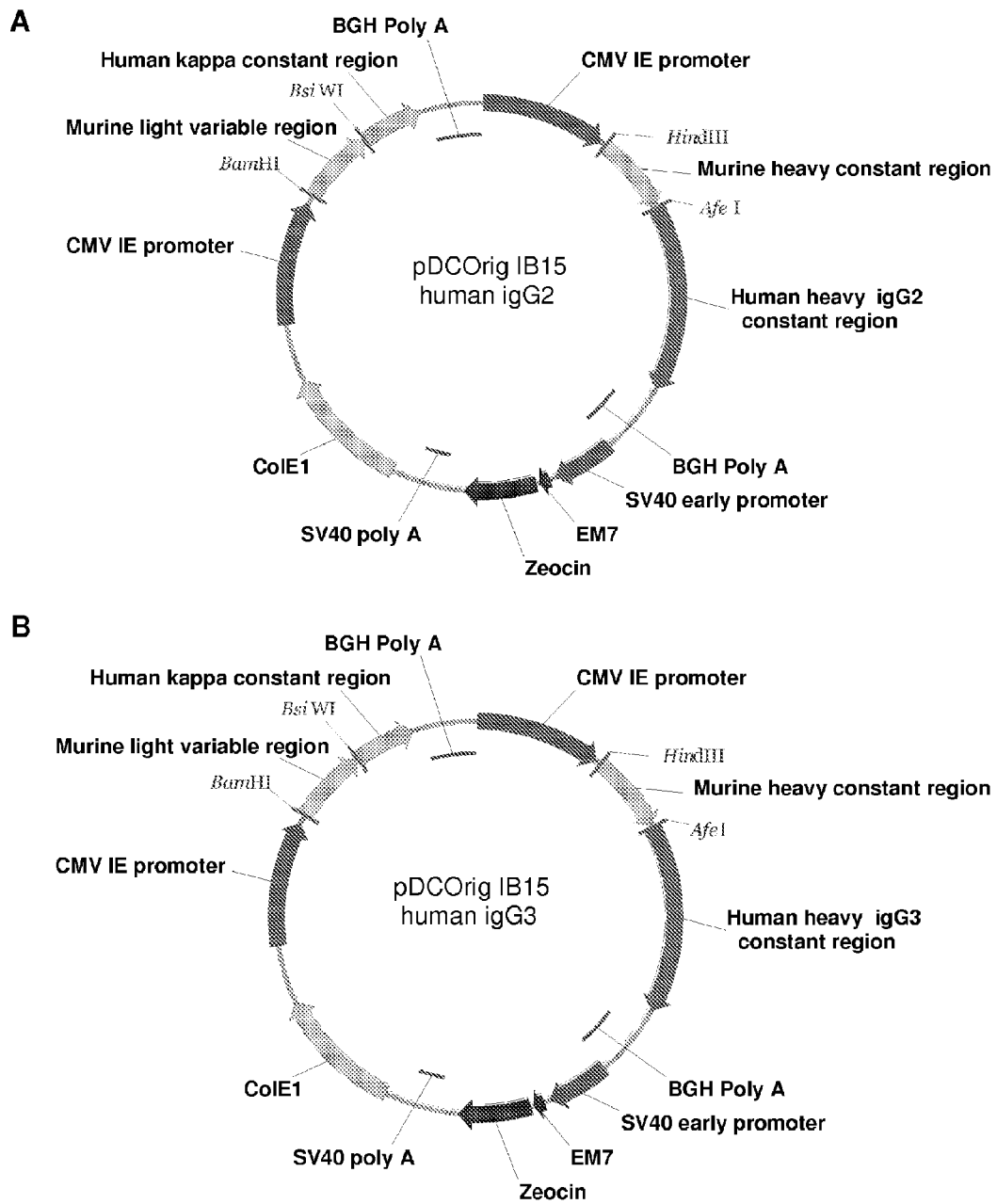

FIG. 14: Human isotypes of the immunobody double expression vector (A) Map of the double expression vector pDCOrigIB15 huigG2.

(B) Map of the double expression vector pDCOrigIB15huigG3. The HindIII/Afe I and BamHI/BsiWI restriction sites utilised in transfer of the variable heavy and light region are highlighted.

FIG. 15: Sequence of DCIB66 heavy chain containing the G2 motif

Nucleotide and amino acid sequence of the chimeric heavy chain. The amino acids E233 L234 L235 within a critical binding motif for interaction with the high affinity FcγR1 (CD64) were substituted with P233 V234 A235 from human igG2 highlighted in bold within a box. Other amino acids within boxes represent the GP100210M epitope in H1 (TIMDQVPFSV-SEQ ID NO: 248) and the TRP2 epitope in H2 (SVYDFFVWL-SEQ ID NO: 9).

The AgeI/AhdI sites highlighted were used in transfer of the section containing the substitutions into pDCOrigIB15 huigG1. The HindIII/Afe I restriction sites utilised in transfer of the variable heavy region are depicted in bold.

FIG. 16: Sequence of DCIB67 heavy chain containing the G1 binding motif

Nucleotide and amino acid sequence of the chimeric heavy chain. The amino acids P233 V234 A235 within the human IgG2 constant region were substituted with the critical binding motif for interaction with the high affinity FcγR1 (CD64) E233 L234 L235 G236 from human IgG1 highlighted in bold within a box. Other amino acids within boxes represent the GP100210M epitope in H1 (TIMDQVPFSV-SEQ ID NO: 248) and the TRP2 epitope in H2 (SVYDFFVWL-SEQ ID NO: 9).

The AgeI/AhdI sites highlighted were used in transfer of the section containing the substitutions into pDCOrigIB15 huigG2. The HindIII/Afe I restriction sites utilised in transfer of the variable heavy region are depicted in bold.

Figure 17:
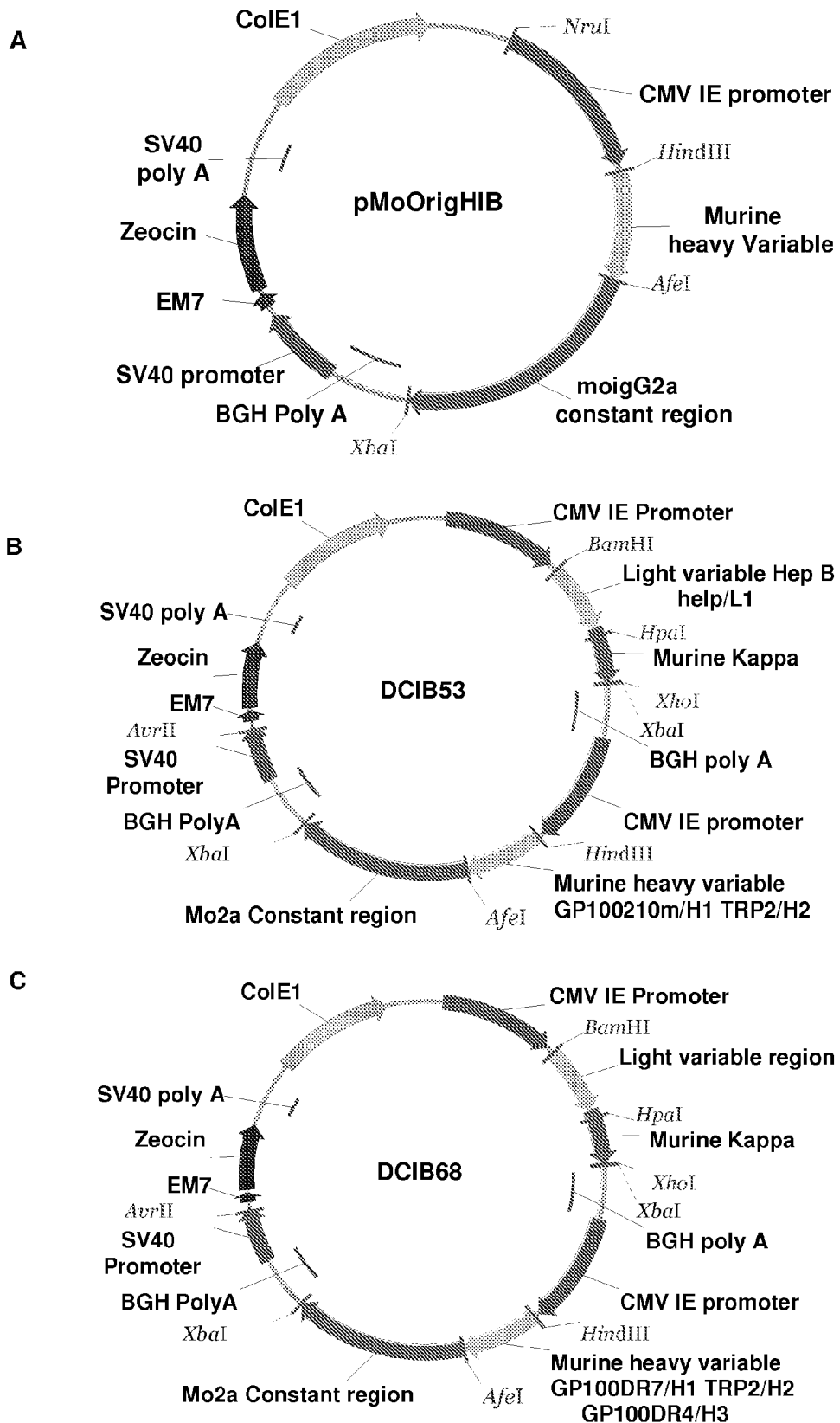

FIG. 17: Murine IgG2a Immunobody expression vectors

Maps of (A) Single chain pMoOrigHIB vector, (B) Double expression vector DCIB53 containing the GP100210M epitope in H1 (TIMDQVPFSV-SEQ ID NO: 248), the TRP2 epitope in H2 (SVYDFFVWL-SEQ ID NO: 9) and the HepB CD4 epitope in L1 (TPPAYRPPNAPIL-SEQ ID NO: 14) and (C). Double expression vector DCIB63containing the HLA-DR7 restricted gp100 CD4 epitope (GTGRAMLGTHT-MEVTVYH-SEQ ID NO: 3) in H1, the TRP2epitope (SVYDFFVWL-SEQ ID NO: 9) in H2 and the HLA-DR4 restricted gp100 CD4 epitope in H3 (WNRQLYPEWTEAQRLD-SEQ ID NO: 15). Restriction sites utilised are depicted.

Figure 18:
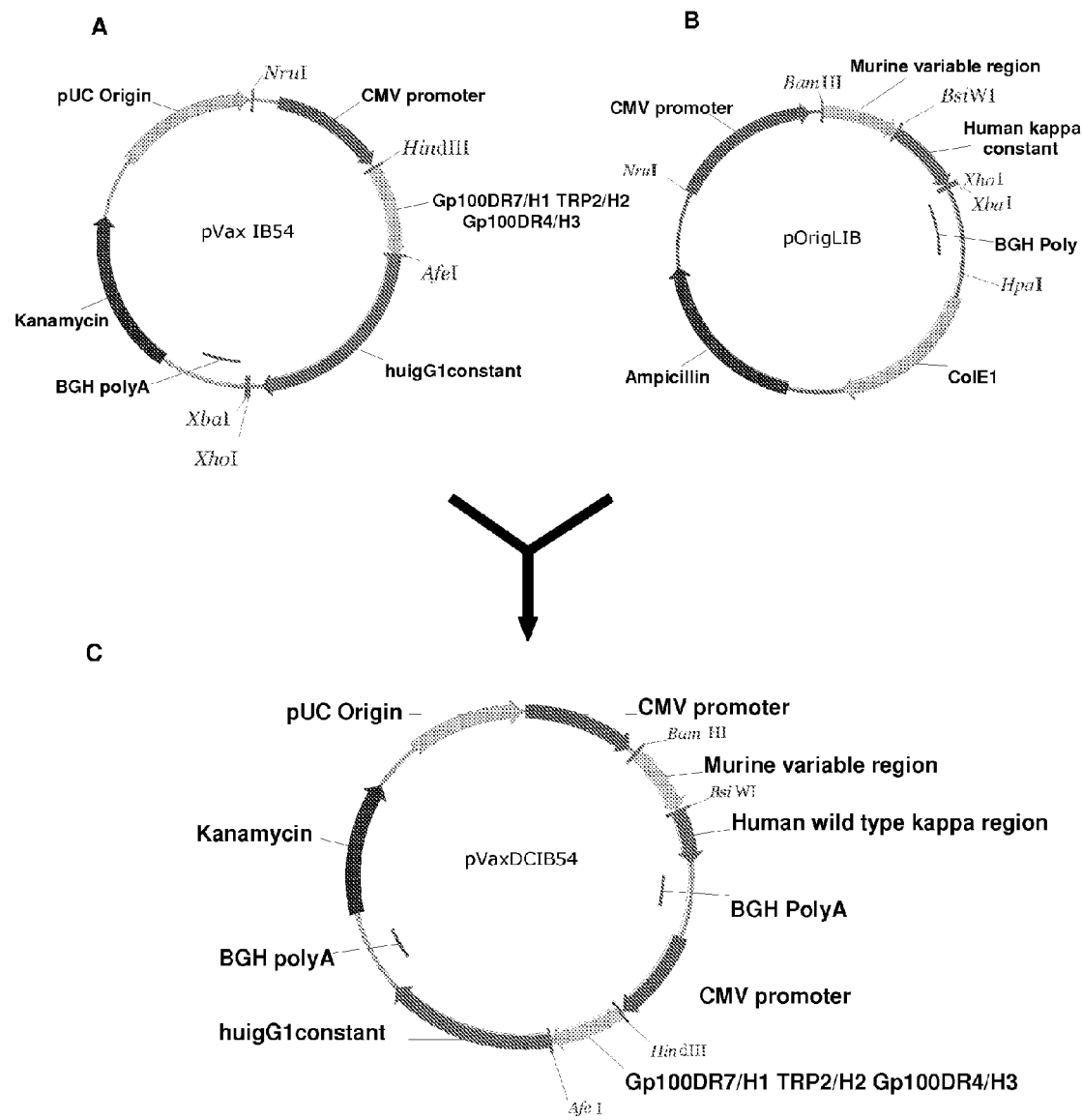

FIG. 18: Schematic diagram to depict construction of the regulatory compliant plasmid pVAXDCIB54

The heavy single chain vector pVaxIB54 HIB (A) was linearised using NruI. The light chain expression cassette from pOrigLIB (B) was excised using NruI and HpaI and cloned into the linearised plasmid to generate the double expression vector pVaxDCIB54 (C). The HindIII/Afe I and BamHI/BsiWI restriction sites utilised in transfer of the variable heavy and light region are highlighted.

FIG. 19: Sequence of DCIB15

Nucleotide and amino acid sequence of the heavy and light variable regions cloned in frame with the human IgG1 Fc and kappa constant regions within the expression vector pDC-Orig. Amino acids within boxes represent the GP100210M epitope in H1 (TIMDQVPFSV-SEQ ID NO: 248), the TRP2 epitope in H2 (SVYDFFVWL-SEQ ID NO: 9) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

FIG. 20: ImmunoBody constructs produce low levels of intact protein.

(A) quantification of the level of ImmunoBody heavy chain by sandwich Elisa from the supernatant of CHO—S cells transfected with ImmunoBody containing gp100/H1, TRP2/H2 and HepB CD4/L1 (DCIB15). Supernatant was used neat and diluted 1 in 3, 1 in 10 and 1 in 30 in media and compared to a human IgG positive control.

(B) Analysis of purified ImmunoBody containing gp100/H1, TRP2/H2 and HepB help/L1 (DCIB15) by sandwich Elisa compare to a positive control.

(C) and (D) Determination of expression of heavy chain and intact ImmunoBody from supernatant of CHO—S transfectants by sandwich Elisa. Plates were coated with an anti-human Fc specific antibody. To detect heavy chain an anti-human IgG Fc specific HRP antibody was used and to detect intact ImmunoBody an anti-human kappa chain specific HRP antibody was used.

(E) Determination of heavy chain, light chain and intact ImmunoBody from supernatant of CHO—S transfectants (DCIB15, DCIB31, DCIB32, DCIB36, DCIB48, DCIB49, DCIB52, DCIB54) by sandwich Elisa. Plates were coated with an anti-human Fc specific antibody or anti-human kappa chain antibody. To detect heavy chain an anti-human IgG Fc specific HRP antibody was used in combination with the anti-human Fc specific coating antibody. To detect intact ImmunoBody an anti-human kappa chain specific HRP antibody was used in combination with anti-human Fc specific coating antibody. To detect light chain anti-human kappa chain specific HRP antibody was used in combination with the anti-human kappa chain specific antibody.

FIG. 21: Sequence of DCIB24

Nucleotide and amino acid sequence of the heavy and light variable regions cloned in frame with the human IgG1 Fc and kappa constant regions within the expression vector pDC-Orig. Amino acids within boxes represent the ovalbumin epitope in H2 (SIINFEKL-SEQ ID NO: 8) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

FIG. 22 Sequence of DCIB25

Nucleotide and amino acid sequence of the heavy and light variable regions cloned in frame with the human IgG1 Fc and kappa constant regions within the expression vector pDC-Orig. Amino acids within boxes represent the GP100210M epitope in H1 (TIMDQVPFSV-SEQ ID NO: 248), the TRP2 epitope in H2 (SVYDFFVWL-SEQ ID NO: 9) and the HepB CD4 epitope in L3 (TPPAYRPPNAPIL-SEQ ID NO: 14). The HindIII/Afe I and BamHI/BsiWI restriction sites utilised in transfer of the variable heavy and light region from the single construct are highlighted.

FIG. 23: Sequence of DCIB31

Nucleotide and amino acid sequence of the heavy and light variable regions cloned inframe with the human IgG1 Fc and kappa constant regions within the expression vector pDC-Orig. Amino acids within boxes represent the TRP2 epitope (SVYDFFVWL-SEQ ID NO: 9) in H3. The HindIII/Afe I and BamHI/BsiWI restriction sites utilised in transfer of the variable heavy and light region from the single construct are highlighted.

FIG. 24: Sequence of DCIB32

Nucleotide and amino acid sequence of the heavy and light variable regions cloned inframe with the human IgG1 Fc and kappa constant regions within the expression vector pDC-Orig. Amino acids within boxes represent the TRP2 epitope (SVYDFFVWL-SEQ ID NO: 9) in H3 and the HepB CD4 epitope in L3 (TPPAYRPPNAPIL-SEQ ID NO: 14). The HindIII/Afe I and BamHI/BsiWI restriction sites utilised in transfer of the variable heavy and light region from the single construct are highlighted.

FIG. 25: Sequence of DCIB36

Nucleotide and amino acid sequence of the heavy and light variable regions cloned inframe with the human IgG1 Fc and kappa constant regions within the expression vector pDC-Orig. Amino acids within boxes represent the TRP2 epitope (SVYDFFVWL-SEQ ID NO: 9) in L3. The HindIII/Afe I and BamHI/BsiWI restriction sites utilised in transfer of the variable heavy and light region from the single construct are highlighted.

FIG. 26: Sequence of DCIB48

Nucleotide and amino acid sequence of the heavy and light variable regions cloned inframe with the human IgG1 Fc and kappa constant regions within the expression vector pDC-Orig. Amino acids within boxes represent the TRP2 epitope (SVYDFFVWL-SEQ ID NO: 9) in H2 and the HLA-DR4 restricted gp100 CD4 epitope in H3(WNRQLYPEW-TEAQRLD-SEQ ID NO: 15). The HindIII/Afe I and BamHI/BsiWI restriction sites utilised in transfer of the variable heavy and light region from the single construct are highlighted.

FIG. 27: Sequence of DCIB49

Nucleotide and amino acid sequence of the heavy and light variable regions cloned inframe with the human IgG1 Fc and kappa constant regions within the expression vector pDC-Orig. Amino acids within boxes represent the HepB CD4 epitope (TPPAYRPPNAPIL-SEQ ID NO: 14) in H3. The HindIII/Afe I and BamHI/BsiWI restriction sites utilised in transfer of the variable heavy and light region from the single construct are highlighted.

FIG. 28: Sequence of DCIB52

Nucleotide and amino acid sequence of the heavy and light variable regions cloned inframe with the human IgG1 Fc and kappa constant regions within the expression vector pDC-Orig. Amino acids within boxes represent the TRP2 epitope (SVYDFFVWL-SEQ ID NO: 9) in H2 and the HepB CD4 epitope (TPPAYRPPNAPIL-SEQ ID NO: 14) in H3. The HindIII/Afe I and BamHI/BsiWI restriction sites utilised in transfer of the variable heavy and light region from the single construct are highlighted.

FIG. 29: Sequence of DCIB54

Nucleotide and amino acid sequence of the heavy and light variable regions cloned inframe with the human IgG1 Fc and kappa constant regions within the expression vector pDC-Orig. Amino acids within boxes represent the HLA-DR7 restricted gp100 CD4 epitope (GTGRAMLGTHT-MEVTVYH-SEQ ID NO: 3) in H1, the TRP2 epitope (SVYDFFVWL-SEQ ID NO: 9) in H2 and the HLA-DR4 restricted gp100 CD4 epitope in H3 (WNRQLYPEWTEAQRLD-SEQ ID NO: 15). The HindIII/Afe I and BamHI/BsiWI restriction sites utilised in transfer of the variable heavy and light region from the single construct are highlighted.

FIG. 30: Sequence of DCIB18

Nucleotide and amino acid sequence of the heavy and light variable regions cloned inframe with the human IgG1 Fc and kappa constant regions within the expression vector pDC-Orig. Amino acids within boxes represent the TRP2 epitope in H2 (SVYDFFVWL-SEQ ID NO: 9) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

Figure 31:
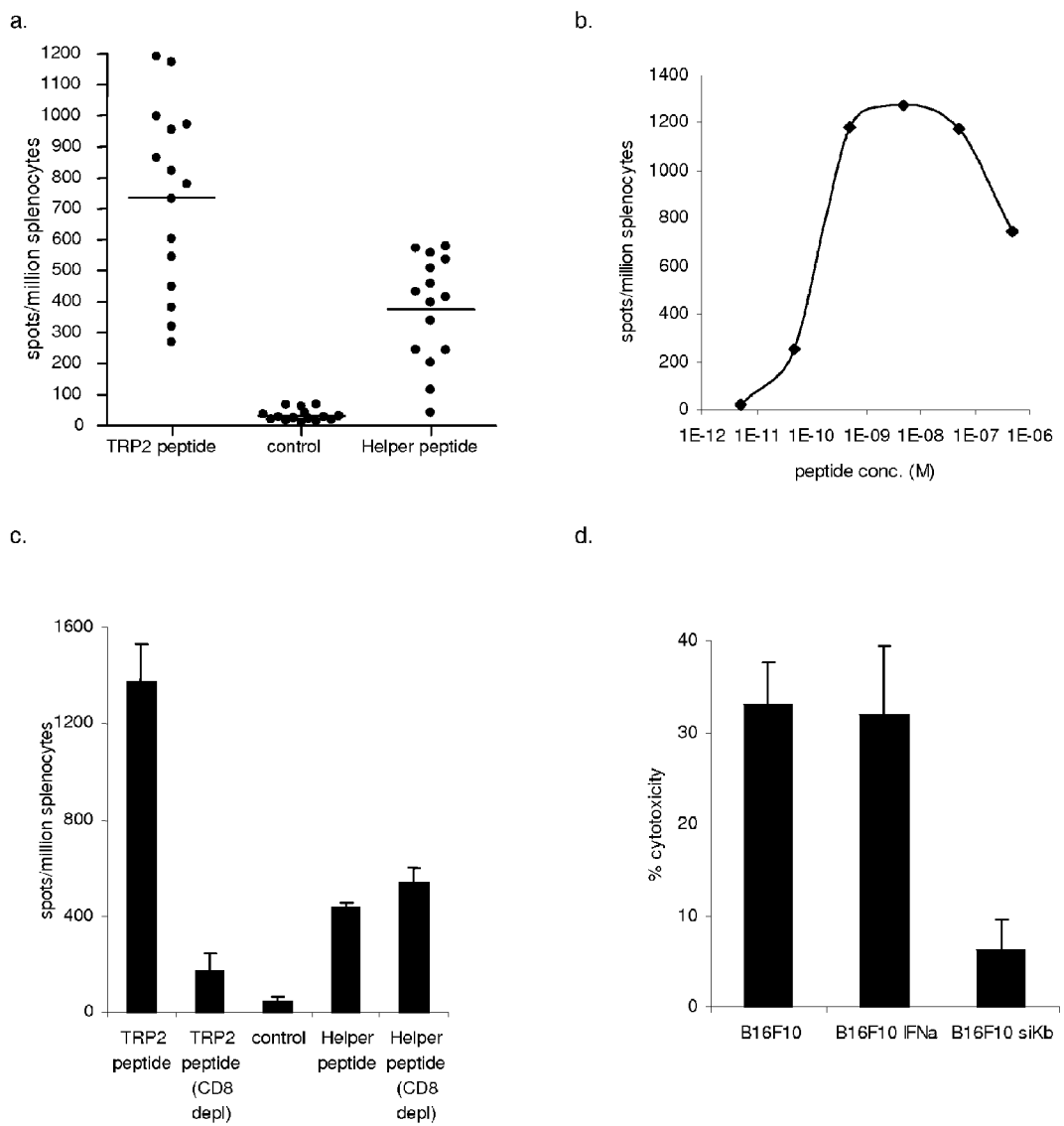

FIG. 31: CTL epitopes incorporated into ImmunoBody framework are processed and presented to elicit an immune response in vivo.

(A) C57B1/6 mice were immunised on days 0, 7, and 14 with an ImmunoBody construct containing the TRP2 epitope in CDR H2 and HepB CD4 epitope in CDR L1 (DCIB18). On day 19 splenocytes were analysed by IFNγ elispot assay against TRP2 peptide, HepB helper peptide and a media control. Responses are measured as spots/million splenocytes.

(B) Splenocytes from immunised mice were assayed for avidity to the TRP2 epitope by measuring responses to increasing peptide concentration in IFNγ elispot assay. Responses are measured as spots/million splenocytes and avidity is assigned as the concentration which gives 50% maximal effector function.

(C) splenocytes from immunised mice were depleted of CD8 T cells and analysed against TRP2 peptide, HepB helper peptide and a media control for the presence epitope specific responses in IFNγ elispot assay. Responses are measured as spots/million splenocytes.

(D) cytotoxicity of splenocytes from immunised mice in a 4 hour $^{51}$Cr-release assay against the B16F10, B16F10 IFNα and B16F10 siKb melanoma cell lines after 6 days in vitro TRP2 peptide stimulation.

(E) C57B1/6 or HLA-DR4 transgenic mice were immunised on days 0, 7, and 14 with ImmunoBody DNA (DCIB15, DCIB31, DCIB32, DCIB36, DCIB48, DCIB52 and DCIB54). On day 19 splenocytes were analysed by IFNγ elispot assay against TRP2 peptide and a media control. Responses are measured as spots/million splenocytes.

(F) Splenocytes from immunised mice were assayed for avidity to the TRP2 epitope by measuring responses to increasing peptide concentration in IFNγ elispot assay. Responses are measured as spots/million splenocytes and avidity is assigned as the concentration which gives 50% maximal effector function.

(G) C57B1/6 or HLA-DR4 transgenic mice were immunised on days 0, 7, and 14 with ImmunoBody DNA (DCIB15, DCIB48, DCIB49, DCIB52 and DCIB54). On day 19 splenocytes were analysed by IFNγ elispot assay against HepB helper peptide (DCIB15, DCIB49 and DCIB52) or gp100DR4 helper peptide (DCIB48 and DCIB54) and a media control. Responses are measured as spots/million splenocytes.

FIG. 32: ImmunoBody DNA immunisation is better than peptide immunisation or immunisation with whole antigen.

(A) ImmunoBody DNA immunisation (DCIB18) was compared to s.c. immunisation with peptide epitope in Incomplete Freund adjuvant or immunisation with a DNA expressing the TRP2 antigen. C57B1/6 mice were immunised on days 0, 7, and 14 and on day 19 splenocytes were analysed by IFNγ elispot assay against TRP2 peptide (■), HepB helper peptide (▨) and a media control (□). Responses are measured as spots/million splenocytes.

(B) Splenocytes from ImmunoBody DNA (◇) and peptide (♦) immunised mice were assayed for avidity to the TRP2 epitope by measuring responses to increasing peptide concentration in IFNγ elispot assay. Responses are measured as spots/million splenocytes and avidity is assigned as the concentration which gives 50% maximal effector function.

(C) cytotoxicity of splenocytes from immunised mice in a 4 hour $^{51}$Cr-release assay against the B16F10 (■), B16F10 IFNα(▨) and B16F10 siKb (□) melanoma cell lines after 6 days in vitro TRP2 peptide stimulation.

(D) ImmunoBody DNA immunisation (DCIB18) was compared to immunisation with TRP2 peptide pulsed DCs. C57B1/6 mice were immunised on days 0, 7, and 14 and on day 19 splenocytes were analysed by IFNγ elispot assay against titrating quantities of TRP2 peptide. Responses are measured as spots/million splenocytes and avidity is assigned as the concentration which gives 50% maximal effector function.

(E) ImmunoBody DNA immunisation (DCIB18) was compared to immunisation with TRP2 peptide pulsed DCs. C57B1/6 mice were immunised on days 0, 7, and 14 and on day 19 splenocytes were stimulated in vitro with TRP2 peptide pulsed LPS blasts. Six days post stimulation CTL lines were assessed by chromium release assay for ability to lyse B16F10 or B16F10 siKb melanoma lines. Responses are measured as cytotoxicity.

(F) ImmunoBody DNA immunisation (DCIB24) was compared to immunisation with SIINFEKL (SEQ ID NO: 8) peptide. C57B1/6 mice were immunised on days 0, 7, and 14 and on day 19 splenocytes were analysed by IFNγ elispot assay against SIINFEKL (SEQ ID NO: 8) peptide and a control peptide. Responses are measured as spots/million splenocytes.

(G) ImmunoBody DNA immunisation (DCIB15) was compared to immunisation with gp100 210M peptide. HHDII mice were immunised on days 0, 7, and 14 and on day 19 splenocytes were analysed by IFNγ elispot assay against titrating quantities of gp100 210M peptide and a control. Responses are measured as spots/million splenocytes.

(H) ImmunoBody DNA immunisation (DCIB24) was compared to immunisation with SIINFEKL (SEQ ID NO: 8) peptide. C57B1/6 mice were immunised on days 0, 7, and 14 and on day 19 splenocytes were analysed by IFNγ elispot assay against titrating quantities of SIINFEKL (SEQ ID NO: 8) peptide. Responses are measured as spots/million splenocytes and avidity is assigned as the concentration which gives 50% maximal effector function.

(I) ImmunoBody DNA immunisation (DCIB15) was compared to immunisation with gp100 210M peptide. HHDII mice were immunised on days 0, 7, and 14 and on day 19 splenocytes were analysed by IFNγ elispot assay against titrating quantities of gp100 210M peptide. Responses are measured as spots/million splenocytes and avidity is assigned as the concentration which gives 50% maximal effector function.

FIG. 33: Sequence of DCIB21

Nucleotide and amino acid sequence of the heavy and light variable regions cloned in frame with the human IgG1 Fc and kappa constant regions within the expression vector pDC-Orig. Amino acids within boxes represent the HepB S Ag epitope in H2 (IPQSLDSWWTSL-SEQ ID NO: 6) and the I-Ad restricted Flu HA CD4 epitope in L1 (FERFEIFPKE-SEQ ID NO: 1). The HindIII/Afe I and BamHI/BsiWI restriction sites utilised in transfer of the variable heavy and light region from the single construct are highlighted.

FIG. 34: Multiple epitopes can be processed from CDR H2 site.

(A) C57B1/6 mice were immunised on days 0, 7 and 14 with ImmunoBody construct containing SIINFEKL (SEQ ID NO: 8) epitope in CDR H2 and HepB CD4epitope in CDR L1 (DCIB24). On day 19, splenocytes were analysed in IFNγ elispot assay against SIINFEKL (SEQ ID NO: 8) peptide, an irrelevant peptide, HepB CD4 peptide and media control. Responses are measured as spots/million splenocytes.

(B) Balb/c mice were immunised on days 0, 7 and 14 with ImmunoBody construct containing HepB CD8 epitope in CDR H2 and Flu HA CD4 epitope in CDR L1 (DCIB21). On day, 19 splenocytes were analysed in IFNγ elispot assay against HepB CD8 peptide, an irrelevant peptide, Flu HA CD4 peptide and media control. Responses are measured as spots/million splenocytes.

FIG. 35: Sequence of DCIB17

Nucleotide and amino acid sequence of the heavy and light variable regions cloned in frame with the human IgG1 Fc and kappa constant regions within the expression vector pDC-Orig. Amino acids within boxes represent the GP100210M epitope in H1 (TIMDQVPFSV-SEQ ID NO: 248) and the HepB CD4 epitope in L1 (TPPAYRPPNAPIL-SEQ ID NO:

14). The HindIII/Afe I and BamHI/BsiWI restriction sites utilised in transfer of the variable heavy and light region from the single construct are highlighted.

FIG. 36: Sequence of DCIB26

Nucleotide and amino acid sequence of the heavy and light variable regions cloned in frame with the human IgG1 Fc and kappa constant regions within the expression vector pDC-Orig. Amino acids within boxes represent the Tie-2 Z84 epitope in H1 (FLPATLTMV-SEQ ID NO: 2) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

Figure 37:
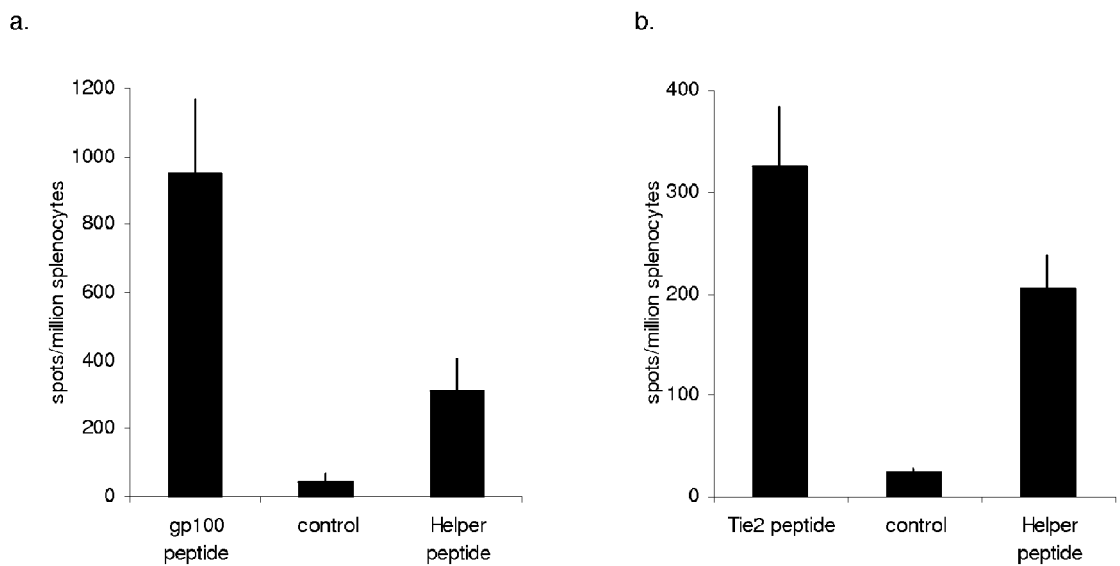

FIG. 37: Multiple CTL epitopes can be processed from the variable region.

(A) HHDII mice were immunised on days 0, 7 and 14 with ImmunoBody construct containing gp100 IMDQVPFSV (SEQ ID NO: 5) epitope in CDR H1 with removal of part of the framework and HepB CD4 epitope in CDR L1 (DCIB17). On day 19, splenocytes were analysed in IFNγ elispot assay against gp100 IMDQVPFSV (SEQ ID NO: 5) peptide, HepB CD4 peptide and media control. Responses are measured as spots/million splenocytes.

(B) HHDII mice were immunised on days 0, 7 and 14 with ImmunoBody construct containing Tie2 epitope in CDR H1 with removal of part of the framework and HepB CD4 epitope in CDR L1 (DCIB26). On day 19, splenocytes were analysed in IFNγ elispot assay against Tie2 peptide, HepB CD4 peptide and media control. Responses are measured as spots/million splenocytes.

Figure 38:
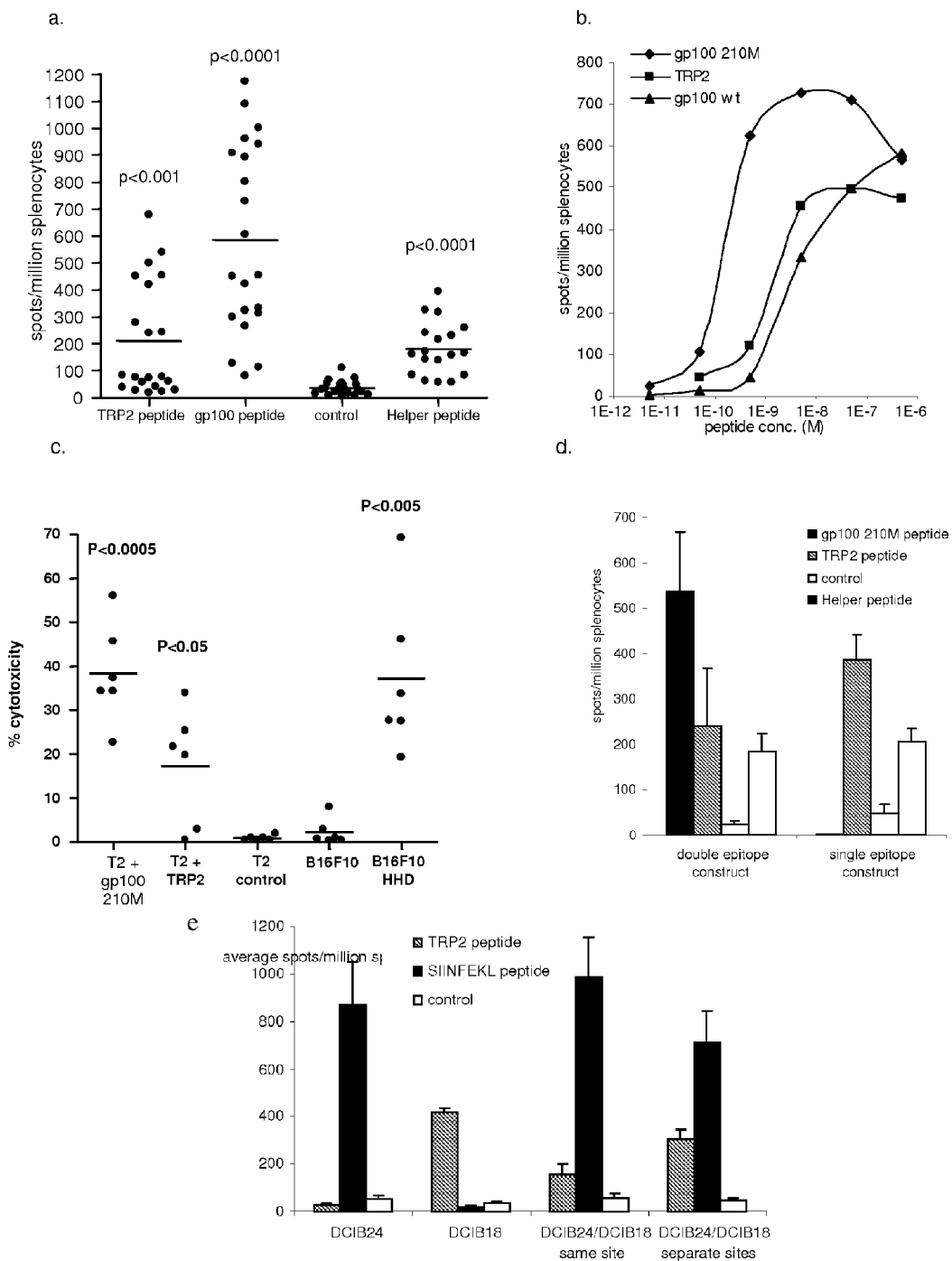

FIG. 38: Multiple CTL responses can be generated from different epitopes within the same ImmunoBody construct.

HLA-A2 restricted gp100 epitope IMDQVPFSV (SEQ ID NO: 5) was engineered into the CDR H1 site alongside the TRP2 epitope SVYDFFVWL (SEQ ID NO: 9) in CDR H2 and the HepB CD4 epitope was present in the CDR L1 site (DCIB15).

(A) HHDII mice were immunised on days 0, 7, and 14 with ImmunoBody DNA. On day 19 splenocytes were analysed by IFNγ elispot assay against gp100 peptide, TRP2 peptide, HepB helper peptide and a media control. Responses are measured as spots/million splenocytes.

(B) Splenocytes from immunised mice were assayed for avidity to the gp100 modified IMDQVPFSV (SEQ ID NO: 5) (♦) epitope, gp100 wt ITDQVPFSV (SEQ ID NO: 7) epitope (▲) and TRP2 epitope (■) by measuring responses to increasing peptide concentration in IFNγ elispot assay. Responses are measured as spots/million splenocytes and avidity is assigned as the concentration which gives 50% maximal effector function.

(C) cytotoxicity of splenocytes from immunised mice in a 4 hour $^{51}$Cr-release assay against T2 cells pulsed with gp100 IMDQVPFSV (SEQ ID NO: 5) peptide, TRP2 peptide or control and the B16F10 and B16F10 HHD melanoma cell lines.

(D) HHDII mice were immunised on days 0, 7, and 14 with ImmunoBody DNA containing either i) gp100 epitope in CDR H1, TRP2 epitope in CDR H2 and HepB CD4 epitope in CDR L1 (DCIB15) or ii) TRP2 epitope in CDR H2 and HepB CD4 epitope in CDR L1 (DCIB18). On day 19, splenocytes were analysed by IFNγ elispot assay against gp100 peptide (■), TRP2 peptide (▨), HepB helper peptide (▦) and a media control (□). Responses are measured as spots/million splenocytes.

(E) C57Bl/6 mice were immunised i.m. with 10 μg DNA solution combined with electroporation. Immunisations were performed three times at weekly intervals in the tibialis muscle. Mice were immunised with DCIB24 or DCIB18 alone, both combined in the same site or with both at the same time but in separate sites. On day 19 splenocytes were analysed for the presence of TRP2, SIINFEKL (SEQ ID NO: 8) peptide specific immune responses. Responses are measured as spots/million splenocytes.

FIG. 39: Sequence of DCIB37

Nucleotide and amino acid sequence of the heavy and light variable regions cloned in frame with the human IgG1 Fc and kappa constant regions within the expression vector pDC-Orig. Amino acids within boxes represent the GP100 F7L epitope in H1 (TITDQVPLSV-SEQ ID NO: 12) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

FIG. 40: Sequence of DCIB40

Nucleotide and amino acid sequence of the heavy and light variable regions cloned in frame with the human IgG1 Fc and kappa constant regions within the expression vector pDC-Orig. Amino acids within boxes represent the GP100 F7I epitope in H1 (TITDQVPISV-SEQ ID NO: 11) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

FIG. 41: Sequence of DCIB41

Nucleotide and amino acid sequence of the heavy and light variable regions cloned in frame with the human IgG1 Fc and kappa constant regions within the expression vector pDC-Orig. Amino acids within boxes represent the GP100 wild type epitope in H1 (TITDQVPFSV-SEQ ID NO: 15) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

FIG. 42: Sequence of DCIB42

Nucleotide and amino acid sequence of the heavy and light variable regions cloned in frame with the human IgG1 Fc and kappa constant regions within the expression vector pDC-Orig. Amino acids within boxes represent the GP100 F7Y epitope in H1 (TITDQVPYSV-SEQ ID NO: 13) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

FIG. 43: Sequence of DCI43

Nucleotide and amino acid sequence of the heavy and light variable regions cloned in frame with the human IgG1 Fc and kappa constant regions within the expression vector pDC-Orig. Amino acids within boxes represent the GP100 V5L epitope in H1 (TITDQLPFSV-SEQ ID NO: 10) and the HepB CD4 epitope in L1 (TPPAYRPPNAPIL-SEQ ID NO: 14). The HindIII/Afe I and BamHI/BsiWI restriction sites utilised in transfer of the variable heavy and light region from the single construct are highlighted.

Figure 44:
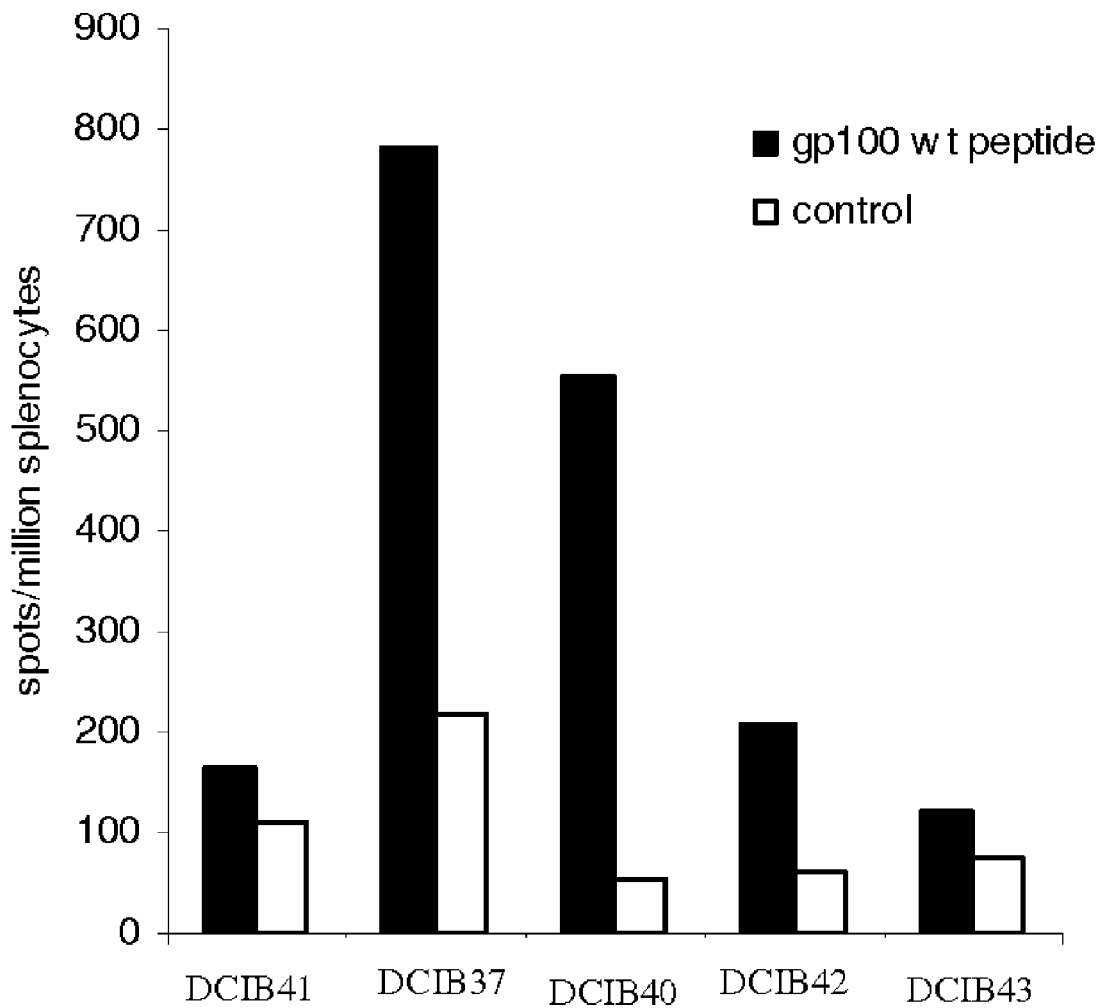

FIG. 44: Modification at non-anchor residues can enhance epitope immunogenicity.

HHDII mice were immunised at days 0, 7 and 14 with ImmunoBody constructs containing modified gp100 epitopes in the CDR H1 region (DCIB37, DCIB40, DCIB41, DCIB42 and DCIB43). On day 19, splenocytes were analysed by IFNγ elispot assay against gp100 wild type epitope peptide and a media control. Responses are measured as spots/million splenocytes.

FIG. 45: Sequence of DCIB35

Nucleotide and amino acid sequence of the heavy and light variable regions cloned in frame with the human IgG1 Fc and kappa constant regions within the expression vector pDC-Orig. Amino acids within boxes represent the GP100210M epitope in H1 (TIMDQVPFSV-SEQ ID NO: 248), the TRP2 epitope in H2(SVYDFFVWL-SEQ ID NO: 9) and the HLA-DR4 restricted gp100 CD4 epitope in L1 (WNRQLYPEW-TEAQRLD-SEQ ID NO: 15). The HindIII/Afe I and BamHI/BsiWI restriction sites utilised in transfer of the variable heavy and light region from the single construct are highlighted.

Figure 46:
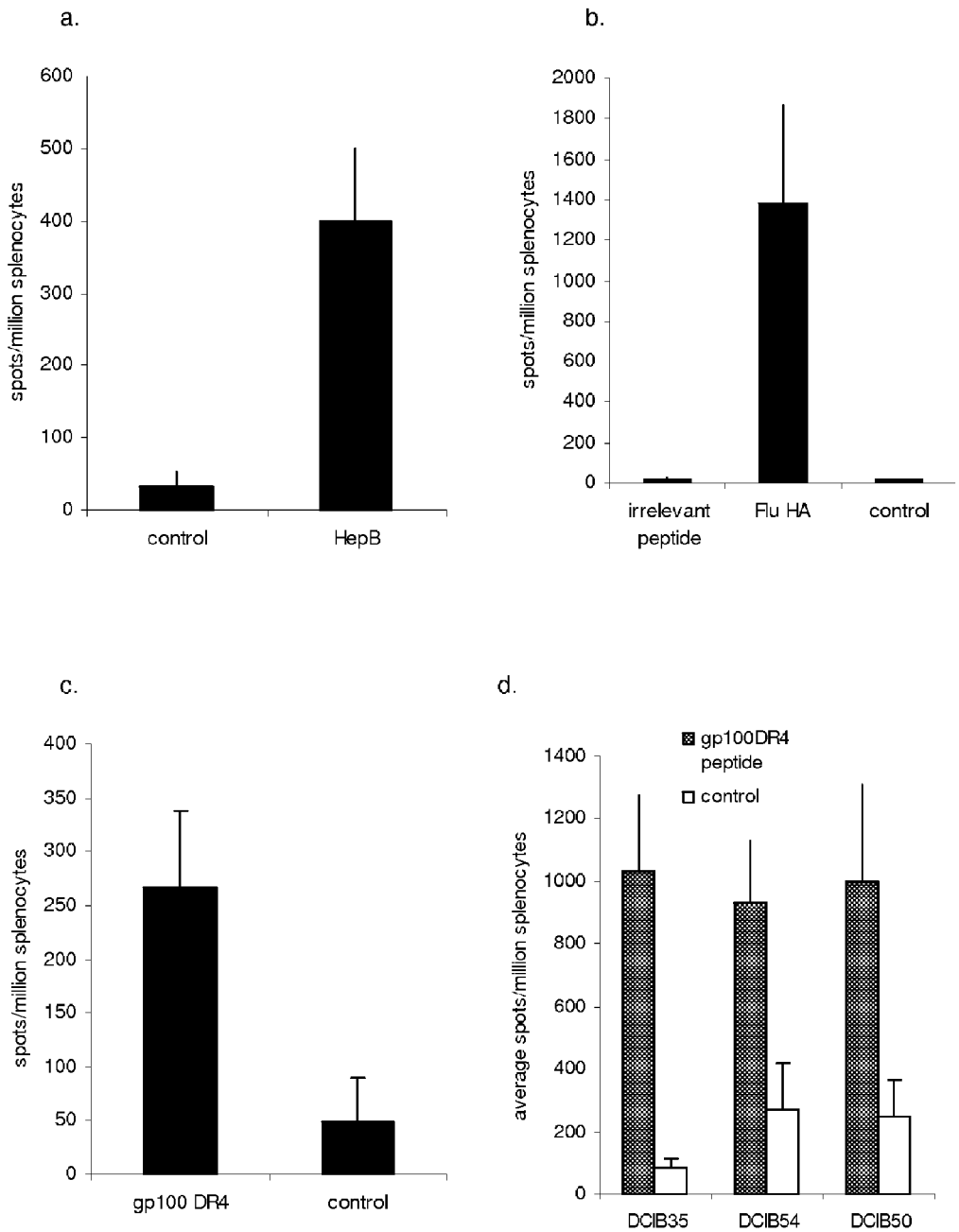

FIG. 46: Multiple CD4 helper responses can be processed and presented to elicit an immune response in vivo.

(A) HHDII or C57B1/6 mice were immunised at days 0, 7 and 14 with ImmunoBody constructs containing the I-Ab restricted HepB CD4 epitope in the CDR L1 region (DCIB15).

(B) Balb/c mice were immunised at days 0, 7 and 14 with ImmunoBody constructs containing the I-Ad restricted Flu HA CD4 epitope in the CDR L1 region (DCIB21).

(C) HLA-DR4 transgenic mice were immunised at days 0, 7 and 14 with ImmunoBody constructs containing the HLA-DR4 restricted gp100 CD4 epitope in the CDR L1 (DCIB35). On day 19, splenocytes were analysed by IFNγ elispot assay against corresponding peptide, an irrelevant peptide and a media control. Responses are measured as spots/million splenocytes.

(D) HLA-DR4 transgenic mice were immunised at days 0, 7 and 14 with ImmunoBody constructs containing the HLA-DR4 restricted gp100 CD4 epitope in the CDR L1 (DCIB35), in the CDR H3 (DCIB54) and in the CDR L3 (DCIB50). On day 19, splenocytes were analysed by IFNγ elispot assay against corresponding peptide, an irrelevant peptide and a media control. Responses are measured as spots/million splenocytes.

FIG. 47: Sequence of DCIB50

Nucleotide and amino acid sequence of the heavy and light variable regions cloned inframe with the human IgG1 Fc and kappa constant regions within the expression vector pDC-Orig. Amino acids within boxes represent the GP100210M epitope (TIMDQVPFSV-SEQ ID NO: 248) in H1, the TRP2 epitope (SVYDFFVWL-SEQ ID NO: 9) in H2 and the HLA-DR4 restricted gp100 CD4 epitope (WNRQLYPEW-TEAQRLD-SEQ ID NO: 15) in L3. The HindIII/Afe I and BamHI/BsiWI restriction sites utilised in transfer of the variable heavy and light region from the single construct are highlighted.

Figure 48:
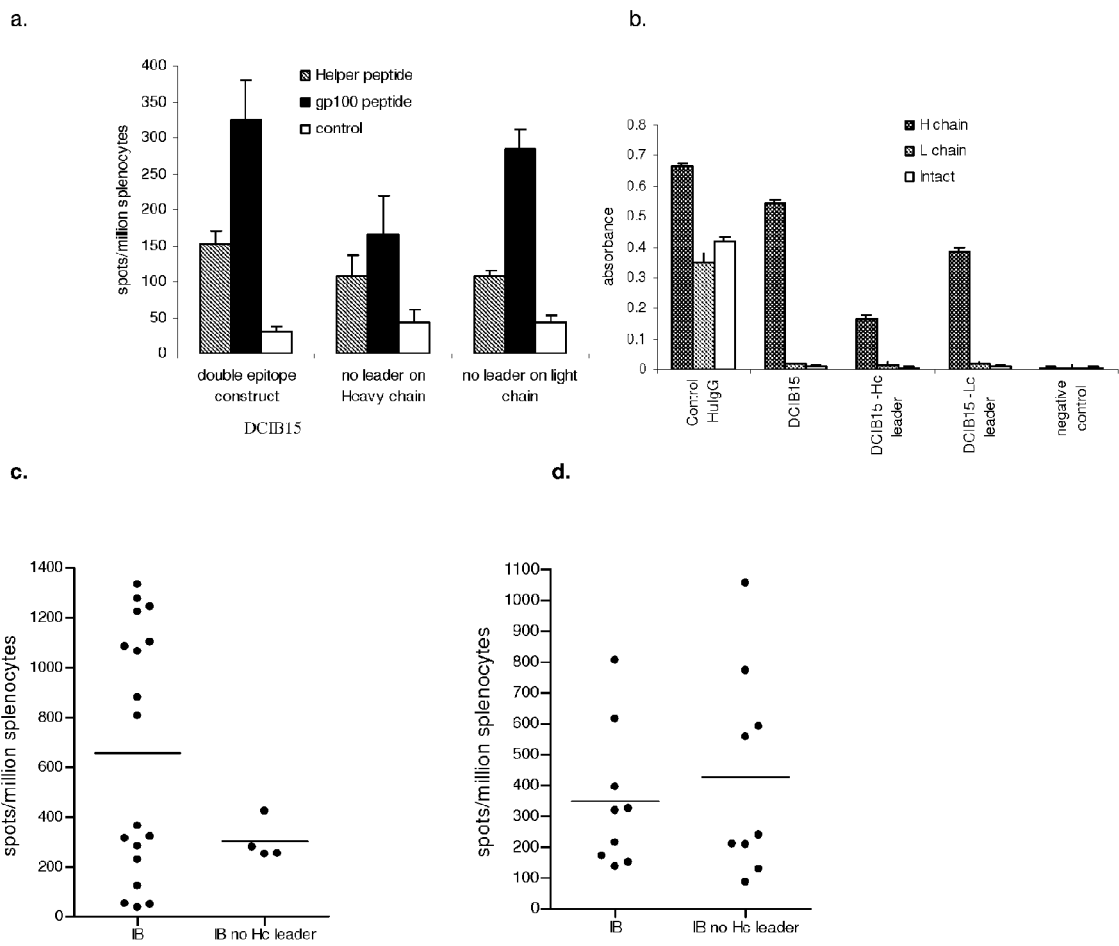

FIG. 48: CD8 T cell responses are partially dependent upon secreted heavy chain but helper responses do not require secreted light chain.

(A) HHDII mice were immunised at day 0, 7 and 14 with ImmunoBody DNA constructs containing i) gp100 epitope in CDR H1, TRP2 epitope in CDR H2 and HepB CD4 epitope in CDR L1 (DCIB15), ii) gp100 epitope in CDR H1, TRP2 epitope in CDR H2 and HepB CD4 epitope in CDR L1 without the leader sequence on the heavy chain, iii) gp100 epitope in CDR H1, TRP2 epitope in CDR H2 and HepB CD4 epitope in CDR L1 without the leader sequence on the light chain. On day 19, splenocytes were analysed by IFNγ elispot assay against gp100 (■) and HepB CD4 (▨) peptides and a media control (□). Responses are measured as spots/million splenocytes.

(B) Determination of heavy chain, light chain and intact ImmunoBody from supernatant of CHO—S transfectants by sandwich Elisa. Plates were coated with an anti-human Fc specific antibody or anti-human kappa chain antibody. To detect heavy chain an anti-human IgG Fc specific HRP antibody was used in combination with the anti-human Fc specific coating antibody. To detect intact ImmunoBody an anti-human kappa chain specific HRP antibody was used in combination with anti-human Fc specific coating antibody. To detect light chain anti-human kappa chain specific HRP antibody was used in combination with the anti-human kappa chain specific antibody.

(C) C57B1/6 mice were immunised at day 0, 7 and 14 with ImmunoBody DNA constructs containing i) gp100 epitope in CDR H1, TRP2 epitope in CDR H2 and HepB CD4 epitope in CDR L1 (DCIB15), ii) gp100 epitope in CDR H1, TRP2 epitope in CDR H2 and HepB CD4 epitope in CDR L1 without the leader sequence on the heavy chain. On day 19, splenocytes were analysed by IFNγ elispot assay against TRP2 peptide. Responses are measured as spots/million splenocytes.

(D) C57B1/6 mice were immunised at day 0, 7 and 14 with ImmunoBody DNA constructs containing i) gp100 epitope in CDR H1, TRP2 epitope in CDR H2 and HepB CD4 epitope in CDR L1 (DCIB15), ii) gp100 epitope in CDR H1, TRP2 epitope in CDR H2 and HepB CD4 epitope in CDR L1 without the leader sequence on the heavy chain. On day 19, splenocytes were analysed by IFNγ elispot assay against HepB helper peptide. Responses are measured as spots/million splenocytes.

Figure 49:
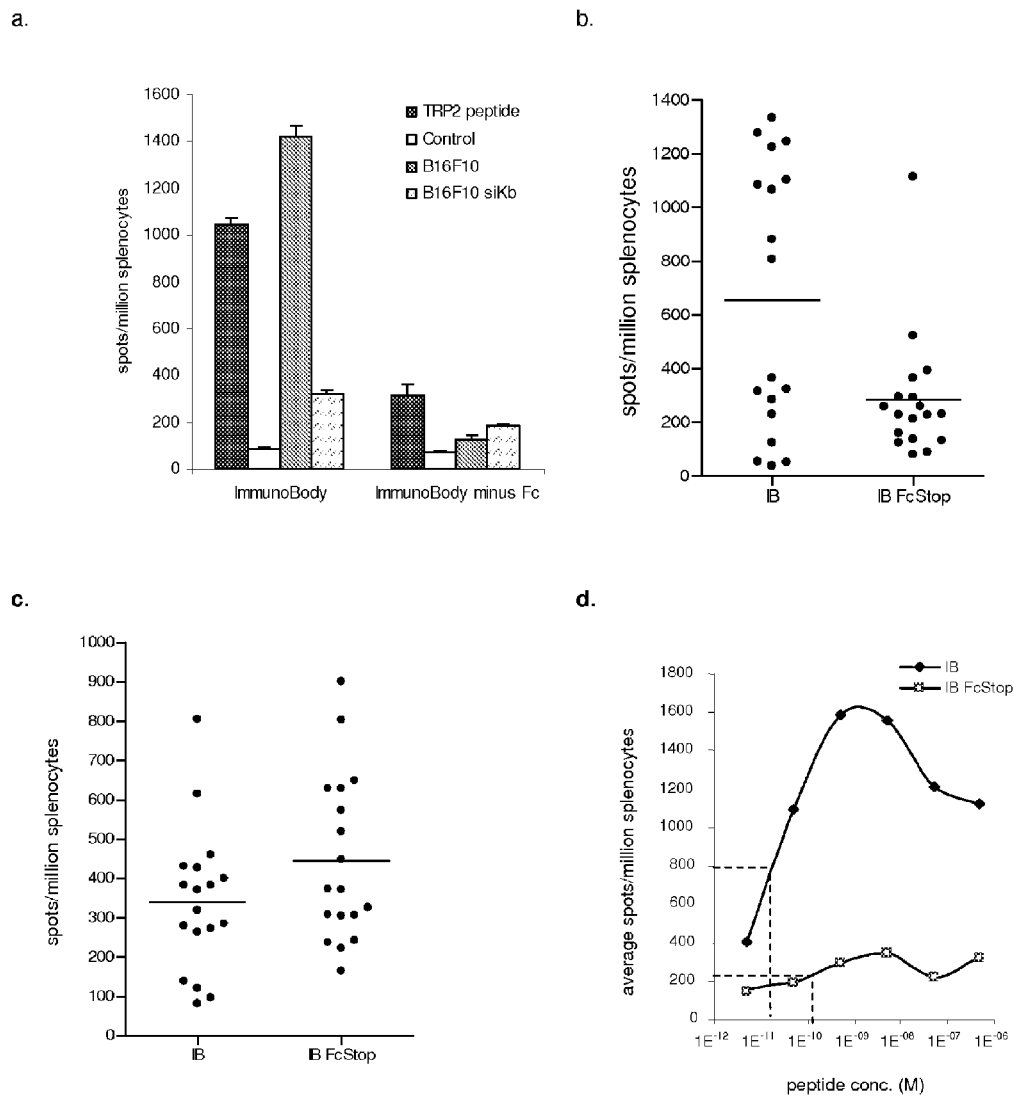
Figure 49:
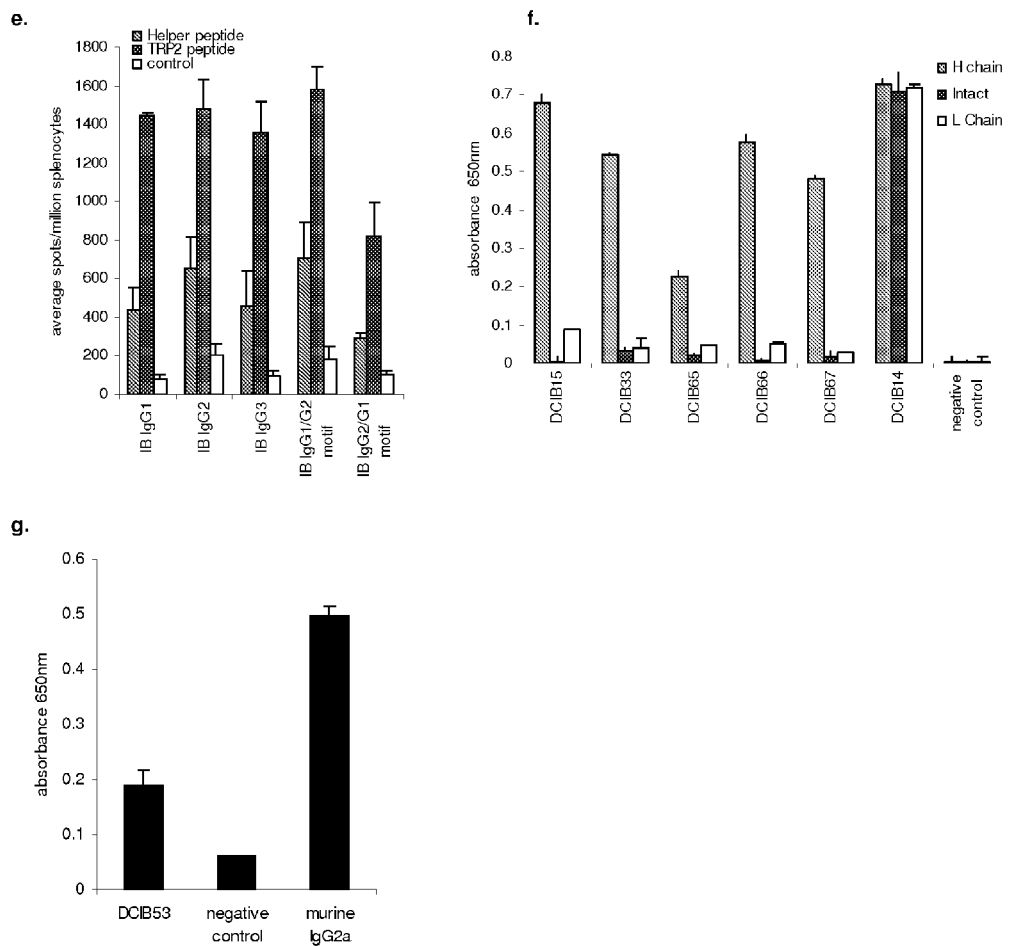

FIG. 49: ImmunoBody Fc region is beneficial for establishing an efficient immune response.

(A) C57B1/6 mice were immunised at day 0, 7 and 14 with ImmunoBody DNA constructs containing i) gp100 epitope in CDR H1, TRP2 epitope in CDR H2 and HepB CD4 epitope in CDR L1 (DCIB15), ii) gp100 epitope in CDR H1, TRP2 epitope in CDR H2 and HepB CD4 epitope in CDR L1 lacking the Fc region. On day 19, splenocytes were analysed by IFNγ elispot assay against TRP2 (▨) peptide, a media control (□), the B16F10 melanoma line (■) and the B16F10 siKb negative control cell line (▨). Responses are measured as spots/million splenocytes.

(B) C57B1/6 mice were immunised at day 0, 7 and 14 with ImmunoBody DNA constructs containing i) gp100 epitope in CDR H1, TRP2 epitope in CDR H2 and HepB CD4 epitope in CDR L1 (DCIB15), ii) gp100 epitope in CDR H1, TRP2 epitope in CDR H2 and HepB CD4 epitope in CDR L1 lacking the Fc region. On day 19, splenocytes were analysed by IFNγ elispot assay against TRP2 peptide. Responses are measured as spots/million splenocytes.

(C) The same mice were analysed for responses specific for the HepB helper peptide. Responses are measured as spots/million splenocytes.

(D) Splenocytes from mice immunised with DCIB15 or DCIB15 lacking the Fc region (DCIB15 FcStop) were assayed for avidity to the TRP2 epitope by measuring responses to increasing peptide concentration in IFNγ elispot assay. Responses are measured as spots/million splenocytes and avidity is assigned as the concentration which gives 50% maximal effector function.

(E) C57B1/6 mice were immunised at day 0, 7 and 14 with ImmunoBody DNA constructs containing i) gp100 epitope in CDR H1, TRP2 epitope in CDR H2 and HepB CD4 epitope in CDR L1 Human IgG1 (DCIB15), ii) The same construct with Human IgG2 constant region (DCIB33), iii) The same construct with Human IgG3 constant region (DCIB65), iv) The same construct with the Human IgG1 binding motif replaced with the binding motif from Human IgG2 (DCIB66) and v) DCIB33 with the binding motif replaced by the motif from Human IgG1 (DCIB67). On day 19, splenocytes were analysed by IFNγ elispot assay against TRP2 peptide (■), a media control (□) and the HepB helper peptide (▨) Responses are measured as spots/million splenocytes.

(F) Determination of heavy chain, light chain and intact ImmunoBody from supernatant of CHO—S transfectants (DCIB15, DCIB33, DCIB65, DCIB66 and DCIB67) by sandwich Elisa. Plates were coated with an anti-human Fc specific antibody or anti-human kappa chain antibody. To detect heavy chain an anti-human IgG Fc specific HRP antibody was used in combination with the anti-human Fc specific coating antibody. To detect intact ImmunoBody an anti-human kappa chain specific HRP antibody was used in combination with anti-human Fc specific coating antibody. To detect light chain anti-human kappa chain specific HRP antibody was used in combination with the anti-human kappa chain specific antibody.

(G) Determination of heavy chain ImmunoBody from supernatant of CHO—S transfected with DCIB53 by sandwich Elisa. Plates were coated with an anti-mouse Fc specific antibody. To detect heavy chain an anti-mouse IgG2a specific HRP antibody was used.

Figure 50:
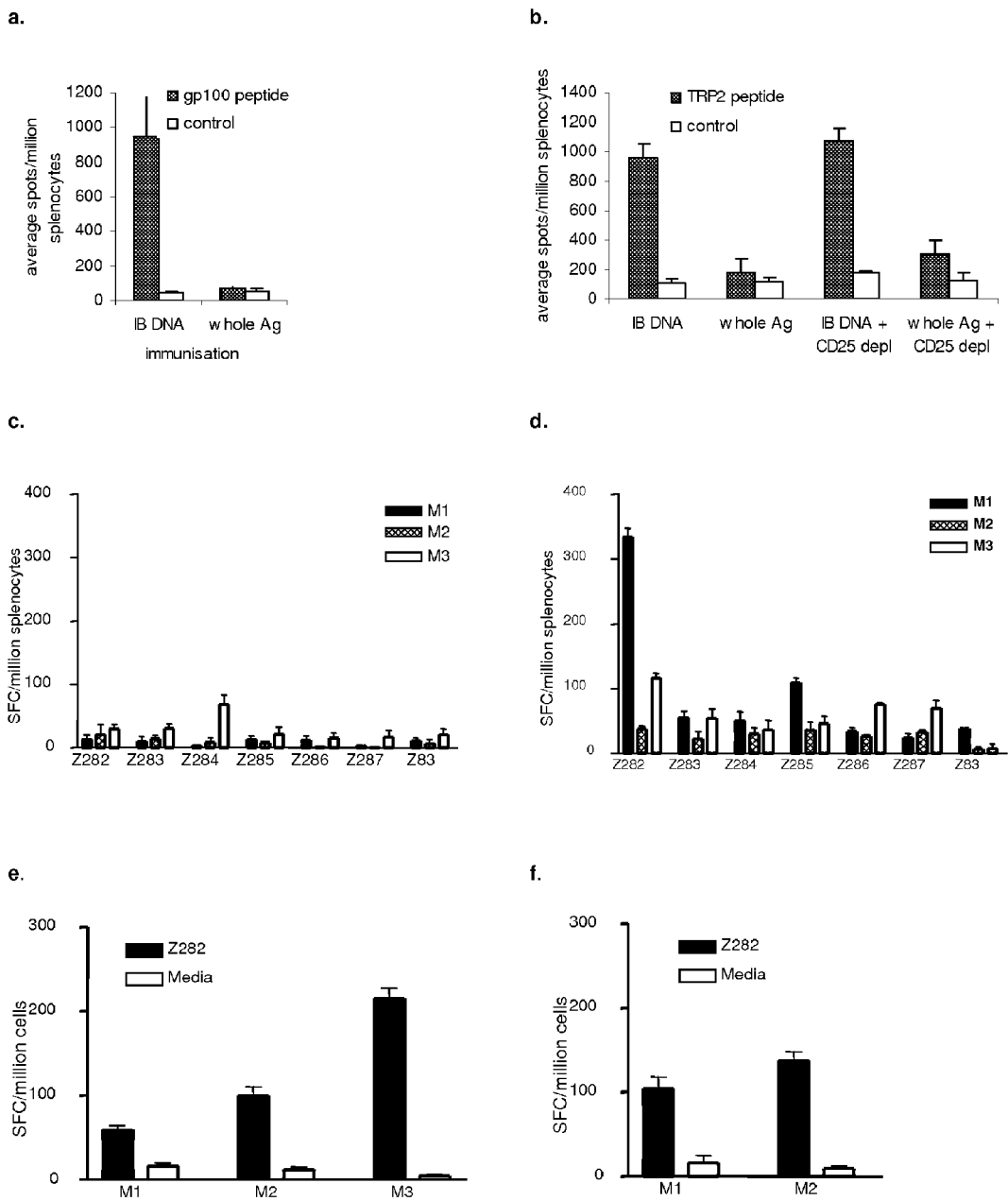
Figure 50:
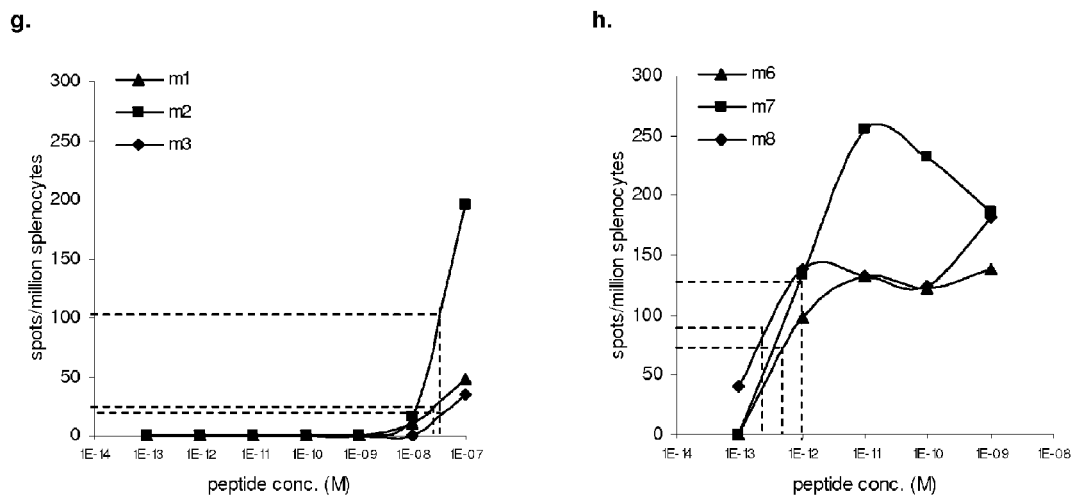

FIG. 50: ImmunoBody immunisation enhances immune responses and overcomes regulation observed from whole antigen.

(A) HLA-A2 transgenic mice (HHDII) were immunised at day 0, 7 and 14 with ImmunoBody DNA constructs DCIB15 or whole gp100 antigen in pcDNA3 vector. On day 19, splenocytes were analysed by IFNγ elispot assay against gp100 peptide or control. Responses are measured as spots/million splenocytes.

(B) C57B1/6 mice were depleted of CD25 positive cells by injection of anti-CD25 antibody (PC61) 400 µg i.p. Both CD25 depleted mice and undepleted animals were subsequently immunised at day 4, 11 and 18 with ImmunoBody DNA constructs DCIB15 or whole TRP2 antigen in pOrig vector. On day 23, splenocytes were analysed by IFNγ elispot assay against TRP2 peptide or control. Responses are measured as spots/million splenocytes.

(C) and (D) HHDII mice were either untreated (c) or treated with 400 µg PC61mAb i.p., (d). 4 days later, all mice were immunized with the Tie2 C200HFc DNA construct. DNA immunizations were repeated at 7 day intervals for a total of 3 immunisations. 6 days after the final immunisation, splenocytes were harvested and restimulated in an ex-vivo IFNγ ELISPOT assay with 1 µg/ml of each of the predicted CTL epitopes from Tie-2. Bars indicate the mean of triplicate values for each individual mouse, normalized to background controls, with error bars representing the standard deviation from the mean.

(E) and (F), HHDII mice were either untreated (e) (n=3) or treated (f) (n=2) with 400 µg PC61 antibody i.p. After 4 days, all mice were immunised with 100 µg Z12 peptide and 100 µg Z48 peptide, mixed 1:1 in IFA (s.c.). Repeat peptide immunisations were administered 7 days after the first peptide immunisation. Splenocytes were harvested 14 days after the final immunisation and restimulated with 1 µg/ml Z12 peptide (black bars) or media alone (open bars) in an IFNγ ELIspot assay. Bars indicate the mean of triplicate values with error bars representing the standard deviation from the mean.

(G) HHDII mice were immunised with 100 µg Z12 peptide mixed 1:1 in IFA (s.c.). Repeat peptide immunisations were administered at days 7 and 14 days after the first peptide immunisation. Splenocytes were harvested 7 days after the final immunisation and analysed for the presence of epitope specific responses to increasing peptide concentration in IFNγ elispot assay. Responses are measured from individual mice as spots/million splenocytes and avidity is assigned as the concentration which gives 50% maximal effector function.

(H) HHDII mice were immunised with ImmunoBody DNA construc DCIB71 via gene gun at days 0, 7 and 14. Splenocytes were harvested 7 days after the final immunisation and analysed for the presence of epitope specific responses to increasing peptide concentration in IFNγ elispot assay. Responses are measured from individual mice as spots/million splenocytes and avidity is assigned as the concentration which gives 50% maximal effector function.

FIG. 51: Sequence of DCIB71

Nucleotide and amino acid sequence of the heavy and light variable regions cloned inframe with the human IgG1 Fc and kappa constant regions within the expression vector pDC-Orig. Amino acids within boxes represent the Tie-2 Z12 epitope (ILINSLPLV-SEQ ID NO: 4) in H1 and the HepB CD4 epitope (TPPAYRPPNAPIL-SEQ ID NO: 14) in L1. The HindIII/Afe I and BamHI/BsiWI restriction sites utilised in transfer of the variable heavy and light region from the single construct are highlighted.

FIG. 52: Sequence of DCIB72

Nucleotide and amino acid sequence of the heavy and light variable regions cloned inframe with the human IgG1 Fc and kappa constant regions within the expression vector pDC-Orig. Amino acids within boxes represent the Tie-2 Z12 epitope (ILINSLPLV-SEQ ID NO: 4) in H2 and the HepB CD4 epitope (TPPAYRPPNAPIL-SEQ ID NO: 14) in L1. The HindIII/Afe I and BamHI/BsiWI restriction sites utilised in transfer of the variable heavy and light region from the single construct are highlighted.

Figure 53:
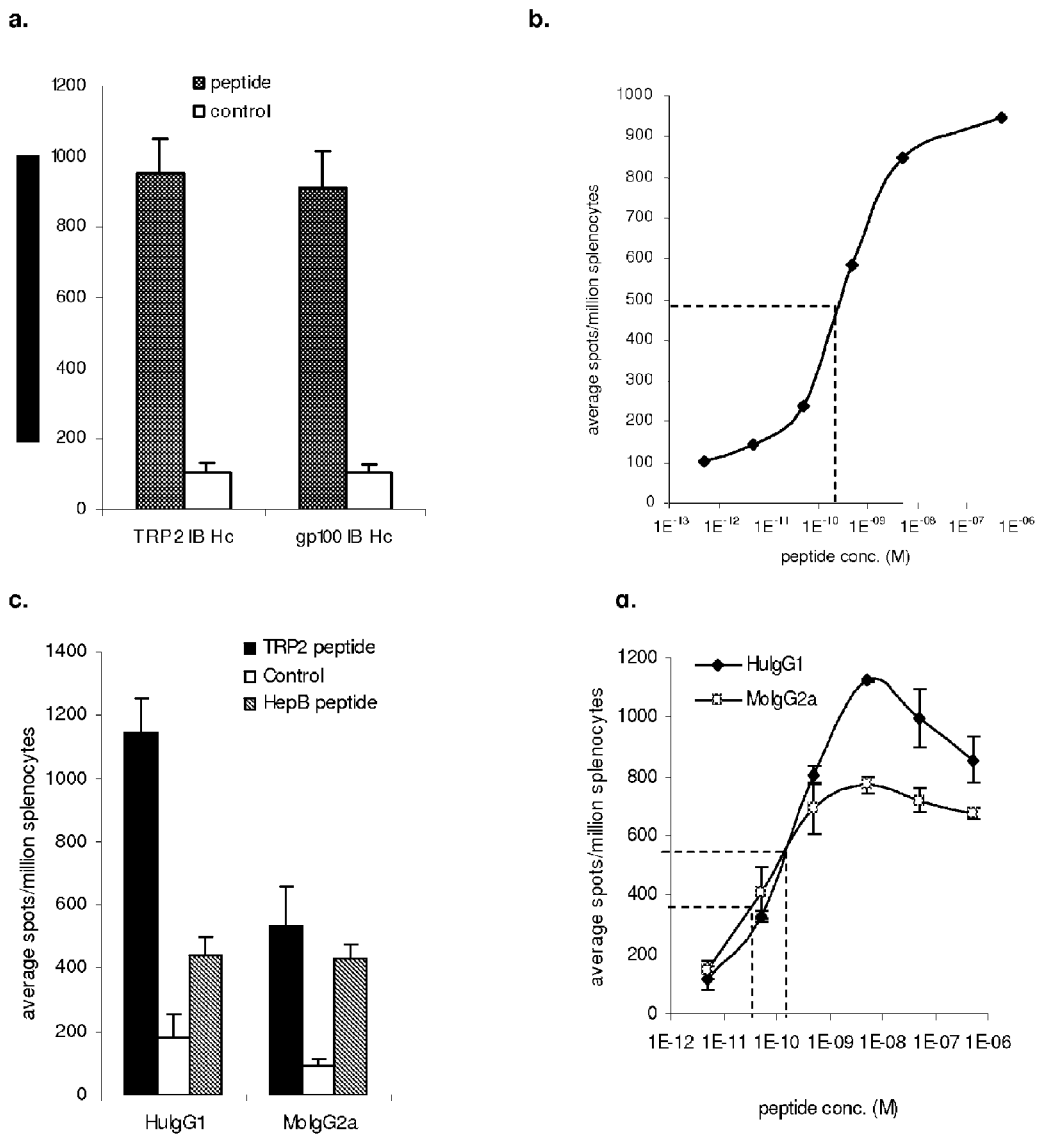
Figure 53:
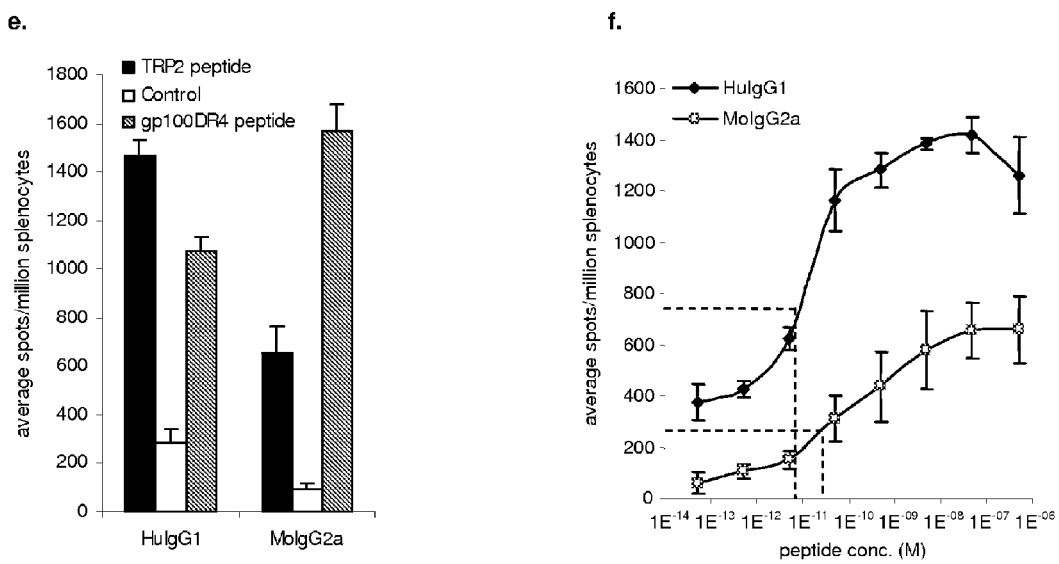

FIG. 53: The role of xenogenic Fc in providing T cell help and the requirement for antigen specific T cell help.

(A) C57B1/6 or HHDII mice were immunised at day 0, 7 and 14 with Heavy chain ImmunoBody DNA constructs containing gp100 epitope in CDR H1 or TRP2 epitope in CDR H2 (IB17 and IB18 respectively). On day 19, splenocytes were analysed by IFNγ elispot assay against gp100 peptide or TRP2 peptide and control. Responses are measured as spots/million splenocytes.

(B) Splenocytes from mice immunised with ImmunoBody heavy chain containing TRP2 epitope in CDR H2 were assayed for avidity to the TRP2 epitope by measuring responses to increasing peptide concentration in IFNγ elispot assay. Responses are measured as spots/million splenocytes and avidity is assigned as the concentration which gives 50% maximal effector function.

(C) C57B1/6 mice were immunised at day 0, 7 and 14 with ImmunoBody DNA constructs containing gp100 epitope in CDR H1, TRP2 epitope in CDR H2 and HepB CD4 epitope in CDR L1 Human IgG1 (DCIB15) or gp100 epitope in CDR H1, TRP2 epitope in CDR H2 and HepB CD4 epitope in CDR L1 with murine IgG2a constant region (DCIB53). On day 19, splenocytes were analysed by IFNγ elispot assay against TRP2 peptide, HepB helper peptide and control. Responses are measured as spots/million splenocytes.

(D) Splenocytes from mice immunised with DCIB15 or DCIB53 were assayed for avidity to the TRP2 epitope by measuring responses to increasing peptide concentration in IFNγ elispot assay. Responses are measured as spots/million splenocytes and avidity is assigned as the concentration which gives 50% maximal effector function.

(E) HLA-DR4 transgenic mice were immunised at day 0, 7 and 14 with ImmunoBody DNA constructs containing gp100DR4 epitope in CDR H1, TRP2 epitope in CDR H2 and gp100DR7 epitope in CDR H3 Human IgG1 (DCIB54) or gp100DR4 epitope in CDR H1, TRP2 epitope in CDR H2 and gp100DR7 epitope in CDR H3 with murine IgG2a constant region (DCIB64). On day 19, splenocytes were analysed by IFNγ elispot assay against TRP2 peptide, gp100DR4 helper peptide and control. Responses are measured as spots/million splenocytes.

(F) Splenocytes from mice immunised with DCIB54 or DCIB64 were assayed for avidity to the TRP2 epitope by measuring responses to increasing peptide concentration in IFNγ elispot assay. Responses are measured as spots/million splenocytes and avidity is assigned as the concentration which gives 50% maximal effector function.

FIG. 54: Sequence of DCIB53

Nucleotide and amino acid sequence of the murine heavy and light full length chains within the expression vector pDC-Orig moigG2a. Amino acids within boxes represent theGP100210M epitope in H1 (TIMDQVPFSV-SEQ ID NO: 248), the TRP2 epitope in H2 (SVYDFFVWL-SEQ ID NO: 9) and the HepB CD4 epitope in L1 (TPPAYRPPNAPIL-SEQ ID NO: 14) in L1. The HindIII/Afe I and BamHI/HpaI restriction sites utilised in transfer of the variable heavy and light region from the single construct are highlighted.

FIG. 55: Sequence of DCIB64

Nucleotide and amino acid sequence of the murine heavy and light full length chains within the expression vector pDC-Orig moigG2a. The stop codon is depicted by an asterisk. Amino acids within boxes represent the HLA-DR7 restricted gp100 CD4 epitope (GTGRAMLGTHTMEVTVYH-SEQ ID NO: 3) in H1, the TRP2 epitope (SVYDFFVWL-SEQ ID NO: 9) in H2 and the HLA-DR4 restricted gp100 CD4 epitope in H3 (WNRQLYPEWTEAQRLD-SEQ ID NO: 15). The HindIII/Afe I and BamHI/HpaI restriction sites utilised in transfer of the variable heavy and light region from the single construct are highlighted.

Figure 56:
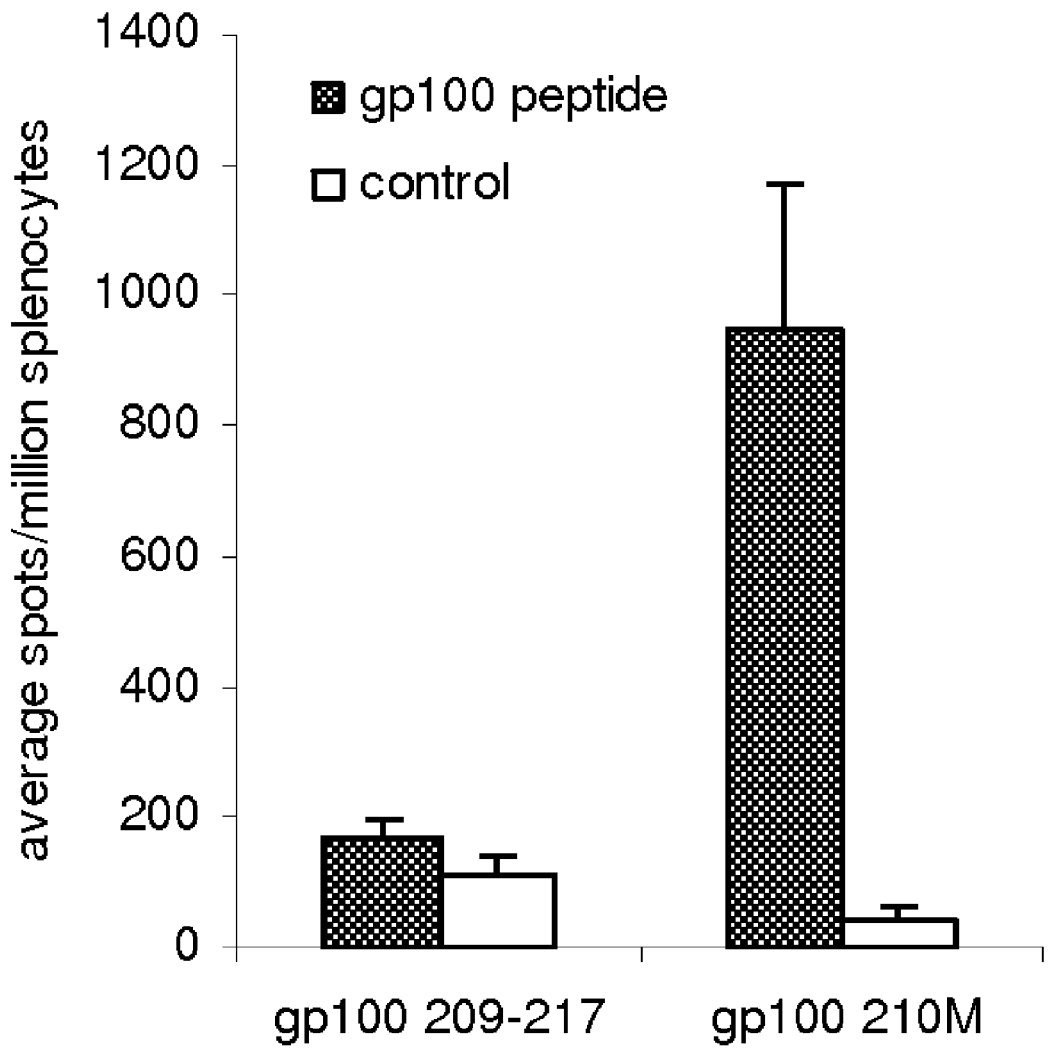

FIG. 56: Immunoproteasome processing is important in the generation of responses from epitopes within Immuno-Body constructs.

HHDII mice were immunised at day 0, 7 and 14 with ImmunoBody constructs containing the gp100$^{209-217}$ epitope in CDR H1 (DCIB41) or the modified version gp100210M in CDR H1 (DCIB15). On day 19, splenocytes were analysed by IFNγ elispot assay against gp100$^{209-217}$ peptide or gp100210M peptide and control. Responses are measured as spots/million splenocytes.

Figure 57:
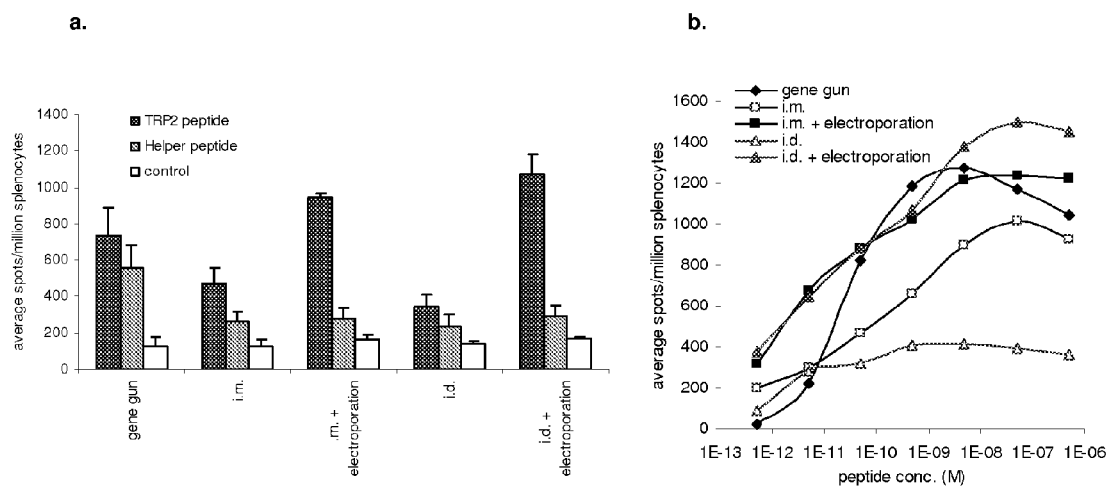

FIG. 57: Different immunisation methods are efficient at eliciting immune responses from ImmunoBody vaccine.

(A) C57B1/6 mice were immunised with ImmunoBody DNA (DCIB15) via gene gun, i.m.+/−electroporation or i.d.+/−electroporation at days 0, 7 and 14. On day 19, splenocytes were analysed by IFNγ elispot assay against TRP2 peptide, HepB helper peptide and control. Responses are measured as spots/million splenocytes.

(B) Splenocytes from mice immunised by different routes were assayed for avidity to the TRP2 epitope by measuring responses to increasing peptide concentration in IFNγ elispot assay. Responses are measured as spots/million splenocytes and avidity is assigned as the concentration which gives 50% maximal effector function.

FIG. 58: ImmunoBody immunisation induces vitiligo-like depigmentation and protects against tumour challenge.

(A) C57B1/6 mice immunised with ImmunoBody DNA containing the TRP2 epitope in CDR H2 and the HepB CD4 epitope in CDR L1 (DCIB18) demonstrate depigmentation in hair growth at the site of immunisation.

(B) Immunised C57B1/6 mice were challenged between 3$^{rd}$ and 4$^{th}$ immunisations with 2×10$^4$ B16F10 IFNα cells i.v. Tumour burden in the lungs was assessed at 49 days post tumour challenge. Tumour burden is expressed as a mean tumour area as a percentage of total lung area. Immunised mice were challenged 7 days post final immunisation with 2×10$^4$ B16F10 IFNα cells s.c. Tumour size was measured at 3-4 day intervals and mice euthanized once tumour growth exceeded limit.

(C) Tumour size assessed at day 46 post tumour injection.
(D) Survival.

Figure 59:
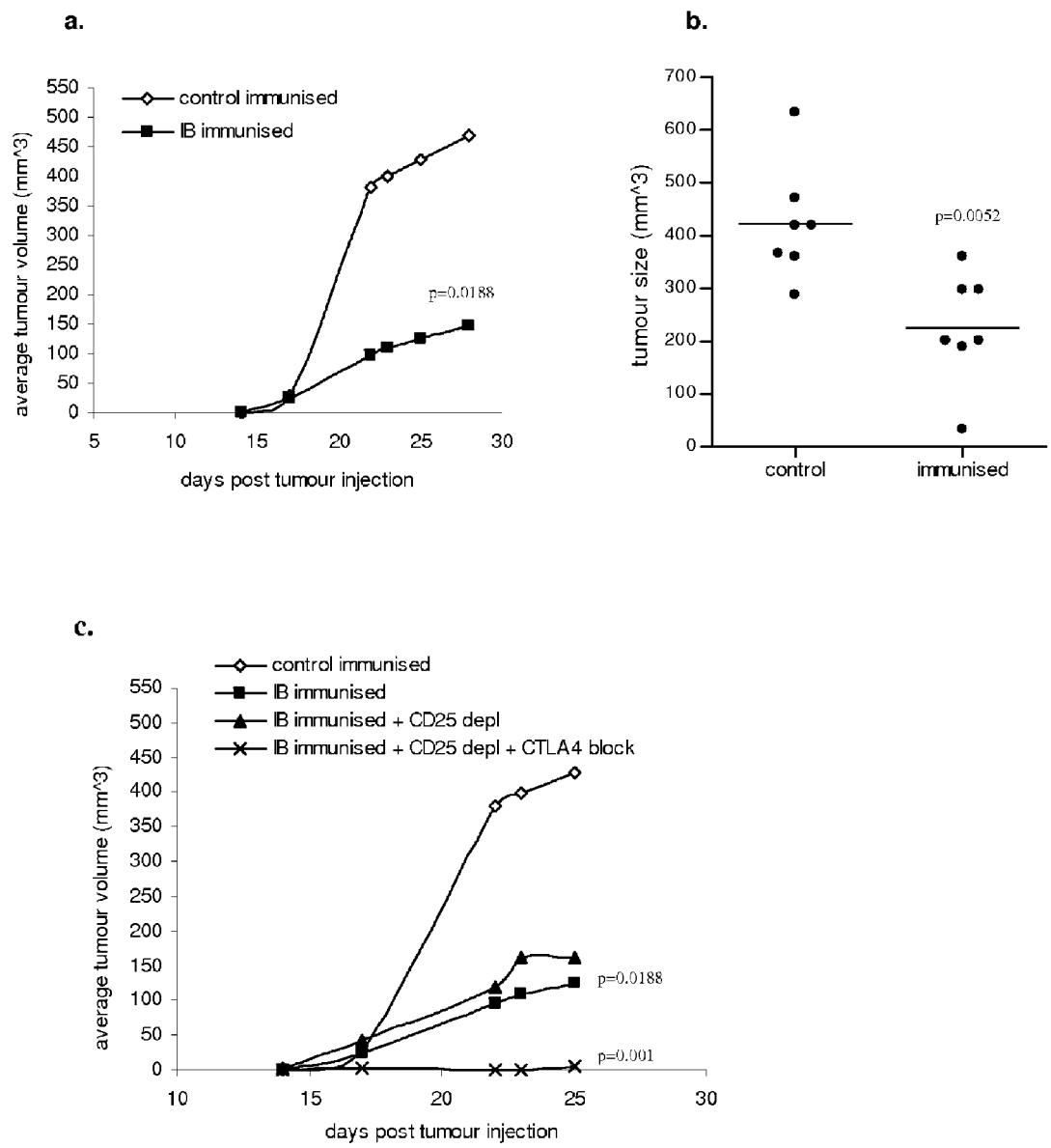

FIG. 59: ImmunoBody Immunisation Significantly Delays Tumour Growth.

(A) C57B16 mice were injected with 2×10$^4$ B16F10 cells s.c. Four days post tumour injection mice were immunised with DCIB52 ImmunoBody DNA. Repeat immunisation were performed at days 11 and 18 post tumour injection. Tumour burden was analysed at 3-4 day intervals and mice euthanized once tumour growth exceeded maximum permitted limit. Tumour volume over time was plotted.

(B) C57B16 mice were injected with 2×10$^4$ B16F10 IFNα cells s.c. Fourteen days post tumour injection mice were immunised with DCIB52 ImmunoBody DNA. Repeat immunisations were performed at days 21 and 28 post tumour injection. Tumour burden was analysed at 3-4 day intervals and mice euthanized once tumour growth exceeded maximum permitted limit. Tumour volume is shown at day 47 post tumour implant.

(C) C57B16 mice were injected with 2×10$^4$ B16F10 cells s.c and anti-CD25 antibody i.p. where appropriate. Four days post tumour injection mice were immunised with DCIB52 ImmunoBody DNA or control ImmunoBody DNA. Repeat immunisations were performed at days 11 and 18 post tumour injection Immunisation at day 11 was combined with the injection of anti-CTLA-4 antibody i.p. where appropriate. Tumour burden was analysed at 3-4 day intervals and mice euthanized once tumour growth exceeded maximum permitted limit. Tumour volume over time was plotted.

FIG. 60: Sequence of DCIB68

Nucleotide and amino acid sequence of the heavy and light variable regions cloned inframe with the human IgG1 Fc and kappa constant regions within the expression vector pDC-Orig. Amino acids within boxes represent the HLA-DR7 restricted gp100 CD4 epitope (GTGRAMLGTHT-MEVTVYH-SEQ ID NO: 3) in H1 and L3, the TRP2 epitope (SVYDFFVWL-SEQ ID NO: 9) in H2 and the HLA-DR4 restricted gp100 CD4 epitope in H3 and L1 (WNRQLYPEW-TEAQRLD-SEQ ID NO: 15). The HindIII/Afe I and BamHI/BsiWI restriction sites utilised in transfer of the variable heavy and light region from the single construct are highlighted.

Figure 61:
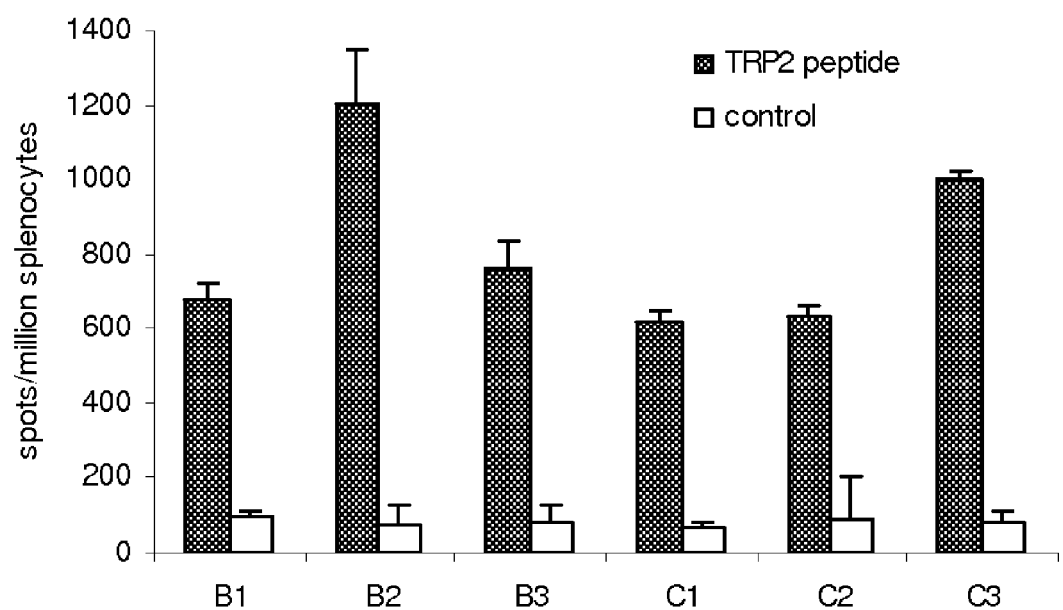

FIG. 61: Immune Responses can be Generated from Immu-noBody Constructs Expressed from Different Vector Backbones.

C57B1/6 mice were immunised at day 0, 7 and 14 with ImmunoBody DNA constructs containing gp100DR4 epitope in CDR H1, TRP2 epitope in CDR H2 and gp100DR7 epitope in CDR H3 Human IgG1 (DCIB54, B1-3) an equivalent construct in the pVax vector (VaxDCIB54, C1-3). On day 19, splenocytes were analysed by IFNγ elispot assay against TRP2 peptide and control. Responses are measured as spots/million splenocytes.

DETAILED DESCRIPTION OF THE INVENTION

In the field of cancer vaccines and chronic viral infections, it is now becoming clear that factors other than frequency, such as functional avidity of tumour specific T cells and route of priming, are major determinants in maximising vaccine efficacy. A number of groups have shown that high avidity CD8+ T cells demonstrate superior anti-tumour activity (Alexander-Miller, *Immunologic Research*, 2005; 31: 13-24, Hodge et al, *J Immunol* 2005; 174: 5994-6004, Valmori et al, *J Immunol* 2002; 168: 4231-40, Zeh et al, *J Immunol* 1999; 162: 989-94). It has been suggested that high avidity T cells play a vital role in tumour regression in patients. This is exemplified in a study where high avidity antigen-specific tumour infiltrating lymphocytes (TIL) were detected in a patient with dramatic tumour regression (Khong & Rosenberg, *J Immunol* 2002; 168: 951-6). Evidence is also emerging demonstrating that adoptive transfer of in vitro stimulated autologous tumour-specific T cells is successful, possibly as in vitro stimulation enables selection of the high avidity T cells (Vignard et al., *J Immunol* 2005; 175: 4797-805, Dudley et al., *J Immunother* 2001; 24: 363-73, Morgan et al, *J Immunol* 2003; 171: 3287-95, Rosenberg & Dudley, *Proceedings of the National Academy of Sciences of the United States of America* 2004; 101 Suppl 2: 14639-45). Hitherto, a number of groups have attempted to raise a cellular immune response against a pre-determined epitope using an antibody as a carrier for that epitope. For example, WO 96/19584 (Bona et al.) discloses chimeric antibodies in which T cell epitopes are inserted into the complementarity determining regions (CDRs) of an antibody, and alleges that such chimeric antibodies are suitable for raising a cytotoxic T cell (CTL) response. However, this document teaches that the DNA must encode a functional protein. Thus in the abstract, it is stated that "the functional capabilities of the epitope and the parent immunoglobulin are retained." Also, on page 21, it is stated "that the insertion of the desired epitope should be at a region of the nucleic acid encoding the parent immunoglobulin molecule that is not essential for expression or function of the parent immunoglobulin molecule." Furthermore, all the examples in WO 96/19584 show that intact immunoglobulin is produced following insertion of the T cell epitope.

U.S. Pat. No. 7,067,110 discloses a method for eliciting an immune response against an antigen using a fusion protein of antibody which lacks an immunoglobulin variable region domain fused to the antigen by a polypeptide bond. The fusion protein retains the ability to bind to Fc.

EP0759944 discloses a method of incorporating T cell epitopes within an antibody molecule that is secreted as an intact immunoglobulin protein and which can target CTL epitopes to tumours to make them better targets for CTLs.

WO 00/64488 discloses that a CTL response can be raised by nucleic acid encoding a chimeric antibody having heterologous T cell epitopes inserted in the CDRs but not the variable region thereof, provided that the nucleic acid is directed for expression in B cells. As B cells cannot stimulate naïve T cell responses, the vaccine described in WO 00/64488 would only be useful in boosting pre-existing T cell responses.

WO 02/092126 discloses that a CTL response can be raised by a polypeptide comprising a heterologous T cell epitope and the part of human Fc which binds to the high affinity CD64 receptor. However, the present inventors have now shown that disruption of the antibody sequence by inserting a T cell epitope, for example within an inappropriate CDR or even within the variable region of an antibody, prevents association of heavy and light chain and no functional antibody is secreted. DNA encoding these mis-folded antibodies unexpectedly generates strong T cell responses. Furthermore, this is not mediated via CD64 as human IgG2—which does not bind to mouse or human CD64—works just as efficiently as human IgG 1.

In one aspect of the present invention, there is provided a nucleic acid which comprises a non-specific promoter and at least one sequence that encodes a polypeptide that has at least one heterologous T cell epitope therein but does not have any regulatory T cell epitopes.

This polypeptide is preferably a homologous carrier, e.g. when used to raise a T cell response in humans it may be a human protein, or a foreign protein or human/foreign chimeric protein that has had all T regulatory epitopes identified and removed.

The polypeptide is preferably one chain of a heterodimer, the heterologous T cell epitope causing disruption of the heterodimer chain such that it cannot bind or associate with the other chain of the heterodimer. Many molecules are herodimeric, with one chain being dependent upon the other for folding and then secretion. If the secondary structure is disrupted due to insertion of a heterologous T cell epitope, folding and secretion is inhibited. In certain embodiments, one chain is secreted and includes a heterologous CTL epitope, and the other chain includes a heterologous helper epitope but, due to disruption of the secondary folding, is not secreted. Thus, the nucleic acid may encode both chains of the heterodimer, wherein one chain includes a heterologous cytotoxic T cell (CTL) epitope and is secreted when expressed, and the other chain includes a heterologous helper epitope and is not secreted when expressed. Alternatively, the respective heterodimer chains may be encoded on separate nucleic acid molecules.

The heterodimer may be an immunoglobulin molecule. The heavy chain of the immunoglobulin molecule may include a heterologous cytotoxic T cell (CTL) epitope and be secreted when expressed, and the light chain of the immunoglobulin molecule may include a heterologous helper epitope and not be secreted when expressed.

The nucleic acid of the first aspect of the present invention encodes an polypeptide that does not include any regulatory T cell (T reg) epitopes. These polypeptides act as inert carriers for the T cell epitope(s) and may be a molecule, or part of a molecule, that can be used by the immune system to stimulate immune responses, as these molecules by definition do not express competing T reg epitopes. Suitable molecules include HLA molecules, T cell receptors, TOL receptors, TOL ligands, cytokines, cytokine receptors, chemokines, chemokine receptors. It is preferred that the molecule is an antibody or part thereof.

Without wishing to be bound by theory, the present invention is based, at least in part, on the concept that a T cell response can be generated against a specific T cell epitope (such as a CTL epitope), by administration of a nucleic acid encoding a polypeptide including the T cell epitope but no regulatory T cell epitopes. It is believed that nucleic acid is either taken up by antigen presenting cells (APCs), migrates to lymph nodes and is directly presented, or is expressed to produce a polypeptide which is secreted and which is then taken up by other APCs. The former nucleic acid is suitable for stimulating helper T cell epitopes and the latter is suitable for stimulating CTL responses. The polypeptide that is encoded by the nucleic acid ideally does not have any natural T cell epitopes. Suitable polypeptides in this regard are immune molecules, such as antibodies. Antibody heavy and light chains which cannot associate so that the light chain remains in the APCs and so that the heavy chain is secreted are suitable for the practice of the present invention, although the present invention is not limited to the use of antibodies as carriers for the T cell epitopes.

A suppressor T cell population was identified approximately 40 years ago, but progress was hampered by the lack of specific techniques to identify the cells and because of scientific skepticism regarding the existence of suppression.

However, Sakaguchi et at resurrected interest in suppressor cells in 1995 by demonstrating that the transfer of lymphocytes depleted of CD4+CD25+ T cells into athymic mice caused the development of various autoimmune diseases in the recipient mice and that reconstitution with CD4+CD25+ T cells prevented autoimmune reactions in these mice (Sakaguchi et al J. Immunol 1995; 155:1151-1164). Subsequently, numerous studies in mice and humans have shown that diverse T cell populations with regulatory activity play an important role in the suppression of immune responses (both innate and adaptive) to self (controlling self tolerance) (Sakaguchi et at J Immunol 1995; 155:1151-1164) as well as foreign antigens (Shevach, *Immunity* 2006; 25: 195-201, Coleman et al, *J. Cell MoL Med.* 2007; 11: 1291-1325). Treg-cell depletion in mouse models of cancer has shown to improve endogenous immune-mediated tumour rejection (Shimizu, et al, *J. Immunol.* 1999; 163: 5211-5218, Onizuka et al, *Cancer Research* 1999; 59: 3128-3133) and antigen-specific anti-tumour immunity (Tanaka, et al, *J. Immunother.* 2002; 25:207-217). In addition, Treg-cell depletion augments tumour immunotherapy including vaccination (Tanaka, et al, *J. Immunother.* 2002; 25:207-217, Dannull et al, *J. Clin. Invest.* 2005; 115:3623-3633) and CTLA-4 blockade (Sutmuller et al, *J. Exp. Med.* 2001; 194:823-832). Furthermore, numbers of Treg-cells are increased in the peripheral blood (Woo et al, *Cancer Research* 2001; 61:4766-4772, Curiel et al, *Nature Medicine* 2004; 10:942-949, Wolf et al, *Clin. Cancer Research* 2003; 9:606-612, Sasada et al, *Cancer* 2003; 98:1089-1099) and populate the tumour microenvironment and draining lymph nodes (Curiel et al, *Nature Medicine* 2004; 10:942-949, Sasada et al, *Cancer* 2003; 98:1089-1099, Liyanage et al, *J. Immunology* 2002; 169:2756-2761, Matsuura et al, *Cancer* 2006; 106:1227-1236, Yang et al, *Blood* 2006; 107:3639-3646, Alvaro et al, *Clin. Cancer Research* 2005; 11:1467-1473) of patients with different cancers. In patients with gastric carcinoma (Sasada et al, *Cancer* 2003; 98:1089-1099, Ichihara et al, *Clinical Cancer Research* 2003; 9:4404-4408) and ovarian cancer (Curiel et al, *Nature Medicine* 2004; 10:942-949), poor prognosis and decreased survival rates were associated with higher Treg-cell frequencies. Treg-cells have also been shown to suppress/inhibit the proliferation, cytokine-production (IFNγ, IL-2) and cytolytic activity of tumour-specific CD8° (Liyanage et al, *J. Immunology* 2002; 169:2756-2761, Piccirillo et al, *J. Immunology* 2001; 167:1137-1140, Mempel et al, *Immunity* 206; 25:129-141, Annacker et al, *J. Immunology* 2001; 166:3008-3018, Woo et al, *J. Immunology* 2002; 168:4272-4276) and CD4+ (Liyanage et al, *J. Immunology* 2002; 169:2756-2761, Ichihara et al, *Clinical Cancer Research* 2003; 9:4404-4408, Nishikawa et al, *Blood* 2005; 106:1008-1011) T cells. In addition, Treg-cells can suppress the functions of dendritic cells (Romagnani et al, *Eur. J. Immunol.* 2005; 35:2452-2458), NK cells (Ralainirina et al, *J. Leukoc. Biol.* 2007; 81:144-153) and B cells (Lim et al, *J. Immunology* 2005; 175:4180-4183). Taken together, these studies suggest an important role of Treg-cells in tumour immunopathology and indicate a close correlation between Treg-cell frequencies and tumour growth.

Treg-cells are divided into natural CD4+CD25+T cells and diverse populations of induced/adaptive Treg-cells (Shevach, *Immunity* 2006; 25: 195-201, Bluestone et al, *Nat. Immunol.* 2005; 6:345-352) (Table 1). About 5%-10% of CD4+ T cells in mice and humans are natural Treg-cells (Sakaguchi et al, *Nat. Immunology* 2005; 6:345-352). Natural Treg-cells develop in the thymus by strong TCR interaction with self peptide (Picca et al, *Current Opinion in Immunology* 2005; 17:131-136, Jordan et al, *Nature Immunology* 2001; 2(4): 301-306, Picca et al, *Immunological Reviews* 2006; 212:74-85), while induced Treg-cells develop from non-regulatory T cells in the periphery. This extrathymic conversion requires special immunological conditions such as continuous exposure to low dose antigen, exposure to a systemic peripheral antigen or exposure to TGFβ (Shevach, *Immunity* 2006; 25: 195-201, Akbar et al, *Nat. Rev. Immunol.* 2007; 7:231-237). Treg-cells may mediate their suppression by one or a combination of the following mechanisms: i) cell-cell contact dependent mechanism, ii) through the secretion of immunosuppressive cytokines like IL-10 or TGFβ or iii) direct killing of the target cells perforin-granzyme pathway (von Boehmer, *Nature Immunology* 2005; 6(4):338-344).

To date, very little is known about the antigen-specificity of human Treg-cells. Wang et al reported the identification of LAGE-1-specific CD4+CD25+GITR+ functional Treg-cell clones in cancer patients (Wang et al, Immunity 2004; 20:107-118). Vence et al. demonstrated the presence of tumour antigen-specific CD4° Treg-cells in the peripheral blood of metastatic melanoma patients (Vence et al, *PNAS* 2007; 104(52):20884-20889). These Treg-cells recognised a broad range of tumour antigens, including TRP1, NY-ESO-1, gp100 and survivin. In addition, Vence et al were the first to demonstrate the presence of NY-ESO-1-specific Treg-cell epitopes within the NY-ESO-1 molecule. Furthermore, vaccination of melanoma patients with dendritic cells either loaded with synthetic peptides or tumour lysates was shown to induce increased frequencies of Treg-cells, concomitant with the expansion of tumour-specific CD8+ T cells (Chakraborty et al, *Hum. Immunology* 2004; 65:794-802). This suggests the possibility that the vaccine contained unidentified Treg-cell epitopes as well as CD8+ T cell epitopes, which lead to the expansion of Treg-cells in vivo by ligand-specific activation through the Treg-cell T cell receptor (TCR). It is widely accepted that Treg-cells require antigen-specific activation through TCR recognition/engagement but mediate antigen-nonspecific bystander suppression (Thorton & Shevach, J. Immunology 2000; 164:183190). Furthermore, Li et at suggested the existence of dominant Treg epitopes within the Hepatitis C Virus core protein that stimulated HCV-specific Treg-cells in infected patients (Li et al, *Immunol. Cell Biol.* 2007; 85(3):197-204). Collectively, these studies in addition to the recent finding that immunization of HHD transgenic mice with the anti-endothelial DNA construct C200Fc, failed to stimulate a significant Tie-$2_{1-196}$-specific anti-tumour immune response and the increased frequency of Tie-$2_{1-196}$-specific IFNγ secreting cells from splenocytes of HHD mice after the depletion of CD4+CD25+ Treg cells (by administration of 400 μg PC61 monoclonal antibody) prior to C200Fc DNA immunization (Middleton, PhD Thesis. University of Nottingham, November 2007) indicates that the Tie-$2_{1-196}$ within the DNA vaccine contains unidentified Treg-cell epitopes as well as the CD8+ epitope. This would explain the failure of the vaccine to break tolerance to the self antigen Tie-2 and to elicit anti-tumour immunity in HHD mice due to abundant antigen-specific expanded Treg-cells suppressing the cell-mediated anti-tumour immune response. There is therefore an advantage to express T effector epitopes with inert immune carriers which fail to express T reg epitopes to direct the immune response to the effector epitope and prevent stimulation of the dominant T reg response.

Advantageously, the nucleic acid of the present invention includes a sequence encoding a sequence, such as a leader sequence, that allows the expressed polynucleotide to be secreted. This allows the polynucleotide to be transferred to antigen presenting cells (APCs). The sequence could be a leader sequence that is naturally expressed with the polynucleotide or could be a heterologous leader sequence, such as an immunoglobulin leader sequence, which is added. The latter is especially suitable where the polynucleotide encodes a membrane-bound molecule.

According to another aspect of the present invention, there is provided a nucleic acid which comprises a non-specific promoter and at least one sequence that encodes a recombinant heavy chain of an immunoglobulin molecule, wherein the heavy chain has at least one heterologous T cell epitope therein such that the heavy chain cannot take its native conformation when the nucleic acid is expressed.

The nucleic acid of the aspect of the present invention encodes a recombinant heavy chain of an immunoglobulin molecule. The structure of such a heavy chain is known to those of skill in the art, and generally includes variable and constant regions. The heavy chain may be from an antibody. The antibody may be monoclonal or polyclonal and may be IgA, IgD, IgE, IgG or IgM, although IgG is preferred. The IgG antibody may be any IgG subclass, such as human IgG1, IgG2, IgG3 or IgG4, or mouse IgG1, IgG2a, IgG2b or IgG3. The IgG antibody may be a human IgG1 antibody having the IgG2 Fc binding domain, or a human IgG2 antibody having the IgG1 Fc binding domain. The heavy chain may have the constant region of a human antibody, and the variable or hypervariable (CDR) region of a mouse monoclonal antibody into which heterologous T cell epitopes have been inserted. The variable region other than the hypervariable region may also be derived from the variable region of a human antibody. When applied to antibodies (i.e. comprising a heavy chain and a light chain), the antibody is said to be humanised. Methods for making humanised antibodies are known in the art. Methods are described, for example, in Winter, U.S. Pat. No. 5,225,539. The variable region of the heavy chain outside of the mouse hypervariable region may also be derived from a mouse monoclonal antibody. In such case, the entire variable region is derived from murine monoclonal antibody and, when applied to antibodies, the antibody is said to be chimerised. Methods for making chimerised antibodies are known in the art. Such methods include, for example, those described in U.S. patents by Boss (Celltech) and by Cabilly (Genentech). See also U.S. Pat. Nos. 4,816,397 and 4,816,567, respectively.

In certain embodiments, the nucleic acid of the present invention further comprises at least one sequence that encodes a light chain of an immunoglobulin molecule. Alternatively, a separate nucleic acid encoding a light chain of an immunoglobulin molecule may be provided. The light chain may have at least one heterologous T cell epitope therein. The T cell epitope may be such that the light chain cannot take its native conformation when the nucleic acid is expressed. The light chain may have any of the features described herein in respect of the heavy chain. Accordingly, the invention also provides a nucleic acid encoding a recombinant light chain of an immunoglobulin molecule, wherein the light chain has at least one heterologous T cell epitope therein such that the light chain cannot take its native conformation when the nucleic acid is expressed. The nucleic acid may include a non-specific promoter. Such nucleic acid(s) encode an immunoglobulin molecule, such as an antibody.

Thus, according to a further aspect of the present invention, there is provided a nucleic acid which comprises a non-specific promoter and at least one sequence that encodes a recombinant immunoglobulin molecule, wherein the immunoglobulin molecule has at least one heterologous T cell epitope therein such that the immunoglobulin molecule cannot take its native conformation when the nucleic acid is expressed. Preferably, the recombinant immunoglobulin molecule, and heavy and light chains described above do not have any regulatory T cell epitopes.

The invention also provides:
a vaccine comprising a nucleic acid of the invention and an adjuvant;
a pharmaceutical composition comprising a nucleic acid of the invention and a pharmaceutically acceptable carrier, excipient or diluent;
a nucleic acid of the invention for use in medicine;
the use of such a nucleic acid of the invention in the manufacture of a medicament for stimulating an immune response against at least one of the T cell epitope(s);
a nucleic acid of the invention for stimulating an immune response against at least one of the T cell epitope(s); and
a method for stimulating an immune response against a T cell epitope, comprising administering to a subject in need of such immune response a therapeutically effective amount of a nucleic acid of the invention.

Surprisingly, the present inventors have found that antibodies, such as monoclonal antibodies, which may be human or non-human, that have pre-determined T cell epitopes cloned within their variable regions, so as to disrupt the primary antibody structure, inhibit folding and/or limit secretion to either just heavy chain or very low amounts of intact antibody, stimulate strong helper and antigen-specific T cell responses. The inventors have also found that this effect can be achieved using nucleic acid encoding the heavy chain of such an antibody. It is believed that the T cell epitope is processed but not destroyed by the immunoproteosome. In certain embodiments, the invention provides a DNA vaccine presenting predefined T cell epitopes within denatured immunoglobulin which enhances the frequency and the avidity of the T cell response. The polypeptides encoded by the nucleic acids of the invention may be referred to herein as "Immunobodies".

The finding that an immune response against a T cell epitope can be stimulated by a nucleic acid encoding at least the heavy chain of an immunoglobulin molecule into which the T cell epitope has been inserted such that the an immunoglobulin molecule cannot take its native conformation runs contrary to the expectations in the art, where it is taught that the antibody must be expressed in a functional form. For example, as discussed above, WO 96/19584 teaches that, where a nucleic acid encodes an antibody in which T cell epitopes are inserted into the CDRs of the antibody, the nucleic acid must encode a functional antibody. Similarly, EP0759944 describes a method of incorporating T cell epitopes within an antibody molecule that is secreted as an intact immunoglobulin protein. Although U.S. Pat. No. 7,067,110 discloses that an immune response can be raised against an antigen by a fusion protein of antibody and the antigen, the antibody is disclosed as lacking an immunoglobulin variable region. In addition, this fusion protein will have regulatory T cell epitopes in the antigen. Thus, although the protein may stimulate an antibody response, it will not stimulate high avidity T cells responses due to regulatory T cell epitopes s in the antigen.

As discussed above, WO 00/64488 discloses a nucleic acid encoding a chimeric antibody having heterologous T cell epitopes inserted in the CDRs but not the variable region thereof, which nucleic acid is directed for expression in B cells. The nucleic acid of the present invention is not directed for expression in B cells, and thus will not target B cells specifically either in vitro or in vivo. The nucleic acid of the present invention can be taken up by any antigen presenting cells, including dendritic cells, and can therefore prime naïve CTL and helper T cell responses, whereas the vaccine described in WO 00/64488 would only be useful in boosting pre-existing T cell responses.

Analysis of the functional avidity of responses induced by nucleic acids in accordance with the invention demonstrated that a high avidity response can be generated when compared to immunisation with synthetic peptide. This also correlated with enhanced ability to recognise and kill tumour cells in vitro and in vivo. This observation is comparable to that documented in other studies where better anti-tumour activity is shown by high avidity TRP2 specific CTL (Zeh et al, *J Immunol* 1999; 162: 989-94, Harada et al, *Immunology* 2001; 104: 67-74).

The nucleic acids of the present invention have a non-specific promoter, i.e. a promoter that will promote expression of the nucleic acid but which has no specificity for cells in which expression is promoted. The promoter preferably causes expression of the nucleic acid in dendritic cells and/or keratinocytes. Examples of suitable promoters include the CMV promoter, the SV40 promoter, and other non-specific promoters known to those of skill in the art. Alternatively, the nucleic acid of the present invention may have one or more promoters that cause specific expression in dendritic cells (e.g. Cd11b promoter) and in keratinocytes (e.g. MHCII promoter, Chin et al., 2001 *J. Immunol.* 167, 5549-5557).

The nucleic acid of certain aspects of the invention encodes an immunoglobulin molecule, preferably an antibody that includes all of the major features of an antibody, that is to say heavy and light chains which include variable and constant regions. The antibody may be monoclonal or polyclonal and may be IgA, IgD, IgE, IgG or IgM, although IgG is preferred. The IgG antibody may be any IgG subclass, such as human IgG1, IgG2, IgG3 or IgG4, or mouse IgG1, IgG2a, IgG2b or IgG3. The IgG antibody may be a human IgG1 antibody having the IgG2 Fc binding domain. The antibody may have the constant region of a human antibody, and the variable or hypervariable region of a mouse monoclonal antibody into which heterologous T cell epitopes have been inserted. The variable region other than the hypervariable region may also be derived from the variable region of a human antibody. Such an antibody is said to be humanised. Methods for making humanised antibodies are known in the art. Methods are described, for example, in Winter, U.S. Pat. No. 5,225,539. The variable region of the antibody outside of the mouse hypervariable region may also be derived from a mouse monoclonal antibody. In such case, the entire variable region is derived from murine monoclonal antibody and the antibody is said to be chimerised. Methods for making chimerised antibodies are known in the art. Such methods include, for example, those described in U.S. patents by Boss (Celltech) and by Cabilly (Genentech). See also U.S. Pat. Nos. 4,816,397 and 4,816,567, respectively.

The nucleic acid of certain aspects of the invention is such that the heavy chain, light chain or immunoglobulin molecule expressed therefrom has at least one heterologous T cell epitope therein so that the heavy chain, light chain or the immunoglobulin molecule cannot take its native conformation. The T cell epitope may disrupt the expressed protein so that the heavy chain or the immunoglobulin molecule can no longer bind to its antigen, so that the heavy and light chains (where present) can no longer associate, or so that the heavy chain or immunoglobulin molecule cannot be secreted properly, for example. The disruption may be in the tertiary structure of the immunoglobulin molecule which may prevent formation of the disulphide bonds.

As discussed in more detail below, where the immunoglobulin molecule is an antibody, the T cell epitope(s) may be inserted into or substituted for the CDR1 and CDR2 regions of the antibody. CDR1 and CDR2 form part of the antibody 13 sheet conformation and are partially submerged within the folded molecule. Any change to their length, amino acid composition or charge will disrupt this structure and prevent heavy and light chain folding and association. CDRH3 is exposed on the surface of the immunoglobulin molecule and is therefore more permissive of alterations. In the present invention, it is preferred if CDR1 and/or CDR2 are substituted with T cell epitope(s). Indeed, in certain embodiments, loss of framework regions at the CDRH junctions completely disrupts antibody folding yet insertion of epitopes in these regions gives good T cell responses. Incorporation of any epitope within the CDRH1 (5 amino acids in length) or CDRH2 (17 amino acids in length) causes sufficient disruption to allows secretion of heavy chain but only very low amounts of intact antibody, even if the light chain has its native sequence. This shows that the secondary structure is important for heavy and light chain pairing. Incorporation of any epitope within CDRL1 of the light chain results in low level secretion of light chain, even if there is only a single epitope incorporated into the CDRH3 of the heavy chain.

"Heterologous T cell epitope" is intended to mean a T cell epitope which is heterologous to the antibody. For example, a heterologous T cell epitope may be one which was not previously present in the antibody. The heterologous T cell epitope may be inserted as a whole, although it may be made up from an inserted amino acid sequence, together with flanking amino acids of the second portion. This is to ensure that the inserted epitope has a similar processing profile in the heterologous nucleic as from the original antigen. One or more CTL/helper epitopes can be inserted within the same variable region.

The T cell epitope(s) can be inserted anywhere in the heavy chain or light chain. It is preferred if the or each epitope is inserted in the variable region of the heavy chain and/or light chain, although nucleic acids encoding heavy chains or antibodies having T cell epitopes inserted in just the constant region, or in the constant region and the variable region of a heavy chain and/or light chain are included within the invention. In the nucleic acids of the present invention, the sequence(s) encoding the T cell epitopes may be inserted into (i.e. added to) the sequence encoding the heavy chain and/or light chain, or may be substituted into the sequence encoding the heavy chain and/or light chain.

In the variable region, the T cell epitope(s) may be inserted in, or substituted for, any one or more the CDRs of the heavy and/or light chain, i.e. L1, L2, L3, H1, H2, or H3. Of these, L1, H1 and H2 are currently preferred. In certain embodiments, the T cell epitopes are inserted in, or substituted for, CDRL1 and/or H1 and/or H2. Preferably the incorporated T cell epitopes are not of similar size and charge to the amino acids of the original CDR of the antibody so that the antibody does not take its native conformation, e.g. does not fold and is not secreted correctly. Alternatively or additionally, they may be inserted in, or substituted for, the framework region surrounding the CDRs.

The inserted T cell epitopes are preferably cytotoxic T cell (CTL or CD8) epitopes. Alternatively or additionally, helper T cell (CD4) epitopes may be inserted. T cell epitopes can be predicted using known T cell algorithms or synthesised as peptides and screened using standard T cell assays. The T cell epitopes may have an amino acid length in the range of from 5 to 50, 7 to 40, 8 to 30 or 9 to 20 amino acids, such as 9, 10, 11, 12, 13, 14, 15, 16, 17, 18, 19, 20, 21, 22, 23, 24, 25, 26, 27, 28, 29 or 30 amino acids. The epitopes may inserted using complementary oligonucleotides that encode the antigenic epitopes, which are annealed and cloned into specific sites of the antibody framework where CDR's (or other region) have been replaced with unique restriction enzyme sites. The ability of the recombinant antibody to stimulate helper and cytotoxic T cell responses can be screened as exemplified herein.

Various combinations are possible within the present invention. In certain embodiments, one or a plurality of CD8 epitopes is/are inserted in, and/or substituted for, the CDR H1 and/or H2, or in the non-CDR variable region, of the heavy chain or the antibody. Additionally or alternatively, one or a plurality of CD4 epitopes may be inserted in, and/or substituted for, the CDR L1, or in the non-CDR variable region, of the light chain or the antibody. Where there is a plurality of T cell epitopes, the T cell epitopes may be the same or different. Those of skill in the art will appreciate that numerous combinations are possible, including:

a CD8 epitope in CDR H1, and a CD4 epitope in CDR L1;
a CD8 epitope in CDR H2, and a CD4 epitope in CDR L1;
a CD8 epitope in CDR H1 and CDR H2, and a CD4 epitope in CDR L1;
2 CD8 epitopes in CDR H1, and a CD4 epitope in CDR L1;
2 CD8 epitopes in CDR H2, and a CD4 epitope in CDR L1;
etc. . . .

Nucleic acids of the present invention can incorporate multiple T cell epitopes from a single target antigen that can bind to the majority of both class I and class II MHC molecules. This may create a vaccine that can be used in widespread population vaccination. Alternatively nucleic acids useful in the invention can incorporate multiple T cell epitopes from multiple target antigens that can bind to the most common class I and class II phenotypes. This may create a vaccine that may prevent selection of antigen loss variants. Target antigens may be from a single pathogen or tumour type or may be selected to give an immune response against a variety of pathogens or cancers. Nucleic acids useful in the present invention targeting specific common HLA phenotypes may incorporate numerous T cell epitopes from a wide variety of cancers and/or pathogens, providing a single vaccine to prevent disease.

Any T cell epitope can be inserted, provided that it stimulates helper and/or cytotoxic T cell responses. T cell epitopes from pathogens such as HIV, Hepatitis C and other infections that require CTLs to clear latent infections may be used, although it is preferred if the epitope is a "self-epitope", i.e. associated with a condition/disorder associated with cell proliferation such as cancer. Preferably, the T cell epitope is such that the heavy chain or antibody cannot fold correctly and be secreted. It is therefore preferred if the inserted epitopes are of not of similar size and amino acid composition to the original variable region. The nucleic acid may have a plurality of different T cell epitopes so as to generate a wide variety of T cell responses. The nucleic acid may incorporate multiple epitopes from a single antigen, thereby ensuring that the majority of individuals with different HLA types respond to the single vaccine. Alternatively, multiple T cell epitopes from multiple antigens targeting a restricted spectrum of HLA types could be used. The nucleic acid molecules of the invention may include a variety of antigens from a single pathogen or cancer type or they could include disparate antigens targeting a wide range of solid tumours or pathogens. The nucleic acid molecules of the invention may even be designed to target different cell populations within a tumour, such as tumour epithelial and endothelial antigens.

Surprisingly the inventors have found that, when T cell epitopes were inserted into structurally confined CDRs or non-CDR regions of the heavy chain, they gave superior CTL responses. This appears to be due to secretion of large amounts of heavy chain, which can only weakly associate with light chain due to the insertion of bulky epitopes into their variable regions. This is contrary to dogma, which states "that only proteins synthesised endogenously by antigen presenting cells are presented on MHC class I molecules and recognised by CTLs"—WO 96/19584. Uptake of exogenous antigen and presentation on MHC class I is a process known as cross presentation and usually requires uptake via specific receptors. This could be the CD64 receptor for human Fcγ1 antibodies. However, it would be predicted that large amounts of intact antibody or antigen-antibody complexes would be better at targeting this receptor. In contrast, the results presented herein clearly show very low levels of intact antibody and large amounts of free heavy chain, which should not bind to CD64, give superior CTL responses. Indeed, it is shown herein that CTL responses can be stimulated when CTL epitopes are inserted in antibodies which cannot bind to CD64, such as IgG2 antibodies or IgG1 molecules with their CD64 binding region replaced with the non-CD64 binding region from IgG2.

The nucleic acid encoding the heavy chain preferably includes a leader sequence to allow it to be secreted. The present inventors have found that, if the leader sequence of the heavy chain is removed to prevent secretion and allow more endogenous protein to be produced, this reduces the CTL response. This is completely contrary to expectations. Whilst not wishing to be bound by theory, the inventors believe that this implies that the nucleic acid is expressed in non-antigen presenting cells, which secrete high levels of heavy chain and low amounts of native protein which can then be taken up by antigen presenting cells. Alternatively, the nucleic acid may directly transfect antigen presenting cells which migrate to the draining lymph node where they secrete low amounts of native protein and large amounts of heavy chain that is taken up by the same or adjacent antigen presenting cells and presented on MHC class Ito naïve CTLs. Therefore, for a nucleic acid vaccine to stimulate efficient CTL responses, it must preferably encode CTL epitopes within a protein that is secreted at very low levels and/or at the same time secretes large amounts of denatured protein. However, a CTL response cannot mature to a high affinity memory response in the absence of helper responses. Therefore, it is preferred if T helper epitopes are inserted into the heavy chain or the immunoglobulin molecule, preferably into the variable region of antibody light chains. Again, surprisingly and in contrast to the dogma which states "only proteins taken up exogenously by the target cells are presented by MHC class II molecules and recognised by helper T cells", light chain was only secreted in very low amounts. Removal of the leader sequence to prevent secretion of the light chain had no effect on the helper responses. Accordingly, the nucleic acid of the present invention may or may not have a leader sequence for the light chain of the antibody. These results imply that the nucleic acid is taken up by the antigen presenting cells which present the T helper epitopes in the context of MHC class II from endogenously-synthesised protein, possibly by autophagy. For helper T cells to assist CTL responses, both the T cell epitopes they recognise must be presented on the same antigen presenting cells in a process known as linked T cell help. This implies that the antigen presenting cell synthesising the light chain, encoded by the nucleic acid, must either also synthesise, secrete and cross present the CTL epitopes themselves or take up heavy chain from an adjacent APC.

The present invention also provides isolated dendritic cells which present the heterologous helper T cell epitopes on MHC class II from endogenously-produced light chain and heterologous CTL epitopes from cross-presented heavy chain. Such dendritic cells may be used in the therapies described herein.

Nucleic acids of the present invention can make existing T cell epitopes more immunogenic by encoding a denatured antibody which leads to an increase in both the frequency and avidity of T cell responses.

The nucleic acid of the invention may be DNA, cDNA, or RNA such as mRNA, obtained by cloning or produced wholly or partly by chemical synthesis. For therapeutic use, the nucleic acid is preferably in a form capable of being expressed in the subject to be treated.

The nucleic acid of the present invention may be recombinant or provided as an isolate, in isolated and/or purified form. It may be free or substantially free of nucleic acid flanking the gene in the human genome, except possibly one or more regulatory sequence(s) for expression. Where nucleic acid according to the invention includes RNA, reference to the sequences shown herein should be construed as reference to the RNA equivalent, with U substituted for T.

Nucleic acids of the present invention can be readily prepared by the skilled person, for example using the information and references contained herein and techniques known in the art (for example, see Sambrook, Fritsch and Maniatis, "Molecular Cloning", A Laboratory Manual, Cold Spring Harbor Laboratory Press, 1989, and Ausubel et al, Short Protocols in Molecular Biology, John Wiley and Sons, 1992), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding the polypeptide may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

In order to obtain expression of the nucleic acid sequences, the sequences can be incorporated into a vector having one or more control sequences operably linked to the nucleic acid to control its expression. The vectors may include other sequences such as promoters or enhancers to drive the expression of the inserted nucleic acid, nucleic acid sequences so that the polypeptide is produced as a fusion and/or nucleic acid encoding secretion signals so that the polypeptide produced in the host cell is secreted from the cell. If desired, polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of *E. coli*, yeast, and eukaryotic cells such as insect cells, and animal cells, for example, COS, CHO cells, Bowes Melanoma and other suitable human cells. Where the present invention relates to nucleic acid(s) encoding the heavy and light chains of an antibody, the respective nucleic acids may be present in the same expression vector, driven by the same or different promoters, or in separate expression vectors.

The nucleic acids of the present invention may be used to stimulate an immune response against at least one of the T cell epitope(s) in a patient such as a mammal, including human. Helper and/or cytotoxic T cell responses may be stimulated. The T cell response against a particular epitope obtained by the present invention may have a higher avidity than that obtained by immunisation with the same epitope as a simple peptide, or by immunisation with the same epitope encoded within an antigen either as a peptide or a nucleic acid. The nucleic acids of the invention may be administered as a combination therapy, i.e., a nucleic acid encoding the light chain and nucleic acid encoding the heavy chain. The nucleic acid may be administered intravenously, intradermally, intramuscularly, orally or by other routes. Intradermal or intramuscular administration is preferred because these tissues contain dendritic cells.

As used herein, the term "treatment" includes any regime that can benefit a human or non-human animal. The treatment may be of an inherited or acquired disease. Preferably, the treatment is of a condition/disorder associated with cell proliferation such as cancer or of infectious disease. Examples of types of cancer that can be treated with the nucleic acid include any solid tumour, colorectal cancer, lung, breast, gastric, ovarian, uterine, liver, kidney, pancreatic, melanoma, bladder, head and neck, brain, oesophageal, pancreatic, and bone tumours, as well as soft tissue cancers, and leukaemias. Examples of infectious diseases that can be treated with the nucleic acid include infection with HIV, Hepatitis C, or any chronic infection that requires T cell immunity for clearance.

The nucleic acid may be employed in combination with a pharmaceutically acceptable carrier or carriers. Such carriers may include, but are not limited to, saline, buffered saline, dextrose, liposomes, water, glycerol, ethanol and combinations thereof.

Adjuvants may be employed to facilitate stimulation of the host's immune response, and may include, aluminium hydroxide, lysolecithin, pluronic, polyols, polyanions, peptides, proteins and oil emulsions.

The nucleic acids useful in the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. intradermal, oral, intravenous, cutaneous or subcutaneous, nasal, intramuscular, intraperitoneal routes. The formulation is preferably nucleic acid as a stable dry powder precipitated onto the surface of microscopic gold particles and suitable for injection via a gene gun. The formulation may be suitable for intradermal or intramuscular administration using electroporation.

The compositions comprising, or for the delivery of, nucleic acids are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. The nucleic acids of the invention are particularly relevant to the treatment of existing cancer and in the prevention of the recurrence of cancer after initial treatment or surgery. Examples of the techniques and protocols mentioned above can be found in Remington's Pharmaceutical Sciences, 16th edition, Oslo, A. (ed.), 1980.

Preferably, the nucleic acid of the invention stimulate helper and/or cytotoxic T cells that can significantly inhibit the growth of tumour cells when administered to a human in an effective amount. The optimal dose can be determined by physicians based on a number of parameters including, for example, age, sex, weight, severity of the condition being treated, the active ingredient being administered and the route of administration. For example, a dose of 1-1000 µg of DNA is sufficient to stimulate both helper and cytotoxic T cell responses.

The nucleic acids of the invention may be administered along with additional pharmaceutically acceptable ingredients. Such ingredients include, for example, immune system stimulators.

A composition may be administered alone or in combination with other treatments, either simultaneously or sequentially dependent upon the condition to be treated. Other cancer treatments include other monoclonal antibodies, other chemotherapeutic agents, other radiotherapy techniques or other immunotherapy known in the art. One particular application of the compositions of the invention are as an adjunct to surgery, i.e., to help to reduce the risk of cancer reoccurring after a tumour is removed.

Injections (id) may be the primary route for therapeutic administration of the nucleic acid of this invention.

The nucleic acids may be administered in a localised manner to a tumour site or other desired site or may be delivered in a manner in which it targets tumour or other cells.

The dose of nucleic acid will be dependent upon the properties of the agent employed, e.g. its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 100 µg of nucleic acid per patient per administration are preferred, although dosages may range from about 10 µg to 1 mg per dose. Different dosages are utilised during a series of sequential inoculations; the practitioner may administer an initial inoculation and then boost with relatively smaller doses of nucleic acid.

In certain other embodiments, the present invention relates to a method of engineering T cell epitopes from target antigens into the variable regions of antibodies, and the use of such engineered antibodies as vaccines to stimulate both helper and cytotoxic T cell responses.

A further aspect of the present invention provides a host cell containing a nucleic acid as disclosed herein. The nucleic acid of the invention may be integrated into the genome (e.g. chromosome) of the host cell. Integration may be promoted by inclusion of sequences that promote recombination with the genome in accordance with standard techniques. The nucleic acid may be on an extra-chromosomal vector within the cell, or otherwise identifiably heterologous or foreign to the cell.

A still further aspect provides a method, which comprises introducing the nucleic acid of the invention into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

The present inventon also provides a method for identifying T cell epitopes in a candidate antigen, comprising:
  depleting T regulatory cells in a non-human animal;
  immunising the non-human animal with a candidate antigen; and
  screening to see whether a T cell response is raised against either peptides to predicted epitopes in the candidate antigen or all the possible overlapping peptides within the candidate antigen.

The method may be carried out in a non-human animal, such as a mouse or a rat. T regulatory cells can be depleted in the non-human animal using anti-CD25 antibodies, which optionally may be conjugated with toxins such as Ontak, or by chemotherapy such as cyclophosphamide which preferentially kills T regulatory cells. Once T regulatory cells have been depleted, the non-human animal may be immunised with DNA encoding the candidate antigen, or by the candidate antigen itself. It is preferred that the candidate antigen is provided as an antigen-Fc fusion protein. In the screening step, the peptide against which any T cell response stimulated in the non-human animal is identified. This can be done in vitro using a technique such as ELISPOT. If a T cell response is elicited to a candidate epitope, this epitope can be used to immunise a non-human animal. If this peptide elicits a T cell response, the avidity and frequency can be enhanced by encoding the epitope within a nucleic acid in accordance with the present invention. This method can allow the identification of T cell epitopes that are processed by the immunoproteosome.

Preferred features of each aspect of the invention are as for each of the other aspects mutatis mutandis. The prior art documents mentioned herein are incorporated to the fullest extent permitted by law.

The invention will now be described further in the following non-limiting examples.

EXAMPLES

Methods
Generation of DNA Vectors

The deimmunised murine heavy and light variable regions of SC100 clone VHd VKb (WO01/88138) within the vectors pSVgptHuigG1 and pSVhygHuCk (Biovation Ltd) were amplified by PCR. $V_H$ and $V_L$ region PCR products were cloned in frame with the human IgG1 and kappa constant regions using HindIII/AfeI and BamHI/BsiWI sites to produce the single chain constructs pOrigHIB and pOrigLIB (see FIGS. 1 and 2). The sequence of the full-length chimeric heavy and kappa chain was confirmed by the dideoxy chain termination method (Sanger et al, *Proceedings of the National Academy of Sciences of the United States of America* 1977; 74: 5463-7). DNA and translated protein sequences for the chimeric heavy and light chain are shown in FIGS. 3 and 4 respectively. Locations of the complementarily determining regions (CDR's) are depicted.

With exception of the heavy CDR2 region that retains six amino acids, the CDRs of the heavy and light chains were completely removed and exchanged for unique restriction enzyme sites. This was achieved by careful examination of the regions either side of the sequence for a removal that will permit a restriction enzyme site to be generated. These unique restriction sites are used to open up the DNA such that an oligonucleotide encoding an antigenic epitope can be inserted. Most framework sequence that is lost on generation of the restriction site is replaced by including in the epitope primers to ensure that, on translation, amino acids are retained and that the sequence remains in frame. Table 1 lists chosen enzyme sites and epitope oligonucleotide sequences for all CDRs.

CDR regions were removed and replaced with unique restriction sites by Overlap Extension PCR as shown in FIG. 5. For the heavy variable region, the oligonucleotides H1, H2 and H3 (see Table 2) were designed to replace each of the three CDR's. Each specific primer contains 10-20 bp of sequence either side of the enzyme site to be incorporated. Used in conjunction with the general reverse primer huHeClonR (see Table 2) that binds to the human IgG1 constant region first round PCR's were set up consisting of $1_i$ µl of the template plasmid pOrigHIB, 2 µl dNTPS (2.5 mM), 5 µl 10×taq polymerase buffer, 1 µl of forward and reverse primer (25 pmols), 5 units of taq polymerase (New England Biolabs) made up to a final volume of 50 µl with sterile distilled water. Reactions were subjected to an initial denaturation of 5 minutes at 95° C. followed by 35 cycles of 30 s at 95° C., 1 minute at 55° C. (annealing) and 1 minutes at 72° C. (extension). The final cycle contained a 10 minute extension using a Techne PHC-1 programmable cyclic reactor. Similarly, for the light variable region, the oligonucleotides L1, L2, and L3 were designed to replace each of the three CDR's (see Table 2). First round PCR's were set up as described above but with the reverse primer huLiClonR (see Table 2) that binds to the constant region of the human kappa chain and the template pOrigLIB.

TABLE 1

List of CDR replacement enzymes and epitope oligonucleotide sequences

| CDR | RE site | Epitope Oligo |
|---|---|---|
| H1 | Fsp I | 5'NNNNNNNTGGGTTCG3' (SEQ ID NO: 16) 3'NNNNNNACCCAAGC5' |
| H2 | Msc I | 5'TNNNNNNNCGATTCA3' (SEQ ID NO: 17) 3'ANNNNNNGCTAAGT5' |
| H3 | Srf I | 5'GANNNNNNTG3' (SEQ ID NO: 18) 3'CTNNNNNNAC5' |

TABLE 1-continued

List of CDR replacement enzymes and epitope oligonucleotide sequences

| CDR | RE site | Epitope Oligo |
|---|---|---|
| L1 | Eco RV | 5'CTCTTGCNNNNNNNTGGT3' (SEQ ID NO: 19) 3'GAGAACGNNNNNNACCA5' |
| L2 | Ssp I | 5'CTACNNNNNNAG3' (SEQ ID NO: 20) 3'GATGNNNNNNTC5' |
| L3 | Hpa I | 5'TATTACTGCNNNNNNNTTCGGTGGAGG3' (SEQ ID NO: 21) 'ATAATGACGNNNNNNAAGCCACCTCC5' |

N represents epitope DNA sequence
The remaining letters represent framework nucleotides that need to be incorporated 1 µl of the resulting PCR products was then used in a subsequent PCR as a reverse primer in conjunction with the CMV forward primer set up as outlined above. The 450 bp amplified DNA fragment was cloned directly into the TA TOPO vector pCR2.1 (Invitrogen) and clones sequenced to confirm amplification of the $V_H$ and $V_L$ region devoid of the CDRs and replacement of restriction site.

CDR's within the variable heavy and light have been replaced with their corresponding enzyme site H1, H2, H3, L1, L2 and L3 singly, in combination and altogether (FIGS. 6 and 7). The different versions were then inserted into pOrig HIB and pOrigLIB using HindIII/AfeI and BamHI/BsiWI with direct replacement of the parental wild type deimmunised SC100 $V_H$ and $V_L$ regions. This allows generation of molecules containing single or multiple epitopes (from the same or different antigens).

TABLE 2

Primers

| Oligonucleotide | Sequence |
|---|---|
| H1 | FspI<br>5'-CCT GAG AAT GTC CTG CTG CGC AGG CTC CGG GGA AG-3' (SEQ ID NO: 22) |
| H2 | MscI<br>5'-CAT TGG TAG TGG TGG CCA TTT CCA GAG AC-3' (SEQ ID NO: 23) |
| H3 | SrfI<br>5'-CCG TGT ATT ACT GTG CCC GGG CCA AGG AAC CAC GGT C-3' (SEQ ID NO: 24) |
| L1 | EcoRV<br>5'-GGA GCC AGC CTC GAT ATC TGC AGA AAC CAG GC-3' (SEQ ID NO: 25) |
| L2 | SspI<br>5'-CCA CAG CTC CTA ATA TTC AGT GGC AGT GGA TC-3' (SEQ ID NO: 26) |
| L3 | HpaI<br>5'-GCT GAG GAT ACC GGA GTT AAC CAA GGT GGA AAT C-3' (SEQ ID NO: 27) |
| huHeClonR | 5'-CGC CTG AGT TCC ACG ACA CC-3' (SEQ ID NO: 28) |
| huLiClonR | 5'-CAG GCA CAC AAC AGA GGC-3' (SEQ ID NO: 29) |

TABLE 2-continued

Primers

| Oligonucleotide | Sequence |
|---|---|
| CMV Forward | 5'-GGC GTG GAT AGC GGT TTG AC-3' (SEQ ID NO: 30) |
| OrigstophuHeCH1 For | 5'-CCA AGG TGG ACA AGA AAG TTT GAC CCA AAT CTT GTG ACA (SEQ ID NO: 31) |
| OrigstophuHeCH1 Rev | 5'-GAG TTT TGT CAC AAG ATT GGG TC AAA CTT TCT TGT CCA CCT TGG-3' (SEQ ID NO: 32) |
| pOrig light no leader For | 5'-AGG ATC CAC CAT GGA TGT GTT GAT GAC CC-3' (SEQ ID NO: 33) |
| pOrig heavy no leader For | 5'-AAA GCT TAT GCA GGT GCA GCT GGT G-3' (SEQ ID NO: 34) |
| huigG3rev2 | 5'-ATC CAT ATC ATT TAC CCG GAG ACA GG-3' (SEQ ID NO: 35) |
| IgG3hufor2 | 5'-ACT GTC TCC AGC GCT TCC ACC AAG-3' (SEQ ID NO: 36) |
| IgG2 for | 5'-AGT CAC CGT TTC CAG CGC TTC CAC-3' (SEQ ID NO: 37) |
| IgG2 rev | 5'-AGT GGA TAT CAT TTA CCC GGA GAC AGG-3' (SEQ ID NO: 38) |
| HIBF | 5'-AAC AGT CTG AGG GCT GAG GA-3' (SEQ ID NO: 39) |
| huigG1PVA REV | 5'-A GAC TGA CGG TCC CCC CGC GAC TGG AGG TGC TGG-3' (SEQ ID NO: 40) |
| HuigG2ELLGRev | 5'-A GAC TGA CGG TCC TCC TAA CAG TTC TGG TGC TGG-3' (SEQ ID NO: 41) |
| SV40premFOR | 5'-A GCT AGC ATC AGC ACG TGT TGA CAA TTA ATC ATC-3' (SEQ ID NO: 42) |
| SV40premREV | 5'-AAC GAT TCC GAA GCC AAA CCT TTC ATA G-3' (SEQ ID NO: 43) |
| migG2aC1AfeiF2 | 5'-TTT ACA GCG CTA AAA CAA CAG CCC CAT CGG TC-3' (SEQ ID NO: 44) |
| migG2aXbaRA | 5'-TCT AGA TCA TTT ACC CGG AGT CCG GGA GAA GCT C-3' (SEQ ID NO: 45) |
| MoLC1BsiF1 | 5'-TTT CGT ACG GAT GCT GCA CCA ACT GTA TCC-3' (SEQ ID NO: 46) |
| MoLCXhoR1 | 5'-TTT CTC GAG TCA ACA CTC ATT CCT GTT GAA GC-3' (SEQ ID NO: 47) |
| MoIgG2BamHI For | 5'-CC TTG ACC TGG AAC TCT GGT TCC CTG TCC AGT GGT G-3' (SEQ ID NO: 48) |
| MoigG2BamHI Rev | 5'-C ACC ACT GGA CAG GGA ACC AGA GTT CCA GGT CAA GG-3' (SEQ ID NO: 49) |
| MoigG2XhoI For | 5'-GC AGC TCA GTG ACT GTA ACT TCG AGC ACC TGG CCC AGC-3' (SEQ ID NO: 50) |
| MoigG2XhoI Rev | 5'-GCT GGG CCA GGT GCT CGA AGT TAC AGT CAC TGA GCT GC-3' (SEQ ID NO: 51) |
| wtkappavarL1for | 5'-C TCT TGC AGA TCT AGT CAG AGC CTG GTA CAT AGT AAT GGA AAC ACC TAT TTA GAA TGG T-3' (SEQ ID NO: 52) |
| wtkappavarL1rev | 5'-A CCA TTC TAA ATA GGT GTT TCC ATT ACT ATG TAC CAG GCT CTG ACT AGA TCT GCA AGA G-3' (SEQ ID NO: 53) |
| Murine TRP2 Forward | 5'-TTT CTA AGC TTA TGG GCC TTG TGG GAT GGG GGC TTC-3' (SEQ ID NO: 54) |
| Murine TRP2 Reverse | 5'-TTT CTG ATA TCT CAG CT TCC TCC GTG TAT CTC TTG C-3' (SEQ ID NO: 55) |
| GP100 Forward | 5'-TTT CTG ATA TCA TGG GTG TCC AGA GAA GGA GCT TC-3' (SEQ ID NO: 56) |
| Gp100 Reverse | 5'-TTT CTC TCG AGT CAG ACC TGC TGT CCA CTG AGG AGC-3' (SEQ ID NO: 57) |

Insertion of Antigenic Epitopes into CDR Sites of Single Chain Vectors

A number of CD8 CTL and CD4 helper epitopes are listed in Table 3, although any epitope can easily be inserted into any of the sites within the single chain vectors. For example, insertion of the TRP2 epitope into the H2 site of the pOrigHIB vector was achieved as follows.

Complementary oligonucleotides were designed to encode nucleotide sequence that on translation expresses the epitope. DNA sequence that encodes the epitope was flanked by the corresponding CDR nucleotides to ensure that, on translation, amino acids were retained and that the sequence remained in frame (see Table 1). Primers were sent for synthesis (MWG) and 5' end phosphorylated.

```
                      S   V   Y   D  F   F   V
5'-Phosphorylated-T AGT GTT TAT GAT TTT TTT GTG
W   L
TGG CTC CGA TTC A-3' (SEQ ID NO: 58)

3'-A TCA CAA ATA CTA AAA AAA CAC ACC GAG GCT AAG
T-Phosphorylated-5'
```

Complementary oligonucleotides were resuspended to a final concentration of 1 mg/ml in sterile double distilled water and annealed together by setting up a reaction with 10 µl of each primer made up to a final volume of 50 µl with TE buffer. The reaction was cycled for 95° C.-5 mins (0.1° C./sec), 72° C.-20 mins 0.1° C./sec, 55° C.-20 mins then held at 4° C.

For insertion into the H2 site, the vector pOrigHIB H2 and/or pOrigHIB H1H2 was linearised by setting up a MscI restriction digest (dependent on CDR to be utilised for insertion of epitope) and incubated overnight at 37° C. The digest was electrophoresed on a 1.5% agarose gel and the cut vector purified by gel extraction. To prevent self ligation of the linearised vector, phosphate groups from the 5' ends of the vector were removed by treatment and overnight incubation at 37° C. with calf intestinal alkaline phosphatase (CIAP) 5 units, 10 µl 10×NEB buffer 3 made up to a final volume of 100 µl with sterile distilled water. Dephosphorylated vector was purified and ligations set up with neat, 1/100 and 1/200 dilutions of the annealed oligonucleotides to clone directly into the H2 site using standard techniques. Epitope insertions were confirmed by sequencing within the single vectors using the universal primer CMV forward.

TABLE 3

CTL and helper epitopes

| PROTEIN | CO-ORDINATES | SEQUENCE | HLA RESTRICTION |
|---|---|---|---|
| TRP2 | 180-188 | SVYDFFVWL (SEQ ID NO: 9) | A2, Kb |
| | | agtgtttatgattttttttgtgtggctc (SEQ ID NO: 59) | |
| GP100 | 209-217 | ITDQVPFSV (SEQ ID NO: 7) | A2 |
| | | accattactgaccaggtgcctttctccgtg (SEQ ID NO: 60) | |
| GP100 (210M) | 209-217(M) | IMDQVPFSV (SEQ ID NO: 5) | A2 |
| | | accattatggaccaggtgcctttctccgtg (SEQ ID NO: 61) | |
| GP100 (F7L) | 209-217 | ITDQVPLSV (SEQ ID NO: 63) | A2 |
| | | accattactgaccaggtgcctttgtccgtg (SEQ ID NO: 62) | |
| GP100 | 44-59 | WNRQLYPEWTEAQRLD (SEQ ID NO: 15) | DR0401 |
| | | tggaacaggcagctgtatccagagtggacagaagcccagagacttgac (SEQ ID NO: 64) | |
| HEPB S AG | 28-39 | IPQSLDSWWTSL (SEQ ID NO: 6) | Kd (CTL) |
| | | ataccgcagagtctagactcgtggtggacttctctc (SEQ ID NO: 65) | |
| HepB nucleoprotein | 128-140 | TPPAYRPPNAPIL (SEQ ID NO: 14) | I-Ab (helper) |
| | | actcctccagcttatagaccaccaaatgcccctatccta (SEQ ID NO: 66) | |
| MAGE3 | 271-279 | FLWGPRALV (SEQ ID NO: 68) | A2 |
| | | ttcctgtggggtccaagggccctcgtt (SEQ ID NO: 67) | |
| Tie2 (Z83) | 124-132 | FLPATLTMT (SEQ ID NO: 70) | A2 |
| | | ttcctaccagctactttaactatgact (SEQ ID NO: 69) | |
| Tie2 (Z84) | 124-132 | FLPATLTMV (SEQ ID NO: 2) | A2 |
| | | ttcctaccagctactttaactatggtt (SEQ ID NO: 71) | |
| Tie2 (Z9) | 431-439 | GMVEKPFNI (SEQ ID NO: 73) | A2 |
| | | gggatggtggaaaagccttcaacatt (SEQ ID NO: 72) | |
| Tie2 (mZ9) | 431-439 | GMVEKPFNV (SEQ ID NO: 75) | A2 |
| | | gggatggtggaaaagcccttcaacgtt (SEQ ID NO: 74) | |
| FLU HA | 111-120 | FERFEIFPKE (SEQ ID NO: 1) | I-Ad (helper) |
| | | tttgaaaggtttgagatattccccaaggaa (SEQ ID NO: 76) | |
| ovalbumin | 258-265 | SIINFEKL (SEQ ID NO: 8) | Kb |
| | | agtataatcaactttgaaaaactg (SEQ ID NO: 77) | |

TABLE 3-continued

CTL and helper epitopes

| PROTEIN | CO-ORDINATES | SEQUENCE | HLA RESTRICTION |
|---|---|---|---|
| Triosephosphate isomerase (wt) | 23-37 | GELIGTLNAAKVPAD (SEQ ID NO: 79) | DR0101 |
| | | ggggagctcatcggcattctgaacgcggcca aggtgccggccgac (SEQ ID NO: 78) | |
| Triosephosphate Isomerase (mI) | 23-37 | GELIGILNAAKVPAD (SEQ ID NO: 81) | DR0101 |
| | | ggggagctcatcggcactctgaacgcggcca aggtgccggccgac (SEQ ID NO: 80) | |
| VEGFR2 | 773-781 | VIAMFFWLL (SEQ ID NO: 83) | A2 |
| | | gtgattgccatgttcttctggctactt (SEQ ID NO: 82) | |
| mVEGFR2 | 773-781 | VLAMFFWLL (SEQ ID NO: 85) | A2 |
| | | gtgcttgccatggttcttctggctactt (SEQ ID NO: 84) | |

Transfer into the Double Expression Vector pDCOrig

Once all epitopes have been incorporated into the $V_H$ and $V_L$ sites within the single vectors, they are transferred into the double expression vector pDCOrig using HindIII/AfeI and BamHI/BsiWI in frame with their respective human constant regions.

To generate the ImmunoBody™ double expression vector pDCOrig, pOrigHIB was linearised using the blunt ended restriction endonuclease NruI located adjacent to the CMV promoter. pOrigLIB was digested with the blunt ended NruI and HpaI endonucleases to excise the entire light chain expression cassette consisting of the CMV promoter, deimmunised human kappa chain and the BGH polyA signal. After gel electrophoresis, isolation and gel extraction of the linerised vector pOrigHIB and the light chain expression cassette the vector was dephosphorylated and light chain expression cassette ligated to form the construct pDCOrig (FIG. 8). Orientation of the light chain cassette within pDC-Orig was confirmed by restriction analysis.

pDCOrig contains both the heavy and light chain gene coding sequences combined within the same construct, eliminating intronic sequences and the two vector system. Expression is driven by the high level CMV Immediate Early promoters and other DNA control elements, such as Bovine Growth Hormone polyadenylation signal. The selection marker Zeocin has also been included to maximise expression and efficiency of production. Careful design of this vector has retained the unique restriction enzyme sites at the junctions of the variable and constant regions and provides a quick and easy method to create different combinations of the variable regions (epitope insertions, see FIG. 8). Table 4 lists some of the pDcOrig IB constructs generated.

TABLE 4 pDCOrig constructs

| | H1 | H2 | H3 | L1 | L3 |
|---|---|---|---|---|---|
| DCIB15 | Gp100 210M TIMDQVPFSV (SEQ ID NO: 248) | TRP2 SVYDFFVWL (SEQ ID NO:9) | | HepB nucleoprotein TPPAYRPPNAPIL (SEQ ID NO: 14) | |
| DCIB17 | Gp100 210M TIMDQVPFSV (SEQ ID NO: 248) | | | HepB nucleoprotein TPPAYRPPNAPIL (SEQ ID NO: 14) | |
| DCIB18 | | TRP2 SVYDFFVWL (SEQ ID NO: 9) | | HepB nucleoprotein TPPAYRPPNAPIL (SEQ ID NO: 14) | |
| DCIB21 | | HepB S Ag IPQSLDSWWTSL (SEQ ID NO: 6) | | Flu HA FERFEIFPKE (SEQ ID NO: 1) | |
| DCIB24 | | OVALBUMIN SIINFEKL (SEQ ID NO: 8) | | HepB nucleoprotein TPPAYRPPNAPIL (SEQ ID NO: 14) | |

TABLE 4-continued pDCOrig constructs

| | H1 | H2 | H3 | L1 | L3 |
|---|---|---|---|---|---|
| DCIB25 | Gp100 210M TIMDQVPFSV (SEQ ID NO: 248) | TRP2 SVYDFFVWL (SEQ ID NO: 9) | | | HepB nucleoprotein TPPAYRPPNAPIL (SEQ ID NO: 14) |
| DCIB26 | Tie-2 Z84 FLPATLTMV (SEQ ID NO: 2) | | | HepB nucleoprotein TPPAYRPPNAPIL (SEQ ID NO: 14) | |
| DCIB30 | Gp100 F7L TITDQVPLSV (SEQ ID NO: 12) | TRP2 SVYDFFVWL (SEQ ID NO: 9) | | HepB nucleoprotein TPPAYRPPNAPIL (SEQ ID NO: 14) | |
| DCIB31 | | | TRP2 SVYDFFVWL (SEQ ID NO: 9) | | |
| DCIB32 | | | TRP2 SVYDFFVWL (SEQ ID NO: 9) | | HepB nucleoprotein TPPAYRPPNAPIL (SEQ ID NO: 14) |
| DCIB33 huIgG2 | Gp100 210M TIMDQVPFSV (SEQ ID NO: 248) | TRP2 SVYDFFVWL (SEQ ID NO: 9) | | HepB nucleoprotein TPPAYRPPNAPIL (SEQ ID NO: 14) | |
| DCIB35 | Gp100 210M TIMDQVPFSV (SEQ ID NO: 248) | TRP2 SVYDFFVWL (SEQ ID NO: 9) | | Gp100 WNRQLYPEWTEAQRLD (SEQ ID NO: 15) | |
| DCIB36 | | | | | TRP2 SVYDFFVWL (SEQ ID NO: 9) |
| DCIB37 | Gp100 F7L TITDQVPLSV (SEQ ID NO: 12) | | | HepB nucleoprotein TPPAYRPPNAPIL (SEQ ID NO: 14) | |
| DCIB40 | Gp100 F7I TITDQVPISV (SEQ ID NO: 11) | | | HepB nucleoprotein TPPAYRPPNAPIL (SEQ ID NO: 14) | |
| DCIB41 | Gp100 wt TITDQVPFSV (SEQ ID NO: 15) | | | HepB nucleoprotein TPPAYRPPNAPIL (SEQ ID NO: 14) | |
| DCIB42 | Gp100 F7Y TITDQVPYSV (SEQ ID NO: 13) | | | HepB nucleoprotein TPPAYRPPNAPIL (SEQ ID NO: 14) | |
| DCIB43 | Gp100 V5L TITDQLPFSV (SEQ ID NO: 10) | | | HepB nucleoprotein TPPAYRPPNAPIL (SEQ ID NO: 14) | |
| DCIB48 | | TRP2 SVYDFFVWL (SEQ ID NO: 9) | Gp100 WNRQLYPEWTEAQRLD (SEQ ID NO: 15) | | |
| DCIB49 | | | HepB nucleoprotein TPPAYRPPNAPIL (SEQ ID NO: 14) | | |
| DCIB50 | Gp100 210M TIMDQVPFSV (SEQ ID NO: 248) | TRP2 SVYDFFVWL (SEQ ID NO: 9) | | | Gp100 WNRQLYPEW TEAQRLD (SEQ ID NO: 15) |
| DCIB52 | | TRP2 SVYDFFVWL (SEQ ID NO: 9) | HepB nucleoprotein TPPAYRPPNAPIL (SEQ ID NO: 14) | | |
| DCIB53 MoIgG2a | Gp100 210M TIMDQVPFSV (SEQ ID NO: 248) | TRP2 SVYDFFVWL (SEQ ID NO: 9) | | HepB nucleoprotein TPPAYRPPNAPIL (SEQ ID NO: 15) | |

TABLE 4-continued pDCOrig constructs

| | H1 | H2 | H3 | L1 | L3 |
|---|---|---|---|---|---|
| DCIB54 | Gp100<br>GTGRAMLGTHTM<br>EVTVYH<br>(SEQ ID NO: 3) | TRP2<br>SVYDFFVWL<br>(SEQ ID NO: 9) | Gp100<br>WNRQLYPEWTEAQRLD<br>(SEQ ID NO: 15) | | |
| DCIB64<br>MoigG2a | Gp100<br>GTGRAMLGTHTM<br>EVTVYH<br>(SEQ ID NO: 3) | TRP2<br>SVYDFFVWL<br>(SEQ ID NO: 9) | Gp100<br>WNRQLYPEWTEAQRLD<br>(SEQ ID NO: 15) | | |
| DCIB65<br>huigG3 | Gp100 210M<br>TIMDQVPFSV<br>(SEQ ID NO: 248) | TRP2<br>SVYDFFVWL<br>(SEQ ID NO: 9) | | HepB nucleoprotein<br>TPPAYRPPNAPIL<br>(SEQ ID NO: 14) | |
| DCIB66<br>huigG1 +<br>G2 motif | Gp100 210M<br>TIMDQVPFSV<br>(SEQ ID NO: 248) | TRP2<br>SVYDFFVWL<br>(SEQ ID NO: 9) | | HepB nucleoprotein<br>TPPAYRPPNAPIL<br>(SEQ ID NO: 14) | |
| DCIB67<br>huigG2 +<br>G1 motif | Gp100 210M<br>TIMDQVPFSV<br>(SEQ ID NO: 248) | TRP2<br>SVYDFFVWL<br>(SEQ ID NO: 9) | | HepB nucleoprotein<br>TPPAYRPPNAPIL<br>(SEQ ID NO: 14) | |
| DCIB68 | Gp100<br>GTGRAMLGTHTM<br>EVTVYH<br>(SEQ ID NO: 3) | TRP2<br>SVYDFFVWL<br>(SEQ ID NO: 9) | Gp100<br>WNRQLYPEWTEAQRLD<br>(SEQ ID NO: 15) | Gp100<br>WNRQLYPEWTEAQRLD<br>(SEQ ID NO: 15) | Gp100<br>GTGRAMLGTHTM<br>EVTVYH<br>(SEQ ID NO: 3) |
| DCIB69<br>MoigG2a | Gp100<br>GTGRAMLGTHTM<br>EVTVYH<br>(SEQ ID NO: 3) | TRP2<br>SVYDFFVWL<br>(SEQ ID NO: 9) | Gp100<br>WNRQLYPEWTEAQRLD<br>(SEQ ID NO: 15) | Gp100<br>WNRQLYPEWTEAQRLD<br>(SEQ ID NO: 15) | Gp100<br>GTGRAMLGTHTM<br>EVTVYH<br>(SEQ ID NO: 3) |
| DCIB71 | Tie-2 Z12<br>ILINSLPLV<br>(SEQ ID NO: 4) | | | HepB nucleoprotein<br>TPPAYRPPNAPIL<br>(SEQ ID NO: 14) | |
| DCIB72 | | Tie-2 Z12<br>ILINSLPLV<br>(SEQ ID NO: 4) | | HepB nucleoprotein<br>TPPAYRPPNAPIL<br>(SEQ ID NO: 14) | |

Generation of pDcOrig IB15 CH1 Stop

A stop codon was incorporated after the CH1 domain of the human IgG1 constant region within the construct pDCOrig IB15 using the Quik change site directed mutagenesis kit (Stratagene) and the complementary oligonucleotides origstophuHeCH1 Forward and OrigstophuHeCH1 reverse primers (see Table 2) as instructed by the manufacturer. Incorporation of the stop codon was confirmed by DNA sequencing (FIG. 9).

Removal of Leader Sequences from pDCOrig IB15

In order to remove the leader sequence from the heavy and light chain of the vector pDCOrig IBIS, PCR's were set up using the template pDCOrig IBIS with the forward primers pOrig light no leader and pOrig heavy no leader in conjunction with the reverse primers huHeClonR and hiLiClonR respectively (Table 2). Amplified fragments were TA TOPO ligated into the vector pCR2.1 (Invitrogen) and clones confirmed by sequencing. Both the IB15 $V_H$ and $V_L$ regions devoid of leader were cloned back into pDCOrig IBIS using HindIII/AfeI and BamHI/BsiWI sites respectively. DNA sequence and translation for the $V_H$ and $V_L$ regions are shown in FIGS. 10 and 11 respectively.

Construction of Human IgG2 and IgG3 Isotypes of the Immunobody™ Double Expression Vector pDCOrig The human IgG3 constant region was amplified by PCR using huigg3 forward and reverse primers (Table 2) incorporating a AfeI and EcoRV respectively with the template pOTB7huigG3 (Image clone 4566267 MGC 45809). Similarly the human IgG2 constant region was amplified using IgG2For and IgG2Rev primers (Table 2) with the template pTOB7 huigG2 (Image clone 6281452 MGC 71314).

Both fragments were TOPO ligated into pCR2.1 and sequence confirmed (FIGS. 12 and 13). The huigG1 constant region within the construct pDCOrigIB15 was effectively replaced with both huigG2 and huigG3 cloned inframe with the heavy variable using AfeI and SapI sites to generate pDC-OrigIB15 huigG2 and pDCOrigIB15huigG3 (FIG. 14). Both the vectors retain the same unique restriction sites at the variable/constant region junction. This permits easy exchange of variable regions between all human isotype single and double chain Immunobody vectors.

Mutation of Human IgG1 Fcγ and Human IgG2 Receptor Binding Domain

To substitute the amino acids E233 L234 L235 of the huigG1 binding motif within the CH2 domain with P233 V234 A235 of huigG2, a short section was reamplified by PCR incorporating the mutation. The reverse primer huigG1PVA Rev containing the substitutions and the constitutive restriction site AhdI was utilised with the forward primer HIBF (Table 2) and the template pDCOrig IB15. The resulting fragment was ligated into the vector pCR2.1 (Invitrogen). After sequence confirmation, the wild type sequence was effectively replaced with the section containing the mutations by inserting into the single cutter AgeI/AhdI sites of the plasmid pDCOrig IB15 huigG1 (FIG. 15).

The amino acids P233 V234 A235 within the huigG2 constant domain of the construct pDCOrig IB15 huigG2 was also substituted with the huigG1 binding motif ELLG. As before, the reverse primer huigG2ELLGRev (Table 2) containing the substitutions and the constitutive restriction site AhdI was utilised with the forward primer HIBF and the template pDC-Orig IB15 human IgG2. The fragment was TA TOPO ligated into the vector pCR2.1. After sequence confirmation, the wild type sequence again was replaced with the section containing the huigG1 binding motif using AgeI/AhdI sites of the plasmid pDCOrig IB15 huigG2 (FIG. 16).

Generation of pDCOrig murine IgG2a plasmids DCIB53 and DCIB63 To construct a murine IgG2a version of the double expression vector pDCOrig, cDNA was synthesised from total RNA isolated from the hybridoma cell line 337. For amplification of the murine IgG2a constant region, the forward primer migG2aClAfeF2 containing the restriction site AfeI was used in conjunction with the reverse primer migG2aXbaRA harbouring a XbaI site after the stop codon. PCR fragment was TOPO ligated into the vector pCR2.1. After sequence confirmation, the murine IgG2a constant region was excised and cloned inframe with the murine heavy variable region into the AfeI/XbaI sites of the vector pOrigHIB effectively replacing human IgG1. A BamHI and XhoI site was removed without altering, on translation, amino acid sequence from the murine IgG2a constant region, sequentially by site directed mutagenesis using Quik change site directed mutagenesis kit (Stratagene) and the complimentary primers MoigG2BamHIFOR and REV, MoigG2XhoIFOR and REV respectively. This generated the single chain ImmunoBody vector pMoOrigHIB (FIG. 17A). A section of pMoOrigHIB containing the MoigG2a constant region was transferred from the single construct into the double expression vector pDCOrig IB15 inframe with the murine heavy variable region using AfeI and the single cutter AvrII located in the SV40 promoter to generate the intermediate vector pDCOrigIB15MoigG2a hukappa still containing a human kappa region.

For amplification of the murine kappa region, the cDNA was used as a template with the primers MoLC1BsiF1 containing a BsiWI site and MoLCXhoI incorporating a XhoI site after the stop codon. The amplified fragment was TOPO cloned into the vector pCR2.1 as before. The murine kappa region was excised and ligated into the ImmunoBody vector pOrigLIB L1 and pOrigLIB hepB help/L1 replacing the human kappa constant using BsiWI/XhoI generating the intermediate vector pMoLIBL1Bsi and pMoLIB HepB help/L1Bsi. The Immunobody system involves transfer of variable regions using a unique restriction site at the junction of the variable and constant regions while the junction between the murine heavy variable and moigG2a constant can accommodate an AfeI site (present within all the human immunobody vectors) and not alter amino acid sequence on translation, the region between the murine variable and kappa is problematic. On analysis of sequence at this junction no unique restriction site could be incorporated that would not alter amino acid sequence. The BsiWI site at the junction was removed to revert to wild type sequence. This was achieved by amplifying the entire murine full length chain by overlapping PCR. A first PCR was set up using the forward primer MoKappaSD-Mfor containing wild type sequence at the junction and flanking region effectively removing BsiWI, the BGH reverse primer and the intermediate light chain vectors pMoLIBL1Bsi and pMoLIB hepB help/L1Bsi as template respectively. Around a 430 bp amplified fragment from the first round of PCR was used as a reverse primer with the forward primer ImmunoLikozFor containing a BamHI site. The amplified full length murine kappa chains were TOPO ligated into pCR2.1 and sequence confirmed. The full length murine kappa chain containing hepB help in the L1 site in pCR2.1 was excised and cloned into the BamHI/XhoI sites of the intermediate double expression vector pDCOrigIB15MoigG2a hukappa replacing the human kappa chain to generate the murine double expression vector pDC-OrigIB GP100210m/H1 TRP2/H2 HepB help/L1 moIgG2a (DCIB 53, FIGS. 17 B and 54).

Similarly, the full length murine kappa chain containing an L1 site was excised and cloned into the BamHI/XhoI sites of the intermediate double expression vector pDCOrigIB15MoigG2a hukappa replacing the human kappa chain to generate the intermediate murine double expression vector pDCOrigIB15moIgG2a with an empty L1 site. To generate the construct with a wild type light variable region, the complimentary 5' phosphorylated primers wtkappavarL1for and rev (Table 2) were annealed and inserted into the L1 site after linearization with EcoRV as described above. Finally the heavy variable region from DCIB 54 containing GP100DR7/H1 TRP2/H2 and GP100DR4/H3 was transferred using HindIII/AfeI to generate pDCOrig GP100DR7/H1 TRP2/H2 GP100DR4/H3 moigG2a wild type kappa (DCIB68 FIGS. 17C and 60).

Removal of the Eukaryotic SV40 Promoter from the Immunobody Double Expression Vector pDCOrig for Regulatory DNA Vaccine Requirements The EM7 bacterial promoter and zeocin gene was amplified using the forward primer SV40PremFOR incorporating a NheI site and SV40remREV reverse primer (Table 2) with the template pOrigHIB. The resultant 511bp PCR fragment was pCR2.1 TOPO ligated and confirmed by sequencing. The EM7 promoter and a section of the zeocin gene was excised using NheI and FseI from pCR2.1 and cloned directly into pOrigHIB H1 effectively removing the SV40 promoter. The NheI site resides before the SV40 promoter while the FseI recognition sequence is a single cutter within the zeocin gene of the vector. After sequence confirmation a larger section was transferred from the single vector into the pDCOrig IB68 vector encoding the tail end of huigG1, BGH polyA, EM7 and part of the zeocin gene digesting with SapI and FseI effectively removing the SV40 promoter from the double expression vector.

Alteration of the pDCOrig Backbone for the FDA Regulatory Compliant One of pVax1 (Invitrogen)

The Immunobody full length human IgG1 heavy chain was excised from the construct DCIB54 using HindIII and XbaI and inserted into these sites within the MCS of the vector pVax1 (FIG. 18 A). In order to generate the pVax version of the double chain expression vector, pVaxIB54HIB was linearised using the blunt ended restriction endonuclease NruI located adjacent to the CMV promoter. pOrigLIB (FIG. 18 B) was digested with the blunt ended NruI and HpaI endonucleases to excise the entire light chain expression cassette consisting of the CMV promoter, Immunobody human kappa chain and the BGH polyA signal. After gel electrophoresis, isolation and gel extraction of the linerised vector pVaxIB54HIB and the light chain expression cassette the vector was dephosphorylated and light chain expression cassette ligated to form the construct pVaxDCIB54 (FIG. 18 C). Orientation of the light chain cassette within pVaxDCIB54 was confirmed by restriction analysis. pVaxDCIB54 retains the same unique restriction sites at the variable/constant region junction permitting easy exchange of variable regions between all human isotype single and double chain Immunobody vectors. For example to generate pVaxDCIB68 (FIG. 60) the murine light variable region containing Gp100DR4/L1 and Gp100DR7/L3 was excised from DCIB68 using BamHI/BsiWI and cloned into pVaxDCIB54 effectively replacing the light wild type variable region.

Generation of pOrig Murine TRP2 and pcDNA3 GP100

To construct pOrig murine TRP2, cDNA synthesised from 5 µg of total RNA isolated from the cell line B16F10 was used as a template for the amplification of full length murine tyrosinase related protein 2 (TRP2) using the primers murine TRP2 forward and reverse (Table 2) with incorporation of a HindIII or EcoRV site respectively. Full length TRP2 was ligated into the HindIII/EcoRV multiple cloning site of the vector pOrigHIB. Full length murine GP100 was also amplified from the cDNA using the designed murine GP100 forward and reverse primers containing EcoRV and XhoI sites respectively (Table 1). The PCR product was cloned into the EcoRV/XhoI sites of the mammalian expression vector pcDNA3 (Invitrogen). Both plasmids were identified by restriction analysis and confirmed by DNA sequencing.

Sandwich Elisas

Falcon 96-well flexible plates were coated, overnight at 4° C., with 50 ul of anti-human IgG, Fc specific antibody (Sigma 12136) or anti-human kappa light chain antibody (Dako A0191) at 10 µm/ml in PBS. Plates were washed three times with 200 µl/well PBS-Tween 20 (0.05%), using a Skan Washer 400 (Molecular Devices), and wells blocked with 1% fish skin gelatin (Sigma) in PBS (1% FSG/PBS). Plates were incubated 1 hr at room temperature and washed with 1% FSG/PBS. Tissue culture supernatant containing expressed ImmunoBody or purified ImmunoBody protein (50 µl) was added to the wells, in triplicate, and plates were incubated for 1 hr at room temperature. Plates were washed with 1% FSG/PBS and bound ImmunoBody was detected by adding 50 µl/well of peroxidase-conjugated anti-human IgG, Fc specific antibody (Sigma A0170) or anti-human kappa light chain antibody (Sigma A7164), diluted 1/2000 in 1% FSG/PBS, and incubated 1 hr at room temperature. Plates were washed with 1% FSG/PBS and developed by adding TMB substrate (R & D Systems) at 50 µl/well. Absorbance was measured at 650 nm in a VERSA max microplate reader (Molecular Devices).

Mice and Immunisations

Animal work was carried out under a Home Office approved project license. Male and female C57B1/6 (Harlan) or HLA-A2 transgenic (HHDII) (Pasteur Institute, Paris) were used between 6 and 12 weeks of age. Synthetic peptides (manufactured by John Keyte, Department of Biomedical Sciences, Nottingham University, UK) were emulsified with incomplete Freunds adjuvant and injected via a sub-cutaneous route. Each mouse received 10 µg peptide/immunisation. DNA was coated onto 1.0 µm gold particles (BioRad, Hemel Hempstead, UK) using the manufacturer's instructions and administered intradermally by the Helios Gene Gun (BioRad). Each mouse received 1 µg DNA/immunisation. Naked DNA solution was also administered i.d. or i.m. (10 µg/immunisation) combined immediately post injection with a short electric pulse. Mice were immunised at 0, 1 and 2 weeks and spleens removed at week 3. Depletion of T cell subsets in vivo was performed by injection of 400 µg anti-CD25 antibody (PC61) i.p. four days prior to immunisation or 200 µg anti-CTLA-4 antibody i.p. concurrent with secondary immunisation.

Restimulations in vitro

Five days post final immunisation, splenocytes ($5 \times 10^6$/ml) were cocultured at 37° C. with syngeneic, irradiated (20 Gy), peptide pulsed lipopolysaccharide (LPS) blasts (0.5 to $1 \times 10^6$ cells/ml) in 2 ml RPMI-1644 with 10% FBS, 2 mM glutamine, 20 mM HEPES buffer, 100 units/ml penicillin, 100 m/ml$^{-1}$ streptomycin and $10^{-5}$M 2-mercaptoethanol in 24 well plates. LPS blasts were obtained by activating splenocytes ($1.5 \times 10^6$ cells/ml) with 25 µm/ml LPS (Sigma) and 7 µg/ml dextran sulphate (Pharmacia, Milton Keynes, UK) for 3 days at 37° C. Before use, $2 \times 10^7$ LPS blasts were cultured with 100 µg/ml synthetic peptide for 1 hr. Cultures were assayed for cytotoxic activity on day 6 in a $^{51}$Cr-release assay.

$^{51}$Cr-Release Assay

Target cells were labelled for 1 hr with 1.85 MBq sodium ($^{51}$Cr) chromate (Amersham, Essex, UK) with or without 100 µg/ml peptide. Post incubation they were washed 3 times in RPMI and incubated for a further 1 hr with 100 µg/ml peptide. $5 \times 10^3$ targets/well of 96-well V-bottomed plates were set up and coincubated with different densities of effector cells in a final volume of 200 µl. After 4 hrs at 37° C., 50 µl of supernatants were removed from each well and transferred to a Lumaplate (Packard, Rigaweg, the Netherlands). Plates were read on a Topcount Microplate Scintillation Counter (Packard). Percentage specific lysis was calculated using the following formula:

specific lysis=100×[(experimental release−spontaneous release)/(maximum release−spontaneous release)]

Ex vivo Elispot Assay

Elispot assays were performed using murine IFNγ capture and detection reagents according to the manufacturer's instructions (Mabtech, Sweden). In brief, anti-IFNγ antibodies were coated onto wells of 96-well Immobilin-P plate and replicate wells were seeded with $5 \times 10^5$ splenocytes. Synthetic peptides (at a variety of concentrations) or $5 \times 10^4$ target melanoma cells were added to these wells and incubated for 40 hrs at 37° C. After incubation, captured IFNγ was detected with by a biotinylated anti-IFNγ antibody and development with a strepatavidin alkaline phosphatase and chromogenic substrate. Spots were analysed and counted using an automated plate reader (CTL). Functional avidity was calculated as the concentration mediating 50% maximal effector function using a graph of effector function versus peptide concentration. Depletion of CD8 T cells from splenocyte populations was performed using CD8 Dynabeads (Dynal) according to manufacturer's instructions and then added to ex vivo elispot assay.

Tumour Studies

C57B1/6 mice were randomised into treatment groups and immunised at weekly intervals for five weeks. Between the third and fourth immunisation they were challenged by i.v. injection into the tail vein with $1 \times 10^4$ B16F10 IFNα melanoma cells. When injected i.v., B16F10 cells migrate to the lungs to form metastases. Mice were monitored for signs of tumour growth and distress. At day 49 post tumour challenge, mice were euthanised and lungs analysed for the presence of metastases. Spleens were analysed for the presence of epitope and tumour specific immune responses in ex vivo elispot assay.

HHDII mice were immunised at weekly intervals for three weeks and 7 days post-final immunisation were challenged s.c. in the right flank with $2 \times 10^4$ B16F10 HHD melanoma cells. Tumour growth was monitored at 3-4 day intervals and size of the tumour was measured using a calliper.

Example 1

ImmunoBody Constructs Produce Low Levels of Intact Antibody

Stable CHO-S cell transfectants were made with an ImmunoBody construct containing the gp100 epitope IMDQVPFSV (SEQ ID NO: 5) and the TRP2 epitope SVY-DFFVWL (SEQ ID NO: 9) in CDR H1 and CDR H2 respectively with the HepB CD4 epitope TPPAYRPPNAPIL (SEQ ID NO: 14) in CDR L1 (DCIB15; FIG. 19).

The supernatant from these transfectants was analysed for expression of ImmunoBody protein by sandwich elisa. Plates were coated with anti-human IgG Fc specific antibody and supernatant added. Bound ImmunoBody was detected using an anti-human Fc specific HRP antibody to detect heavy chain. Heavy chain was detected in the supernatant at a concentration of approximately 1 µg/ml compared to the control (FIG. 20a). ImmunoBody was purified from the supernatant using a protein A affinity column and analysed for presence of ImmunoBody. Purification of ImmunoBody yielded far lower quantities of protein than previously expected compared to the control (FIG. 20b). Since such low yields of intact protein could be purified, ImmunoBody constructs were analysed for the expression of both heavy chain and intact antibody in the supernatant of transfected cells by sandwich ELISA.

Constructs with the HepB CD4 epitope in CDR L1 and the SIINFEKL (SEQ ID NO: 8) epitope in CDR H2 (DCIB24; FIG. 21) or the gp100 epitope IMDQVPFSV (SEQ ID NO: 5) and the TRP2 epitope SVYDFFVWL (SEQ ID NO: 9) in CDR H1 and CDR H2 respectively with the HepB CD4 epitope TPPAYRPPNAPIL (SEQ ID NO: 14) in CDR L3 (DCIB25; FIG. 22) were also tested. Plates were coated with anti-human IgG Fc specific antibody and supernatant added. Bound ImmunoBody was detected using an anti-human Fc specific HRP antibody to detect heavy chain or an anti-human kappa chain specific HRP antibody to detect intact ImmunoBody. ImmunoBody transfectants show high level of heavy chain secretion but very low levels of intact ImmunoBody (FIG. 20c and d).

This data indicates that the incorporation of CD8 and CD4 T cell epitopes into the heavy and light chain variable regions has disrupted the overall structure of the ImmunoBody preventing formation of intact antibody.

Additional data on analysis of supernatant from transfected CHO—S cells demonstrates that only constructs with CTL epitopes incorporated into the CDRH3 or CDRL3 are secreted as intact antibody (FIG. 20e). In contrast, incorporation of any epitope within the CDRH1 or CDRH2 allowed secretion of heavy but low amounts of intact antibody even if there was nothing incorporated within the light chain and it was secreted. Incorporation of any epitope within CDRL1 any of the light chain resulted in low level secretion of light chain even if there was only an epitopes incorporated into the CDRH3 of the heavy chain.

Example 2

CTL Epitopes Incorporated into ImmunoBody Framework are Processed and Presented to Elicit an Immune Response in vivo The previously-published CTL epitope from TRP2, aa280-288 (Bloom et al, *The Journal of Experimental Medicine* 1997; 185: 453-9), was engineered into the CDR H2 region of the ImmunoBody construct alongside a Hepatitis B universal CD4 epitope in CDR L1 (DCIB18; FIG. 30). C57B1/6 mice were immunised three times at weekly intervals intradermally with ImmunoBody DNA via the gene gun. Splenocytes were subsequently analysed by IFNγ elispot for TRP2 specific responses. Mice immunised with ImmunoBody DNA demonstrated considerable TRP2 peptide specific responses compared to control but lower level responses specific for the HepB CD4 peptide (FIG. 31a). The avidity of the TRP2 specific responses were also studied by peptide titration in IFNγ elispot. Over the fifteen mice tested within five different experiments, the avidity of the responses ranges from $10^{-9}$ M to $10^{-11}$ M peptide. A representative example is shown in FIG. 31b.

In order to confirm that this TRP2 specific response was mediated by CD8 T cells, the C57B1/6 mice were immunised three times with ImmunoBody DNA at weekly intervals. Six days after the last immunisation splenocytes were isolated and analysed in vitro for specific responses by IFNγ elispot. To determine if the TRP-2 specific response was mediated by CD8 T cells, CD8 T cells were depleted prior to analysis in elispot assay. Depletion of CD8 T cells led to abolition of the TRP2-specific response; however CD8 depletion did not affect the HepB CD4 peptide response, suggesting it is most likely mediated by CD4 T cells (FIG. 31c).

To determine if the responses generated by ImmunoBody DNA immunisation are capable of killing target cells in vitro, splenocytes were stimulated with TRP2 peptide pulsed LPS blasts in vitro for 6 days and analysed in a chromium release assay against B16F10 melanoma cells. Splenocytes from ImmunoBody DNA immunised mice demonstrated superior lysis of both B16F10 cells, which have low levels of surface MHC class I, and of B16F10 IFNα cells, which have high surface MHC class I expression compared to that of B16F10 line that expresses no H-2 Kb molecules (B16F10 siKb). The abolition of killing against the B16F10 siKb cell line demonstrates that killing is CD8 dependent and restricted through H-2 Kb (FIG. 31d).

These results show that TRP2 (SVYDFFVWL-(SEQ ID NO: 9) CD8 epitope incorporated into the CDR H2 region of the ImmunoBody framework is processed and presented to elicit high frequency responses mediated via MHC class I. The HepB CD4epitope is also processed and presented in the context of MHC class II to elicit good CD4 mediated responses from DNA immunisation.

TRP2 epitope specific responses were also analysed from other TRP2 epitope containing constructs using identical methodology. Incorporation of the TRP2 epitope into CDRs within the heavy chain resulted in high frequency peptide specific responses (FIG. 31e). In contrast incorporation of CTL epitopes within the light chain resulted in a significant reduction in CTL frequency (DCIB36). Analysis of the avidity of the TRP2 epitope specific responses reveals that they are of high avidity when generated from epitopes within the heavy chain but this is considerably lower upon expression of epitopes from the light chain (FIG. 31f). High frequency high avidity helper responses where observed for all constructs (FIG. 31g). Suggesting that secretion of heavy chain was an advantage for stimulating CTL responses but not for helper responses.

Example 3

ImmunoBody DNA Immunisation is Better than Peptide Immunisation or Immunisation with Whole Antigen To analyse the efficiency of ImmunoBody DNA immunisation, it was compared to s.c. immunisation with peptide epitope in Incomplete Freund's adjuvant or immunisation with a DNA expressing the TRP2 antigen.

C57B1/6 mice received three weekly immunisations with DNA or peptide comprising of the TRP2 epitope linked to the universal helper epitope in IFA. TRP2 and helper peptide specific responses generated in ImmunoBody immunised mice were far superior in magnitude to those elicited by peptide immunisation or immunisation with the whole TRP2 antigen (FIG. 32a). Further analysis of the avidity of these peptide specific responses revealed that responses generated by mice immunised with ImmunoBody DNA have greater than a log higher avidity than those from peptide immunised individuals (FIG. 32b). The responses generated in C57B1/6 mice were subsequently analysed for cytotoxic ability in vitro against the B16F10 cell line and, as a negative control, the B16F10 siKb cell line. FIG. 32c shows that ImmunoBody DNA immunised mice are capable of anti-tumour activity in vitro that is H-2 Kb restricted and both peptide immunised mice and whole antigen immunised mice are unsuccessful at killing the same melanoma cell lines.

ImmunoBody immunisation was also compared to immunisation with DC+peptide. C57B1/6 mice received three weekly immunisations with DNA or DC+peptide. TRP2 peptide specific responses were of comparable frequency but ImmunoBody immunised mice generated higher avidity responses compared to those immunised with DC+peptide (FIG. 32d). This is also demonstrated when these responses were analysed for ability to kill B16F10 melanoma cells in vitro (FIG. 32e). The responses generated by ImmunoBody immunisation showed higher killing of B16F10 melanoma at lower effector to target ratio than responses from DC+peptide immunised mice. They also showed higher specific lysis of the B16F20 siKb melanoma line which has knocked down levels of H-2 Kb.

ImmunoBody constructs containing the H-2Kb restricted Ovalbumin epitope, SIINFEKL (SEQ ID NO: 8), and the anchor modified HLA-A2 restricted gp100 epitope, IMDQVPFSV (SEQ ID NO: 5) (210M) were compared with the corresponding epitope peptide immunisation in C57B1/6 or HHDII mice respectively. Mice received three weekly immunisations with DNA or peptide in IFA. Analysis of the responses after the final immunisation reveals that ImmunoBody DNA immunised mice generate higher frequency peptide specific responses compared to peptide immunised mice (FIG. 32f and g). These responses were also analysed for avidity by peptide titration. ImmunoBody immunisation elicits significantly higher avidity responses than peptide immunisation (FIG. 32h and i).

The magnitude of TRP2 specific response generated by the ImmunoBody DNA vaccine is far superior to that generated by either synthetic peptide or whole TRP2 antigen. However, evidence from clinical trials suggests that the presence of a high frequency of tumour specific CD8 T cells does not necessarily lead to tumour regression and generally in vaccine trials the objective clinical response rate is very low (Rosenberg et al, *J Immunol* 2005; 175: 6169-76; Rosenberg et al, *Nature Medicine* 2004; 10: 909-15). It is now becoming clear that factors other than frequency such as functional avidity of tumour specific T cells and route of priming are major determinants in maximising vaccine efficacy. A number of groups have shown that high avidity CD8 T cells demonstrate superior anti-tumour activity (Alexander-Miller, Immunologic research, 2005; 31: 13-24; Hodge et al, J Immunol 2005; 174: 5994-6004; Valmori et al, J Immunol 2002; 168: 4231-40; Zeh et al, J Immunol 1999; 162: 989-94; Alexander-Miller et al, Proceedings of the National Academy of Sciences of the United States of America 1996; 93: 4102-7). In our study, analysis of the functional avidity of ImmunoBody induced TRP2 specific responses demonstrated that a high avidity response can be generated when compared to immunisation with synthetic peptide. This high avidity response also correlated with the enhanced ability to recognise and kill tumour cells in vitro. The signal from the APC or route of priming of the response is also crucial for the induction of high avidity immune responses (Oh et al, J Immunol 2003; 170: 2523-30).

Example 4

Multiple Epitopes can be Processed from CDR H2 Site

To demonstrate that multiple epitopes can be processed and presented from CDR H2 to elicit an immune response, the H-2Kb restricted epitope SIINFEKL (SEQ ID NO: 8) (DCIB24; FIG. 21) from ovalbumin and the H-2Kd restricted Hepatitis B epitope IPQSLDSWWTSL (SEQ ID NO: 6) (DCIB21; FIG. 33) were engineered into the H2 site in the heavy variable region. These ImmunoBody constructs also contained a I-Ab restricted (TPPAYRPPNAPIL-SEQ ID NO: 14) epitope Hepatitis B CD4 epitope or I-Ad restricted Influenza haemagluttinin (FERFEIFPKE-SEQ ID NO: 1) epitope in the CDR L1 site in the light variable region.

C57B1/6 or Balb/c mice were immunised three times at weekly intervals intradermally with ImmunoBody DNA via the gene gun. Splenocytes were subsequently analysed by IFNγ elispot for the presence of epitope specific CD8 and CD4 responses.

C57B1/6 immunised mice demonstrated high frequency SIINFEKL (SEQ ID NO: 8) specific responses but lower responses specific for the helper epitope (FIG. 34a). Balb/c mice also created high frequency Hepatitis B epitope specific CD8 responses with similar level responses to the helper epitope (FIG. 34b).

This data suggests that processing and presentation of CD8 epitopes from the CDR H2 site is not restricted by specific epitope sequence or length.

Example 5

Multiple CTL Epitopes can be Processed from the Variable Region

To demonstrate that epitopes can be processed and presented from the variable region and not solely the CDR regions, epitopes were incorporated into the CDR H1 site with the removal of part of the framework region.

Example epitopes are the modified HLA-A2 restricted epitopes IMDQVPFSV (SEQ ID NO: 5) (DCIB17; FIG. 35) from gp100 and FLPATLTMV (SEQ ID NO: 2) from Tie-2 (DCIB26; FIG. 36). ImmunoBody constructs also contained the Hepatitis B CD4 epitope in the CDR L1 site.

HLA-A2 transgenic mice (HHDII) mice were immunised three times at weekly intervals intradermally with ImmunoBody DNA via the gene gun. Splenocytes were subsequently analysed by IFNγ elispot for the presence of epitope specific CD8 and CD4 responses.

HHDII mice elicited high frequency gp100 210M epitope specific responses with reasonable responses to the HepB CD4 epitope (FIG. 37a). Responses in HHDII mice immunised with the Tie2 epitope containing construct were not of as high frequency but considerable responses were generated specific for both the Tie2 epitope and the HepB CD4 epitope (FIG. 37b).

Data in this example indicates that epitopes inserted within the variable region can be processed and presented to elicit an immune response in vivo. It is also apparent that this is not restricted to one epitope sequence.

Example 6

Multiple CTL Responses can be Generated from Different Epitopes within the Same ImmunoBody Construct The previously-mentioned HLA-A2 restricted gp100 epitope IMDQVPFSV (SEQ ID NO: 5) was engineered into the CDR H1 site alongside the TRP2 epitope SVYDFFVWL (SEQ ID NO: 9) which is also restricted through HLA-A2 in the CDR H2 site of the same construct. The HepB CD4 epitope was present in the CDR L1 site (DCIB15; FIG. 19).

HHDII mice were immunised three times at weekly intervals intradermally with ImmunoBody DNA via the gene gun. Splenocytes were subsequently analysed by IFNγ elispot for the presence of epitope specific CD8 and CD4 responses.

FIG. 38a shows that responses are generated specific for both the gp100 and TRP2 epitopes, although the frequency of the TRP2 specific responses are lower. Responses to the HepB CD4 peptide are also generated. The avidity of the TRP2 specific responses were also studied by peptide titration in IFNγ elispot. The avidity of the responses ranges from $10^{-10}$ M to $10^{-11}$ M peptide for the gp100 epitope and $10^{-9}$ M to $10^{-10}$ M peptide for the TRP2 epitope. Representative examples are shown in FIG. 38b. To determine if the responses are capable of killing target cells in vitro, splenocytes were stimulated with TRP2 and gp100 peptide pulsed LPS blasts in vitro for 6 days and analysed in a chromium release assay against peptide labelled T2 cells and B16F10 HHD melanoma cells. Specific killing of B16F10 HHD melanoma line compared to the control B16F10 melanoma line. Responses also demonstrated specific lysis of peptide labelled T2 cells compared to control (FIG. 38c).

Combining two CD8 epitopes in a single ImmunoBody construct appears to result in a degree of immunodominance between epitopes. The immunodominant epitope is the epitope with the highest affinity for MHC class I. When mice are immunised with the construct containing both gp100 and TRP2 CD8 epitopes are compared to those immunised with a construct containing only the TRP2 CD8 epitope, the frequency of the TRP2 response decreases (FIG. 38d).

This data demonstrates that epitope specific immune responses can be generated from the same DNA construct specific for two different CD8 epitopes. These are also capable of anti-tumour activity in vitro. However, there is a degree of immunodominance that governs the frequency of the response to the subdominant epitope.

A similar study was performed with separate ImmunoBody constructs containing the TRP2 epitope in CDRH2 (DCIB18) or the SIINFEKL (SEQ ID NO: 8) epitope in CDRH2 (DCIB24). Mice were immunised with either DCIB18 or DCIB24 alone, DCIB18 and DCIB24 combined in the same site or DCIB18 and DCIB24 at the same time but in separate sites. Immunisations were performed three times at weekly intervals and DNA was injected i.m in the tibialis muscle combined with electroporation. Analysis of the immune responses generated shows that high frequency peptide specific responses can be elicited when mice were immunised with DCIB18 or DCIB24 alone (FIG. 38e). Immunising mice with these constructs in the same site results in significant loss of the TRP2 peptide specific response. This suggests that the SIINFEKL (SEQ ID NO: 8) epitope is dominant over the TRP2epitope. The TRP2 specific response can be recovered if mice are immunised with constructs in separate sites (p=0.0026). This data suggests that immunodominance does influence immune responses generated by IB immunisation but this can be resolved by immunisation in spatially separate sites.

Example 7

Non Anchor Residue Modifications can Enhance T Cell Recognition

The previous example shows that the modified gp100 epitope IMDQVPFSV (SEQ ID NO: 5) is immunodominant and has a high affinity for HLA-A2 (predicted using the SYFPEITHI algorithm and demonstrated in T2 stabilisation assay - Table 5). Since the wild type gp100 epitope ITDQVPFSV (SEQ ID NO: 7) is not immunogenic, modifications were made at non anchor residues that would have a similar HLA-A2 binding affinity to the wild type epitope but also enhance the immunogenicity. These modified epitopes were engineered into the CDR H1 site of the ImmunoBody construct and tested alongside the wild type epitope (DCIB37, DCIB40, DCIB41, DCIB42, DCIB43; FIGS. 39-43).

HHDII mice were immunised three times at weekly intervals intradermally with ImmunoBody heavy chain DNA alone via the gene gun. Splenocytes were subsequently analysed by IFNγ elispot for the presence of epitope specific CD8 responses. Two modifications (F7L and F7I; DCIB37; FIG. 39, DCIB40; FIG. 40) to the wild type gp100 epitope which retain affinity for HLA-A2 (Table 5) demonstrated superior ability to induce epitope specific immune responses compared to the wild type epitope (FIG. 44a).

TABLE 5

| Antigen | Epitope | T2 stabilisation assay (m.f.i) | SYFPEI-THI score |
|---|---|---|---|
| Gp100 (210M) | IMDQVPFSV (SEQ ID NO: 5) | 23.1 | 22 |
| Gp100 (wt) | ITDQVPFSV (SEQ ID NO: 7) | 18.5 | 18 |
| Gp100 (F7L) | ITDQVPLSV (SEQ ID NO: 63) | 18 | 19 |
| Gp100 (F7I) | ITDQVPISV (SEQ ID NO: 11) | Nd | 18 |
| TRP2 | SVYDFFVWL (SEQ ID NO: 9) | 19 | 21 |
| Control | | 7.29 | - |

Example 8

Multiple CD4 Helper Responses can be Processed and Presented to Elicit an Immune Response in vivo To examine if CD4 helper epitopes could be processed and presented to elicit an immune response in vivo, different epitopes were engineered independently into the CDR L1 site of the ImmunoBody construct. These included the I-Ad restricted epitope FERFEIFPKE (SEQ ID NO: 1) (DCIB21; FIG. 33) from Influenza haemagluttinin, the I-Ab restricted epitope TPPAYRPPNAPIL (SEQ ID NO: 14) from HBcAg (DCIB15; FIG. 19) and the HLA-DR4 restricted epitope WNRQLYPEWTEAQRLD (SEQ ID NO: 15) from gp100 (DCIB35; FIG. 45).

Balb/c, C57B1/6 or HHDII and DR4 transgenic mice were immunised three times at weekly intervals intradermally with ImmunoBody DNA via the gene gun. Splenocytes were subsequently analysed by IFNγ elispot for the presence of epitope specific CD4 responses. FIGS. 46*a*, *b* and *c* demonstrate that all three CD4 helper epitopes can be processed and presented from the CDR L1 site to elict an epitope specific immune response in vivo.

The gp100 HLA-DR4 restricted epitope was also tested for processing and presentation from different CDRs. Constructs incorporating the epitope into CDRL1 (DCIB35; FIG. 45), CDRH3 (DCIB54; FIG. 29) or CDRL3 (DCIB50; FIG. 47) were used to immunise HLA-DR4 transgenic mice three times at weekly intervals. FIG. 46*d* shows that helper epitope can be efficiently processed from different CDRs to elicit high frequency helper responses.

Example 9

CTL Responses are Partially Dependent Upon Secreted Heavy Chain but Helper Responses do not Require Secreted Light Chain Classically CD4 T cell epitopes are processed from proteins that are acquired exogenously and CD8 T cell epitopes from endogenously produced proteins. There is evidence now for the cross presentation of epitopes from exogenously acquired antigen to elicit a CD8 T cell mediated response. This route of priming has also been proposed to be more efficient in the development of CD8 T cell-mediated immune responses. Recently there have been similar findings for CD4-mediated responses. Mounting evidence suggests that CD4 T cell epitopes derived from intracellular proteins can be processed and presented in the context of MHC class II.

In order to determine if secreted ImmunoBody is required for the induction of CD8 and CD4 T cell responses, ImmunoBody constructs containing the HLA-A2 restricted gp100 epitope IMDQVPFSV (SEQ ID NO: 5) in the CDR H1 site and the I-Ab restricted HepB helper epitope TPPAYRPPNAPIL (SEQ ID NO: 14) in the CDR L1 site were made without leader sequences on the heavy chain or light chain (FIGS. 10 and 11).

HHDII mice were immunised three times at weekly intervals intradermally with ImmunoBody DNA via the gene gun. Splenocytes were subsequently analysed by IFNγ elispot for the presence of epitope specific CD8 and CD4 T cell responses. When the responses were analysed for gp100 specific CD8 response, it was observed that removal of the leader sequence from the heavy chain of the ImmunoBody construct resulted in a decrease in epitope specific responses however the CD4 responses was not affected (FIG. 48*a*). Removal of the leader sequence from the heavy chain affected secretion of heavy chain by transfected CHO—S cells (FIG. 48*b*). Removal of the leader sequence from the light chain, thus preventing light chain secretion, did not appear to affect the epitope specific CD8 or CD4 responses (FIG. 48*c*). CD8 responses were significantly reduced in the absence of a leader sequence on the heavy chain but CD4 responses remained unaffected (FIGS. 48*c* and *d*).

This data implies that the secretion of heavy chain is important for the efficient induction of a CD8 T cell response, suggesting that CD8 epitopes are undergoing cross presentation. Secondly, it implies that CD4 epitopes are derived from intracellular ImmunoBody to elicit an immune response.

Example 10

Reduced CTL Responses without Fc Due to Lack of Protein Secretion

This experiment examines whether the presence of the Fc region is beneficial for establishing an efficient immune response. The Fc region has been removed from the ImmunoBody construct, containing the H-2Kb restricted TRP2 epitope SVYDFFVWL (SEQ ID NO: 9) in CDR H2 and the I-Ab restricted HepB CD4 epitope TPPAYRPPNAPIL (SEQ ID NO: 14) in CDR L1 (DCIB15), by incorporating a stop codon before the Fc to prevent transcription and translation (FIG. 9).

C57B1/6 mice were immunised three times at weekly intervals intradermally with ImmunoBody DNA via the gene gun. Splenocytes were subsequently analysed by IFNγ elispot for the presence of epitope specific CD8 and CD4 T cell responses.

Mice immunised with the ImmunoBody construct lacking the Fc region generated a low level TRP2 peptide specific response that was capable of very low level recognition of the tumour cell line B16F10 compared to a construct with the Fc region (FIG. 49*a*). Analysis of both the TRP2 and HepB helper peptide specific responses from a number of experiments demonstrates that constructs lacking the Fc region generate significantly lower TRP2 peptide specific responses (FIG. 49*b*). However the HepB helper responses is unaffected by removal of the Fc region (FIG. 49*c*). This is consistent with our previous results showing that help works best in the light chain where it is not secreted and is therefore working by direct presentation. In contrast CTL responses are stimulated by both direct and indirect presentation and the latter may benefit from Fc targeting. Alternatively the Fc stop construct results in lower secretion of the truncated heavy chain which may explain the reduced response. An ImmunoBody encoding TRP-2 was therefore engineered with an IgG2 (DCIB33) and an IgG3 constant region (DCIB65) the former should not bind to CD64 but can bind to CD32 and may also bind to Fc receptor IV in mice. Human IgG3 can bind to both CD32 and CD64. Both ImmunoBodies stimulated strong CTL responses (FIG. 49*e*). This suggests that Fc targeting is not a strong component of the indirect presentation. To further verify this issue, the Fc targeting domain of IgG1 was replaced with the equivalent IgG2 domain and vica versa (DCIB66, 67, FIGS. 15 and 16). Both constructs stimulated strong CTL responses (FIG. 49*e*). This may be due to the ImmunoBody™ vaccines only secreting heavy chain which may not associate and allow Fc binding (FIGS. 49*f* and *g*).

Example 11

ImmunoBody Immunisation Enhances Immune Responses and Overcomes Regulation Observed from Whole Antigen. It Also Allows Identification of New Heterologous T Cell Epitopes This may lead to the second benefit of immunising with a human antibody encoding T cell epitope which is that, in contrast to most self antigens, it is an inert carrier that does not express regulatory epitopes. An ImmunoBody™ expressing either a gp100 epitope or a TRP-2 epitope stimulated a high frequency, high avidity T cell response (frequency $\frac{1}{10^3}$ avidity $10^{-10}$ M) whereas immunisation with the whole gp100 of TRP-2 antigen stimulated T cells with low frequency and avidity (frequency $\frac{1}{10^5}$ avidity $10^{-7}$M). CD25 depletion partially restored the response to the antigen but ImmunoBody was still 100 fold superior (FIGS. 50a and b).

Similarly immunisation with DNA encoding the first 200 amino acids of Tie-2 linked to -Fc, failed to stimulate an immune response to the top 10 predicted epitopes. The sequence of the first 196 amino acids of Tie-2 was entered into the EpiJen and NetCTL online prediction algorithms. Both of these methods take into account proteasomal cleavage and TAP transport in addition to predicting HLA-A*0201 binding affinity. The MHCpred and Syfpeithi algorithms were also used as examples of the older prediction algorithms that only take into account predicted MHC binding affinity. The whole Tie-2 molecule could contain additional CTL epitopes that may exert an immunodominant effect over those present in the first 196 amino acids. The whole sequence of Tie-2 was therefore also entered into the same algorithms in order to obtain the ranks of each predicted epitope from the whole molecule. Peptides that were not homologous in mouse and man were discounted. Six of the remaining peptides that were consistently predicted to represent good CTL epitopes by several different prediction algorithms were selected. The relative scores obtained with the different algorithms for each of these peptides, along with the results for Z83 (a previously identified epitope), are summarised in Table 6.

Additional data on analysis of supernatant from transfected CHO—S cells demonstrates that only constructs with CTL epitopes incorporated into the CDRH3 or CDRL3 are secreted as intact antibody (FIG. 20e). In contrast, incorporation of any epitope within the CDRH1 or CDRH2 allowed secretion of heavy but low amounts of intact antibody even if there was nothing incorporated within the light chain and it was secreted. Incorporation of any epitope within CDRL1 any of the light chain resulted in low level secretion of light chain even if there was only an epitopes incorporated into the CDRH3 of the heavy chain.

In order to determine whether a T cell repertoire exists in HLA-A*0201 transgenic mice that recognizes any of the predicted CTL epitopes from Tie-2, animals were immunised with the native Tie2 C200hFc DNA construct (Ramage et al, Int. J. Cancer 2004; 110:245-250) and splenocytes were screened for peptide specific IFNγ responses in an ELISPOT assay. A separate group of mice were immunized with C200hFc following treatment with PC61 mAb, as before, 4 days prior to DNA immunisation.

Mice that were immunised with the native C200HFc DNA construct did not mount an IFNγ response that recognised Z83, regardless of whether the animals were depleted of CD25$^+$ regulatory T cells prior to immunisation or not. There were no significant IFNγ responses to any of the new peptides tested from animals that were not depleted of regulatory T cells prior to immunisation, with the exception of Z284 which appeared to stimulate a response in one animal (M3) with a mean of 69 SFC/million splenocytes (FIGS. 50c and d). From the animals that were depleted of regulatory T cells prior to DNA immunisation, 2/3 animals (M1 and M3) demonstrated an IFNγ response to restimulation with Z282 peptide, with mean values of 320 and 94 SFC/million splenocytes respectively. M1 also demonstrated a partial response to restimulation with Z285, with a mean of 85 SFC/million splenocytes.

The apparently conflicting results from the in vivo screen of the predicted CD8$^+$ epitopes from Tie-2 could be the result of immunodominance, as the IFNγ responses from mice that were immunized with the native C200HFc construct in the absence of CD25$^+$ cells appeared to be skewed towards one predominant peptide. In order to further investigate the T cell repertoire that is available to respond to the Z282 epitope, in the absence of competition from other potential CD8$^+$ epitopes, a group of HHD mice were immunized with the Z282 peptide in IFA in the presence or absence of CD25$^+$ regulatory T cells.

All of the mice immunised with Z282 mounted peptide-specific IFNγ responses, even when immunised in the presence of CD25$^+$ regulatory T cells. Mouse 3 of the non-depleted animals mounted the highest response, with a mean value of 215 SFC/million cells. The highest response from the depleted animals was observed from mouse 2 with a mean value of 137 SFC/million cells (FIGS. 50e and f).

Responses induced by peptide immunisation remain of low frequency. To examine if higher frequency responses can be generated if the epitope is removed from any regulatory influence generated by the whole antigen, the z282 (also known as z12) epitope was engineered into the H1 site of an ImmunoBody construct alongside Hep B CD4 in L1 (DCIB71, FIG. 51) HLA-A2 transgenic mice were then immunised with z12 peptide or ImmunoBody DNA (via gene gun) three times at weekly intervals and then analysed for the presence of epitope specific immune responses. All mice immunised with z12 peptide exhibit low frequency and avidity epitope specific responses (FIG. 50g). However when the z12 epitope is engineered into the ImmunoBody construct higher frequency and avidity responses are induced in all mice (FIG. 50h).

To summarize, if CD25 cells were depleted prior to immunisation an immune response was stimulated to 3/10 of the Tie2 epitopes. Similarly if one of these epitopes was presented as a peptide, weak immune responses could be generated. However if this epitope was presented within an ImmunoBody™ construct high frequency and high avidity T cell responses were generated. These results suggest that there are T-reg epitopes within the first 200 amino acids of Tie-2 which inhibit CTL responses. If these T-regs or their epitopes are removed it is possible to uncover a response to self antigens which can be further enhanced by presentation within an ImmunoBody.

TABLE 6

Predicted HLA-A*0201 restricted CTL epitopes from Tie-2.

| Name [1] | Start | [2]Peptide [3] | EpiJen [4] | | NetCTL [5] | | Syfpeithi [6] | | MHCPred [7] | |
|---|---|---|---|---|---|---|---|---|---|---|
| | | | Score (IC50 nM) | Rank | Score | Rank | Score | Rank | Score (IC50 nM) | Rank |
| Z83 | 124 | F L P A T L T M T (SEQ ID NO: 70) | — | — | 0.73 | 9 (27) | 19 | 18 (55) | 2978 | 96 (633) |
| Z282 | 27 | I L I N S L P L V (SEQ ID NO: 4) | 0.05 | 1 | 1.39* | 1 | 29 | 1 (2) | 16 | 2 (6) |

TABLE 6-continued

Predicted HLA-A*0201 restricted CTL epitopes from Tie-2.

| Name [1] | Start | [2]Peptide [3] | EpiJen [4] Score (IC50 nM) | Rank | NetCTL [5] Score | Rank | Syfpeithi [6] Score | Rank | MHCPred [7] Score (IC50 nM) | Rank |
|---|---|---|---|---|---|---|---|---|---|---|
| Z283 | 146 | V L I K E E D A V (SEQ ID NO: 89) | 0.23 | 2 (5) | 0.7 | 10 (31) | 24 | 5 (11) | 89 | 9 (34) |
| Z284 | 64 | L M N Q H Q D P L (SEQ ID NO: 90) | 0.98 | 3 (7) | 0.88* | 3 (11) | 21 | 9 (32) | 113 | 11 (51) |
| Z285 | 8 | V L C G V S L L L (SEQ ID NO: 91) | 1.19 | 4 (10) | 0.94* | 2 (9) | 24 | 4 (10) | 242 | 21 (125) |
| Z286 | 34 | L V S D A E T S L (SEQ ID NO: 92) | — | — | 0.74 | 8 (26) | 19 | 15 (52) | 887 | 65 (349) |
| Z287 | 26 | L I L I N S L P L (SEQ ID NO: 93) | — | — | 0.88* | 4 (12) | 23 | 7 (16) | 607 | 57 (271) |
| Z18 | (flu) | G I L G F V F T L (SEQ ID NO: 94) | 0.19 | (1) | 1.29 | (2) | 30 | | 419 | (87) |

[1] Name of peptide.
[2] Amino acid residue start position within Tie-2 molecule.
[3] Peptide sequence.
[4] Prediction using the EpiJen web server. The score is given in units of $IC_{50}$ nM, with lower scores representing higher affinity peptides.
[5] Prediction using the NetCTL 1.2 web server. Score represents the weighted sum of three individual prediction methods, with a relative weighting on MHC binding of 1.
*indicates a score above the threshold value of 0.75 identified as the cut off point for CTL epitopes from the dataset obtained for known epitopes.
[6] Prediction using the SYFPEITHI programme. Maximal score for HLA-A*0201 binding peptides is 36.
[7] Prediction using the MHCPred additive method to predict peptide affinity for MHC and TAP. The score is again given in units of $IC_{50}$ nM, with lower scores representing higher affinity peptides.
Suggested $IC_{50}$ values are between 0.01 to 5000 nM. For all prediction methods, the rank values indicate the order in which epitopes are predicted from the 196 amino acid fragment, with values in brackets representing the rank predictions from the whole Tie-2 molecule.
Values obtained for the known Z18 CTL epitope derived from the matrix protein of Influenza A virus are included for comparison.

Example 12

The Role of Xenogenic Fc in Providing T Cell Help and the Requirement for Antigen Specific T Cell Help Stimulation of high avidity T cell responses usually requires T cell help during the priming. It was originally conceived that this would be provided by the Hep B foreign helper epitope encoded within the light chain. Indeed strong helper responses were generated to this epitope. However as the heavy chain was secreted and the light chain was not although the hep B epitope could have provided help for direct presentation when both chains would be produced by the same APC it is unlikely that it could be providing help for the indirectly presented heavy chain as this is unlikely to be taken up by the same antigen presenting cell. Mice were therefore immunised with a DNA vector only encoding heavy chain. High frequency, high avidity CTL responses were still generated (FIG. 53 a and b). This implies that either help is not required or that the human Fc which is xenogenic in mice is providing linked foreign help. A mouse IgG2a construct was therefore assessed for secretion of Heavy and light chains (FIG. 49g) and screened for generation of immune responses (DCIB53 FIG. 54). Although it still gave high frequency high avidity T cell responses these were not as strong as the equivalent human construct suggesting that the xenogenic Fc was providing linked help (FIGS. 53c and d). An HLA-DR4 gp100 epitope was then incorporated into the mouse IgG2a construct (DCIB64, FIG. 55) to provide both linked help for CTL generation but also antigen specific T cell help to stimulate inflammation within the tumour environment. These constructs stimulate high frequency and high avidity CTL and helper responses (FIGS. 53e and f). A hIgG1 construct expressing the same epitope can be used in human patients.

Example 13

Immunoproteasome Processing is Important in the Generation of Responses from Epitopes within ImmunoBody Constructs It has been suggested that the immunoproteasome has the ability to alter the array of epitopes generated from self antigens as it possess a different pattern of cleavage. In some cases, new epitopes are generated upon upregulation of the immunoproteasome and in others epitopes are destroyed. There is evidence that the immunoproteasome is unable to generate several epitopes derived from melanoma antigens namely MelanA/MART-1, gp100$^{209-217}$ and Tyrosinase$^{369-377}$ (Chapiro et al 2006. J Immunol; 176: 1053-61). Chapiro and colleagues have suggested that the ability to process and present the gp100 epitope is related to the upregulation of the immunoproteasome. Mature DCs are believed to be responsible for the priming of immune responses and are known to constitutively express the immunoproteasome (Macagno et al. 2001. Eur J Immunol; 31: 3271-80). The gp100$^{209-217}$ epitope was therefore engineered into the CDRH1 site of an ImmunoBody construct and tested for its ability to induce peptide specific immune responses in HLA-A2 transgenic mice. No peptide specific responses were observed from this construct (FIG. 56). However when the epitope was modified to possess a methionine at position 210 (210M) instead of threonine this prevents its cleavage by the immunoproteasome and epitope specific responses were observed (FIG. 56).

A HLA-A2 restricted peptide derived from VEGFR2 (aa 773-781 VIAMFFWLL- SEQ ID NO: 83) and two modified hTERT peptides (aa 572-580 YLFFYRKSV (SEQ ID NO: 96) and aa 988-997 YLQVNSLQTV (SEQ ID NO: 97) were also tested for generation of responses from ImmunoBody constructs. These epitopes were initially discovered by in silico epitope prediction and peptide immunisation therefore negating the requirement for proteasomal processing. However they are presented upon the surface of host endothelial/tumour cells which suggests they are processed from whole antigen via the constitutive proteasome. None of these epitopes generated responses when engineered into the ImmunoBody construct suggesting that processing via the immunoproteasome may be required for efficient generation of immune responses.

Example 14

Different Immunisation Methods are Efficient at Eliciting Immune Responses from ImmunoBody Vaccine ImmunoBody vaccine has been shown to be effective at eliciting high frequency and avidity CD8 and CD4 responses when administered via gene gun. ImmunoBody vaccine was subsequently tested for generation of T cell responses using other methods of immunisation.

C57B1/6 mice were immunised with ImmunoBody DNA containing the TRP2 epitope in CDRH2 via either the i.d. or i.m. route. Immunisations were combined with and without electroporation and performed three times at weekly intervals.

Mice immunised with gene gun show high frequency TRP2 peptide specific responses. These are comparable in mice immunised either via i.m. or i.d. route combined with electroporation. Immunisation via i.m. or i.d. route in absence of electroporation generated lower frequency TRP2 peptide specific responses (FIG. 57a). All TRP2 peptide specific responses are of high avidity as measured by peptide titration (FIG. 57b).

Example 15

ImmunoBody Immunisation Induces Vitiligo-Like Depigmentation and Protects Against Tumour Challenge Since mice immunised with ImmunoBody DNA generate immune responses capable of cytotoxic activity against the highly metastatic and poorly immunogenic tumour cell line B16F10, the vaccine was tested for protective efficacy in vivo.

Mice were immunised with IB DNA (DCIB18; FIG. 30) via gene gun into shaved skin of the abdomen at five weekly intervals. Part way through the schedule of immunisations, mice were injected i.v with 1×10$^4$ B16F10 cells expressing IFNα which forms metastatic tumours in the lung. When the hair was permitted to grow back after last immunisation, mice immunised with ImmunoBody DNA were observed to have growth of white hair at the site of immunisation (FIG. 58a). Seven weeks post tumour cell injection, mice were sacrificed and the number of internal and external lung metastases analysed. ImmunoBody DNA immunised mice exhibited a significant reduction in the number of lung metastases compared to untreated control mice (FIG. 58b).

Mice were also immunised with IB DNA (DCIB18) via gene gun at three weekly intervals. Seven days post final immunisation mice were challenged with 2×10$^4$ B16F10 cells expressing IFNα subcutaneously. Mice were monitored for tumour growth and survival. Mice were euthanized once tumours reached the maximum limit according to Home Office regulations. ImmunoBody DNA immunised mice exhibited significantly slower subcutaneous tumour growth and prolonged survival (FIGS. 58c & d).

The TRP2 specific response is CD8 mediated as depletion of the CD8$^+$ cells abrogates the response. CD8 T cells have been identified as a major player in anti-tumour immunity and our results show that ImmunoBody DNA immunisation elicits in vivo anti-tumour immunity in a mouse model. All immunised mice with no signs of disease exhibited vitiligo-like depigmentation of fur at the site of immunisation. Previously vitiligo is often associated with tumour protection in mice and has been highly correlated with successful IL-2 immunotherapy in patients with metastatic melanoma (Overwijk et al, *Proceedings of the National Academy of Sciences of the United States of America* 1999; 96: 2982-7; Lane et al, *Cancer Research* 2004; 64: 1509-14; Steitz et al, *Cancer Immunol Immunother* 2006; 55: 246-53; Rosenberg & White, *J Immunother Emphasis Tumor Immunol* 1996; 19: 81-4).

Example 16

ImmunoBody Immunisation Significantly Delays Tumour Growth

ImmunoBody immunisation has previously shown to significantly protect against tumour challenge. The vaccine was subsequently tested for efficacy in a therapeutic setting.

C57B1/6 mice were injected s.c. with 2×10$^4$ B16F10 tumour cells. Four days post injection mice were immunised with ImmunoBody DNA containing TRP2 epitope in CDRH2 or control ImmunoBody DNA. Repeat immunisations were performed at days 11 and 18 post tumour injection. Tumour growth was monitored at 3-4 day intervals. ImmunoBody immunised mice demonstrate a significant delay in growth of the aggressive B16F10 melanoma compared to control immunised mice (FIG. 59a).

A similar study was also performed using the less aggressive B16F10 IFNalpha tumour line. C57B1/6 mice were injected with 2×10$^4$ tumour cells s.c. and immunised at day 14 with ImmunoBody DNA or control DNA. Repeat immunisation were performed at days 21 and 28 post tumour injection. ImmunoBody immunised mice exhibited significantly lower tumour growth than control immunised mice at day 47 post tumour injection (FIG. 59b).

Previous data has suggested that depletion of T regulatory cells enhances generation of immune responses therefore an anti-tumour study was performed. In this study mice were injected with 2×10$^4$ B16F10 tumour cells s.c. and immunised at day 4, 11 and 18 with ImmunoBody DNA or control DNA. On day 0 mice were depleted of T regulatory cells via injection of anti-CD25 antibody (PC61). Concurrent with the second immunisation mice were also injected with anti-CTLA-4 antibody as blockade of CTLA-4 has also shown to be beneficial in the inhibition of regulatory T cells. Tumour growth was monitored and although ImmunoBody immunisation significantly delays the tumour growth (p=0.0188) this was further enhanced by treatment with anti-CD25 and anti-CTLA-4 antibodies (p=0.001) (FIG. 59c). The treatment with anti-CD25 antibody did not appear to significantly delay the tumour growth observed in ImmunoBody immunised mice.

Example 17

Immune Responses can be Generated from ImmunoBody Constructs Expressed from Different Vector Backbones Responses were analysed when ImmunoBody constructs were expressed from different vector backbones. ImmunoBody construct containing gp100DR7 epitope in CDRH1, TRP2 epitope in CDRH2 and gp100DR4 epitope in CDRH3 with wildtype light chain was engineered into the double expression vectors DCOrig and DCVax (DCIB54, FIGS. 18 and 29). HLA-DR4 transgenic mice were immunised via gene gun three times at weekly intervals and responses analysed ex vivo by IFNγ elispot assay.

Similar experiments were performed using an ImmunoBody construct containing gp100DR7 epitope in CDRH1 and CDRL3, TRP2 epitope in CDRH2, gp100DR4 epitope in CDRH3 and CDRL1 (DCIB68, FIG. 60). This construct was engineered into both the DCOrig, DCOrig devoid of the SV40 promoter and DCVax vector backbones.

Mice immunised with the ImmunoBody construct in the Orig vector (B1-3) demonstrate similar frequency epitope responses compared to the Immunobody cionstruct in the pVax vector (C1-3) (FIG. 61).

In summary, ImmunoBody technology has superior ability to elicit high frequency and avidity CD8 and CD4 immune responses from a non-immunogenic antibody framework that can efficiently prevent tumour growth in vivo. It has the ability to target up to six different antigens simultaneously and has the capability to avert the problem of regulatory T cells that often occurs when whole antigen immunogens are used. This technology presents a novel approach to vaccination and demonstrates the potential for the ImmunoBody system to be used as a multivalent vaccine for many other cancer types and micro-organism related diseases.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
<160> NUMBER OF SEQ ID NOS: 248

<210> SEQ ID NO 1
<211> LENGTH: 10
<212> TYPE: PRT
<213> ORGANISM: Artificial Sequence
<220> FEATURE:
<223> OTHER INFORMATION: I-Ad restricted epitope from Influenza
      haemagluttinin

<400> SEQUENCE: 1

Phe Glu Arg Phe Glu Ile Phe Pro Lys Glu
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: Tie-2 Z84 epitope

<400> SEQUENCE: 2

Phe Leu Pro Ala Thr Leu Thr Met Val
 1               5

<210> SEQ ID NO 3
<211> LENGTH: 18
<212> TYPE: PRT
<213> ORGANISM: Artificial Sequence
<220> FEATURE:
<223> OTHER INFORMATION: HLA-DR7 restricted gp100 CD4 epitope

<400> SEQUENCE: 3

Gly Thr Gly Arg Ala Met Leu Gly Thr His Thr Met Glu Val Thr Val
 1               5                  10                  15

Tyr His

<210> SEQ ID NO 4
<211> LENGTH: 9
<212> TYPE: PRT
<213> ORGANISM: Artificial Sequence
```

```
<220> FEATURE:
<223> OTHER INFORMATION: Tie-2 Z12 epitope

<400> SEQUENCE: 4

Ile Leu Ile Asn Ser Leu Pro Leu Val
1               5

<210> SEQ ID NO 5
<211> LENGTH: 9
<212> TYPE: PRT
<213> ORGANISM: Artificial Sequence
<220> FEATURE:
<223> OTHER INFORMATION: HLA-A2 restricted gp100 epitope

<400> SEQUENCE: 5

Ile Met Asp Gln Val Pro Phe Ser Val
1               5

<210> SEQ ID NO 6
<211> LENGTH: 12
<212> TYPE: PRT
<213> ORGANISM: Artificial Sequence
<220> FEATURE:
<223> OTHER INFORMATION: HepB S Ag epitope

<400> SEQUENCE: 6

Ile Pro Gln Ser Leu Asp Ser Trp Trp Thr Ser Leu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: gp100 wt ITDQVPFSV epitope

<400> SEQUENCE: 7

Ile Thr Asp Gln Val Pro Phe Ser Val
1               5

<210> SEQ ID NO 8
<211> LENGTH: 8
<212> TYPE: PRT
<213> ORGANISM: Artificial Sequence
<220> FEATURE:
<223> OTHER INFORMATION: ovalbumin epitope

<400> SEQUENCE: 8

Ser Ile Ile Asn Phe Glu Lys Leu
1               5

<210> SEQ ID NO 9
<211> LENGTH: 9
<212> TYPE: PRT
<213> ORGANISM: Artificial Sequence
<220> FEATURE:
<223> OTHER INFORMATION: TRP2 epitope

<400> SEQUENCE: 9

Ser Val Tyr Asp Phe Phe Val Trp Leu
1               5

<210> SEQ ID NO 10
<211> LENGTH: 10
<212> TYPE: PRT
<213> ORGANISM: Artificial Sequence
<220> FEATURE:
<223> OTHER INFORMATION: GP100 wild type/ GP100210M epitope
```

```
<400> SEQUENCE: 10

Thr Ile Thr Asp Gln Val Pro Phe Ser Val
1               5                   10

<210> SEQ ID NO 11
<211> LENGTH: 10
<212> TYPE: PRT
<213> ORGANISM: Artificial Sequence
<220> FEATURE:
<223> OTHER INFORMATION: GP100 F7I epitope

<400> SEQUENCE: 11

Thr Ile Thr Asp Gln Val Pro Ile Ser Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: GP100 F7L epitope

<400> SEQUENCE: 12

Thr Ile Thr Asp Gln Val Pro Leu Ser Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: GP100 F7Y epitope

<400> SEQUENCE: 13

Thr Ile Thr Asp Gln Val Pro Tyr Ser Val
1               5                   10

<210> SEQ ID NO 14
<211> LENGTH: 13
<212> TYPE: PRT
<213> ORGANISM: Artificial Sequence
<220> FEATURE:
<223> OTHER INFORMATION: I-Ab restricted epitope/ HepB CD4 epitope

<400> SEQUENCE: 14

Thr Pro Pro Ala Tyr Arg Pro Pro Asn Ala Pro Ile Leu
1               5                   10

<210> SEQ ID NO 15
<211> LENGTH: 16
<212> TYPE: PRT
<213> ORGANISM: Artificial Sequence
<220> FEATURE:
<223> OTHER INFORMATION: HLA-DR4 restricted gp100 CD4 epitope

<400> SEQUENCE: 15

Trp Asn Arg Gln Leu Tyr Pro Glu Trp Thr Glu Ala Gln Arg Leu Asp
1               5                   10                  15

<210> SEQ ID NO 16
<211> LENGTH: 14
<212> TYPE: DNA
<213> ORGANISM: Artificial Sequence
<220> FEATURE:
<223> OTHER INFORMATION: Chosen enzyme site (Fsp I) and epitope
      oligonucleotide sequence for CDR H1
<220> FEATURE:
```

```
<221> NAME/KEY: misc_feature
<222> LOCATION: 1,2,3,4,5,6
<223> OTHER INFORMATION: n = A,T,C or G

<400> SEQUENCE: 16
nnnnnntggg ttcg                                                         14

<210> SEQ ID NO 17
<211> LENGTH: 14
<212> TYPE: DNA
<213> ORGANISM: Artificial Sequence
<220> FEATURE:
<223> OTHER INFORMATION: Chosen enzyme site (Msc I) and epitope
      oligonucleotide sequence for CDR H2
<220> FEATURE:
<221> NAME/KEY: misc_feature
<222> LOCATION: 2,3,4,5,6,7
<223> OTHER INFORMATION: n = A,T,C or G

<400> SEQUENCE: 17
tnnnnnncga ttca                                                         14

<210> SEQ ID NO 18
<211> LENGTH: 10
<212> TYPE: DNA
<213> ORGANISM: Artificial Sequence
<220> FEATURE:
<223> OTHER INFORMATION: Chosen enzyme site (Srf I) and epitope
      oligonucleotide sequence for CDR H3
<220> FEATURE:
<221> NAME/KEY: misc_feature
<222> LOCATION: 3,4,5,6,7,8
<223> OTHER INFORMATION: n = A,T,C or G

<400> SEQUENCE: 18 gannnnnntg                                                              10

<210> SEQ ID NO 19
<211> LENGTH: 17
<212> TYPE: DNA
<213> ORGANISM: Artificial Sequence
<220> FEATURE:
<223> OTHER INFORMATION: Chosen enzyme site (Eco RV) and epitope
      oligonucleotide sequence for CDR L1
<220> FEATURE:
<221> NAME/KEY: misc_feature
<222> LOCATION: 8,9,10,11,12,13
<223> OTHER INFORMATION: n = A,T,C or G

<400> SEQUENCE: 19
ctcttgcnnn nnntggt                                                      17

<210> SEQ ID NO 20
<211> LENGTH: 12
<212> TYPE: DNA
<213> ORGANISM: Artificial Sequence
<220> FEATURE:
<223> OTHER INFORMATION: Chosen enzyme site (Ssp I) and epitope
      oligonucleotide sequence for CDR L2
<220> FEATURE:
<221> NAME/KEY: misc_feature
<222> LOCATION: 5,6,7,8,9,10
<223> OTHER INFORMATION: n = A,T,C or G

<400> SEQUENCE: 20
ctacnnnnnn ag                                                           12

<210> SEQ ID NO 21
<211> LENGTH: 26
<212> TYPE: DNA
```

<213> ORGANISM: Artificial Sequence
<220> FEATURE:
<223> OTHER INFORMATION: Chosen enzyme site (Hpa I) and epitope
      oligonucleotide sequence for CDR L3
<220> FEATURE:
<221> NAME/KEY: misc_feature
<222> LOCATION: 10,11,12,13,14,15
<223> OTHER INFORMATION: n = A,T,C or G

<400> SEQUENCE: 21
tattactgcn nnnnnttcgg tggagg                                        26

<210> SEQ ID NO 22
<211> LENGTH: 35
<212> TYPE: DNA
<213> ORGANISM: Artificial Sequence
<220> FEATURE:
<223> OTHER INFORMATION: Primer H1

<400> SEQUENCE: 22
cctgagaatg tcctgctgcg caggctccgg ggaag                              35

<210> SEQ ID NO 23
<211> LENGTH: 29
<212> TYPE: DNA
<213> ORGANISM: Artificial Sequence
<220> FEATURE:
<223> OTHER INFORMATION: Primer H2

<400> SEQUENCE: 23
cattggtagt ggtggccatt tccagagac                                     29

<210> SEQ ID NO 24
<211> LENGTH: 37
<212> TYPE: DNA
<213> ORGANISM: Artificial Sequence
<220> FEATURE:
<223> OTHER INFORMATION: Primer H3

<400> SEQUENCE: 24
ccgtgtatta ctgtgcccgg gccaaggaac cacggtc                            37

<210> SEQ ID NO 25
<211> LENGTH: 32
<212> TYPE: DNA
<213> ORGANISM: Artificial Sequence
<220> FEATURE:
<223> OTHER INFORMATION: Primer L1

<400> SEQUENCE: 25
ggagccagcc tcgatatctg cagaaaccag gc                                 32

<210> SEQ ID NO 26
<211> LENGTH: 32
<212> TYPE: DNA
<213> ORGANISM: Artificial Sequence
<220> FEATURE:
<223> OTHER INFORMATION: Primer L2

<400> SEQUENCE: 26
ccacagctcc taatattcag tggcagtgga tc                                 32

<210> SEQ ID NO 27
<211> LENGTH: 33
<212> TYPE: DNA
<213> ORGANISM: Artificial Sequence
<220> FEATURE:
<223> OTHER INFORMATION: Primer L3

```
<400> SEQUENCE: 27
gctgaggata ccggagttaa ccaaggtgga aat                              33

<210> SEQ ID NO 28
<211> LENGTH: 20
<212> TYPE: DNA
<213> ORGANISM: Artificial Sequence
<220> FEATURE:
<223> OTHER INFORMATION: Primer huHeClonR

<400> SEQUENCE: 28
cgcctgagtt ccacgacacc                                            20

<210> SEQ ID NO 29
<211> LENGTH: 18
<212> TYPE: DNA
<213> ORGANISM: Artificial Sequence
<220> FEATURE:
<223> OTHER INFORMATION: Primer huLiClonR

<400> SEQUENCE: 29
caggcacaca acagaggc                                              18

<210> SEQ ID NO 30
<211> LENGTH: 20
<212> TYPE: DNA
<213> ORGANISM: Artificial Sequence
<220> FEATURE:
<223> OTHER INFORMATION: Primer CMV Forward

<400> SEQUENCE: 30
ggcgtggata gcggtttgac                                            20

<210> SEQ ID NO 31
<211> LENGTH: 39
<212> TYPE: DNA
<213> ORGANISM: Artificial Sequence
<220> FEATURE:
<223> OTHER INFORMATION: Primer OrigstophuHeCH1 For

<400> SEQUENCE: 31
ccaaggtgga caagaaagtt tgacccaaat cttgtgaca                       39

<210> SEQ ID NO 32
<211> LENGTH: 45
<212> TYPE: DNA
<213> ORGANISM: Artificial Sequence
<220> FEATURE:
<223> OTHER INFORMATION: Primer OrigstophuHeCH1 Rev

<400> SEQUENCE: 32
gagttttgtc acaagatttg ggtcaaactt tcttgtccac cttgg                45

<210> SEQ ID NO 33
<211> LENGTH: 29
<212> TYPE: DNA
<213> ORGANISM: Artificial Sequence
<220> FEATURE:
<223> OTHER INFORMATION: Primer pOrig light no leader For

<400> SEQUENCE: 33
aggatccacc atggatgtgt tgatgaccc                                  29

<210> SEQ ID NO 34
<211> LENGTH: 25
```

```
<212> TYPE: DNA
<213> ORGANISM: Artificial Sequence
<220> FEATURE:
<223> OTHER INFORMATION: Primer pOrig heavy no leader For

<400> SEQUENCE: 34
aaagcttatg caggtgcagc tggtg                                      25

<210> SEQ ID NO 35
<211> LENGTH: 26
<212> TYPE: DNA
<213> ORGANISM: Artificial Sequence
<220> FEATURE:
<223> OTHER INFORMATION: Primer huigG3rev2#

<400> SEQUENCE: 35
atcgatatca tttacccgga gacagg                                     26

<210> SEQ ID NO 36
<211> LENGTH: 24
<212> TYPE: DNA
<213> ORGANISM: Artificial Sequence
<220> FEATURE:
<223> OTHER INFORMATION: Primer IgG3hufor2

<400> SEQUENCE: 36
actgtctcca gcgcttccac caag                                       24

<210> SEQ ID NO 37
<211> LENGTH: 24
<212> TYPE: DNA
<213> ORGANISM: Artificial Sequence
<220> FEATURE:
<223> OTHER INFORMATION: Primer IgG2 for

<400> SEQUENCE: 37
agtcaccgtt tccagcgctt ccac                                       24

<210> SEQ ID NO 38
<211> LENGTH: 27
<212> TYPE: DNA
<213> ORGANISM: Artificial Sequence
<220> FEATURE:
<223> OTHER INFORMATION: Primer IgG2 rev

<400> SEQUENCE: 38
agtggatatc atttacccgg agacagg                                    27

<210> SEQ ID NO 39
<211> LENGTH: 20
<212> TYPE: DNA
<213> ORGANISM: Artificial Sequence
<220> FEATURE:
<223> OTHER INFORMATION: Primer HIBF

<400> SEQUENCE: 39
aacagtctga gggctgagga                                            20

<210> SEQ ID NO 40
<211> LENGTH: 34
<212> TYPE: DNA
<213> ORGANISM: Artificial Sequence
<220> FEATURE:
<223> OTHER INFORMATION: Primer huigG1PVA REV

<400> SEQUENCE: 40
agactgacgg tcccccccgcg actggaggtg ctgg                           34
```

```
<210> SEQ ID NO 41
<211> LENGTH: 34
<212> TYPE: DNA
<213> ORGANISM: Artificial Sequence
<220> FEATURE:
<223> OTHER INFORMATION: Primer HuigG2ELLGRev

<400> SEQUENCE: 41
agactgacgg tcctcctaac agttctggtg ctgg                              34

<210> SEQ ID NO 42
<211> LENGTH: 34
<212> TYPE: DNA
<213> ORGANISM: Artificial Sequence
<220> FEATURE:
<223> OTHER INFORMATION: Primer SV40premFOR

<400> SEQUENCE: 42
agctagcatc agcacgtgtt gacaattaat catc                              34

<210> SEQ ID NO 43
<211> LENGTH: 28
<212> TYPE: DNA
<213> ORGANISM: Artificial Sequence
<220> FEATURE:
<223> OTHER INFORMATION: Primer SV40premREV

<400> SEQUENCE: 43
aacgattccg aagcccaacc tttcatag                                     28

<210> SEQ ID NO 44
<211> LENGTH: 32
<212> TYPE: DNA
<213> ORGANISM: Artificial Sequence
<220> FEATURE:
<223> OTHER INFORMATION: Primer migG2aC1Afe1F2

<400> SEQUENCE: 44
tttacagcgc taaaacaaca gccccatcgg tc                                32

<210> SEQ ID NO 45
<211> LENGTH: 34
<212> TYPE: DNA
<213> ORGANISM: Artificial Sequence
<220> FEATURE:
<223> OTHER INFORMATION: Primer migG2aXbaRA

<400> SEQUENCE: 45
tctagatcat ttacccggag tccgggagaa gctc                              34

<210> SEQ ID NO 46
<211> LENGTH: 30
<212> TYPE: DNA
<213> ORGANISM: Artificial Sequence
<220> FEATURE:
<223> OTHER INFORMATION: Primer MoLC1BsiF1

<400> SEQUENCE: 46
tttcgtacgg atgctgcacc aactgtatcc                                   30

<210> SEQ ID NO 47
<211> LENGTH: 32
<212> TYPE: DNA
<213> ORGANISM: Artificial Sequence
<220> FEATURE:
<223> OTHER INFORMATION: Primer MoLCXhoR1
```

<400> SEQUENCE: 47
tttctcgagt caacactcat tcctgttgaa gc                                32

<210> SEQ ID NO 48
<211> LENGTH: 36
<212> TYPE: DNA
<213> ORGANISM: Artificial Sequence
<220> FEATURE:
<223> OTHER INFORMATION: Primer MoIgG2BamHI For

<400> SEQUENCE: 48
ccttgacctg gaactctggt tccctgtcca gtggtg                            36

<210> SEQ ID NO 49
<211> LENGTH: 36
<212> TYPE: DNA
<213> ORGANISM: Artificial Sequence
<220> FEATURE:
<223> OTHER INFORMATION: Primer MoigG2BamHI Rev

<400> SEQUENCE: 49
caccactgga cagggaacca gagttccagg tcaagg                            36

<210> SEQ ID NO 50
<211> LENGTH: 38
<212> TYPE: DNA
<213> ORGANISM: Artificial Sequence
<220> FEATURE:
<223> OTHER INFORMATION: Primer MoigG2XhoI For

<400> SEQUENCE: 50
gcagctcagt gactgtaact tcgagcacct ggcccagc                          38

<210> SEQ ID NO 51
<211> LENGTH: 38
<212> TYPE: DNA
<213> ORGANISM: Artificial Sequence
<220> FEATURE:
<223> OTHER INFORMATION: Primer MoigG2XhoI Rev

<400> SEQUENCE: 51
gctgggccag gtgctcgaag ttacagtcac tgagctgc                          38

<210> SEQ ID NO 52
<211> LENGTH: 59
<212> TYPE: DNA
<213> ORGANISM: Artificial Sequence
<220> FEATURE:
<223> OTHER INFORMATION: Primer wtkappavarL1for

<400> SEQUENCE: 52
ctcttgcaga tctagtcaga gcctggtaca tagtaatgga aacacctatt tagaatggt   59

<210> SEQ ID NO 53
<211> LENGTH: 59
<212> TYPE: DNA
<213> ORGANISM: Artificial Sequence
<220> FEATURE:
<223> OTHER INFORMATION: Primer wtkappavarL1 rev

<400> SEQUENCE: 53
accattctaa ataggtgttt ccattactat gtaccaggct ctgactagat ctgcaagag   59

<210> SEQ ID NO 54
<211> LENGTH: 36

```
<212> TYPE: DNA
<213> ORGANISM: Artificial Sequence
<220> FEATURE:
<223> OTHER INFORMATION: Primer Murine TRP2 Forward

<400> SEQUENCE: 54
tttctaagct tatgggcctt gtgggatggg ggcttc                                36

<210> SEQ ID NO 55
<211> LENGTH: 37
<212> TYPE: DNA
<213> ORGANISM: Artificial Sequence
<220> FEATURE:
<223> OTHER INFORMATION: Primer Murine TRP2 Reverse

<400> SEQUENCE: 55
tttctgatat ctcaggcttc ctccgtgtat ctcttgc                               37

<210> SEQ ID NO 56
<211> LENGTH: 35
<212> TYPE: DNA
<213> ORGANISM: Artificial Sequence
<220> FEATURE:
<223> OTHER INFORMATION: Primer GP100 Forward

<400> SEQUENCE: 56
tttctgatat catgggtgtc cagagaagga gcttc                                 35

<210> SEQ ID NO 57
<211> LENGTH: 36
<212> TYPE: DNA
<213> ORGANISM: Artificial Sequence
<220> FEATURE:
<223> OTHER INFORMATION: Primer Gp100 Reverse

<400> SEQUENCE: 57
tttctctcga gtcagacctg ctgtccactg aggagc                                36

<210> SEQ ID NO 58
<211> LENGTH: 35
<212> TYPE: DNA
<213> ORGANISM: Artificial Sequence
<220> FEATURE:
<223> OTHER INFORMATION: Phosphorylated primer (TRP2 epitope example)

<400> SEQUENCE: 58
tagtgtttat gattttttg tgtggctccg attca                                  35

<210> SEQ ID NO 59
<211> LENGTH: 27
<212> TYPE: DNA
<213> ORGANISM: Artificial Sequence
<220> FEATURE:
<223> OTHER INFORMATION: CD8 CTL or CD4 helpter epitope (TRP2, HLA
      restriction A2, Kb)

<400> SEQUENCE: 59
agtgtttatg atttttttgt gtggctc                                          27

<210> SEQ ID NO 60
<211> LENGTH: 30
<212> TYPE: DNA
<213> ORGANISM: Artificial Sequence
<220> FEATURE:
<223> OTHER INFORMATION: CD8 CTL or CD4 helpter epitope (GP100, HLA
      restriction A2)

<400> SEQUENCE: 60
```
accattactg accaggtgcc tttctccgtg                                        30

<210> SEQ ID NO 61
<211> LENGTH: 30
<212> TYPE: DNA
<213> ORGANISM: Artificial Sequence
<220> FEATURE:
<223> OTHER INFORMATION: CD8 CTL or CD4 helper epitope (GP100 (210M),
      HLA restriction A2)

<400> SEQUENCE: 61
accattatgg accaggtgcc tttctccgtg                                        30

<210> SEQ ID NO 62
<211> LENGTH: 30
<212> TYPE: DNA
<213> ORGANISM: Artificial Sequence
<220> FEATURE:
<223> OTHER INFORMATION: CD8 CTL or CD4 helper epitope (GP100 (F7L))

<400> SEQUENCE: 62
accattactg accaggtgcc tttgtccgtg                                        30

<210> SEQ ID NO 63
<211> LENGTH: 9
<212> TYPE: PRT
<213> ORGANISM: Artificial Sequence
<220> FEATURE:
<223> OTHER INFORMATION: GP100 (F7L) epitope, HLA restriction A2

<400> SEQUENCE: 63

Ile Thr Asp Gln Val Pro Leu Ser Val
 1               5

<210> SEQ ID NO 64
<211> LENGTH: 48
<212> TYPE: DNA
<213> ORGANISM: Artificial Sequence
<220> FEATURE:
<223> OTHER INFORMATION: CD8 CTL or CD4 helper epitope (GP100, HLA
      restriction DR0401)

<400> SEQUENCE: 64
tggaacaggc agctgtatcc agagtggaca gaagcccaga gacttgac                    48

<210> SEQ ID NO 65
<211> LENGTH: 36
<212> TYPE: DNA
<213> ORGANISM: Artificial Sequence
<220> FEATURE:
<223> OTHER INFORMATION: CD8 CTL or CD4 helper epitope (HEPB S AG, HLA
      restriction Kd(CTL))

<400> SEQUENCE: 65
ataccgcaga gtctagactc gtggtggact tctctc                                 36

<210> SEQ ID NO 66
<211> LENGTH: 39
<212> TYPE: DNA
<213> ORGANISM: Artificial Sequence
<220> FEATURE:
<223> OTHER INFORMATION: CD8 CTL or CD4 helper epitope (HepB
      nucleoprotein, HLA
      restriction I-Ab (helper))

<400> SEQUENCE: 66
actcctccag cttatagacc accaaatgcc cctatccta                              39

<210> SEQ ID NO 67
<211> LENGTH: 27
<212> TYPE: DNA
<213> ORGANISM: Artificial Sequence
<220> FEATURE:
<223> OTHER INFORMATION: CD8 CTL or CD4 helpter epitope (MAGE3, HLA
      restriction A2)

<400> SEQUENCE: 67
ttcctgtggg gtccaagggc cctcgtt                                         27

<210> SEQ ID NO 68
<211> LENGTH: 9
<212> TYPE: PRT
<213> ORGANISM: Artificial Sequence
<220> FEATURE:
<223> OTHER INFORMATION: CD8 CTL or CD4 helpter epitope (MAGE3, HLA
      restriction A2)

<400> SEQUENCE: 68

Phe Leu Trp Gly Pro Arg Ala Leu Val
 1               5

<210> SEQ ID NO 69
<211> LENGTH: 27
<212> TYPE: DNA
<213> ORGANISM: Artificial Sequence
<220> FEATURE:
<223> OTHER INFORMATION: CD8 CTL or CD4 helpter epitope (Tie2 (Z83), HLA
      restriction A2)

<400> SEQUENCE: 69
ttcctaccag ctactttaac tatgact                                         27

<210> SEQ ID NO 70
<211> LENGTH: 9
<212> TYPE: PRT
<213> ORGANISM: Artificial Sequence
<220> FEATURE:
<223> OTHER INFORMATION: CD8 CTL or CD4 helpter epitope (Tie2 (Z83), HLA
      restriction A2)

<400> SEQUENCE: 70

Phe Leu Pro Ala Thr Leu Thr Met Thr
 1               5

<210> SEQ ID NO 71
<211> LENGTH: 27
<212> TYPE: DNA
<213> ORGANISM: Artificial Sequence
<220> FEATURE:
<223> OTHER INFORMATION: CD8 CTL or CD4 helpter epitope (Tie2 (Z84), HLA
      restriction A2)

<400> SEQUENCE: 71
ttcctaccag ctactttaac tatggtt                                         27

<210> SEQ ID NO 72
<211> LENGTH: 9
<212> TYPE: PRT
<213> ORGANISM: Artificial Sequence
<220> FEATURE:
<223> OTHER INFORMATION: CD8 CTL or CD4 helpter epitope (Tie2 (Z84), HLA
      restriction A2)

<400> SEQUENCE: 72

Phe Leu Pro Ala Thr Leu Thr Met Val

<210> SEQ ID NO 73
<211> LENGTH: 27
<212> TYPE: DNA
<213> ORGANISM: Artificial Sequence
<220> FEATURE:
<223> OTHER INFORMATION: CD8 CTL or CD4 helpter epitope (Tie2 (Z9), HLA
      restriction A2)

<400> SEQUENCE: 73
gggatggtgg aaaagccctt caacatt                                         27

<210> SEQ ID NO 74
<211> LENGTH: 9
<212> TYPE: PRT
<213> ORGANISM: Artificial Sequence
<220> FEATURE:
<223> OTHER INFORMATION: CD8 CTL or CD4 helpter epitope (Tie2 (Z9), HLA
      restriction A2)

<400> SEQUENCE: 74

Gly Met Val Glu Lys Pro Phe Asn Ile
1               5

<210> SEQ ID NO 75
<211> LENGTH: 27
<212> TYPE: DNA
<213> ORGANISM: Artificial Sequence
<220> FEATURE:
<223> OTHER INFORMATION: CD8 CTL or CD4 helpter epitope (Tie2 (mZ9), HLA
      restriction A2)

<400> SEQUENCE: 75
gggatggtgg aaaagccctt caacgtt                                         27

<210> SEQ ID NO 76
<211> LENGTH: 9
<212> TYPE: PRT
<213> ORGANISM: Artificial Sequence
<220> FEATURE:
<223> OTHER INFORMATION: CD8 CTL or CD4 helpter epitope (Tie2 (mZ9), HLA
      restriction A2)

<400> SEQUENCE: 76

Gly Met Val Glu Lys Pro Phe Asn Val
1               5

<210> SEQ ID NO 77
<211> LENGTH: 30
<212> TYPE: DNA
<213> ORGANISM: Artificial Sequence
<220> FEATURE:
<223> OTHER INFORMATION: CD8 CTL or CD4 helpter epitope (FLU HA, HLA
      restriction I-Ad (helper))

<400> SEQUENCE: 77
tttgaaaggt ttgagatatt ccccaaggaa                                      30

<210> SEQ ID NO 78
<211> LENGTH: 24
<212> TYPE: DNA
<213> ORGANISM: Artificial Sequence
<220> FEATURE:
<223> OTHER INFORMATION: CD8 CTL or CD4 helpter epitope (ovalbumin, HLA
      restriction Kb)

<400> SEQUENCE: 78
agtataatca actttgaaaa actg                                          24

<210> SEQ ID NO 79
<211> LENGTH: 45
<212> TYPE: DNA
<213> ORGANISM: Artificial Sequence
<220> FEATURE:
<223> OTHER INFORMATION: CD8 CTL or CD4 helpter epitope (Triosephosphate
      isomerase (wt), HLA restriction DR0101)

<400> SEQUENCE: 79
ggggagctca tcggcattct gaacgcggcc aaggtgccgg ccgac                   45

<210> SEQ ID NO 80
<211> LENGTH: 15
<212> TYPE: PRT
<213> ORGANISM: Artificial Sequence
<220> FEATURE:
<223> OTHER INFORMATION: CD8 CTL or CD4 helpter epitope (Triosephosphate
      isomerase (wt), HLA restriction DR0101)

<400> SEQUENCE: 80

Gly Glu Leu Ile Gly Thr Leu Asn Ala Ala Lys Val Pro Ala Asp
1               5                   10                  15

<210> SEQ ID NO 81
<211> LENGTH: 45
<212> TYPE: DNA
<213> ORGANISM: Artificial Sequence
<220> FEATURE:
<223> OTHER INFORMATION: CD8 CTL or CD4 helpter epitope (Triosephosphate
      Isomerase (mI), HLA restriction DR0101)

<400> SEQUENCE: 81
ggggagctca tcggcactct gaacgcggcc aaggtgccgg ccgac                   45

<210> SEQ ID NO 82
<211> LENGTH: 15
<212> TYPE: PRT
<213> ORGANISM: Artificial Sequence
<220> FEATURE:
<223> OTHER INFORMATION: CD8 CTL or CD4 helpter epitope (Triosephosphate
      Isomerase (mI), HLA restriction DR0101)

<400> SEQUENCE: 82

Gly Glu Leu Ile Gly Ile Leu Asn Ala Ala Lys Val Pro Ala Asp
1               5                   10                  15

<210> SEQ ID NO 83
<211> LENGTH: 27
<212> TYPE: DNA
<213> ORGANISM: Artificial Sequence
<220> FEATURE:
<223> OTHER INFORMATION: CD8 CTL or CD4 helpter epitope (VEGFR2, HLA
      restriction A2)

<400> SEQUENCE: 83
gtgattgcca tgttcttctg gctactt                                       27

<210> SEQ ID NO 84
<211> LENGTH: 9
<212> TYPE: PRT
<213> ORGANISM: Artificial Sequence
<220> FEATURE:
<223> OTHER INFORMATION: CD8 CTL or CD4 helpter epitope (VEGFR2, HLA
      restriction A2)

<400> SEQUENCE: 84

-continued

Val Ile Ala Met Phe Phe Trp Leu Leu
1               5

<210> SEQ ID NO 85
<211> LENGTH: 28
<212> TYPE: DNA
<213> ORGANISM: Artificial Sequence
<220> FEATURE:
<223> OTHER INFORMATION: CD8 CTL or CD4 helpter epitope (mVEGFR2, HLA
      restriction A2)

<400> SEQUENCE: 85
gtgcttgcca tggttcttct ggctactt                                      28

<210> SEQ ID NO 86
<211> LENGTH: 9
<212> TYPE: PRT
<213> ORGANISM: Artificial Sequence
<220> FEATURE:
<223> OTHER INFORMATION: CD8 CTL or CD4 helpter epitope (mVEGFR2, HLA
      restriction A2)

<400> SEQUENCE: 86

Val Leu Ala Met Phe Phe Trp Leu Leu
1               5

<210> SEQ ID NO 87
<211> LENGTH: 10
<212> TYPE: PRT
<213> ORGANISM: Artificial Sequence
<220> FEATURE:
<223> OTHER INFORMATION: Gp100 V5L epitope

<400> SEQUENCE: 87

Thr Ile Thr Asp Gln Leu Pro Phe Ser Val
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Predicted HLA-A*0201 restricted CTL epitope
      from Tie-2 (Z282)

<400> SEQUENCE: 88

Ile Leu Ile Asn Ser Leu Pro Leu Val
1               5

<210> SEQ ID NO 89
<211> LENGTH: 9
<212> TYPE: PRT
<213> ORGANISM: Artificial Sequence
<220> FEATURE:
<223> OTHER INFORMATION: Predicted HLA-A*0201 restricted CTL epitope
      from Tie-2 (Z283)

<400> SEQUENCE: 89

Val Leu Ile Lys Glu Glu Asp Ala Val
1               5

<210> SEQ ID NO 90
<211> LENGTH: 9
<212> TYPE: PRT
<213> ORGANISM: Artificial Sequence
<220> FEATURE:
<223> OTHER INFORMATION: Predicted HLA-A*0201 restricted CTL epitope
      from Tie-2 (Z284)

```
<400> SEQUENCE: 90

Leu Met Asn Gln His Gln Asp Pro Leu
 1               5

<210> SEQ ID NO 91
<211> LENGTH: 9
<212> TYPE: PRT
<213> ORGANISM: Artificial Sequence
<220> FEATURE:
<223> OTHER INFORMATION: Predicted HLA-A*0201 restricted CTL epitope
      from Tie-2 (Z285)

<400> SEQUENCE: 91

Val Leu Cys Gly Val Ser Leu Leu Leu
 1               5

<210> SEQ ID NO 92
<211> LENGTH: 9
<212> TYPE: PRT
<213> ORGANISM: Artificial Sequence
<220> FEATURE:
<223> OTHER INFORMATION: Predicted HLA-A*0201 restricted CTL epitope
      from Tie-2 (Z286)

<400> SEQUENCE: 92

Leu Val Ser Asp Ala Glu Thr Ser Leu
 1               5

<210> SEQ ID NO 93
<211> LENGTH: 9
<212> TYPE: PRT
<213> ORGANISM: Artificial Sequence
<220> FEATURE:
<223> OTHER INFORMATION: Predicted HLA-A*0201 restricted CTL epitope
      from Tie-2 (Z287)

<400> SEQUENCE: 93

Leu Ile Leu Ile Asn Ser Leu Pro Leu
 1               5

<210> SEQ ID NO 94
<211> LENGTH: 9
<212> TYPE: PRT
<213> ORGANISM: Artificial Sequence
<220> FEATURE:
<223> OTHER INFORMATION: Predicted HLA-A*0201 restricted CTL epitope
      from Tie-2 (Z18)

<400> SEQUENCE: 94

Gly Ile Leu Gly Phe Val Phe Thr Leu
 1               5

<210> SEQ ID NO 95
<211> LENGTH: 9
<212> TYPE: PRT
<213> ORGANISM: Artificial Sequence
<220> FEATURE:
<223> OTHER INFORMATION: HLA-A2 restricted peptide derived from VEGFR2

<400> SEQUENCE: 95

Val Ile Ala Met Phe Phe Trp Leu Leu
 1               5

<210> SEQ ID NO 96
<211> LENGTH: 9
<212> TYPE: PRT
<213> ORGANISM: Artificial Sequence
<220> FEATURE:
```

<223> OTHER INFORMATION: modified hTERT peptides

<400> SEQUENCE: 96

Tyr Leu Phe Phe Tyr Arg Lys Ser Val
1               5

<210> SEQ ID NO 97
<211> LENGTH: 10
<212> TYPE: PRT
<213> ORGANISM: Artificial Sequence
<220> FEATURE:
<223> OTHER INFORMATION: modified hTERT peptide

<400> SEQUENCE: 97

Tyr Leu Gln Val Asn Ser Leu Gln Thr Val
1               5                   10

<210> SEQ ID NO 98
<211> LENGTH: 1489
<212> TYPE: DNA
<213> ORGANISM: Unknown
<220> FEATURE:
<223> OTHER INFORMATION: Immunobody chimeric heavy chain

<400> SEQUENCE: 98

| | | |
|---|---|---|
| aagcttacca tgggatggag ctgtatcatc ctcttcttgg tagcaacagc taccggagtc | 60 |
| cactcccagg tgcagctggt ggagactggg ggaggcttaa tccagcctgg agggtccctg | 120 |
| agaatgtcct gtgcagcctc tggattcgct ttcaatacct atgacatgtc ttgggttcgc | 180 |
| caggctccgg ggaaggggct ggagtggatc gcatacattg gtagtggtgg tgatagaacc | 240 |
| tactatccag acactgtgaa gggccgattc accatttcca gagacaatag caagaacacc | 300 |
| ctgtatttgc aattgaacag tctgagggct gaggacacag ccgtgtatta ctgtgcaaga | 360 |
| cattatggtc actacgtgga ctatgctgtg gactactggg gtcaaggaac cacggtcacc | 420 |
| gtctccagcg cttccaccaa gggcccatcg gtcttccccc tggcaccctc ctccaagagc | 480 |
| acctctgggg gcacagcggc cctgggctgc ctggtcaagg actacttccc cgaaccggtg | 540 |
| acggtgtcgt ggaactcagg cgccctgacc agcggcgtgc acaccttccc ggctgtccta | 600 |
| cagtcctcag gactctactc cctcagcagc gtggtgaccg tgccctccag cagcttgggc | 660 |
| acccagacct acatctgcaa cgtgaatcac aagcccagca acaccaaggt ggacaagaaa | 720 |
| gttgagccca atcttgtgca aaaactcaca catgcccac cgtgcccagc acctgaactc | 780 |
| ctggggggac cgtcagtctt cctcttcccc ccaaaaccca aggacaccct catgatctcc | 840 |
| cggacccctg aggtcacatg cgtggtggtg gacgtgagcc acgaagaccc tgaggtcaag | 900 |
| ttcaactggt acgtggacgg cgtggaggtg cataatgcca agacaaagcc gcgggaggag | 960 |
| cagtacaaca gcacgtaccg tgtggtcagc gtcctcaccg tcctgcacca ggactggctg | 1020 |
| aatggcaagg agtacaagtg caaggtctcc aacaaagccc tcccagcccc catcgagaaa | 1080 |
| accatctcca aagccaaagg gcagccccga gaaccacagg tgtacaccct gcccccatcc | 1140 |
| cgggatgagc tgaccaagaa ccaggtcagc ctgacctgcc tggtcaaagg cttctatccc | 1200 |
| agcgacatcg ccgtggagtg ggagagcaat gggcagccgg agaacaacta caagaccacg | 1260 |
| cctcccgtgc tggactccga cggctccttc ttcctctaca gcaagctcac cgtggacaag | 1320 |
| agcaggtggc agcaggggaa cgtcttctca tgctccgtga tgcatgaggc tctgcacaac | 1380 |
| cactacacgc agaagagcct ctccctgtct ccgggtaaat gatctaaagg gcgaattcgc | 1440 |
| ccttaagggc gaatttttgca gatatccatc acactggcgg ccgctcgag | 1489 |

```
<210> SEQ ID NO 99
<211> LENGTH: 467
<212> TYPE: PRT
<213> ORGANISM: Unknown
<220> FEATURE:
<223> OTHER INFORMATION: Immunobody chimeric heavy chain

<400> SEQUENCE: 99
```

| | | | | | | | | | | | | | | |
|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly |
| 1 | | | | 5 | | | | | 10 | | | | | 15 |
| Val | His | Ser | Gln | Val | Gln | Leu | Val | Glu | Thr | Gly | Met | Gly | Trp | Ser | Cys |
| | | | 20 | | | | | 25 | | | | | 30 | | |
| Ile | Ile | Leu | Phe | Leu | Val | Ala | Thr | Ala | Thr | Gly | Val | His | Ser | Gln | Val |
| | | 35 | | | | | 40 | | | | | 45 | | | |
| Gln | Leu | Val | Glu | Thr | Gly | Gln | Ala | Pro | Gly | Lys | Gly | Leu | Glu | Trp | Ile |
| | 50 | | | | | 55 | | | | | 60 | | | | |
| Ala | Tyr | Ile | Gly | Ser | Gly | Gly | Asp | Arg | Thr | Tyr | Tyr | Pro | Asp | Thr | Val |
| 65 | | | | | 70 | | | | | 75 | | | | | 80 |
| Lys | Gly | Arg | Phe | Thr | Ile | Ser | Arg | Asp | Asn | Ser | Lys | Asn | Thr | Leu | Tyr |
| | | | | 85 | | | | | 90 | | | | | 95 | |
| Leu | Gln | Leu | Asn | Ser | Leu | Arg | Ala | Glu | Asp | Thr | Ala | Val | Tyr | Tyr | Cys |
| | | | | 100 | | | | | 105 | | | | | 110 | |
| Ala | Arg | His | Tyr | Gly | His | Tyr | Val | Asp | Tyr | Ala | Val | Asp | Tyr | Trp | Gly |
| | | | 115 | | | | | 120 | | | | | 125 | | |
| Gln | Gly | Thr | Thr | Val | Thr | Val | Ser | Ser | Ala | Ser | Thr | Lys | Gly | Pro | Ser |
| | 130 | | | | | 135 | | | | | 140 | | | | |
| Val | Phe | Pro | Leu | Ala | Pro | Ser | Ser | Lys | Ser | Thr | Ser | Gly | Gly | Thr | Ala |
| 145 | | | | | 150 | | | | | 155 | | | | | 160 |
| Ala | Leu | Gly | Cys | Leu | Val | Lys | Asp | Tyr | Phe | Pro | Glu | Pro | Val | Thr | Val |
| | | | | 165 | | | | | 170 | | | | | 175 | |
| Ser | Trp | Asn | Ser | Gly | Ala | Leu | Thr | Ser | Gly | Val | His | Thr | Phe | Pro | Ala |
| | | | | 180 | | | | | 185 | | | | | 190 | |
| Val | Leu | Gln | Ser | Ser | Gly | Leu | Tyr | Ser | Leu | Ser | Ser | Val | Val | Thr | Val |
| | | | 195 | | | | | 200 | | | | | 205 | | |
| Pro | Ser | Ser | Leu | Gly | Thr | Gln | Thr | Tyr | Ile | Cys | Asn | Val | Asn | His |
| | 210 | | | | | 215 | | | | | 220 | | | | |
| Lys | Pro | Ser | Asn | Thr | Lys | Val | Asp | Lys | Val | Glu | Pro | Lys | Ser | Cys |
| 225 | | | | | 230 | | | | | 235 | | | | | 240 |
| Asp | Lys | Thr | His | Thr | Cys | Pro | Pro | Cys | Pro | Ala | Pro | Glu | Leu | Leu | Gly |
| | | | | 245 | | | | | 250 | | | | | 255 | |
| Gly | Pro | Ser | Val | Phe | Leu | Phe | Pro | Pro | Lys | Pro | Lys | Asp | Thr | Leu | Met |
| | | | | 260 | | | | | 265 | | | | | 270 | |
| Ile | Ser | Arg | Thr | Pro | Glu | Val | Thr | Cys | Val | Val | Val | Asp | Val | Ser | His |
| | | | 275 | | | | | 280 | | | | | 285 | | |
| Glu | Asp | Pro | Glu | Val | Lys | Phe | Asn | Trp | Tyr | Val | Asp | Gly | Val | Glu | Val |
| | 290 | | | | | 295 | | | | | 300 | | | | |
| His | Asn | Ala | Lys | Thr | Lys | Pro | Arg | Glu | Glu | Gln | Tyr | Asn | Ser | Thr | Tyr |
| 305 | | | | | 310 | | | | | 315 | | | | | 320 |
| Arg | Val | Val | Ser | Val | Leu | Thr | Val | Leu | His | Gln | Asp | Trp | Leu | Asn | Gly |
| | | | | 325 | | | | | 330 | | | | | 335 | |
| Lys | Glu | Tyr | Lys | Cys | Lys | Val | Ser | Asn | Lys | Ala | Leu | Pro | Ala | Pro | Ile |
| | | | | 340 | | | | | 345 | | | | | 350 | |
| Glu | Lys | Thr | Ile | Ser | Lys | Ala | Lys | Gly | Gln | Pro | Arg | Glu | Pro | Gln | Val |
| | | | 355 | | | | | 360 | | | | | 365 | | |
| Tyr | Thr | Leu | Pro | Pro | Ser | Arg | Asp | Glu | Leu | Thr | Lys | Asn | Gln | Val | Ser |

```
                370                 375                 380
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 100
<211> LENGTH: 732
<212> TYPE: DNA
<213> ORGANISM: Unknown
<220> FEATURE:
<223> OTHER INFORMATION: Immunbody chimeric kappa chain

<400> SEQUENCE: 100
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctccatct cttgcagatc tagtcagagc ctggtacata gtaatggaaa cacctattta     180
gaatggtacc tgcagaaacc aggccagtct ccacagctcc tgatctacaa gtttccaac      240 cgatttctg gggtcccaga cagattcagt ggcagtggat cagggacaga tttcacactc      300
aagatcagca gagtggaggc tgaggatacc ggagtgtatt actgctttca aggttcacat     360
gttccgtgga cgttcggtgg aggcaccaag gtggaaatca agcgtacggt agcggcccca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccaccaggg cctgagctcg cccgtcacaa agagcttcaa caggggagag     720
tgttgactcg ag                                                        732

<210> SEQ ID NO 101
<211> LENGTH: 238
<212> TYPE: PRT
<213> ORGANISM: Unknown
<220> FEATURE:
<223> OTHER INFORMATION: Immunbody chimeric kappa chain

<400> SEQUENCE: 101

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
                20                  25                  30

Thr Pro Gly Glu Pro Ala Ser Ile Ser Cys Arg Ser Ser Gln Ser Leu
            35                  40                  45

Val His Ser Asn Gly Asn Thr Tyr Leu Glu Trp Tyr Leu Gln Lys Pro
        50                  55                  60

Gly Gln Ser Pro Gln Leu Leu Ile Tyr Lys Val Ser Asn Arg Phe Ser
65                  70                  75                  80
```

Gly Val Pro Asp Arg Phe Ser Gly Ser Gly Thr Asp Phe Thr
            85                  90                  95

Leu Lys Ile Ser Arg Val Glu Ala Glu Asp Thr Gly Val Tyr Tyr Cys
            100                 105                 110

Phe Gln Gly Ser His Val Pro Trp Thr Phe Gly Gly Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

```
<210> SEQ ID NO 102
<211> LENGTH: 376
<212> TYPE: DNA
<213> ORGANISM: Unknown
<220> FEATURE:
<223> OTHER INFORMATION: ImmunoBody heavy chain variable region (H1)

<400> SEQUENCE: 102
atgggatgga gctgtatcat cctcttcttg gtagcaacag ctaccggagt ccactcccag     60
gtgcagctgg tggagactgg gggaggctta atccagcctg agggtccct  gagaatgtcc   120 tgcgcaggct ccggggaagg ggctggagtg gatcgcatac attggtagtg gtggtgatag   180
aacctactat ccagacactg tgaagggccg attcaccatt tccagagaca atagcaagaa   240 cacccctgtat ttgcaattga acagtctgag ggctgaggac acagccgtgt attactgtgc   300
aagacattat ggtcactacg tggactatgc tgtggactac tggggtcaag gtaccacggt   360
caccgtctcc agcgct                                                    376

<210> SEQ ID NO 103
<211> LENGTH: 125
<212> TYPE: PRT
<213> ORGANISM: Unknown
<220> FEATURE:
<223> OTHER INFORMATION: ImmunoBody heavy chain variable region (H1)

<400> SEQUENCE: 103
```

Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Gln Ala Pro Gly Lys Gly Leu
            35                  40                  45

Glu Trp Ile Ala Tyr Ile Gly Ser Gly Gly Asp Arg Thr Tyr Tyr Pro
50                  55                  60

Asp Thr Val Lys Gly Arg Phe Thr Ile Ser Arg Asp Asn Ser Lys Asn
65                  70                  75                  80

```
Thr Leu Tyr Leu Gln Leu Asn Ser Leu Arg Ala Glu Asp Thr Ala Val
            85                  90                  95

Tyr Tyr Cys Ala Arg His Tyr Gly His Tyr Val Asp Tyr Ala Val Asp
            100                 105                 110

Tyr Trp Gly Gln Gly Thr Thr Val Thr Val Ser Ser Ala
            115                 120             125

<210> SEQ ID NO 104
<211> LENGTH: 382
<212> TYPE: DNA
<213> ORGANISM: Unknown
<220> FEATURE:
<223> OTHER INFORMATION: ImmunoBody heavy chain variable region (H2)

<400> SEQUENCE: 104
atgggatgga gctgtatcat cctcttcttg gtagcaacag ctaccggagt ccactcccag     60
gtgcagctgg tggagactgg gggaggctta atccagcctg agggtccct gagaatgtcc     120 tgtgcagcct ctggattcgc tttcaatacc tatgacatgt cttgggttcg ccaggctccg     180
gggaaggggc tggagtggat cgcatacatt ggtagtggtg ccatttcca gagacaatag     240 caagaacacc ctgtatttgc aattgaacag tctgagggct gaggacacag ccgtgtatta     300
ctgtgcaaga cattatggtc actacgtgga ctatgctgtg gactactggg gtcaaggtac     360
cacggtcacc gtctccagcg ct                                             382

<210> SEQ ID NO 105
<211> LENGTH: 126
<212> TYPE: PRT
<213> ORGANISM: Unknown
<220> FEATURE:
<223> OTHER INFORMATION: ImmunoBody heavy chain variable region (H2)

<400> SEQUENCE: 105

Met Gly Trp Ser Cys Ile Ile Leu Phe Leu Val Ala Thr Ala Thr Gly
  1               5                  10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
            35                  40                  45

Asn Thr Tyr Asp Met Ser Trp Val Arg Gln Ala Pro Gly Lys Gly Leu
        50                  55                  60

Glu Trp Ile Ala Tyr Ile Gly Ser Gly Ile Ser Arg Asp Asn Ser Lys
 65                  70                  75                  80

Asn Thr Leu Tyr Leu Gln Leu Asn Ser Leu Arg Ala Glu Asp Thr Ala
            85                  90                  95

Val Tyr Tyr Cys Ala Arg His Tyr Gly His Tyr Val Asp Tyr Ala Val
            100                 105                 110

Asp Tyr Trp Gly Gln Gly Thr Thr Val Thr Val Ser Ser Ala
            115                 120                 125

<210> SEQ ID NO 106
<211> LENGTH: 383
<212> TYPE: DNA
<213> ORGANISM: Unknown
<220> FEATURE:
<223> OTHER INFORMATION: ImmunoBody heavy chain variable region (H3)

<400> SEQUENCE: 106
atgggatgga gctgtatcat cctcttcttg gtagcaacag ctaccggagt ccactcccag     60
gtgcagctgg tggagactgg gggaggctta atccagcctg agggtccct gagaatgtcc    120
```

-continued

```
tgtgcagcct ctggattcgc tttcaatacc tatgacatgt cttgggttcg ccaggctccg    180 gggaagggc tggagtggat cgcatacatt ggtagtggtg gtgatagaac ctactatcca    240
gacactgtga agggccgatt caccatttcc agagacaata gcaagaacac cctgtatttg    300
caattgaaca gtctgagggc tgaggacaca gccgtgtatt actgtgcccg ggccaaggta    360
ccacggtcac cgtctccagc gct                                            383

<210> SEQ ID NO 107
<211> LENGTH: 127
<212> TYPE: PRT
<213> ORGANISM: Unknown
<220> FEATURE:
<223> OTHER INFORMATION: ImmunoBody heavy chain variable region (H3)

<400> SEQUENCE: 107

Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
                20                  25                  30

Pro Gly Gly Ser Leu Arg Met Ser Cys Ala Ala Ser Gly Phe Ala Phe
            35                  40                  45

Asn Thr Tyr Asp Met Ser Trp Val Arg Gln Ala Pro Gly Lys Gly Leu
        50                  55                  60

Glu Trp Ile Ala Tyr Ile Gly Ser Gly Gly Asp Arg Thr Tyr Tyr Pro
 65                 70                  75                  80

Asp Thr Val Lys Gly Arg Phe Thr Ile Ser Arg Asp Asn Ser Lys Asn
                85                  90                  95

Thr Leu Tyr Leu Gln Leu Asn Ser Leu Arg Ala Glu Asp Thr Ala Val
            100                 105                 110

Tyr Tyr Cys Ala Gly Gln Gly Thr Thr Val Thr Val Ser Ser Ala
        115                 120                 125

<210> SEQ ID NO 108
<211> LENGTH: 335
<212> TYPE: DNA
<213> ORGANISM: Unknown
<220> FEATURE:
<223> OTHER INFORMATION: ImmunoBody heavy chain variable region (H1/H2)

<400> SEQUENCE: 108
atgggatgga gctgtatcat cctcttcttg gtagcaacag ctaccggagt ccactcccag    60
gtgcagctgg tggagactgg gggaggctta atccagcctg agggtccct gagaatgtcc    120 tgcgcaggct ccggggaagg ggctggagtg gatcgcatac attggtagtg gtggccattt    180
ccagagacaa tagcaagaac accctgtatt tgcaattgaa cagtctgagg gctgaggaca    240
cagccgtgta ttactgtgca agacattatg gtcactacgt ggactatgct gtggactact    300
ggggtcaagg taccacggtc accgtctcca gcgct                               335

<210> SEQ ID NO 109
<211> LENGTH: 110
<212> TYPE: PRT
<213> ORGANISM: Unknown
<220> FEATURE:
<223> OTHER INFORMATION: ImmunoBody heavy chain variable region (H1/H2)

<400> SEQUENCE: 109

Met Gly Trp Ser Cys Ile Ile Leu Phe Leu Val Ala Thr Ala Thr Gly
 1               5                  10                  15
```

-continued

Val His Ser Gln Val Gln Leu Val Glu Thr Gly Gly Gly Leu Ile Gln
         20                  25                  30

Pro Gly Gly Ser Leu Arg Met Ser Cys Gln Ala Pro Gly Lys Gly Leu
         35                  40                  45

Glu Trp Ile Ala Tyr Ile Gly Ser Gly Ile Ser Arg Asp Asn Ser Lys
 50                  55                  60

Asn Thr Leu Tyr Leu Gln Leu Asn Ser Leu Arg Ala Glu Asp Thr Ala
 65                  70                  75                  80

Val Tyr Tyr Cys Ala Arg His Tyr Gly His Tyr Val Asp Tyr Ala Val
                 85                  90                  95

Asp Tyr Trp Gly Gln Gly Thr Thr Val Thr Val Ser Ser Ala
                100                 105                 110

<210> SEQ ID NO 110
<211> LENGTH: 336
<212> TYPE: DNA
<213> ORGANISM: Unknown
<220> FEATURE:
<223> OTHER INFORMATION: ImmunoBody heavy chain variable region (H1/H3)

<400> SEQUENCE: 110
atgggatgga gctgtatcat cctcttcttg gtagcaacag ctaccggagt ccactcccag    60
gtgcagctgg tggagactgg gggaggctta atccagcctg agggtccct gagaatgtcc    120 tgcgcaggct ccggggaagg ggctggagtg gatcgcatac attggtagtg gtggtgatag    180
aacctactat ccagacactg tgaagggccg attcaccatt tccagagaca atagcaagaa    240
caccctgtat ttgcaattga acagtctgag ggctgaggac acagccgtgt attactgtgc    300
ccgggccaag gtaccacggt caccgtctcc agcgct    336

<210> SEQ ID NO 111
<211> LENGTH: 111
<212> TYPE: PRT
<213> ORGANISM: Unknown
<220> FEATURE:
<223> OTHER INFORMATION: ImmunoBody heavy chain variable region (H1/H3)

<400> SEQUENCE: 111

Met Gly Trp Ser Cys Ile Ile Leu Phe Leu Val Ala Thr Ala Thr Gly
 1               5                   10                  15

Val His Ser Gln Val Gln Leu Val Glu Thr Gly Gly Gly Leu Ile Gln
         20                  25                  30

Pro Gly Gly Ser Leu Arg Met Ser Cys Gln Ala Pro Gly Lys Gly Leu
         35                  40                  45

Glu Trp Ile Ala Tyr Ile Gly Ser Gly Gly Asp Arg Thr Tyr Tyr Pro
 50                  55                  60

Asp Thr Val Lys Gly Arg Phe Thr Ile Ser Arg Asp Asn Ser Lys Asn
 65                  70                  75                  80

Thr Leu Tyr Leu Gln Leu Asn Ser Leu Arg Ala Glu Asp Thr Ala Val
                 85                  90                  95

Tyr Tyr Cys Ala Gly Gln Gly Thr Thr Val Thr Val Ser Ser Ala
                100                 105                 110

<210> SEQ ID NO 112
<211> LENGTH: 342
<212> TYPE: DNA
<213> ORGANISM: Unknown
<220> FEATURE:
<223> OTHER INFORMATION: ImmunoBody heavy chain variable region (H2/H3)

<400> SEQUENCE: 112
atgggatgga gctgtatcat cctcttcttg gtagcaacag ctaccggagt ccactcccag     60
gtgcagctgg tggagactgg gggaggctta atccagcctg agggtccct gagaatgtcc     120 tgtgcagcct ctggattcgc tttcaatacc tatgacatgt cttgggttcg ccaggctccg    180 gggaagggc tggagtggat cgcatacatt ggtagtggtg gccatttcca gagacaatag    240
caagaacacc ctgtatttgc aattgaacag tctgagggct gaggacacag ccgtgtatta    300
ctgtgcccgg gccaaggtac acggtcacc gtctccagcg ct                       342

<210> SEQ ID NO 113
<211> LENGTH: 112
<212> TYPE: PRT
<213> ORGANISM: Unknown
<220> FEATURE:
<223> OTHER INFORMATION: ImmunoBody heavy chain variable region (H2/H3)

<400> SEQUENCE: 113

Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
        35                  40                  45

Asn Thr Tyr Asp Met Ser Trp Val Arg Gln Ala Pro Gly Lys Gly Leu
    50                  55                  60

Glu Trp Ile Ala Tyr Ile Gly Ser Gly Ile Ser Arg Asp Asn Ser Lys
65                  70                  75                  80

Asn Thr Leu Tyr Leu Gln Leu Asn Ser Leu Arg Ala Glu Asp Thr Ala
                85                  90                  95

Val Tyr Tyr Cys Ala Gly Gln Gly Thr Thr Val Thr Val Ser Ser Ala
            100                 105                 110

<210> SEQ ID NO 114
<211> LENGTH: 295
<212> TYPE: DNA
<213> ORGANISM: Unknown
<220> FEATURE:
<223> OTHER INFORMATION: ImmunoBody heavy chain variable region
      (H1/H2/H3)

<400> SEQUENCE: 114
atgggatgga gctgtatcat cctcttcttg gtagcaacag ctaccggagt ccactcccag     60
gtgcagctgg tggagactgg gggaggctta atccagcctg agggtccct gagaatgtcc     120 tgcgcaggct ccggggaagg ggctggagtg gatcgcatac attggtagtg gtggccattt    180
ccagagacaa tagcaagaac accctgtatt tgcaattgaa cagtctgagg gctgaggaca    240
cagccgtgta ttactgtgcc cgggccaagg taccacggtc accgtctcca gcgct         295

<210> SEQ ID NO 115
<211> LENGTH: 96
<212> TYPE: PRT
<213> ORGANISM: Unknown
<220> FEATURE:
<223> OTHER INFORMATION: ImmunoBody heavy chain variable region
      (H1/H2/H3)

<400> SEQUENCE: 115

Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln

```
                  20                  25                  30

Pro Gly Gly Ser Leu Arg Met Ser Cys Gln Ala Pro Gly Lys Gly Leu
            35                  40                  45

Glu Trp Ile Ala Tyr Ile Gly Ser Gly Ile Ser Arg Asp Asn Ser Lys
50                  55                  60

Asn Thr Leu Tyr Leu Gln Leu Asn Ser Leu Arg Ala Glu Asp Thr Ala
65                  70                  75                  80

Val Tyr Tyr Cys Ala Gly Gln Gly Thr Thr Val Thr Val Ser Ser Ala
                85                  90                  95

<210> SEQ ID NO 116
<211> LENGTH: 340
<212> TYPE: DNA
<213> ORGANISM: Unknown
<220> FEATURE:
<223> OTHER INFORMATION: Immunobody kappa chain variable region (L1)

<400> SEQUENCE: 116
atgggatgga gctgtatcat cctcttcttg gtagcaacag ctaccggagt ccactccgat      60
gtgttgatga cccaatctcc actctccctg cctgtcactc ctggggagcc agcctcgata     120
tctgcagaaa ccaggccagt ctccacagct cctgatctac aaagtttcca accgattttc     180
tggggtccca gacagattca gtggcagtgg atcaggacag atttcacact caagatcag      240 cagagtggag gctgaggata ccggagtgta ttactgcttt caaggttcac atgttccgtg     300
gacgttcggt ggaggcacca aggtggaaat caagcgtacg                           340

<210> SEQ ID NO 117
<211> LENGTH: 110
<212> TYPE: PRT
<213> ORGANISM: Unknown
<220> FEATURE:
<223> OTHER INFORMATION: Immunobody kappa chain variable region (L1)

<400> SEQUENCE: 117

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
                20                  25                  30

Thr Pro Gly Glu Pro Ala Ser Leu Gln Lys Pro Gly Gln Ser Pro Gln
            35                  40                  45

Leu Leu Ile Tyr Lys Val Ser Asn Arg Phe Ser Gly Val Pro Asp Arg
50                  55                  60

Phe Ser Gly Ser Gly Ser Gly Thr Asp Phe Thr Leu Lys Ile Ser Arg
65                  70                  75                  80

Val Glu Ala Glu Asp Thr Gly Val Tyr Tyr Cys Phe Gln Gly Ser His
                85                  90                  95

Val Pro Trp Thr Phe Gly Gly Gly Thr Lys Val Glu Ile Lys
            100                 105                 110

<210> SEQ ID NO 118
<211> LENGTH: 360
<212> TYPE: DNA
<213> ORGANISM: Unknown
<220> FEATURE:
<223> OTHER INFORMATION: Immunobody kappa chain variable region (L2)

<400> SEQUENCE: 118
atgggatgga gctgtatcat cctcttcttg gtagcaacag ctaccggagt ccactccgat      60
gtgttgatga cccaatctcc actctccctg cctgtcactc ctggggagcc agcctccatc     120
```

```
tcttgcagat ctagtcagag cctggtacat agtaatggaa acacctattt agaatggtac    180
ctgcagaaac caggccagtc tccacagctc ctaatattca gtggcagtgg atcagggaca    240
gatttcacac tcaagatcag cagagtggag gctgaggata ccggagtgta ttactgcttt    300
caaggttcac atgttccgtg gacgttcggt ggaggcacca aggtggaaat caagcgtacg    360
```

```
<210> SEQ ID NO 119
<211> LENGTH: 117
<212> TYPE: PRT
<213> ORGANISM: Unknown
<220> FEATURE:
<223> OTHER INFORMATION: Immunobody kappa chain variable region (L2)

<400> SEQUENCE: 119
```

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
    50                  55                  60

Gly Gln Ser Pro Gln Leu Leu Phe Ser Gly Ser Gly Ser Gly Thr Asp
65                  70                  75                  80

Phe Thr Leu Lys Ile Ser Arg Val Glu Ala Glu Asp Thr Gly Val Tyr
                85                  90                  95

Tyr Cys Phe Gln Gly Ser His Val Pro Trp Thr Phe Gly Gly Gly Thr
            100                 105                 110

Lys Val Glu Ile Lys
        115

```
<210> SEQ ID NO 120
<211> LENGTH: 352
<212> TYPE: DNA
<213> ORGANISM: Unknown
<220> FEATURE:
<223> OTHER INFORMATION: Immunobody kappa chain variable region (L3)

<400> SEQUENCE: 120
atgggatgga gctgtatcat cctcttcttg gtagcaacag ctaccggagt ccactccgat    60
gtgttgatga cccaatctcc actctccctg cctgtcactc tggggagcc agcctccatc    120 tcttgcagat ctagtcagag cctggtacat agtaatggaa acacctattt agaatggtac    180
ctgcagaaac caggccagtc tccacagctc ctgatctaca agtttccaa ccgattttct    240 ggggtcccag acagattcag tggcagtgga tcagggacag atttcacact caagatcagc    300
agagtggagg ctgaggatac cggagttaac caaggtggaa atcaagcgta cg            352
```

```
<210> SEQ ID NO 121
<211> LENGTH: 115
<212> TYPE: PRT
<213> ORGANISM: Unknown
<220> FEATURE:
<223> OTHER INFORMATION: Immunobody kappa chain variable region (L3)

<400> SEQUENCE: 121
```

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
            20                  25                  30

```
Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
 50                  55                  60

Gly Gln Ser Pro Gln Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Thr Gly Val Thr Lys Val
            100                 105                 110

Glu Ile Lys
        115

<210> SEQ ID NO 122
<211> LENGTH: 301
<212> TYPE: DNA
<213> ORGANISM: Unknown
<220> FEATURE:
<223> OTHER INFORMATION: Immunobody kappa chain variable region (L1/L3)

<400> SEQUENCE: 122
atgggatgga gctgtatcat cctcttcttg gtagcaacag ctaccggagt ccactccgat      60
gtgttgatga cccaatctcc actctccctg cctgtcactc tggggagcc agcctcgata     120 tctgcagaaa ccaggccagt ctccacagct cctaatattc agtggcagtg atcagggac     180 agatttcaca ctcaagatca gcagagtgga ggctgaggat accggagtgt attactgctt     240
tcaaggttca catgttccgt ggacgttcgg tggaggcacc aaggtggaaa tcaagcgtac     300
g                                                                    301

<210> SEQ ID NO 123
<211> LENGTH: 96
<212> TYPE: PRT
<213> ORGANISM: Unknown
<220> FEATURE:
<223> OTHER INFORMATION: Immunobody kappa chain variable region (L1/L3)

<400> SEQUENCE: 123

Met Gly Trp Ser Cys Ile Ile Leu Phe Leu Val Ala Thr Ala Thr Gly
  1               5                  10                  15

Val His Ser Asp Val Leu Met Thr Gln Ser Pro Leu Ser Leu Pro Val
             20                  25                  30

Thr Pro Gly Glu Pro Ala Ser Leu Gln Lys Pro Gly Gln Ser Pro Gln
        35                  40                  45

Leu Leu Phe Ser Gly Ser Gly Ser Gly Thr Asp Phe Thr Leu Lys Ile
 50                  55                  60

Ser Arg Val Glu Ala Glu Asp Thr Gly Val Tyr Tyr Cys Phe Gln Gly
 65                  70                  75                  80

Ser His Val Pro Trp Thr Phe Gly Gly Gly Thr Lys Val Glu Ile Lys
                 85                  90                  95

<210> SEQ ID NO 124
<211> LENGTH: 313
<212> TYPE: DNA
<213> ORGANISM: Unknown
<220> FEATURE:
<223> OTHER INFORMATION: Immunobody kappa chain variable region (L2/L3)

<400> SEQUENCE: 124
atgggatgga gctgtatcat cctcttcttg gtagcaacag ctaccggagt ccactccgat      60
```

```
gtgttgatga cccaatctcc actctccctg cctgtcactc ctggggagcc agcctccatc     120
tcttgcagat ctagtcagag cctggtacat agtaatggaa acacctattt agaatggtac     180
ctgcagaaac caggccagtc tccacagctc ctaatattca gtggcagtgg atcagggaca     240
gatttcacac tcaagatcag cagagtggag gctgaggata ccggagttaa ccaaggtgga     300
aatcaagcgt acg                                                        313
```

<210> SEQ ID NO 125
<211> LENGTH: 101
<212> TYPE: PRT
<213> ORGANISM: Unknown
<220> FEATURE:
<223> OTHER INFORMATION: Immunobody kappa chain variable region (L2/L3)

<400> SEQUENCE: 125

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
    50                  55                  60

Gly Gln Ser Pro Gln Leu Leu Phe Ser Gly Ser Gly Ser Gly Thr Asp
65                  70                  75                  80

Phe Thr Leu Lys Ile Ser Arg Val Glu Ala Glu Asp Thr Gly Val Thr
                85                  90                  95

Lys Val Glu Ile Lys
            100
```

<210> SEQ ID NO 126
<211> LENGTH: 254
<212> TYPE: DNA
<213> ORGANISM: Unknown
<220> FEATURE:
<223> OTHER INFORMATION: Immunobody kappa chain variable region
     (L1/L2/L3)

<400> SEQUENCE: 126

```
atgggatgga gctgtatcat cctcttcttg gtagcaacag ctaccggagt ccactccgat     60
gtgttgatga cccaatctcc actctccctg cctgtcactc ctggggagcc agcctcgata     120
tctgcagaaa ccaggccagt ctccacagct cctaatattc agtggcagtg gatcagggac     180
agatttcaca ctcaagatca gcagagtgga ggctgaggat accggagtta accaaggtgg     240
aaatcaagcg tacg                                                       254
```

<210> SEQ ID NO 127
<211> LENGTH: 80
<212> TYPE: PRT
<213> ORGANISM: Unknown
<220> FEATURE:
<223> OTHER INFORMATION: Immunobody kappa chain variable region
     (L1/L2/L3)

<400> SEQUENCE: 127

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30
```

```
Thr Pro Gly Glu Pro Ala Ser Leu Gln Lys Pro Gly Gln Ser Pro Gln
        35                  40                  45

Leu Leu Phe Ser Gly Ser Gly Ser Gly Thr Asp Phe Thr Leu Lys Ile
    50                  55                  60

Ser Arg Val Glu Ala Glu Asp Thr Gly Val Thr Lys Val Glu Ile Lys
65                  70                  75                  80

<210> SEQ ID NO 128
<211> LENGTH: 293
<212> TYPE: DNA
<213> ORGANISM: Unknown
<220> FEATURE:
<223> OTHER INFORMATION: Immunobody kappa chain variable region (L1/L3)

<400> SEQUENCE: 128
atgggatgga gctgtatcat cctcttcttg gtagcaacag ctaccggagt ccactccgat      60
gtgttgatga cccaatctcc actctccctg cctgtcactc tgggggagcc agcctcgata     120
tctgcagaaa ccaggccagt ctccacagct cctgatctac aaagtttcca accgattttc     180
tggggtccca gacagattca gtggcagtgg atcagggaca gatttcacac tcaagatcag     240
cagagtggag gctgaggata ccggagttaa ccaaggtgga aatcaagcgt acg            293

<210> SEQ ID NO 129
<211> LENGTH: 94
<212> TYPE: PRT
<213> ORGANISM: Unknown
<220> FEATURE:
<223> OTHER INFORMATION: Immunobody kappa chain variable region (L1/L3)

<400> SEQUENCE: 129

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
                20                  25                  30

Thr Pro Gly Glu Pro Ala Ser Leu Gln Lys Pro Gly Gln Ser Pro Gln
        35                  40                  45

Leu Leu Ile Tyr Lys Val Ser Asn Arg Phe Ser Gly Val Pro Asp Arg
    50                  55                  60

Phe Ser Gly Ser Gly Ser Gly Thr Asp Phe Thr Leu Lys Ile Ser Arg
65                  70                  75                  80

Val Glu Ala Glu Asp Thr Gly Val Thr Lys Val Glu Ile Lys
                85                  90

<210> SEQ ID NO 130
<211> LENGTH: 720
<212> TYPE: DNA
<213> ORGANISM: Unknown
<220> FEATURE:
<223> OTHER INFORMATION: Immunobody IB15 heavy chain

<400> SEQUENCE: 130
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gcaccattat ggaccaggtg cctttctccg tgtgggttcg gcaggctccg     180 gggaagggc tggagtggat cgcatacatt ggtagtggtg gtagtgttta tgattttttt     240
gtgtggctcc gattcaccat ttccagagac aatagcaaga acaccctgta tttgcaattg     300
aacagtctga gggctgagga cacagccgtg tattactgtg cgagacatta tggtcactac     360
gtggactatg ctgtggacta ctggggtcaa ggtaccacgg tcaccgtctc cagcgcttcc     420
```

```
accaagggcc catcggtctt ccccctggca ccctcctcca agagcacctc tgggggcaca        480
gcggccctgg gctgcctggt caaggactac ttccccgaac cggtgacggt gtcgtggaac        540
tcaggcgccc tgaccagcgg cgtgcacacc ttcccggctg tcctacagtc ctcaggactc        600
tactccctca gcagcgtggt gaccgtgccc tccagcagct gggcaccca gacctacatc         660 tgcaacgtga atcacaagcc cagcaacacc aaggtggaca gaaagtttg acccaaatct         720
```

<210> SEQ ID NO 131
<211> LENGTH: 236
<212> TYPE: PRT
<213> ORGANISM: Unknown
<220> FEATURE:
<223> OTHER INFORMATION: Immunobody IB15 heavy chain

<400> SEQUENCE: 131

```
Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
                20                  25                  30

Pro Gly Gly Ser Leu Arg Met Ser Cys Thr Ile Met Asp Gln Val Pro
            35                  40                  45

Phe Ser Val Trp Val Arg Gln Ala Pro Gly Lys Gly Leu Glu Trp Ile
        50                  55                  60

Ala Tyr Ile Gly Ser Gly Gly Ser Val Tyr Asp Phe Phe Val Trp Leu
65                  70                  75                  80

Arg Phe Thr Ile Ser Arg Asp Asn Ser Lys Asn Thr Leu Tyr Leu Gln
                85                  90                  95

Leu Asn Ser Leu Arg Ala Glu Asp Thr Ala Val Tyr Tyr Cys Ala Arg
            100                 105                 110

His Tyr Gly His Tyr Val Asp Tyr Ala Val Asp Tyr Trp Gly Gln Gly
        115                 120                 125

Thr Thr Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Pro Lys Ser
225                 230                 235
```

<210> SEQ ID NO 132
<211> LENGTH: 363
<212> TYPE: DNA
<213> ORGANISM: Unknown
<220> FEATURE:
<223> OTHER INFORMATION: DCIB15 heavy variable region without a leader
      (heavy chain)

<400> SEQUENCE: 132

```
aagcttacca tgcaggtgca gctggtggag actgggggag cttaatcca gcctggaggg         60 tccctgagaa tgtcctgcac cattatggac caggtgcctt tctccgtgtg ggttcggcag       120
```

```
gctccgggga aggggctgga gtggatcgca tacattggta gtggtggtag tgtttatgat    180
ttttttgtgt ggctccgatt caccatttcc agagacaata gcaagaacac cctgtatttg    240
caattgaaca gtctgagggc tgaggacaca gccgtgtatt actgtgcgag acattatggt    300
cactacgtgg actatgctgt ggactactgg ggtcaaggta ccacggtcac cgtctccagc    360
gct                                                                 363
```

<210> SEQ ID NO 133
<211> LENGTH: 117
<212> TYPE: PRT
<213> ORGANISM: Unknown
<220> FEATURE:
<223> OTHER INFORMATION: DCIB15 heavy variable region without a leader
      (heavy chain)

<400> SEQUENCE: 133

```
Met Gln Val Gln Leu Val Glu Thr Gly Gly Gly Leu Ile Gln Pro Gly
  1               5                  10                  15

Gly Ser Leu Arg Met Ser Cys Thr Ile Met Asp Gln Val Pro Phe Ser
             20                  25                  30

Val Trp Val Arg Gln Ala Pro Gly Lys Gly Leu Glu Trp Ile Ala Tyr
         35                  40                  45

Ile Gly Ser Gly Gly Ser Val Tyr Asp Phe Phe Val Trp Leu Arg Phe
     50                  55                  60

Thr Ile Ser Arg Asp Asn Ser Lys Asn Thr Leu Tyr Leu Gln Leu Asn
 65                  70                  75                  80

Ser Leu Arg Ala Glu Asp Thr Ala Val Tyr Tyr Cys Ala Arg His Tyr
                 85                  90                  95

Gly His Tyr Val Asp Tyr Ala Val Asp Tyr Trp Gly Gln Gly Thr Thr
            100                 105                 110

Val Thr Val Ser Ser
        115
```

<210> SEQ ID NO 134
<211> LENGTH: 345
<212> TYPE: DNA
<213> ORGANISM: Unknown
<220> FEATURE:
<223> OTHER INFORMATION: DCIB15 kappa variable region without a leader
      (light chain)

<400> SEQUENCE: 134

```
ggatccacca tggatgtgtt gatgacccaa tctccactct ccctgcctgt cactcctggg     60
gagccagcct ccatctcttg cactcctcca gcttatagac accaaatgc cctatcctg    120 tggtatctgc agaaaccagg ccagtctcca cagctcctga tctacaaagt ttccaaccga    180
ttttctgggg tcccagacag attcagtggc agtggatcag gacagattt cacactcaag    240 atcagcagag tggaggctga ggatccgga gtgtattact gctttcaagg ttcacatgtt    300
ccgtggacgt tcggtggagg caccaaggtg gaaatcaagc gtacg                   345
```

<210> SEQ ID NO 135
<211> LENGTH: 110
<212> TYPE: PRT
<213> ORGANISM: Unknown
<220> FEATURE:
<223> OTHER INFORMATION: DCIB15 kappa variable region without a leader
      (light chain)

<400> SEQUENCE: 135

```
Met Asp Val Leu Met Thr Gln Ser Pro Leu Ser Leu Pro Val Thr Pro
1               5                   10                  15

Gly Glu Pro Ala Ser Ile Ser Cys Thr Pro Pro Ala Tyr Arg Pro Pro
                20                  25                  30

Asn Ala Pro Ile Leu Trp Tyr Leu Gln Lys Pro Gly Gln Ser Pro Gln
                35                  40                  45

Leu Leu Ile Tyr Lys Val Ser Asn Arg Phe Ser Gly Val Pro Asp Arg
        50                  55                  60

Phe Ser Gly Ser Gly Ser Gly Thr Asp Phe Thr Leu Lys Ile Ser Arg
65                  70                  75                  80

Val Glu Ala Glu Asp Thr Gly Val Tyr Tyr Cys Phe Gln Gly Ser His
                85                  90                  95

Val Pro Trp Thr Phe Gly Gly Gly Thr Lys Val Glu Ile Lys
                100                 105                 110

<210> SEQ ID NO 136
<211> LENGTH: 857
<212> TYPE: DNA
<213> ORGANISM: Homo sapiens

<400> SEQUENCE: 136
agcgcttcca ccaagggccc atcggtcttc cccctggcgc cctgctccag gagcacctcc     60
gagagcacag cggccctggg ctgcctggtc aaggactact cccccgaacc ggtgacggtg    120
tcgtggaact caggcgctct gaccagcggc gtgcacacct tcccggctgt cctacagtcc    180
tcaggactct actccctcag cagcgtggtg accgtgccct ccagcaactt cggcacccag    240
acctacacct gcaacgtaga tcacaagccc agcaacacca aggtggacaa gacagttgag    300
cgcaaatgtt gtgtcgagtg cccaccgtgc ccagcaccac ctgtggcagg accgtcagtc    360
ttcctcttcc ccccaaaacc caaggacacc ctcatgatct cccggacccc tgaggtcacg    420
tgcgtggtgg tggacgtgag ccacgaagac cccgaggtcc agttcaactg gtacgtggac    480
ggcgtggagg tgcataatgc caagacaaag ccacgggagg agcagttcaa cagcacgttc    540
cgtgtggtca gcgtcctcac cgtcgtgcac caggactggc tgaacggcaa ggagtacaag    600
tgcaaggtct ccaacaaagg cctcccagcc cccatcgaga aaaccatctc caaaaccaaa    660
gggcagcccc gagaaccaca ggtgtacacc ctgcccccat cccgggagga gatgaccaag    720
aaccaggtca gcctgacctg cctggtcaaa ggcttctacc ccagcgacat cgccgtggag    780
tgggagagca atgggcagcc ggagaacaac ctaagggcga attctgcaga tatccagcac    840
agtggcggcc gctcgag                                                   857

<210> SEQ ID NO 137
<211> LENGTH: 654
<212> TYPE: PRT
<213> ORGANISM: Homo sapiens

<400> SEQUENCE: 137

Ser Ala Ser Thr Lys Gly Pro Ser Val Phe Pro Leu Ala Pro Cys Ser
1               5                   10                  15

Arg Ser Thr Ser Glu Ser Thr Ala Ala Leu Gly Cys Leu Val Lys Asp
                20                  25                  30

Tyr Phe Pro Glu Pro Val Thr Val Ser Trp Asn Ser Gly Ala Leu Thr
                35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Asn Phe Gly Thr Gln
```

-continued

```
                65                  70                  75                  80
Thr Tyr Thr Cys Asn Val Asp His Lys Pro Ser Asn Thr Lys Val Asp
                    85                  90                  95

Lys Thr Val Glu Arg Lys Cys Cys Val Glu Cys Pro Pro Cys Pro Ala
                100                 105                 110

Pro Val Ala Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser His Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Phe Arg Val Val Ser Val Leu Thr Val Val His Gln Asp
                180                 185                 190

Trp Leu Asn Gly Lys Glu Tyr Lys Cys Lys Val Ser Asn Lys Gly Leu
            195                 200                 205

Pro Ala Pro Ile Glu Lys Thr Ile Ser Lys Thr Lys Gly Gln Pro Arg
        210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Met Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys Ser Ala Ser Thr Lys Gly Pro Ser Val
                325                 330                 335

Phe Pro Leu Ala Pro Cys Ser Arg Ser Thr Ser Glu Ser Thr Ala Ala
                340                 345                 350

Leu Gly Cys Leu Val Lys Asp Tyr Phe Pro Glu Pro Val Thr Val Ser
            355                 360                 365

Trp Asn Ser Gly Ala Leu Thr Ser Gly Val His Thr Phe Pro Ala Val
        370                 375                 380

Leu Gln Ser Ser Gly Leu Tyr Ser Leu Ser Ser Val Val Thr Val Pro
385                 390                 395                 400

Ser Ser Asn Phe Gly Thr Gln Thr Tyr Thr Cys Asn Val Asp His Lys
                405                 410                 415

Pro Ser Asn Thr Lys Val Asp Lys Thr Val Glu Arg Lys Cys Cys Val
                420                 425                 430

Glu Cys Pro Pro Cys Pro Ala Pro Pro Val Ala Gly Pro Ser Val Phe
            435                 440                 445

Leu Phe Pro Pro Lys Pro Lys Asp Thr Leu Met Ile Ser Arg Thr Pro
        450                 455                 460

Glu Val Thr Cys Val Val Val Asp Val Ser His Glu Asp Pro Glu Val
465                 470                 475                 480

Gln Phe Asn Trp Tyr Val Asp Gly Val Glu Val His Asn Ala Lys Thr
                485                 490                 495
```

```
Lys Pro Arg Glu Glu Gln Phe Asn Ser Thr Phe Arg Val Val Ser Val
            500                 505                 510
Leu Thr Val Val His Gln Asp Trp Leu Asn Gly Lys Glu Tyr Lys Cys
        515                 520                 525
Lys Val Ser Asn Lys Gly Leu Pro Ala Pro Ile Glu Lys Thr Ile Ser
    530                 535                 540
Lys Thr Lys Gly Gln Pro Arg Glu Pro Gln Val Tyr Thr Leu Pro Pro
545                 550                 555                 560
Ser Arg Glu Glu Met Thr Lys Asn Gln Val Ser Leu Thr Cys Leu Val
                565                 570                 575
Lys Gly Phe Tyr Pro Ser Asp Ile Ala Val Glu Trp Glu Ser Asn Gly
            580                 585                 590
Gln Pro Glu Asn Asn Tyr Lys Thr Thr Pro Pro Met Leu Asp Ser Asp
        595                 600                 605
Gly Ser Phe Phe Leu Tyr Ser Lys Leu Thr Val Asp Lys Ser Arg Trp
    610                 615                 620
Gln Gln Gly Asn Val Phe Ser Cys Ser Val Met His Glu Ala Leu His
625                 630                 635                 640
Asn His Tyr Thr Gln Lys Ser Leu Ser Leu Ser Pro Gly Lys
                645                 650
```

<210> SEQ ID NO 138
<211> LENGTH: 1164
<212> TYPE: DNA
<213> ORGANISM: Homo sapiens

<400> SEQUENCE: 138

```
agcgcttcca ccaagggccc atcggtcttc cccctggcgc cctgctccag gagcacctct    60
ggggggcacag cggccctggg ctgcctggtc aaggactact ccccgaaccc ggtgacggtg   120
tcgtggaact caggcgccct gaccagcggc gtgcacacct tcccggctgt cctacagtcc   180
tcaggactct actccctcag cagcgtggtg accgtgccct ccagcagctt gggcacccag   240
acctacacct gcaacgtgaa tcacaagccc agcaacacca aggtggacaa gagagttgag   300
ctcaaaaccc cacttggtga cacaactcac acatgcccac ggtgcccaga gcccaaatct   360
tgtgacacac ctcccccgtg cccacggtgc ccagagccca atcttgtga cacacctccc   420
ccatgcccac ggtgcccaga gcccaaatct tgtgacacac ctccccccatg cccacggtgc   480
ccagcacctg aactcctggg aggaccgtca gtcttcctct tccccccaaa acccaaggat   540
acccttatga tttcccggac ccctgaggtc acgtgcgtgg tggtggacgt gagccacgaa   600
gaccccgagg tccagttcaa gtggtacgtg gacggcgtgg aggtgcataa tgccaagaca   660
aagccgcggg aggagcagtt caacagcacg ttccgtgtgg tcagcgtcct caccgtcctg   720
caccaggact ggctgaacgg caaggagtac aagtgcaagg tctccaacaa agccctccca   780
gccccccatcg agaaaaccat ctccaaaacc aaaggacagc ccgagaacc acaggtgtac   840
accctgcccc catcccggga ggagatgacc aagaaccagg tcagcctgac ctgcctggtc   900
aaaggcttct accccagcga catcgccgtg gagtgggaga gcagcgggca gccggagaac   960
aactacaaca ccacgcctcc catgctggac tccgacggct ccttcttcct ctacagcaag  1020
ctcaccgtgg acaagagcag gtggcagcag gggaacatct tctcatgctc cgtgatgcat  1080
gaggctctgc acaaccgctt cacgcagaag agcctctccc tgtctccggg taaatgatat  1140
ccatcacact ggcggccgct cgag                                         1164
```

<210> SEQ ID NO 139

```
<211> LENGTH: 377
<212> TYPE: PRT
<213> ORGANISM: Homo sapiens

<400> SEQUENCE: 139

Ser Ala Ser Thr Lys Gly Pro Ser Val Phe Pro Leu Ala Pro Cys Ser
1               5                   10                  15

Arg Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Thr Cys Asn Val Asn His Lys Pro Ser Asn Thr Lys Val Asp
                85                  90                  95

Lys Arg Val Glu Leu Lys Thr Pro Leu Gly Asp Thr Thr His Thr Cys
            100                 105                 110

Pro Arg Cys Pro Glu Pro Lys Ser Cys Asp Thr Pro Pro Pro Cys Pro
        115                 120                 125

Arg Cys Pro Glu Pro Lys Ser Cys Asp Thr Pro Pro Pro Cys Pro Arg
    130                 135                 140

Cys Pro Glu Pro Lys Ser Cys Asp Thr Pro Pro Pro Cys Pro Arg Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Gln Phe Lys Trp
        195                 200                 205

Tyr Val Asp Gly Val Glu Val His Asn Ala Lys Thr Lys Pro Arg Glu
    210                 215                 220

Glu Gln Phe Asn Ser Thr Phe Arg Val Val Ser Val Leu Thr Val His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 140
```

<211> LENGTH: 1440
<212> TYPE: DNA
<213> ORGANISM: Unknown
<220> FEATURE:
<223> OTHER INFORMATION: DCIB66 heavy chain

<400> SEQUENCE: 140

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattat ggaccaggtg cctttctccg tgtgggttcg gcaggctccg   180
gggaaggggc tggagtggat cgcatacatt ggtagtggtg gtagtgttta tgatttttt    240
gtgtggctcc gattcaccat ttccagagac aatagcaaga caccctgta tttgcaattg    300
aacagtctga gggctgagga cacagccgtg tattactgtg cgagacatta tggtcactac   360
gtggactatg ctgtggacta ctggggtcaa ggtaccacgg tcaccgtctc cagcgcttcc   420
accaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660
tgcaacgtga atcacaagcc cagcaacacc aaggtggaca gaaagttga gcccaaatct    720
tgtgacaaaa ctcacacatg cccaccgtgc ccagcacctc cagtcgcggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccgcggg aggagcagta caacagcacg   960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga tgagctgacc  1140
aagaaccagg tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctccggg taaatgatct aaagggcgaa ttcgcccta agggcgaatt   1440
```

<210> SEQ ID NO 141
<211> LENGTH: 465
<212> TYPE: PRT
<213> ORGANISM: Unknown
<220> FEATURE:
<223> OTHER INFORMATION: DCIB66 heavy chain

<400> SEQUENCE: 141

```
Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Thr Ile Met Asp Gln Val Pro
        35                  40                  45

Phe Ser Val Trp Val Arg Gln Ala Pro Gly Lys Gly Leu Glu Trp Ile
    50                  55                  60

Ala Tyr Ile Gly Ser Gly Gly Ser Val Tyr Asp Phe Phe Val Trp Leu
65                  70                  75                  80
```

Arg Phe Thr Ile Ser Arg Asp Asn Ser Lys Asn Thr Leu Tyr Leu Gln
                85                  90                  95

Leu Asn Ser Leu Arg Ala Glu Asp Thr Ala Val Tyr Tyr Cys Ala Arg
            100                 105                 110

His Tyr Gly His Tyr Val Asp Tyr Ala Val Asp Tyr Trp Gly Gln Gly
        115                 120                 125

Thr Thr Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Pro Val Ala Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465

<210> SEQ ID NO 142
<211> LENGTH: 1440
<212> TYPE: DNA

<213> ORGANISM: Unknown
<220> FEATURE:
<223> OTHER INFORMATION: DCIB67 heavy chain containing G1 binding motif

<400> SEQUENCE: 142

```
aagcttacca tgggatggag ctgtatcatc ctcttcttgg tagcaacagc taccggagtc      60
cactcccagg tgcagctggt ggagactggg ggaggcttaa tccagc

```
                    85                  90                  95
Leu Asn Ser Leu Arg Ala Glu Asp Thr Ala Val Tyr Tyr Cys Ala Arg
                100                 105                 110

His Tyr Gly His Tyr Val Asp Tyr Ala Val Asp Tyr Trp Gly Gln Gly
                115                 120                 125

Thr Thr Val Thr Val Ser Ser Ala Ser Thr Lys Gly Pro Ser Val Phe
            130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Gln Phe Asn Trp Tyr Val Asp Gly Val Glu Val His Asn Ala Lys Thr
        290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
                340                 345                 350

Lys Thr Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 144
<211> LENGTH: 417
<212> TYPE: DNA
<213> ORGANISM: Unknown
<220> FEATURE:
<223> OTHER INFORMATION: Nucleotide and amino acid sequence of the heavy
      and light variable regions cloned in frame with the
      human IgG1 Fc and kappa constant regions within the expression
``` vector pDCOrig (heavy variable)

<400> SEQUENCE: 144

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattat ggaccaggtg cctttctccg tgtgggttcg caggctccg    180
gggaaggggc tggagtggat cgcatacatt ggtagtggtg gtagtgttta tgattttttt   240
gtgtggctcc gattcaccat ttccagagac aatagcaaga caccctgta tttgcaattg    300
aacagtctga gggctgagga cacagccgtg tattactgtg cgagacatta tggtcactac   360
gtggactatg ctgtggacta ctggggtcaa ggtaccacgg tcaccgtctc cagcgct      417
```

<210> SEQ ID NO 145
<211> LENGTH: 135
<212> TYPE: PRT
<213> ORGANISM: Unknown
<220> FEATURE:
<223> OTHER INFORMATION: Nucleotide and amino acid sequence of the heavy
and light variable regions cloned in frame with the
human IgG1 Fc and kappa constant regions within the expression
vector pDCOrig

<400> SEQUENCE: 145

```
Met Gly Trp Ser Cys Ile Ile Leu Phe Leu Val Ala Thr Ala Thr Gly
 1               5                  10                  15
Val His Ser Gln Val Gln Leu Val Glu Thr Gly Gly Gly Leu Ile Gln
            20                  25                  30
Pro Gly Gly Ser Leu Arg Met Ser Cys Thr Ile Met Asp Gln Val Pro
        35                  40                  45
Phe Ser Val Trp Val Arg Gln Ala Pro Gly Lys Gly Leu Glu Trp Ile
    50                  55                  60
Ala Tyr Ile Gly Ser Gly Gly Ser Val Tyr Asp Phe Phe Val Trp Leu
65                  70                  75                  80
Arg Phe Thr Ile Ser Arg Asp Asn Ser Lys Asn Thr Leu Tyr Leu Gln
                85                  90                  95
Leu Asn Ser Leu Arg Ala Glu Asp Thr Ala Val Tyr Tyr Cys Ala Arg
            100                 105                 110
His Tyr Gly His Tyr Val Asp Tyr Ala Val Asp Tyr Trp Gly Gln Gly
        115                 120                 125
Thr Thr Val Thr Val Ser Ser
    130                 135
```

<210> SEQ ID NO 146
<211> LENGTH: 309
<212> TYPE: DNA
<213> ORGANISM: Unknown
<220> FEATURE:
<223> OTHER INFORMATION: Nucleotide and amino acid sequence of the heavy
and light variable regions cloned in frame with the
human IgG1 Fc and kappa constant regions within the expression
vector pDCOrig (light variable)

<400> SEQUENCE: 146

```
ctctccctgc ctgtcactcc tggggagcca gcctcgatct cttgcactcc tccagcttat    60
agaccaccaa atgcccctat cctatggtat ctgcagaaac caggccagtc tccacagctc   120
ctgatctaca aagtttccaa ccgatttct ggggtcccag acagattcag tggcagtgga   180
tcagggacag atttcacact caagatcagc agagtggagg ctgaggatac cggagtgtat   240
tactgctttc aaggttcaca tgttccgtgg acgttcggtg aggcaccaa ggtggaaatc    300
```

<210> SEQ ID NO 147
<211> LENGTH: 128
<212> TYPE: PRT
<213> ORGANISM: Unknown
<220> FEATURE:
<223> OTHER INFORMATION: Nucleotide and amino acid sequence of the heavy
and light variable regions cloned in frame with the
human IgG1 Fc and kappa constant regions within the expression
vector pDCOrig (light variable)

<400> SEQUENCE: 147

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Thr Pro Pro Ala Tyr Arg
        35                  40                  45

Pro Pro Asn Ala Pro Ile Leu Trp Tyr Leu Gln Lys Pro Gly Gln Ser
    50                  55                  60

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
        115                 120                 125
```

<210> SEQ ID NO 148
<211> LENGTH: 422
<212> TYPE: DNA
<213> ORGANISM: Unknown
<220> FEATURE:
<223> OTHER INFORMATION: Nucleotide and amino acid sequence of the heavy
and light variable regions cloned in frame with the
human IgG1 Fc and kappa constant regions within the expression
vector pDCOrig (heavy varaible) (Sequence of DCIB24)

<400> SEQUENCE: 148

```
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gtgcagcctc tggattcgct ttcaatacct atgacatgtc ttgggttcgc     180
aggctccggg gaaggggctg gagtggatcg catacattgg tagtggtggt agtataatca     240
actttgaaaa actgcgattc accatttcca gagacaatag caagaacacc ctgtatttgc     300
aattgaacag tctgagggct gaggacacag ccgtgtatta ctgtgcaaga cattatggtc     360
actacgtgga ctatgctgtg gactactggg gtcaaggaac cacggtcacc gtctccagcg     420
ct                                                                     422
```

<210> SEQ ID NO 149
<211> LENGTH: 137
<212> TYPE: PRT
<213> ORGANISM: Unknown
<220> FEATURE:
<223> OTHER INFORMATION: Nucleotide and amino acid sequence of the heavy
and light variable regions cloned in frame with the
human IgG1 Fc and kappa constant regions within the expression
vector pDCOrig (heavy varaible) (Sequence of DCIB24)

<400> SEQUENCE: 149

```
Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
        35                  40                  45

Asn Thr Tyr Asp Met Ser Trp Val Arg Gln Ala Pro Lys Gly Leu
    50                  55                  60

Glu Trp Ile Ala Tyr Ile Gly Ser Gly Gly Ser Ile Ile Asn Phe Glu
 65                 70                  75                  80

Lys Leu Arg Phe Thr Ile Ser Arg Asp Asn Ser Lys Asn Thr Leu Tyr
                85                  90                  95

Leu Gln Leu Asn Ser Leu Arg Ala Glu Asp Thr Ala Val Tyr Tyr Cys
            100                 105                 110

Ala Arg His Tyr Gly His Tyr Val Asp Tyr Ala Val Asp Tyr Trp Gly
        115                 120                 125

Gln Gly Thr Thr Val Thr Val Ser Ser
    130                 135
```

<210> SEQ ID NO 150
<211> LENGTH: 398
<212> TYPE: DNA
<213> ORGANISM: Unknown
<220> FEATURE:
<223> OTHER INFORMATION: Nucleotide and amino acid sequence of the heavy
      and light variable regions cloned in frame with the
      human IgG1 Fc and kappa constant regions within the expression
      vector pDCOrig (light varaible) (Sequence of DCIB24)

<400> SEQUENCE: 150

```
ggatccacca tgggatggag ctgtatcatc ctcttcttgg tagcaacagc taccggagtc    60
cactccgatg tgttgatgac ccaatctcca ctctccctgc ctgtcactcc tggggagcca   120
gcctcgatct cttgcactcc tccagcttat agaccaccaa atgcccctat cctatggtat   180
tgcagaaacc aggccagtct ccacagctcc tgatctacaa agtttccaac cgattttctg   240
gggtcccaga cagattcagt ggcagtggat cagggacaga tttcacactc aagatcagca   300
gagtggaggc tgaggatacc ggagtgtatt actgctttca aggttcacat gttccgtgga   360
cgttcggtgg aggcaccaag gtggaaatca agcgtacg                           398
```

<210> SEQ ID NO 151
<211> LENGTH: 128
<212> TYPE: PRT
<213> ORGANISM: Unknown
<220> FEATURE:
<223> OTHER INFORMATION: Nucleotide and amino acid sequence of the heavy
      and light variable regions cloned in frame with the
      human IgG1 Fc and kappa constant regions within the expression
      vector pDCOrig (light varaible) (Sequence of DCIB24)

<400> SEQUENCE: 151

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Thr Pro Pro Ala Tyr Arg
        35                  40                  45

Pro Pro Asn Ala Pro Ile Leu Trp Tyr Leu Gln Lys Pro Gly Gln Ser
    50                  55                  60
```

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
        115                 120                 125

<210> SEQ ID NO 152
<211> LENGTH: 417
<212> TYPE: DNA
<213> ORGANISM: Unknown
<220> FEATURE:
<223> OTHER INFORMATION: Nucleotide and amino acid sequence of the heavy
      and light variable regions cloned in frame with the
      human IgG1 Fc and kappa constant regions within the expression
      vector pDCOrig (heavy variable) (Sequence of DCIB25)

<400> SEQUENCE: 152
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gcaccattat ggaccaggtg cctttctccg tgtgggttcg gcaggctccg     180
gggaaggggc tggagtggat cgcatacatt ggtagtggtg gtagtgttta tgatttttt     240 gtgtggctcc gattcaccat ttccagagac aatagcaaga cacccctgta tttgcaattg     300
aacagtctga gggctgagga cacagccgtg tattactgtg cgagacatta tggtcactac     360
gtggactatg ctgtggacta ctggggtcaa ggtaccacgg tcaccgtctc cagcgct       417

<210> SEQ ID NO 153
<211> LENGTH: 420
<212> TYPE: DNA
<213> ORGANISM: Unknown
<220> FEATURE:
<223> OTHER INFORMATION: Nucleotide and amino acid sequence of the heavy
      and light  variable regions cloned in frame with the
      human IgG1 Fc and kappa constant regions within the expression
      vector pDCOrig (light variable) (Sequence of DCIB25)

<400> SEQUENCE: 153
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctccatct cttgcagatc tagtcagagc ctggtacata gtaatggaaa cacctattta     180
gaatggtacc tgcagaaacc aggccagtct ccacagctcc tgatctacaa agtttccaac     240
cgattttctg ggtcccaga cagattcagt ggcagtggat cagggacaga tttcacactc     300
aagatcagca gtggaggc tgaggatacc ggagtgtatt actgcactcc tccagcttat     360
agaccaccaa atgccctat cctattcggt ggaggcacca aggtggaaat caagcgtacg     420

<210> SEQ ID NO 154
<211> LENGTH: 135
<212> TYPE: PRT
<213> ORGANISM: Unknown
<220> FEATURE:
<223> OTHER INFORMATION: Nucleotide and amino acid sequence of the heavy
      and light variable regions cloned in frame with the
      human IgG1 Fc and kappa constant regions within the expression
      vector pDCOrig (light variable) (Sequence of DCIB25)

<400> SEQUENCE: 154

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
                20                  25                  30

Thr Pro Gly Glu Pro Ala Ser Ile Ser Cys Arg Ser Ser Gln Ser Leu
            35                  40                  45

Val His Ser Asn Gly Asn Thr Tyr Leu Glu Trp Tyr Leu Gln Lys Pro
        50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Thr Gly Val Tyr Tyr Cys
            100                 105                 110

Thr Pro Pro Ala Tyr Arg Pro Pro Asn Ala Pro Ile Leu Phe Gly Gly
        115                 120                 125

Gly Thr Lys Val Glu Ile Lys
    130                 135

<210> SEQ ID NO 155
<211> LENGTH: 135
<212> TYPE: PRT
<213> ORGANISM: Unknown
<220> FEATURE:
<223> OTHER INFORMATION: Nucleotide and amino acid sequence of the heavy
      and light variable regions cloned in frame with the
      human IgG1 Fc and kappa constant regions within the expression
      vector pDCOrig (heavy variable) (Sequence of DCIB25)

<400> SEQUENCE: 155

Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
                20                  25                  30

Pro Gly Gly Ser Leu Arg Met Ser Cys Thr Ile Met Asp Gln Val Pro
            35                  40                  45

Phe Ser Val Trp Val Arg Gln Ala Pro Gly Lys Gly Leu Glu Trp Ile
        50                  55                  60

Ala Tyr Ile Gly Ser Gly Gly Ser Val Tyr Asp Phe Phe Val Trp Leu
65                  70                  75                  80

Arg Phe Thr Ile Ser Arg Asp Asn Ser Lys Asn Thr Leu Tyr Leu Gln
                85                  90                  95

Leu Asn Ser Leu Arg Ala Glu Asp Thr Ala Val Tyr Tyr Cys Ala Arg
            100                 105                 110

His Tyr Gly His Tyr Val Asp Tyr Ala Val Asp Tyr Trp Gly Gln Gly
        115                 120                 125

Thr Thr Val Thr Val Ser Ser
    130                 135

<210> SEQ ID NO 156
<211> LENGTH: 423
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa  constant regions within the expression
      vector pDCOrig (heavy variable) (Sequence of DCIB31)

<400> SEQUENCE: 156

-continued

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gtgcagcctc tggattcgct ttcaatacct atgacatgtc ttgggttcgc   180
caggctccgg ggaaggggct ggagtggatc gcatacattg gtagtggtgg tgatagaacc   240
tactatccag acactgtgaa gggccgattc accatttcca gagacaatag caagaacacc   300
ctgtatttgc aattgaacag tctgagggct gaggacacac cgtgtatta ctgtgcccga    360 agtgtttatg atttttttgt gtggctctgg ggccaaggaa ccacggtcac cgtctccagc   420
gct                                                                 423
```

<210> SEQ ID NO 157
<211> LENGTH: 137
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB31)

<400> SEQUENCE: 157

```
Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
             20                  25                  30

Pro Gly Gly Ser Leu Arg Met Ser Cys Ala Ala Ser Gly Phe Ala Phe
         35                  40                  45

Asn Thr Tyr Asp Met Ser Trp Val Arg Gln Ala Pro Gly Lys Gly Leu
     50                  55                  60

Glu Trp Ile Ala Tyr Ile Gly Ser Gly Gly Asp Arg Thr Tyr Tyr Pro
 65                  70                  75                  80

Asp Thr Val Lys Gly Arg Phe Thr Ile Ser Arg Asp Asn Ser Lys Asn
                 85                  90                  95

Thr Leu Tyr Leu Gln Leu Asn Ser Leu Arg Ala Glu Asp Thr Ala Val
            100                 105                 110

Tyr Tyr Cys Ala Arg Ser Val Tyr Asp Phe Phe Val Trp Leu Trp Gly
        115                 120                 125

Gln Gly Thr Thr Val Thr Val Ser Ser
    130                 135
```

<210> SEQ ID NO 158
<211> LENGTH: 407
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB31)

<400> SEQUENCE: 158

```
ggatccacca tgggatggag ctgtatcatc ctcttcttgg tagcaacagc taccggagtc    60
cactccgatg tgttgatgac ccaatctcca ctctccctgc ctgtcactcc tggggagcca   120
gcctccatct cttgcagatc tagtcagagc ctggtacata gtaatggaaa cacctattta   180
gaatggtacc tgcagaaacc aggccagtct ccacagctcc tgatctacaa agtttccaac   240
cgattttctg ggtcccccaga cagattcagt gcagtggatc agggacagat tcacactca   300 agatcagcag agtggaggct gaggataccg gagtgtatta ctgctttcaa ggttcacatg   360
```
ttccgtggac gttcggtgga ggcaccaagg tggaaatcaa gcgtacg        407

<210> SEQ ID NO 159
<211> LENGTH: 131
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB31)

<400> SEQUENCE: 159

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Thr Gly Val Tyr Tyr Cys
            100                 105                 110

Phe Gln Gly Ser His Val Pro Trp Thr Phe Gly Gly Gly Thr Lys Val
        115                 120                 125

Glu Ile Lys
    130

<210> SEQ ID NO 160
<211> LENGTH: 423
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB32)

<400> SEQUENCE: 160
aagcttacca tgggatggag ctgtatcatc ctcttcttgg tagcaacagc taccggagtc        60
cactcccagg tgcagctggt ggagactggg ggaggcttaa tccagcctgg agggtccctg       120
agaatgtcct gtgcagcctc tggattcgct ttcaatacct atgacatgtc ttgggttcgc       180
caggctccgg ggaaggggct ggagtggatc gcatacattg gtagtggtgg tgatagaacc       240
tactatccag acactgtgaa gggccgattc accatttcca gagacaatag caagaacacc       300
ctgtatttgc aattgaacag tctgagggct gaggacacag ccgtgtatta ctgtgcccga       360
agtgtttatg attttttgt gtggctctgg ggccaaggaa ccacggtcac cgtctccagc       420
gct                                                                    423

<210> SEQ ID NO 161
<211> LENGTH: 137
<212> TYPE: PRT
<213> ORGANISM: Unknown
<220> FEATURE:
<223> OTHER INFORMATION: Nucleotide and amino acid sequence of the heavy
      and light variable regions cloned inframe with the human IgG1 Fc and kappa constant regions within the expression
vector pDCOrig (heavy variable) (Sequence of DCIB32)

<400> SEQUENCE: 161

Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
        35                  40                  45

Asn Thr Tyr Asp Met Ser Trp Val Arg Gln Ala Pro Gly Lys Gly Leu
    50                  55                  60

Glu Trp Ile Ala Tyr Ile Gly Ser Gly Gly Asp Arg Thr Tyr Tyr Pro
65                  70                  75                  80

Asp Thr Val Lys Gly Arg Phe Thr Ile Ser Arg Asp Asn Ser Lys Asn
                85                  90                  95

Thr Leu Tyr Leu Gln Leu Asn Ser Leu Arg Ala Glu Asp Thr Ala Val
            100                 105                 110

Tyr Tyr Cys Ala Arg Ser Val Tyr Asp Phe Phe Val Trp Leu Trp Gly
        115                 120                 125

Gln Gly Thr Thr Val Thr Val Ser Ser
    130                 135

<210> SEQ ID NO 162
<211> LENGTH: 420
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB32)

<400> SEQUENCE: 162
ggatccacca tgggatggag ctgtatcatc ctcttcttgg tagcaacagc taccggagtc      60
cactccgatg tgttgatgac ccaatctcca ctctccctgc tgtcactcc tggggagcca     120 gcctccatct cttgcagatc tagtcagagc ctggtacata gtaatggaaa cacctattta     180
gaatggtacc tgcagaaacc aggccagtct ccacagctcc tgatctacaa agttccaac     240 cgattttctg gggtcccaga cagattcagt ggcagtggat cagggacaga tttcacactc     300
aagatcagca gagtggaggc tgaggatacc ggagtgtatt actgcactcc tccagcttat     360
agaccaccaa atgcccctat cctattcggt ggaggcacca aggtggaaat caagcgtacg     420

<210> SEQ ID NO 163
<211> LENGTH: 432
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB36)

<400> SEQUENCE: 163
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gtcagcctc tggattcgct ttcaatacct atgacatgtc ttgggttcgc     180
caggctccgg ggaagggct ggagtggatc gcatacattg gtagtggtgg tgatagaacc     240

```
tactatccag acactgtgaa gggccgattc accatttcca gagacaatag caagaacacc      300
ctgtatttgc aattgaacag tctgagggct gaggacacag ccgtgtatta ctgtgcaaga      360
cattatggtc actacgtgga ctatgctgtg gactactggg gtcaaggaac cacggtcacc      420
gtctccagcg ct                                                         432
```

<210> SEQ ID NO 164
<211> LENGTH: 140
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB36)

<400> SEQUENCE: 164

```
Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
        35                  40                  45

Asn Thr Tyr Asp Met Ser Trp Val Arg Gln Ala Pro Gly Lys Gly Leu
    50                  55                  60

Glu Trp Ile Ala Tyr Ile Gly Ser Gly Gly Asp Arg Thr Tyr Tyr Pro
65                  70                  75                  80

Asp Thr Val Lys Gly Arg Phe Thr Ile Ser Arg Asp Asn Ser Lys Asn
                85                  90                  95

Thr Leu Tyr Leu Gln Leu Asn Ser Leu Arg Ala Glu Asp Thr Ala Val
            100                 105                 110

Tyr Tyr Cys Ala Arg His Tyr Gly His Tyr Val Asp Tyr Ala Val Asp
        115                 120                 125

Tyr Trp Gly Gln Gly Thr Thr Val Thr Val Ser Ser
    130                 135                 140
```

<210> SEQ ID NO 165
<211> LENGTH: 408
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB36)

<400> SEQUENCE: 165

```
ggatccacca tgggatggag ctgtatcatc ctcttcttgg tagcaacagc taccggagtc       60
cactccgatg tgttgatgac ccaatctcca ctctccctgc ctgtcactcc tggggagcca      120
gcctccatct cttgcagatc tagtcagagc ctggtacata gtaatggaaa cacctattta      180
gaatggtacc tgcagaaacc aggccagtct ccacagctcc tgatctacaa agtttccaac      240
cgattttctg ggtcccccaga cagattcagt ggcagtggat cagggacaga tttcacactc      300
aagatcagca gagtggaggc tgaggatacc ggagtgtatt actgcagtgt tatgatttt      360 tttgtgtggc tcttcggtgg aggcaccaag gtggaaatca agcgtacg                   408
```

<210> SEQ ID NO 166
<211> LENGTH: 131
<212> TYPE: PRT
<213> ORGANISM: Unknown

```
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB36)

<400> SEQUENCE: 166

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Thr Gly Val Tyr Tyr Cys
            100                 105                 110

Ser Val Tyr Asp Phe Phe Val Trp Leu Phe Gly Gly Gly Thr Lys Val
        115                 120                 125

Glu Ile Lys
        130

<210> SEQ ID NO 167
<211> LENGTH: 438
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB48)

<400> SEQUENCE: 167
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gtgcagcctc tggattcgct ttcaatacct atgacatgtc ttgggttcgc     180
caggctccgg ggaaggggct ggagtggatc gcatacattg gtagtggtgg tagtgtttat     240 gattttttg tgtggctccg attccaccat tccagagaca atagcaagaa caccctgtat      300
ttgcaattga acagtctgag ggctgaggac acagccgtgt attactgtgc ccgatggaac     360
aggcagctgt atccagagtg gacagaagcc cagagacttg actggggcca aggaaccacg     420
gtcaccgtct ccagcgct                                                   438

<210> SEQ ID NO 168
<211> LENGTH: 142
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB48)

<400> SEQUENCE: 168

Met Gly Trp Ser Cys Ile Ile Leu Phe Leu Val Ala Thr Ala Thr Gly
1               5                   10                  15
```

```
Val His Ser Gln Val Gln Leu Val Glu Thr Gly Gly Leu Ile Gln
         20                  25                  30

Pro Gly Gly Ser Leu Arg Met Ser Cys Ala Ala Ser Gly Phe Ala Phe
         35                  40                  45

Asn Thr Tyr Asp Met Ser Trp Val Arg Gln Ala Pro Gly Lys Gly Leu
 50                  55                  60

Glu Trp Ile Ala Tyr Ile Gly Ser Gly Gly Ser Val Tyr Asp Phe Phe
 65                  70                  75                  80

Val Trp Leu Arg Phe Thr Ile Ser Arg Asp Asn Ser Lys Asn Thr Leu
                 85                  90                  95

Tyr Leu Gln Leu Asn Ser Leu Arg Ala Glu Asp Thr Ala Val Tyr Tyr
            100                 105                 110

Cys Ala Arg Trp Asn Arg Gln Leu Tyr Pro Glu Trp Thr Glu Ala Gln
             115                 120                 125

Arg Leu Asp Trp Gly Gln Gly Thr Thr Val Thr Val Ser Ser
         130                 135                 140

<210> SEQ ID NO 169
<211> LENGTH: 317
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB48)

<400> SEQUENCE: 169
ggatccacca tgggatggag ctgtatcatc ctcttcttgg tagcaacagc taccggagtc    60
cactccgatg tgttgatgac ccaatctcca ctctccctgc ctgtcactcc tggggagcca   120
gcctccatct cttgcagatc tagtcagagc ctggtacata gtaatggaaa cacctattta   180
gcagtggatc aggacagat tcacactca agatcagcag agtggaggct gaggataccg    240
gagtgtatta ctgctttcaa ggttcacatg ttccgtggac gttcggtgga ggcaccaagg   300
tggaaatcaa gcgtacg                                                  317

<210> SEQ ID NO 170
<211> LENGTH: 435
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB49)

<400> SEQUENCE: 170
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gtgcagcctc tggattcgct ttcaatacct atgacatgtc ttgggttcgc   180
caggctccgg ggaagggct ggagtggatc gcatacattg gtagtggtgg tgatagaacc    240
tactatccag acactgtgaa ggccgattc accatttcca gagacaatag caagaacacc   300
ctgtatttgc aattgaacag tctgagggct gaggacacac cgtgtatta ctgtgcccga   360 actcctccag cttatagacc accaaatgcc cctatcctat ggggccaagg aaccacggtc   420
accgtctcca gcgct                                                   435

<210> SEQ ID NO 171
```

```
<211> LENGTH: 141
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB49)

<400> SEQUENCE: 171

Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
        35                  40                  45

Asn Thr Tyr Asp Met Ser Trp Val Arg Gln Ala Pro Gly Lys Gly Leu
    50                  55                  60

Glu Trp Ile Ala Tyr Ile Gly Ser Gly Gly Asp Arg Thr Tyr Tyr Pro
65                  70                  75                  80

Asp Thr Val Lys Gly Arg Phe Thr Ile Ser Arg Asp Asn Ser Lys Asn
                85                  90                  95

Thr Leu Tyr Leu Gln Leu Asn Ser Leu Arg Ala Glu Asp Thr Ala Val
            100                 105                 110

Tyr Tyr Cys Ala Arg Thr Pro Pro Ala Tyr Arg Pro Pro Asn Ala Pro
        115                 120                 125

Ile Leu Trp Gly Gln Gly Thr Thr Val Thr Val Ser Ser
    130                 135                 140

<210> SEQ ID NO 172
<211> LENGTH: 408
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB49)

<400> SEQUENCE: 172
ggatccacca tgggatggag ctgtatcatc ctcttcttgg tagcaacagc taccggagtc      60
cactccgatg tgttgatgac ccaatctcca ctctccctgc ctgtcactcc tggggagcca    120
gcctccatct cttgcagatc tagtcagagc ctggtacata gtaatggaaa cacctattta    180
gaatggtacc tgcagaaacc aggccagtct ccacagctcc tgatctacaa agtttccaac    240
cgattttctg gggtcccaga cagattcagt ggcagtggat cagggacaga tttcacactc    300
aagatcagca gagtggaggc tgaggatacc ggagtgtatt actgctttca aggttcacat    360
gttccgtgga cgttcggtgg aggcaccaag gtggaaatca agcgtacg                 408

<210> SEQ ID NO 173
<211> LENGTH: 429
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB52)

<400> SEQUENCE: 173
aagcttacca tgggatggag ctgtatcatc ctcttcttgg tagcaacagc taccggagtc      60
```

```
cactcccagg tgcagctggt ggagactggg ggaggcttaa tccagcctgg agggtccctg    120
agaatgtcct gtgcagcctc tggattcgct ttcaatacct atgacatgtc ttgggttcgc    180
caggctccgg ggaagggct ggagtggatc gcatacattg gtagtggtgg tagtgtttat    240 gattttttg tgtggctccg attcaccatt tccagagaca atagcaagaa cacctgtat    300 ttgcaattga acagtctgag ggctgaggac acagccgtgt attactgtgc ccgaactcct    360
ccagcttata gaccaccaaa tgccctatc ctatggggcc aaggaaccac ggtcaccgtc    420
tccagcgct                                                           429
```

<210> SEQ ID NO 174
<211> LENGTH: 139
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB52)

<400> SEQUENCE: 174

```
Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
             20                  25                  30

Pro Gly Gly Ser Leu Arg Met Ser Cys Ala Ala Ser Gly Phe Ala Phe
         35                  40                  45

Asn Thr Tyr Asp Met Ser Trp Val Arg Gln Ala Pro Gly Lys Gly Leu
     50                  55                  60

Glu Trp Ile Ala Tyr Ile Gly Ser Gly Gly Ser Val Tyr Asp Phe Phe
 65                  70                  75                  80

Val Trp Leu Arg Phe Thr Ile Ser Arg Asp Asn Ser Lys Asn Thr Leu
                 85                  90                  95

Tyr Leu Gln Leu Asn Ser Leu Arg Ala Glu Asp Thr Ala Val Tyr Tyr
            100                 105                 110

Cys Ala Arg Thr Pro Pro Ala Tyr Arg Pro Pro Asn Ala Pro Ile Leu
        115                 120                 125

Trp Gly Gln Gly Thr Thr Val Thr Val Ser Ser
    130                 135
```

<210> SEQ ID NO 175
<211> LENGTH: 407
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB52)

<400> SEQUENCE: 175

```
ggatccacca tgggatggag ctgtatcatc ctcttcttgg tagcaacagc taccggagtc    60
cactccgatg tgttgatgac ccaatctcca ctctccctgc tgtcactcc tggggagcca    120 gcctccatct cttgcagatc tagtcagagc ctggtacata gtaatggaaa cacctatttg    180
aatggtacct gcagaaacca ggccagtctc cacagctcct gatctacaaa gtttccaacc    240
gattttctgg ggtcccagac agattcagtg gcagtggatc agggacagat ttcacactca    300
agatcagcag agtggaggct gaggatacccg gagtgtatta ctgctttcaa ggttcacatg    360
ttccgtggac gttcggtgga ggcaccaagg tggaaatcaa gcgtacg                 407
```

<210> SEQ ID NO 176
<211> LENGTH: 453
<212> TYPE: DNA
<213> ORGANISM: Unknown
<220> FEATURE:
<223> OTHER INFORMATION: Nucleotide and amino acid sequence of the heavy
and light variable regions cloned inframe with the
human IgG1 Fc and kappa constant regions within the expression
vector pDCOrig (heavy variable) (Sequence of DCIB54)

<400> SEQUENCE: 176

```
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gcgggacagg cagggcaatg ctgggcacac acaccatgga agtaactgtc     180
taccattggg ttcggcaggc tccggggaag gggctggagt ggatcgcata cattggtagt     240
ggtggtagtg tttatgattt ttttgtgtgg ctccgattca ccatttccag agacaatagc     300
aagaacaccc tgtatttgca attgaacagt ctgagggctg aggacacagc cgtgtattac     360
tgtgcccgat ggaacaggca gctgtatcca gagtggacag aagcccagag acttgactgg     420
ggccaaggta ccacggtcac cgtctccagc gct                                  453
```

<210> SEQ ID NO 177
<211> LENGTH: 147
<212> TYPE: PRT
<213> ORGANISM: Unknown
<220> FEATURE:
<223> OTHER INFORMATION: Nucleotide and amino acid sequence of the heavy
and light variable regions cloned inframe with the
human IgG1 Fc and kappa constant regions within the expression
vector pDCOrig (heavy variable) (Sequence of DCIB54)

<400> SEQUENCE: 177

```
Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
            20                  25                  30

Pro Gly Gly Ser Leu Arg Met Ser Cys Gly Thr Gly Arg Ala Met Leu
        35                  40                  45

Gly Thr His Thr Met Glu Val Thr Val Tyr His Trp Val Arg Gln Ala
    50                  55                  60

Pro Gly Lys Gly Leu Glu Trp Ile Ala Tyr Ile Gly Ser Gly Gly Ser
65                  70                  75                  80

Val Tyr Asp Phe Phe Val Trp Leu Arg Phe Thr Ile Ser Arg Asp Asn
                85                  90                  95

Ser Lys Asn Thr Leu Tyr Leu Gln Leu Asn Ser Leu Arg Ala Glu Asp
            100                 105                 110

Thr Ala Val Tyr Tyr Cys Ala Arg Trp Asn Arg Gln Leu Tyr Pro Glu
        115                 120                 125

Trp Thr Glu Ala Gln Arg Leu Asp Trp Gly Gln Gly Thr Thr Val Thr
    130                 135                 140

Val Ser Ser
145
```

<210> SEQ ID NO 178
<211> LENGTH: 131
<212> TYPE: PRT
<213> ORGANISM: Unknown
<220> FEATURE:
<223> OTHER INFORMATION: Nucleotide and amino acid sequence of the heavy -continued and light variable regions cloned inframe with the
human IgG1 Fc and kappa constant regions within the expression
vector pDCOrig (light variable) (Sequence of DCIB52)

<400> SEQUENCE: 178

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
 50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Thr Gly Val Tyr Tyr Cys
            100                 105                 110

Phe Gln Gly Ser His Val Pro Trp Thr Phe Gly Gly Gly Thr Lys Val
        115                 120                 125

Glu Ile Lys
    130
```

<210> SEQ ID NO 179
<211> LENGTH: 408
<212> TYPE: DNA
<213> ORGANISM: Unknown
<220> FEATURE:
<223> OTHER INFORMATION: Nucleotide and amino acid sequence of the heavy
      and light  variable regions cloned inframe with the
      human IgG1 Fc and kappa constant regions within the expression
      vector pDCOrig (light variable) (Sequence of DCIB54)

<400> SEQUENCE: 179

```
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctccatct cttgcagatc tagtcagagc ctggtacata gtaatggaaa cacctattta     180
gaatggtacc tgcagaaacc aggccagtct ccacagctcc tgatctacaa agtttccaac     240
cgattttctg gggtcccaga cagattcagt ggcagtggat cagggacaga tttcacactc     300
aagatcagca gagtggaggc tgaggatacc ggagtgtatt actgctttca aggttcacat     360
gttccgtgga cgttcggtgg aggcaccaag gtggaaatca agcgtacg                  408
```

<210> SEQ ID NO 180
<211> LENGTH: 131
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB54)

<400> SEQUENCE: 180

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
```

```
                35                  40                  45

Val His Ser Asn Gly Asn Thr Tyr Leu Glu Trp Tyr Leu Gln Lys Pro
 50                  55                  60

Gly Gln Ser Pro Gln Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Thr Gly Val Tyr Tyr Cys
            100                 105                 110

Phe Gln Gly Ser His Val Pro Trp Thr Phe Gly Gly Gly Thr Lys Val
        115                 120                 125

Glu Ile Lys
        130

<210> SEQ ID NO 181
<211> LENGTH: 426
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB18)

<400> SEQUENCE: 181
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gtgcagcctc tggattcgct ttcaatacct atgacatgtc ttgggttcgc     180
caggctccgg ggaaggggct ggagtggatc gcatacattg gtagtggtgg tagtgtttat     240 gattttttg tgtggctccg attcaccatt ccagagaca atagcaagaa caccctgtat       300
ttgcaattga acagtctgag ggctgaggac acagccgtgt attactgtgc aagacattat    360
ggtcactacg tggactatgc tgtggactac tggggtcaag gaaccacggt caccgtctcc    420
agcgct                                                                426

<210> SEQ ID NO 182
<211> LENGTH: 138
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (heavy variable) (Sequence of DCIB18)

<400> SEQUENCE: 182

Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
             20                  25                  30

Pro Gly Gly Ser Leu Arg Met Ser Cys Ala Ala Ser Gly Phe Ala Phe
         35                  40                  45

Asn Thr Tyr Asp Met Ser Trp Val Arg Gln Ala Pro Gly Lys Gly Leu
     50                  55                  60

Glu Trp Ile Ala Tyr Ile Gly Ser Gly Gly Ser Val Tyr Asp Phe Phe
 65                  70                  75                  80

Val Trp Leu Arg Phe Thr Ile Ser Arg Asp Asn Ser Lys Asn Thr Leu
                 85                  90                  95
```

```
Tyr Leu Gln Leu Asn Ser Leu Arg Ala Glu Asp Thr Ala Val Tyr Tyr
            100                 105                 110

Cys Ala Arg His Tyr Gly His Tyr Val Asp Tyr Ala Val Asp Tyr Trp
            115                 120                 125

Gly Gln Gly Thr Thr Val Thr Val Ser Ser
            130                 135

<210> SEQ ID NO 183
<211> LENGTH: 398
<212> TYPE: DNA
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB18)

<400> SEQUENCE: 183
ggatccacca tgggatggag ctgtatcatc ctcttcttgg tagcaacagc taccggagtc      60
cactccgatg tgttgatgac ccaatctcca ctctccctgc ctgtcactcc tggggagcca    120
gcctcgatct cttgcactcc tccagcttat agaccaccaa atgcccctat cctatggtat    180
tgcagaaacc aggccagtct ccacagctcc tgatctacaa agtttccaac cgattttctg    240
gggtcccaga cagattcagt ggcagtggat cagggacaga tttcacactc aagatcagca    300
gagtggaggc tgaggatacc ggagtgtatt actgctttca aggttcacat gttccgtgga    360
cgttcggtgg aggcaccaag gtggaaatca agcgtacg                            398

<210> SEQ ID NO 184
<211> LENGTH: 128
<212> TYPE: PRT
<213> ORGANISM: Unknown
<220> FEATURE:
<223> OTHER INFORMATION: Nucleotide and amino acid sequence of the heavy
      and light variable regions cloned inframe with the
      human IgG1 Fc and kappa constant regions within the expression
      vector pDCOrig (light variable) (Sequence of DCIB18)

<400> SEQUENCE: 184

Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
             20                  25                  30

Thr Pro Gly Glu Pro Ala Ser Ile Ser Cys Thr Pro Pro Ala Tyr Arg
         35                  40                  45

Pro Pro Asn Ala Pro Ile Leu Trp Tyr Leu Gln Lys Pro Gly Gln Ser
     50                  55                  60

Pro Gln Leu Leu Ile Tyr Lys Val Ser Asn Arg Phe Ser Gly Val Pro
 65                  70                  75                  80

Asp Arg Phe Ser Gly Ser Gly Ser Gly Thr Asp Phe Thr Leu Lys Ile
                 85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
            115                 120                 125

<210> SEQ ID NO 185
<211> LENGTH: 135
<212> TYPE: PRT
<213> ORGANISM: Unknown
<220> FEATURE:
<223> OTHER INFORMATION: Nucleotide and amino acid sequence of the heavy
```

-continued and light variable regions cloned inframe with the
human IgG1 Fc and kappa constant regions within the expression
vector pDCOrig (light variable) (Sequence of DCIB32)

<400> SEQUENCE: 185

```
Met Gly Trp Ser Cys Ile Ile Leu Phe Leu Val Ala Thr Ala Thr Gly
  1               5                  10                  15

Val His Ser Asp Val Leu Met Thr Gln Ser Pro Leu Ser Leu Pro Val
             20                  25                  30

Thr Pro Gly Glu Pro Ala Ser Ile Ser Cys Arg Ser Ser Gln Ser Leu
         35                  40                  45

Val His Ser Asn Gly Asn Thr Tyr Leu Glu Trp Tyr Leu Gln Lys Pro
     50                  55                  60

Gly Gln Ser Pro Gln Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Thr Gly Val Tyr Tyr Cys
            100                 105                 110

Thr Pro Pro Ala Tyr Arg Pro Pro Asn Ala Pro Ile Leu Phe Gly Gly
        115                 120                 125

Gly Thr Lys Val Glu Ile Lys
    130                 135
```

<210> SEQ ID NO 186
<211> LENGTH: 131
<212> TYPE: PRT
<213> ORGANISM: Unknown
<220> FEATURE:
<223> OTHER INFORMATION: Nucleotide and amino acid sequence of the heavy
    and light variable regions cloned inframe with the
    human IgG1 Fc and kappa constant regions within the expression
    vector pDCOrig (light variable) (Sequence of DCIB48)

<400> SEQUENCE: 186

```
Met Gly Trp Ser Cys Ile Ile Leu Phe Leu Val Ala Thr Ala Thr Gly
  1               5                  10                  15

Val His Ser Asp Val Leu Met Thr Gln Ser Pro Leu Ser Leu Pro Val
             20                  25                  30

Thr Pro Gly Glu Pro Ala Ser Ile Ser Cys Arg Ser Ser Gln Ser Leu
         35                  40                  45

Val His Ser Asn Gly Asn Thr Tyr Leu Glu Trp Tyr Leu Gln Lys Pro
     50                  55                  60

Gly Gln Ser Pro Gln Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Thr Gly Val Tyr Tyr Cys
            100                 105                 110

Phe Gln Gly Ser His Val Pro Trp Thr Phe Gly Gly Gly Thr Lys Val
        115                 120                 125

Glu Ile Lys
    130
```

<210> SEQ ID NO 187
<211> LENGTH: 131
<212> TYPE: PRT
<213> ORGANISM: Unknown
<220> FEATURE:
<223> OTHER INFORMATION: Nucleotide and amino acid sequence of the heavy and light variable regions cloned inframe with the
human IgG1 Fc and kappa constant regions within the expression
vector pDCOrig (light variable) (Sequence of DCIB49)

<400> SEQUENCE: 187

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Thr Gly Val Tyr Tyr Cys
            100                 105                 110

Phe Gln Gly Ser His Val Pro Trp Thr Phe Gly Gly Gly Thr Lys Val
        115                 120                 125

Glu Ile Lys
    130

<210> SEQ ID NO 188
<211> LENGTH: 435
<212> TYPE: DNA
<213> ORGANISM: Unknown
<220> FEATURE:
<223> OTHER INFORMATION: Sequence of DCIB21 - Heavy variable

<400> SEQUENCE: 188
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gtgcagcctc tggattcgct ttcaatacct atgacatgtc ttgggttcgc     180
caggctccgg ggaaggggct ggagtggatc gcatacattg gtagtggtgg tataccgcag     240
agtctagact cgtggtggac ttctctccga ttcaccattt ccagagacaa tagcaagaac     300
accctgtatt tgcaattgaa cagtctgagg gctgaggaca cagccgtgta ttactgtgca     360
agacattatg gtcactacgt ggactatgct gtggactact ggggtcaagg aaccacggtc     420
accgtctcca gcgct                                                     435

<210> SEQ ID NO 189
<211> LENGTH: 141
<212> TYPE: PRT
<213> ORGANISM: Unknown
<220> FEATURE:
<223> OTHER INFORMATION: Sequence of DCIB21 - Heavy variable

<400> SEQUENCE: 189

Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
        35                  40                  45

Asn Thr Tyr Asp Met Ser Trp Val Arg Gln Ala Pro Gly Lys Gly Leu
    50                  55                  60

Glu Trp Ile Ala Tyr Ile Gly Ser Gly Gly Ile Pro Gln Ser Leu Asp
65                  70                  75                  80

Ser Trp Trp Thr Ser Leu Arg Phe Thr Ile Ser Arg Asp Asn Ser Lys
                85                  90                  95

Asn Thr Leu Tyr Leu Gln Leu Asn Ser Leu Arg Ala Glu Asp Thr Ala
            100                 105                 110

Val Tyr Tyr Cys Ala Arg His Tyr Gly His Tyr Val Asp Tyr Ala Val
        115                 120                 125

Asp Tyr Trp Gly Gln Gly Thr Thr Val Thr Val Ser Ser
130                 135                 140

<210> SEQ ID NO 190
<211> LENGTH: 390
<212> TYPE: DNA
<213> ORGANISM: Unknown
<220> FEATURE:
<223> OTHER INFORMATION: Sequence of DCIB21 - Light variable

<400> SEQUENCE: 190
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctccatct cttgctttga aaggtttgag atattcccca ggaatggta cctgcagaaa      180 ccaggccagt ctccacagct cctgatctac aaagtttcca accgattttc tggggtccca     240
gacagattca gtggcagtgg atcagggaca gatttcacac tcaagatcag cagagtggag     300
gctgaggata ccggagtgta ttactgcttt caaggttcac atgttccgtg gacgttcggt     360
ggaggcacca aggtggaaat caagcgtacg                                      390

<210> SEQ ID NO 191
<211> LENGTH: 125
<212> TYPE: PRT
<213> ORGANISM: Unknown
<220> FEATURE:
<223> OTHER INFORMATION: Sequence of DCIB21 - Light variable

<400> SEQUENCE: 191

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
                20                  25                  30

Thr Pro Gly Glu Pro Ala Ser Ile Ser Cys Phe Glu Arg Phe Glu Ile
            35                  40                  45

Phe Pro Lys Glu Trp Tyr Leu Gln Lys Pro Gly Gln Ser Pro Gln Leu
        50                  55                  60

Leu Ile Tyr Lys Val Ser Asn Arg Phe Ser Gly Val Pro Asp Arg Phe
65                  70                  75                  80

Ser Gly Ser Gly Ser Gly Thr Asp Phe Thr Leu Lys Ile Ser Arg Val
                85                  90                  95

Glu Ala Glu Asp Thr Gly Val Tyr Tyr Cys Phe Gln Gly Ser His Val
            100                 105                 110

Pro Trp Thr Phe Gly Gly Gly Thr Lys Val Glu Ile Lys
        115                 120                 125

<210> SEQ ID NO 192
<211> LENGTH: 423
<212> TYPE: DNA
<213> ORGANISM: Unknown
<220> FEATURE:

<223> OTHER INFORMATION: Sequence of DCIB26 - Heavy variable

<400> SEQUENCE: 192

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattat ggaccaggtg cctttctccg tgtgggttcg gcaggctccg   180
gggaaggggc tggagtggat cgcatacatt ggtagtggtg gtgatagaac ctactatcca   240
gacactgtga agggccgatt caccatttcc agagacaata gcaagaacac cctgtatttg   300
caattgaaca gtctgagggc tgaggacaca gccgtgtatt actgtgcaag acattatggt   360
cactacgtgg actatgctgt ggactactgg ggtcaaggaa ccacggtcac cgtctccagc   420
gct                                                                 423
```

<210> SEQ ID NO 193
<211> LENGTH: 137
<212> TYPE: PRT
<213> ORGANISM: Unknown
<220> FEATURE:
<223> OTHER INFORMATION: Sequence of DCIB26 - Heavy variable

<400> SEQUENCE: 193

```
Met Gly Trp Ser Cys Ile Ile Leu Phe Leu Val Ala Thr Ala Thr Gly
 1               5                  10                  15
Val His Ser Gln Val Gln Leu Val Glu Thr Gly Gly Gly Leu Ile Gln
            20                  25                  30
Pro Gly Gly Ser Leu Arg Met Ser Cys Thr Ile Met Asp Gln Val Pro
        35                  40                  45
Phe Ser Val Trp Val Arg Gln Ala Pro Gly Lys Gly Leu Glu Trp Ile
    50                  55                  60
Ala Tyr Ile Gly Ser Gly Gly Asp Arg Thr Tyr Tyr Pro Asp Thr Val
65                  70                  75                  80
Lys Gly Arg Phe Thr Ile Ser Arg Asp Asn Ser Lys Asn Thr Leu Tyr
                85                  90                  95
Leu Gln Leu Asn Ser Leu Arg Ala Glu Asp Thr Ala Val Tyr Tyr Cys
            100                 105                 110
Ala Arg His Tyr Gly His Tyr Val Asp Tyr Ala Val Asp Tyr Trp Gly
        115                 120                 125
Gln Gly Thr Thr Val Thr Val Ser Ser
    130                 135
```

<210> SEQ ID NO 194
<211> LENGTH: 399
<212> TYPE: DNA
<213> ORGANISM: Unknown
<220> FEATURE:
<223> OTHER INFORMATION: Sequence of DCIB26 - Light variable

<400> SEQUENCE: 194

```
ggatccacca tgggatggag ctgtatcatc ctcttcttgg tagcaacagc taccggagtc    60
cactccgatg tgttgatgac ccaatctcca ctctccctgc ctgtcactcc tggggagcca   120
gcctcgatct cttgcactcc tccagcttat agaccaccaa atgcccctat cctatggtat   180
ctgcagaaac caggccagtc tccacagctc ctgatctaca agtttccaa ccgatttttct   240
ggggtcccag acagattcag tggcagtgga tcagggacag atttcacact caagatcagc   300
agagtggagg ctgaggatac cggagtgtat tactgctttc aaggttcaca tgttccgtgg   360
acgttcggtg gaggcaccaa ggtggaaatc aagcgtacg                           399
```

<210> SEQ ID NO 195
<211> LENGTH: 128
<212> TYPE: PRT
<213> ORGANISM: Unknown
<220> FEATURE:
<223> OTHER INFORMATION: Sequence of DCIB26 - Light variable

<400> SEQUENCE: 195

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
            20                  25                  30

Thr Pro Gly Glu Pro Ala Ser Ile Ser Cys Thr Pro Pro Ala Tyr Arg
        35                  40                  45

Pro Pro Asn Ala Pro Ile Leu Trp Tyr Leu Gln Lys Pro Gly Gln Ser
    50                  55                  60

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
        115                 120                 125

<210> SEQ ID NO 196
<211> LENGTH: 420
<212> TYPE: DNA
<213> ORGANISM: Unknown
<220> FEATURE:
<223> OTHER INFORMATION: Sequence of DCIB26 - Heavy Variable

<400> SEQUENCE: 196
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gcttcctacc agctacttta actatggttt gggttcggca ggctccgggg     180
aaggggctgg agtggatcgc atacattggt agtggtggtg atagaaccta ctatccagac     240
actgtgaagg gccgattcac catttccaga gacaatagca gaacaccct  gtatttgcaa     300 ttgaacagtc tgagggctga ggacacagcc gtgtattact gtgcaagaca ttatggtcac     360
tacgtggact atgctgtgga ctactgggt caaggaacca cggtcaccgt ctccagcgct      420

<210> SEQ ID NO 197
<211> LENGTH: 136
<212> TYPE: PRT
<213> ORGANISM: Unknown
<220> FEATURE:
<223> OTHER INFORMATION: Sequence of DCIB26 - Heavy Variable

<400> SEQUENCE: 197

Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Phe Leu Pro Ala Thr Leu Thr
        35                  40                  45

Met Val Trp Val Arg Gln Ala Pro Gly Lys Gly Leu Glu Trp Ile Ala
    50                  55                  60

Tyr Ile Gly Ser Gly Gly Asp Arg Thr Tyr Tyr Pro Asp Thr Val Lys
65                  70                  75                  80

Gly Arg Phe Thr Ile Ser Arg Asp Asn Ser Lys Asn Thr Leu Tyr Leu
            85                  90                  95

Gln Leu Asn Ser Leu Arg Ala Glu Asp Thr Ala Val Tyr Tyr Cys Ala
                100                 105                 110

Arg His Tyr Gly His Tyr Val Asp Tyr Ala Val Asp Tyr Trp Gly Gln
        115                 120                 125

Gly Thr Thr Val Thr Val Ser Ser
        130                 135

<210> SEQ ID NO 198
<211> LENGTH: 399
<212> TYPE: DNA
<213> ORGANISM: Unknown
<220> FEATURE:
<223> OTHER INFORMATION: Sequence of DCIB26 - Light Variable

<400> SEQUENCE: 198
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctcgatct cttgcactcc tccagcttat agaccaccaa atgcccctat cctatggtat     180
ctgcagaaac caggccagtc tccacagctc ctgatctaca agtttccaac cgatttctct     240
ggggtcccag acagattcag tggcagtgga tcagggacag atttcacact caagatcagc     300
agagtggagg ctgaggatac cggagtgtat tactgctttc aaggttcaca tgttccgtgg     360
acgttcggtg gaggcaccaa ggtggaaatc aagcgtacg                            399

<210> SEQ ID NO 199
<211> LENGTH: 128
<212> TYPE: PRT
<213> ORGANISM: Unknown
<220> FEATURE:
<223> OTHER INFORMATION: Sequence of DCIB26 - Light Variable

<400> SEQUENCE: 199

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
                20                  25                  30

Thr Pro Gly Glu Pro Ala Ser Ile Ser Cys Thr Pro Pro Ala Tyr Arg
            35                  40                  45

Pro Pro Asn Ala Pro Ile Leu Trp Tyr Leu Gln Lys Pro Gly Gln Ser
    50                  55                  60

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
                100                 105                 110

Ser His Val Pro Trp Thr Phe Gly Gly Gly Thr Lys Val Glu Ile Lys
        115                 120                 125

<210> SEQ ID NO 200
<211> LENGTH: 423
<212> TYPE: DNA
<213> ORGANISM: Unknown
<220> FEATURE:

<223> OTHER INFORMATION: Sequence of DCIB37 - heavy variable

<400> SEQUENCE: 200

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattac tgaccaggtg cctttgtccg tgtgggttcg gcaggctccg   180
gggaaggggc tggagtggat cgcatacatt ggtagtggtg gtgatagaac ctactatcca   240
gacactgtga agggccgatt caccatttcc agagacaata gcaagaacac cctgtatttg   300
caattgaaca gtctgagggc tgaggacaca gccgtgtatt actgtgcaag acattatggt   360
cactacgtgg actatgctgt ggactactgg ggtcaaggaa ccacggtcac cgtctccagc   420
gct                                                                 423
```

<210> SEQ ID NO 201
<211> LENGTH: 137
<212> TYPE: PRT
<213> ORGANISM: Unknown
<220> FEATURE:
<223> OTHER INFORMATION: Sequence of DCIB37 - heavy variable

<400> SEQUENCE: 201

```
Met Gly Trp Ser Cys Ile Ile Leu Phe Leu Val Ala Thr Ala Thr Gly
  1               5                  10                  15
Val His Ser Gln Val Gln Leu Val Glu Thr Gly Gly Gly Leu Ile Gln
                 20                  25                  30
Pro Gly Gly Ser Leu Arg Met Ser Cys Thr Ile Thr Asp Gln Val Pro
             35                  40                  45
Leu Ser Val Trp Val Arg Gln Ala Pro Gly Lys Gly Leu Glu Trp Ile
         50                  55                  60
Ala Tyr Ile Gly Ser Gly Gly Asp Arg Thr Tyr Tyr Pro Asp Thr Val
 65                  70                  75                  80
Lys Gly Arg Phe Thr Ile Ser Arg Asp Asn Ser Lys Asn Thr Leu Tyr
                 85                  90                  95
Leu Gln Leu Asn Ser Leu Arg Ala Glu Asp Thr Ala Val Tyr Tyr Cys
            100                 105                 110
Ala Arg His Tyr Gly His Tyr Val Asp Tyr Ala Val Asp Tyr Trp Gly
        115                 120                 125
Gln Gly Thr Thr Val Thr Val Ser Ser
    130                 135
```

<210> SEQ ID NO 202
<211> LENGTH: 399
<212> TYPE: DNA
<213> ORGANISM: Unknown
<220> FEATURE:
<223> OTHER INFORMATION: Sequence of DCIB37 - light variable

<400> SEQUENCE: 202

```
ggatccacca tgggatggag ctgtatcatc ctcttcttgg tagcaacagc taccggagtc    60
cactccgatg tgttgatgac ccaatctcca ctctccctgc ctgtcactcc tggggagcca   120
gcctcgatct cttgcactcc tccagcttat agaccaccaa atgcccctat cctatggtat   180
ctgcagaaac caggccagtc tccacagctc ctgatctaca agtttccaac cgatttttct   240
ggggtcccag acagattcag tggcagtgga tcagggacag atttcacact caagatcagc   300
agagtggagg ctgaggatac cggagtgtat tactgctttc aaggttcaca tgttccgtgg   360
acgttcggtg gaggcaccaa ggtggaaatc aagcgtacg                          399
```

<210> SEQ ID NO 203
<211> LENGTH: 128
<212> TYPE: PRT
<213> ORGANISM: Unknown
<220> FEATURE:
<223> OTHER INFORMATION: Sequence of DCIB37 - light variable

<400> SEQUENCE: 203

```
Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
            20                  25                  30

Thr Pro Gly Glu Pro Ala Ser Ile Ser Cys Thr Pro Pro Ala Tyr Arg
        35                  40                  45

Pro Pro Asn Ala Pro Ile Leu Trp Tyr Leu Gln Lys Pro Gly Gln Ser
    50                  55                  60

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
        115                 120                 125
```

<210> SEQ ID NO 204
<211> LENGTH: 423
<212> TYPE: DNA
<213> ORGANISM: Unknown
<220> FEATURE:
<223> OTHER INFORMATION: Sequence of DCIB40 - heavy variable

<400> SEQUENCE: 204

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattac tgaccaggtg cctatctccg tgtgggttcg gcaggctccg   180
gggaaggggc tggagtggat cgcatacatt ggtagtggtg gtgatagaac ctactatcca   240
gacactgtga agggccgatt caccatttcc agagacaata gcaagaacac cctgtatttg   300
caattgaaca gtctgagggc tgaggacaca gccgtgtatt actgtgcaag acattatggt   360
cactacgtgg actatgctgt ggactactgg ggtcaaggaa ccacggtcac cgtctccagc   420
gct                                                                 423
```

<210> SEQ ID NO 205
<211> LENGTH: 137
<212> TYPE: PRT
<213> ORGANISM: Unknown
<220> FEATURE:
<223> OTHER INFORMATION: Sequence of DCIB40 - heavy variable

<400> SEQUENCE: 205

```
Met Gly Trp Ser Cys Ile Ile Leu Phe Leu Val Ala Thr Ala Thr Gly
1               5                   10                  15

Val His Ser Gln Val Gln Leu Val Glu Thr Gly Gly Gly Leu Ile Gln
            20                  25                  30

Pro Gly Gly Ser Leu Arg Met Ser Cys Thr Ile Thr Asp Gln Val Pro
        35                  40                  45
```

```
Ile Ser Val Trp Val Arg Gln Ala Pro Gly Lys Gly Leu Glu Trp Ile
 50                  55                  60

Ala Tyr Ile Gly Ser Gly Asp Arg Thr Tyr Tyr Pro Asp Thr Val
 65                  70                  75                  80

Lys Gly Arg Phe Thr Ile Ser Arg Asp Asn Ser Lys Asn Thr Leu Tyr
                 85                  90                  95

Leu Gln Leu Asn Ser Leu Arg Ala Glu Asp Thr Ala Val Tyr Tyr Cys
             100                 105                 110

Ala Arg His Tyr Gly His Tyr Val Asp Tyr Ala Val Asp Tyr Trp Gly
         115                 120                 125

Gln Gly Thr Thr Val Thr Val Ser Ser
     130                 135
```

<210> SEQ ID NO 206
<211> LENGTH: 399
<212> TYPE: DNA
<213> ORGANISM: Unknown
<220> FEATURE:
<223> OTHER INFORMATION: Sequence of DCIB40 - light variable

<400> SEQUENCE: 206

```
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctcgatct cttgcactcc tccagcttat agaccaccaa atgccctat cctatggtat      180
ctgcagaaac caggccagtc tccacagctc ctgatctaca agtttccaa ccgattttct      240
ggggtcccag acagattcag tggcagtgga tcaggacag atttcacact caagatcagc      300
agagtggagg ctgaggatac cggagtgtat tactgctttc aaggttcaca tgttccgtgg     360
acgttcggtg gaggcaccaa ggtggaaatc aagcgtacg                            399
```

<210> SEQ ID NO 207
<211> LENGTH: 128
<212> TYPE: PRT
<213> ORGANISM: Unknown
<220> FEATURE:
<223> OTHER INFORMATION: Sequence of DCIB40 - light variable

<400> SEQUENCE: 207

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
             20                  25                  30

Thr Pro Gly Glu Pro Ala Ser Ile Ser Cys Thr Pro Pro Ala Tyr Arg
         35                  40                  45

Pro Pro Asn Ala Pro Ile Leu Trp Tyr Leu Gln Lys Pro Gly Gln Ser
     50                  55                  60

Pro Gln Leu Leu Ile Tyr Lys Val Ser Asn Arg Phe Ser Gly Val Pro
 65                  70                  75                  80

Asp Arg Phe Ser Gly Ser Gly Ser Gly Thr Asp Phe Thr Leu Lys Ile
                 85                  90                  95

Ser Arg Val Glu Ala Glu Asp Thr Gly Val Tyr Tyr Cys Phe Gln Gly
             100                 105                 110

Ser His Val Pro Trp Thr Phe Gly Gly Gly Thr Lys Val Glu Ile Lys
         115                 120                 125
```

<210> SEQ ID NO 208
<211> LENGTH: 423
<212> TYPE: DNA

<213> ORGANISM: Unknown
<220> FEATURE:
<223> OTHER INFORMATION: Sequence of DCIB41 - heavy variable

<400> SEQUENCE: 208

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattac tgaccaggtg cctttctccg tgtgggttcg gcaggctccg   180
gggaaggggc tggagtggat cgcatacatt ggtagtggtg gtgatagaac ctactatcca   240
gacactgtga agggccgatt caccatttcc agagacaata gcaagaacac cctgtatttg   300
caattgaaca gtctgagggc tgaggacaca gccgtgtatt actgtgcaag acattatggt   360
cactacgtgg actatgctgt ggactactgg ggtcaaggaa ccacggtcac cgtctccagc   420
gct                                                                 423
```

<210> SEQ ID NO 209
<211> LENGTH: 399
<212> TYPE: DNA
<213> ORGANISM: Unknown
<220> FEATURE:
<223> OTHER INFORMATION: Sequence of DCIB41 - light variable

<400> SEQUENCE: 209

```
ggatccacca tgggatggag ctgtatcatc ctcttcttgg tagcaacagc taccggagtc    60
cactccgatg tgttgatgac ccaatctcca ctctccctgc ctgtcactcc tggggagcca   120
gcctcgatct cttgcactcc tccagcttat agaccaccaa atgcccctat cctatggtat   180
ctgcagaaac caggccagtc tccacagctc ctgatctaca agtttccaa ccgatttct    240
ggggtcccag acagattcag tggcagtgga tcagggacag atttcacact caagatcagc   300
agagtggagg ctgaggatac cggagtgtat tactgctttc aaggttcaca tgttccgtgg   360
acgttcggtg aggcaccaa ggtggaaatc aagcgtacg                           399
```

<210> SEQ ID NO 210
<211> LENGTH: 128
<212> TYPE: PRT
<213> ORGANISM: Unknown
<220> FEATURE:
<223> OTHER INFORMATION: Sequence of DCIB41 - light variable

<400> SEQUENCE: 210

```
Met Gly Trp Ser Cys Ile Ile Leu Phe Leu Val Ala Thr Ala Thr Gly
 1               5                   10                  15

Val His Ser Asp Val Leu Met Thr Gln Ser Pro Leu Ser Leu Pro Val
            20                  25                  30

Thr Pro Gly Glu Pro Ala Ser Ile Ser Cys Thr Pro Pro Ala Tyr Arg
        35                  40                  45

Pro Pro Asn Ala Pro Ile Leu Trp Tyr Leu Gln Lys Pro Gly Gln Ser
    50                  55                  60

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
        115                 120                 125
```

```
<210> SEQ ID NO 211
<211> LENGTH: 423
<212> TYPE: DNA
<213> ORGANISM: Unknown
<220> FEATURE:
<223> OTHER INFORMATION: Sequence of DCIB42 - heavy variable

<400> SEQUENCE: 211
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gcaccattac tgaccaggtg ccttactccg tgtgggttcg gcaggctccg     180
gggaaggggc tggagtggat cgcatacatt ggtagtggtg gtgatagaac ctactatcca     240
gacactgtga aggccgatt caccattcc agagacaata gcaagaacac cctgtatttg       300
caattgaaca gtctgagggc tgaggacaca gccgtgtatt actgtgcaag acattatggt     360
cactacgtgg actatgctgt ggactactgg ggtcaaggaa ccacggtcac cgtctccagc     420
gct                                                                   423

<210> SEQ ID NO 212
<211> LENGTH: 137
<212> TYPE: PRT
<213> ORGANISM: Unknown
<220> FEATURE:
<223> OTHER INFORMATION: Sequence of DCIB42 - heavy variable

<400> SEQUENCE: 212

Met Gly Trp Ser Cys Ile Ile Leu Phe Leu Val Ala Thr Ala Thr Gly
  1               5                  10                  15

Val His Ser Gln Val Gln Leu Val Glu Thr Gly Gly Gly Leu Ile Gln
                 20                  25                  30

Pro Gly Gly Ser Leu Arg Met Ser Cys Thr Ile Thr Asp Gln Val Pro
             35                  40                  45

Tyr Ser Val Trp Val Arg Gln Ala Pro Gly Lys Gly Leu Glu Trp Ile
         50                  55                  60

Ala Tyr Ile Gly Ser Gly Gly Asp Arg Thr Tyr Tyr Pro Asp Thr Val
 65                  70                  75                  80

Lys Gly Arg Phe Thr Ile Ser Arg Asp Asn Ser Lys Asn Thr Leu Tyr
                 85                  90                  95

Leu Gln Leu Asn Ser Leu Arg Ala Glu Asp Thr Ala Val Tyr Tyr Cys
            100                 105                 110

Ala Arg His Tyr Gly His Tyr Val Asp Tyr Ala Val Asp Tyr Trp Gly
        115                 120                 125

Gln Gly Thr Thr Val Thr Val Ser Ser
    130                 135

<210> SEQ ID NO 213
<211> LENGTH: 399
<212> TYPE: DNA
<213> ORGANISM: Unknown
<220> FEATURE:
<223> OTHER INFORMATION: Sequence of DCIB42 - light variable

<400> SEQUENCE: 213
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctcgatct cttgcactcc tccagcttat agaccaccaa atgcccctat cctatggtat     180
ctgcagaaac aggccagtc tccacagctc ctgatctaca aagtttccaa ccgattttct     240
```

```
ggggtcccag acagattcag tggcagtgga tcagggacag atttcacact caagatcagc    300
agagtggagg ctgaggatac cggagtgtat tactgctttc aaggttcaca tgttccgtgg    360
acgttcggtg gaggcaccaa ggtggaaatc aagcgtacg                           399
```

```
<210> SEQ ID NO 214
<211> LENGTH: 128
<212> TYPE: PRT
<213> ORGANISM: Unknown
<220> FEATURE:
<223> OTHER INFORMATION: Sequence of DCIB42 - light variable

<400> SEQUENCE: 214
```

```
Met Gly Trp Ser Cys Ile Ile Leu Phe Leu Val Ala Thr Ala Thr Gly
  1               5                  10                  15

Val His Ser Asp Val Leu Met Thr Gln Ser Pro Leu Ser Leu Pro Val
             20                  25                  30

Thr Pro Gly Glu Pro Ala Ser Ile Ser Cys Thr Pro Pro Ala Tyr Arg
         35                  40                  45

Pro Pro Asn Ala Pro Ile Leu Trp Tyr Leu Gln Lys Pro Gly Gln Ser
     50                  55                  60

Pro Gln Leu Leu Ile Tyr Lys Val Ser Asn Arg Phe Ser Gly Val Pro
 65                  70                  75                  80

Asp Arg Phe Ser Gly Ser Gly Ser Gly Thr Asp Phe Thr Leu Lys Ile
                 85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
        115                 120                 125
```

```
<210> SEQ ID NO 215
<211> LENGTH: 423
<212> TYPE: DNA
<213> ORGANISM: Unknown
<220> FEATURE:
<223> OTHER INFORMATION: Sequence of DCIB43 - heavy variable

<400> SEQUENCE: 215
```

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattac tgaccagctg cctttctccg tgtgggttcg gcaggctccg   180 gggaagggc tggagtggat cgcatacatt ggtagtggtg gtgatagaac ctactatcca    240
gacactgtga agggccgatt caccatttcc agagacaata gcaagaacac cctgtatttg   300
caattgaaca gtctgagggc tgaggacaca gccgtgtatt actgtgcaag acattatggt   360
cactacgtgg actatgctgt ggactactgg ggtcaaggaa ccacggtcac cgtctccagc   420
gct                                                                 423
```

```
<210> SEQ ID NO 216
<211> LENGTH: 136
<212> TYPE: PRT
<213> ORGANISM: Unknown
<220> FEATURE:
<223> OTHER INFORMATION: Sequence of DCIB43 - heavy variable

<400> SEQUENCE: 216
```

```
Met Gly Trp Ser Cys Ile Ile Leu Phe Leu Val Ala Thr Ala Thr Gly
  1               5                  10                  15
```

Val His Ser Gln Val Gln Leu Val Glu Thr Gly Gly Gly Leu Ile Gln
         20                  25                  30

Pro Gly Gly Ser Leu Arg Met Ser Cys Thr Ile Thr Asp Gln Leu Pro
             35                  40                  45

Phe Ser Val Trp Val Arg Gln Ala Pro Gly Lys Gly Leu Glu Trp Ile
 50                  55                  60

Ala Tyr Ile Gly Ser Gly Gly Asp Arg Thr Tyr Tyr Pro Asp Thr Val
 65                  70                  75                  80

Lys Gly Arg Phe Thr Ile Arg Asp Asn Ser Lys Asn Thr Leu Tyr Leu
                 85                  90                  95

Gln Leu Asn Ser Leu Arg Ala Glu Asp Thr Ala Val Tyr Tyr Cys Ala
             100                 105                 110

Arg His Tyr Gly His Tyr Val Asp Tyr Ala Val Asp Tyr Trp Gly Gln
             115                 120                 125

Gly Thr Thr Val Thr Val Ser Ser
             130                 135

<210> SEQ ID NO 217
<211> LENGTH: 128
<212> TYPE: PRT
<213> ORGANISM: Unknown
<220> FEATURE:
<223> OTHER INFORMATION: Sequence of DCIB43 - light variable

<400> SEQUENCE: 217

Met Gly Trp Ser Cys Ile Ile Leu Phe Leu Val Ala Thr Ala Thr Gly
 1               5                   10                  15

Val His Ser Asp Val Leu Met Thr Gln Ser Pro Leu Ser Leu Pro Val
             20                  25                  30

Thr Pro Gly Glu Pro Ala Ser Ile Ser Cys Thr Pro Ala Tyr Arg
             35                  40                  45

Pro Pro Asn Ala Pro Ile Leu Trp Tyr Leu Gln Lys Pro Gly Gln Ser
 50                  55                  60

Pro Gln Leu Leu Ile Tyr Lys Val Ser Asn Arg Phe Ser Gly Val Pro
 65                  70                  75                  80

Asp Arg Phe Ser Gly Ser Gly Ser Gly Thr Asp Phe Thr Leu Lys Ile
                 85                  90                  95

Ser Arg Val Glu Ala Glu Asp Thr Gly Val Tyr Tyr Cys Phe Gln Gly
             100                 105                 110

Ser His Val Pro Trp Thr Phe Gly Gly Gly Thr Lys Val Glu Ile Lys
             115                 120                 125

<210> SEQ ID NO 218
<211> LENGTH: 137
<212> TYPE: PRT
<213> ORGANISM: Unknown
<220> FEATURE:
<223> OTHER INFORMATION: Sequence of DCIB41 - heavy variable

<400> SEQUENCE: 218

Met Gly Trp Ser Cys Ile Ile Leu Phe Leu Val Ala Thr Ala Thr Gly
 1               5                   10                  15

Val His Ser Gln Val Gln Leu Val Glu Thr Gly Gly Gly Leu Ile Gln
             20                  25                  30

Pro Gly Gly Ser Leu Arg Met Ser Cys Thr Ile Thr Asp Gln Val Pro
             35                  40                  45

Phe Ser Val Trp Val Arg Gln Ala Pro Gly Lys Gly Leu Glu Trp Ile
 50                  55                  60

```
Ala Tyr Ile Gly Ser Gly Gly Asp Arg Thr Tyr Tyr Pro Asp Thr Val
 65                  70                  75                  80

Lys Gly Arg Phe Thr Ile Ser Arg Asp Asn Ser Lys Asn Thr Leu Tyr
                 85                  90                  95

Leu Gln Leu Asn Ser Leu Arg Ala Glu Asp Thr Ala Val Tyr Tyr Cys
            100                 105                 110

Ala Arg His Tyr Gly His Tyr Val Asp Tyr Ala Val Asp Tyr Trp Gly
        115                 120                 125

Gln Gly Thr Thr Val Thr Val Ser Ser
        130                 135
```

<210> SEQ ID NO 219
<211> LENGTH: 399
<212> TYPE: DNA
<213> ORGANISM: Unknown
<220> FEATURE:
<223> OTHER INFORMATION: Sequence of DCIB43 - light variable

<400> SEQUENCE: 219

```
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctcgatct cttgcactcc tccagcttat agaccaccaa atgcccctat cctatggtat     180
ctgcagaaac caggccagtc tccacagctc ctgatctaca agtttccaa ccgattttct      240
ggggtcccag acagattcag tggcagtgga tcaggacag atttcacact caagatcagc      300
agagtggagg ctgaggatac cggagtgtat tactgctttc aaggttcaca tgttccgtgg     360
acgttcggtg gaggcaccaa ggtggaaatc aagcgtacg                            399
```

<210> SEQ ID NO 220
<211> LENGTH: 417
<212> TYPE: DNA
<213> ORGANISM: Unknown
<220> FEATURE:
<223> OTHER INFORMATION: Sequence of DCIB35 - heavy variable

<400> SEQUENCE: 220

```
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gcaccattat ggaccaggtg cctttctccg tgtgggttcg gcaggctccg     180
gggaaggggc tggagtggat cgcatacatt ggtagtggtg gtagtgttta tgatttttt      240
gtgtggctcc gattcaccat tccagagac aatagcaaga cacctgta tttgcaattg       300
aacagtctga gggctgagga cacagccgtg tattactgtg cgagacatta tggtcactac     360
gtggactatg ctgtggacta ctggggtcaa ggtaccacgg tcaccgtctc cagcgct        417
```

<210> SEQ ID NO 221
<211> LENGTH: 135
<212> TYPE: PRT
<213> ORGANISM: Unknown
<220> FEATURE:
<223> OTHER INFORMATION: Sequence of DCIB35 - heavy variable

<400> SEQUENCE: 221

```
Met Gly Trp Ser Cys Ile Ile Leu Phe Leu Val Ala Thr Ala Thr Gly
  1               5                  10                  15

Val His Ser Gln Val Gln Leu Val Glu Thr Gly Gly Gly Leu Ile Gln
             20                  25                  30

Pro Gly Gly Ser Leu Arg Met Ser Cys Thr Ile Met Asp Gln Val Pro
```

```
                35                  40                  45
Phe Ser Val Trp Val Arg Gln Ala Pro Gly Lys Gly Leu Glu Trp Ile
 50                  55                  60

Ala Tyr Ile Gly Ser Gly Gly Ser Val Tyr Asp Phe Val Trp Leu
 65                  70                  75                  80

Arg Phe Thr Ile Ser Arg Asp Asn Ser Lys Asn Thr Leu Tyr Leu Gln
                 85                  90                  95

Leu Asn Ser Leu Arg Ala Glu Asp Thr Ala Val Tyr Tyr Cys Ala Arg
                100                 105                 110

His Tyr Gly His Tyr Val Asp Tyr Ala Val Asp Tyr Trp Gly Gln Gly
                115                 120                 125

Thr Thr Val Thr Val Ser Ser
                130                 135

<210> SEQ ID NO 222
<211> LENGTH: 408
<212> TYPE: DNA
<213> ORGANISM: Unknown
<220> FEATURE:
<223> OTHER INFORMATION: Sequence of DCIB35 - light variable

<400> SEQUENCE: 222
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctcgatct cttgctggaa caggcagctg tatccagagt ggacagaagc ccagagactt     180
gactggtatc tgcagaaacc aggccagtct ccacagctcc tgatctacaa agtttccaac     240
cgattttctg gggtcccaga cagattcagt ggcagtggat cagggacaga tttcacactc     300
aagatcagca gagtggaggc tgaggatacc ggagtgtatt actgctttca aggttcacat     360
gttccgtgga cgttcggtgg aggcaccaag gtggaaatca agcgtacg                  408

<210> SEQ ID NO 223
<211> LENGTH: 131
<212> TYPE: PRT
<213> ORGANISM: Unknown
<220> FEATURE:
<223> OTHER INFORMATION: Sequence of DCIB35 - light variable

<400> SEQUENCE: 223

Met Gly Trp Ser Cys Ile Ile Leu Phe Leu Val Ala Thr Ala Thr Gly
  1               5                  10                  15

Val His Ser Asp Val Leu Met Thr Gln Ser Pro Leu Ser Leu Pro Val
                 20                  25                  30

Thr Pro Gly Glu Pro Ala Ser Ile Ser Cys Trp Asn Arg Gln Leu Tyr
                 35                  40                  45

Pro Glu Trp Thr Glu Ala Gln Arg Leu Asp Trp Tyr Leu Gln Lys Pro
 50                  55                  60

Gly Gln Ser Pro Gln Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Thr Gly Val Tyr Tyr Cys
                100                 105                 110

Phe Gln Gly Ser His Val Pro Trp Thr Phe Gly Gly Gly Thr Lys Val
                115                 120                 125

Glu Ile Lys
                130
```

<210> SEQ ID NO 224
<211> LENGTH: 417
<212> TYPE: DNA
<213> ORGANISM: Unknown
<220> FEATURE:
<223> OTHER INFORMATION: Sequence of DCIB50 - heavy variable

<400> SEQUENCE: 224

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcaccattat ggaccaggtg cctttctccg tgtgggttcg gcaggctccg   180
gggaagggc tggagtggat cgcatacatt ggtagtggtg gtagtgttta tgattttttt    240
gtgtggctcc gattcaccat ttccagagac aatagcaaga cacccctgta tttgcaattg   300
aacagtctga gggctgagga cacagccgtg tattactgtg cgagacatta tggtcactac   360
gtggactatg ctgtggacta ctggggtcaa ggtaccacgg tcaccgtctc cagcgct      417
```

<210> SEQ ID NO 225
<211> LENGTH: 135
<212> TYPE: PRT
<213> ORGANISM: Unknown
<220> FEATURE:
<223> OTHER INFORMATION: Sequence of DCIB50 - heavy variable

<400> SEQUENCE: 225

```
Met Gly Trp Ser Cys Ile Ile Leu Phe Leu Val Ala Thr Ala Thr Gly
 1               5                  10                  15
Val His Ser Gln Val Gln Leu Val Glu Thr Gly Gly Gly Leu Ile Gln
            20                  25                  30
Pro Gly Gly Ser Leu Arg Met Ser Cys Thr Ile Met Asp Gln Val Pro
        35                  40                  45
Phe Ser Val Trp Val Arg Gln Ala Pro Gly Lys Gly Leu Glu Trp Ile
    50                  55                  60
Ala Tyr Ile Gly Ser Gly Gly Ser Val Tyr Asp Phe Phe Val Trp Leu
65                  70                  75                  80
Arg Phe Thr Ile Ser Arg Asp Asn Ser Lys Asn Thr Leu Tyr Leu Gln
                85                  90                  95
Leu Asn Ser Leu Arg Ala Glu Asp Thr Ala Val Tyr Tyr Cys Ala Arg
            100                 105                 110
His Tyr Gly His Tyr Val Asp Tyr Ala Val Asp Tyr Trp Gly Gln Gly
        115                 120                 125
Thr Thr Val Thr Val Ser Ser
    130                 135
```

<210> SEQ ID NO 226
<211> LENGTH: 431
<212> TYPE: DNA
<213> ORGANISM: Unknown
<220> FEATURE:
<223> OTHER INFORMATION: Sequence of DCIB50 - light variable

<400> SEQUENCE: 226

```
ggatccacca tgggatggag ctgtatcatc ctcttcttgg tagcaacagc taccggagtc    60
cactccgatg tgttgatgac ccaatctcca ctctccctgc ctgtcactcc tggggagcca   120
gcctccatct cttgcagatc tagtcagagc ctggtacata gtaatggaaa cacctattta   180
gaatggtacc tgcagaaacc aggccagtct ccacagctcc tgatctacaa agtttccaac   240
```

-continued

```
cgatttttctg gggtcccaga cagattcagt ggcagtggat cagggacaga tttcacactc      300
aagatcagca gagtggaggc tgaggatacc ggagtgtatt actgctgaa caggcagctg       360 tatccagagt ggacagaagc ccagagactt gacttcggtg gaggcaccaa ggtggaaatc      420
aagcgtacgm g                                                           431
```

<210> SEQ ID NO 227
<211> LENGTH: 138
<212> TYPE: PRT
<213> ORGANISM: Unknown
<220> FEATURE:
<223> OTHER INFORMATION: Sequence of DCIB50 - light variable

<400> SEQUENCE: 227

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Thr Gly Val Tyr Tyr Cys
            100                 105                 110

Trp Asn Arg Gln Leu Tyr Pro Glu Trp Thr Glu Ala Gln Arg Leu Asp
        115                 120                 125

Phe Gly Gly Gly Thr Lys Val Glu Ile Lys
    130                 135
```

<210> SEQ ID NO 228
<211> LENGTH: 420
<212> TYPE: DNA
<213> ORGANISM: Unknown
<220> FEATURE:
<223> OTHER INFORMATION: Sequence of DCIB71 - Heavy variable

<400> SEQUENCE: 228

```
aagcttacca tgggatggag ctgtatcatc ctcttcttgg tagcaacagc taccggagtc      60
cactcccagg tgcagctggt ggagactggg ggaggcttaa tccagcctgg agggtccctg     120
agaatgtcct gcatcttgat caattcccta cctcttgtat gggttcggca ggctccgggg    180
aaggggctgg agtggatcgc atacattggt agtggtggtg atagaaccta ctatccagac    240
actgtgaagg gccgattcac catttccaga gacaatagca gaacaccct gtatttgcaa     300 ttgaacagtc tgagggctga ggacacagcc gtgtattact gtgcaagaca ttatggtcac    360
tacgtggact atgctgtgga ctactggggt caaggaacca cggtcaccgt ctccagcgct    420
```

<210> SEQ ID NO 229
<211> LENGTH: 136
<212> TYPE: PRT
<213> ORGANISM: Unknown
<220> FEATURE:
<223> OTHER INFORMATION: Sequence of DCIB71 - Heavy variable

<400> SEQUENCE: 229

Met Gly Trp Ser Cys Ile Ile Leu Phe Leu Val Ala Thr Ala Thr Gly

|  1 |  |  |  | 5 |  |  |  |  | 10 |  |  |  |  | 15 |
|---|---|---|---|---|---|---|---|---|---|---|---|---|---|---|
Val His Ser Gln Val Gln Leu Val Glu Thr Gly Gly Gly Leu Ile Gln
                20                  25                  30

Pro Gly Gly Ser Leu Arg Met Ser Cys Ile Leu Ile Asn Ser Leu Pro
            35                  40                  45

Leu Val Trp Val Arg Gln Ala Pro Gly Lys Gly Leu Glu Trp Ile Ala
    50                  55                  60

Tyr Ile Gly Ser Gly Gly Asp Arg Thr Tyr Tyr Pro Asp Thr Val Lys
65                  70                  75                  80

Gly Arg Phe Thr Ile Ser Arg Asp Asn Ser Lys Asn Thr Leu Tyr Leu
                85                  90                  95

Gln Leu Asn Ser Leu Arg Ala Glu Asp Thr Ala Val Tyr Tyr Cys Ala
            100                 105                 110

Arg His Tyr Gly His Tyr Val Asp Tyr Ala Val Asp Tyr Trp Gly Gln
        115                 120                 125

Gly Thr Thr Val Thr Val Ser Ser
            130                 135

<210> SEQ ID NO 230
<211> LENGTH: 399
<212> TYPE: DNA
<213> ORGANISM: Unknown
<220> FEATURE:
<223> OTHER INFORMATION: Sequence of DCIB71 - Light variable

<400> SEQUENCE: 230
ggatccacca tgggatggag ctgtatcatc ctcttcttgg tagcaacagc taccggagtc     60
cactccgatg tgttgatgac ccaatctcca ctctccctgc ctgtcactcc tggggagcca    120
gcctcgatct cttgcactcc tccagcttat agaccaccaa atgccectat cctatggtat    180 ctgcagaaac caggccagtc tccacagctc ctgatctaca agtttccaa ccgattttct     240 ggggtcccag acagattcag tggcagtgga tcagggacag atttcacact caagatcagc    300
agagtggagg ctgaggatac cggagtgtat tactgctttc aaggttcaca tgttccgtgg    360
acgttcggtg gaggcaccaa ggtggaaatc aagcgtacg                           399

<210> SEQ ID NO 231
<211> LENGTH: 128
<212> TYPE: PRT
<213> ORGANISM: Unknown
<220> FEATURE:
<223> OTHER INFORMATION: Sequence of DCIB71 - Light variable

<400> SEQUENCE: 231

Met Gly Trp Ser Cys Ile Ile Leu Phe Leu Val Ala Thr Ala Thr Gly
1               5                   10                  15

Val His Ser Asp Val Leu Met Thr Gln Ser Pro Leu Ser Leu Pro Val
                20                  25                  30

Thr Pro Gly Glu Pro Ala Ser Ile Ser Cys Thr Pro Pro Ala Tyr Arg
            35                  40                  45

Pro Pro Asn Ala Pro Ile Leu Trp Tyr Leu Gln Lys Pro Gly Gln Ser
    50                  55                  60

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
            100                 105                 110

```
Ser His Val Pro Trp Thr Phe Gly Gly Gly Thr Lys Val Glu Ile Lys
        115                 120                 125
```

```
<210> SEQ ID NO 232
<211> LENGTH: 426
<212> TYPE: DNA
<213> ORGANISM: Unknown
<220> FEATURE:
<223> OTHER INFORMATION: Sequence of DCIB72 - heavy variable

<400> SEQUENCE: 232
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gtgcagcctc tggattcgct ttcaatacct atgacatgtc ttgggttcgc   180
caggctccgg ggaaggggct ggagtggatc gcatacattg gtagtggtgg tatcttgatc   240
aattccctac ctcttgtacg attcaccatt tccagagaca atagcaagaa cacectgtat   300 ttgcaattga acagtctgag ggctgaggac acagccgtgt attactgtgc aagacattat   360
ggtcactacg tggactatgc tgtggactac tggggtcaag gaaccacggt caccgtctcc   420
agcgct                                                             426
```

```
<210> SEQ ID NO 233
<211> LENGTH: 138
<212> TYPE: PRT
<213> ORGANISM: Unknown
<220> FEATURE:
<223> OTHER INFORMATION: Sequence of DCIB72 - heavy variable

<400> SEQUENCE: 233

Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
            20                  25                  30

Pro Gly Gly Ser Leu Arg Met Ser Cys Ala Ala Ser Gly Phe Ala Phe
        35                  40                  45

Asn Thr Tyr Asp Met Ser Trp Val Arg Gln Ala Pro Gly Lys Gly Leu
    50                  55                  60

Glu Trp Ile Ala Tyr Ile Gly Ser Gly Gly Ile Leu Ile Asn Ser Leu
65                  70                  75                  80

Pro Leu Val Arg Phe Thr Ile Ser Arg Asp Asn Ser Lys Asn Thr Leu
                85                  90                  95

Tyr Leu Gln Leu Asn Ser Leu Arg Ala Glu Asp Thr Ala Val Tyr Tyr
            100                 105                 110

Cys Ala Arg His Tyr Gly His Tyr Val Asp Tyr Ala Val Asp Tyr Trp
        115                 120                 125

Gly Gln Gly Thr Thr Val Thr Val Ser Ser
    130                 135
```

```
<210> SEQ ID NO 234
<211> LENGTH: 399
<212> TYPE: DNA
<213> ORGANISM: Unknown
<220> FEATURE:
<223> OTHER INFORMATION: Sequence of DCIB72 - light variable

<400> SEQUENCE: 234
ggatccacca tgggatggag ctgtatcatc ctcttcttgg tagcaacagc taccggagtc    60
cactccgatg tgttgatgac ccaatctcca ctctccctgc ctgtcactcc tggggagcca   120
```

```
gcctcgatct cttgcactcc tccagcttat agaccaccaa atgcccctat cctatggtat    180
ctgcagaaac caggccagtc tccacagctc ctgatctaca aagtttccaa ccgatttttct   240 ggggtcccag acagattcag tggcagtgga tcagggacag atttcacact caagatcagc    300
agagtggagg ctgaggatac cggagtgtat tactgctttc aaggttcaca tgttccgtgg    360
acgttcggtg gaggcaccaa ggtggaaatc aagcgtacg                            399
```

<210> SEQ ID NO 235
<211> LENGTH: 128
<212> TYPE: PRT
<213> ORGANISM: Unknown
<220> FEATURE:
<223> OTHER INFORMATION: Sequence of DCIB72 - light variable

<400> SEQUENCE: 235

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Thr Pro Pro Ala Tyr Arg
        35                  40                  45

Pro Pro Asn Ala Pro Ile Leu Trp Tyr Leu Gln Lys Pro Gly Gln Ser
    50                  55                  60

Pro Gln Leu Leu Ile Tyr Lys Val Ser Asn Arg Phe Ser Gly Val Pro
65                  70                  75                  80

Asp Arg Phe Ser Gly Ser Gly Ser Gly Thr Asp Phe Thr Leu Lys Ile
                85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
        115                 120                 125
```

<210> SEQ ID NO 236
<211> LENGTH: 1413
<212> TYPE: DNA
<213> ORGANISM: Unknown
<220> FEATURE:
<223> OTHER INFORMATION: Sequence of DCIB53 - heavy variable

<400> SEQUENCE: 236

```
aagcttacca tgggatggag ctgtatcatc ctcttcttgg tagcaacagc taccggagtc     60
cactcccagg tgcagctggt ggagactggg ggaggcttaa tccagcctgg agggtccctg    120
agaatgtcct gcaccattat ggaccaggtg ccttctctccg tgtgggttcg gcaggctccg   180
gggaaggggc tggagtggat cgcatacatt ggtagtggtg gtagtgttta tgatttttt    240 gtgtggctcc gattcaccat ttccagagac aatagcaaga cacccctgta tttgcaattg    300
aacagtctga gggctgagga cacagccgtg tattactgtg cgagacatta tggtcactac   360
gtggactatg ctgtgactac tggggtcaa ggtaccacgg tcaccgtctc cagcgctaaa   420
acaacagccc catcggtcta tccactggcc cctgtgtgtg agatacaac tggctcctcg   480 gtgactctag gatgcctggt caagggttat tccctgagc cagtgacctt gacctggaac    540
tctggttccc tgtccagtgg tgtgcacacc ttcccagctg tcctgcagtc tgacctctac   600
accctcagca gctcagtgac tgtaacttcg agcacctggc cagccagtc catcacctgc    660 aatgtggccc acccggcaag cagcaccaag gtggacaaga aaattgagcc cagagggccc    720
acaatcaagc cctgtcctcc atgcaaatgc ccagcaccta acctcttggg tggaccatcc    780
```

-continued

```
gtcttcatct tccctccaaa gatcaaggat gtactcatga tctccctgag ccccatagtc    840
acatgtgtgg tggtggatgt gagcgaggat gacccagatg tccagatcag ctggtttgtg    900
aacaacgtgg aagtacacac agctcagaca caaacccata gagaggatta acacagtact    960
ctccgggtgg tcagtgccct ccccatccag caccaggact ggatgagtgg caaggagttc   1020
aaatgcaagg tcaacaacaa agacctccca gcgcccatcg agagaaccat ctcaaaaccc   1080
aaagggtcag taagagctcc acaggtatat gtcttgcctc caccagaaga agagatgact   1140
aagaaacagg tcactctgac ctgcatggtc acagacttca tgcctgaaga catttacgtg   1200
gagtggacca acaacgggaa aacagagcta actacaaga cactgaacc agtcctggac     1260 tctgatggtt cttacttcat gtacagcaag ctgagagtgg aaaagaagaa ctgggtggaa   1320
agaaatagct actcctgttc agtggtccac gagggtctgc acaatcacca cacgactaag   1380
agcttctccc ggactccggg taaatgatct aga                                1413
```

<210> SEQ ID NO 237
<211> LENGTH: 465
<212> TYPE: PRT
<213> ORGANISM: Unknown
<220> FEATURE:
<223> OTHER INFORMATION: Sequence of DCIB53 - heavy variable

<400> SEQUENCE: 237

```
Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
            20                  25                  30

Pro Gly Gly Ser Leu Arg Met Ser Cys Thr Ile Met Asp Gln Val Pro
        35                  40                  45

Phe Ser Val Trp Val Arg Gln Ala Pro Gly Lys Gly Leu Glu Trp Ile
    50                  55                  60

Ala Tyr Ile Gly Ser Gly Gly Ser Val Tyr Asp Phe Phe Val Trp Leu
65                  70                  75                  80

Arg Phe Thr Ile Ser Arg Asp Asn Ser Lys Asn Thr Leu Tyr Leu Gln
                85                  90                  95

Leu Asn Ser Leu Arg Ala Glu Asp Thr Ala Val Tyr Tyr Cys Ala Arg
            100                 105                 110

His Tyr Gly His Tyr Val Asp Tyr Ala Val Asp Tyr Trp Gly Gln Gly
        115                 120                 125

Thr Thr Val Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Val Thr Val Thr Ser Ser
        195                 200                 205

Thr Trp Pro Ser Gln Ser Ile Thr Cys Asn Val Ala His Pro Ala Ser
    210                 215                 220

Ser Thr Lys Val Asp Lys Lys Ile Glu Pro Arg Gly Pro Thr Ile Lys
225                 230                 235                 240

Pro Cys Pro Pro Cys Lys Cys Pro Ala Pro Asn Leu Leu Gly Gly Pro
                245                 250                 255
```

```
Ser Val Phe Ile Phe Pro Pro Lys Ile Lys Asp Val Leu Met Ile Ser
        260                 265                 270
Leu Ser Pro Ile Val Thr Cys Val Val Asp Val Ser Glu Asp Asp
    275                 280                 285
Pro Asp Val Gln Ile Ser Trp Phe Val Asn Asn Val Glu Val His Thr
290                 295                 300
Ala Gln Thr Gln Thr His Arg Glu Asp Tyr Asn Ser Thr Leu Arg Val
305                 310                 315                 320
Val Ser Ala Leu Pro Ile Gln His Gln Asp Trp Met Ser Gly Lys Glu
            325                 330                 335
Phe Lys Cys Lys Val Asn Asn Lys Asp Leu Pro Ala Pro Ile Glu Arg
        340                 345                 350
Thr Ile Ser Lys Pro Lys Gly Ser Val Arg Ala Pro Gln Val Tyr Val
        355                 360                 365
Leu Pro Pro Pro Glu Glu Glu Met Thr Lys Lys Gln Val Thr Leu Thr
    370                 375                 380
Cys Met Val Thr Asp Phe Met Pro Glu Asp Ile Tyr Val Glu Trp Thr
385                 390                 395                 400
Asn Asn Gly Lys Thr Glu Leu Asn Tyr Lys Asn Thr Glu Pro Val Leu
            405                 410                 415
Asp Ser Asp Gly Ser Tyr Phe Met Tyr Ser Lys Leu Arg Val Glu Lys
        420                 425                 430
Lys Asn Trp Val Glu Arg Asn Ser Tyr Ser Cys Ser Val Val His Glu
        435                 440                 445
Gly Leu His Asn His His Thr Thr Lys Ser Phe Ser Arg Thr Pro Gly
        450                 455                 460
Lys
465

<210> SEQ ID NO 238
<211> LENGTH: 729
<212> TYPE: DNA
<213> ORGANISM: Unknown
<220> FEATURE:
<223> OTHER INFORMATION: Sequence of DCIB53 - light variable

<400> SEQUENCE: 238
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctcgatct cttgcactcc tccagcttat agaccaccaa atgccctat cctatggtat      180
ctgcagaaac caggccagtc tccacagctc ctgatctaca agtttccaa ccgattttct      240
ggggtcccag acagattcag tggcagtgga tcaggacag atttcacact caagatcagc      300
agagtggagg ctgaggatac cggagtgtat tactgctttc aaggttcaca tgttccgtgg     360
acgttcggtg gaggcaccaa ggtggaaatc aagcgtgcag atgctgcacc aactgtatcg     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag acagcaaag acagcaccta cagcatgagc     600
agcaccctca cgttgaccaa ggacgagtat aacgacata acagctatac ctgtgaggcc     660
actcacaaga catctacttc acccattgtc aagagcttca caggaatga gtgttagctc     720
gagtctaga                                                            729
```

<210> SEQ ID NO 239
<211> LENGTH: 235
<212> TYPE: PRT
<213> ORGANISM: Unknown
<220> FEATURE:
<223> OTHER INFORMATION: Sequence of DCIB53 - light variable

<400> SEQUENCE: 239

```
Met Gly Trp Ser Cys Ile Ile Leu Phe Leu Val Ala Thr Ala Thr Gly
  1               5                  10                  15

Val His Ser Asp Val Leu Met Thr Gln Ser Pro Leu Ser Leu Pro Val
             20                  25                  30

Thr Pro Gly Glu Pro Ala Ser Ile Ser Cys Thr Pro Ala Tyr Arg
         35                  40                  45

Pro Pro Asn Ala Pro Ile Leu Trp Tyr Leu Gln Lys Pro Gly Gln Ser
 50                  55                  60

Pro Gln Leu Leu Ile Tyr Lys Val Ser Asn Arg Phe Ser Gly Val Pro
 65                  70                  75                  80

Asp Arg Phe Ser Gly Ser Gly Ser Gly Thr Asp Phe Thr Leu Lys Ile
                 85                  90                  95

Ser Arg Val Glu Ala Glu Asp Thr Gly Val Tyr Tyr Cys Phe Gln Gly
            100                 105                 110

Ser His Val Pro Trp Thr Phe Gly Gly Gly Thr Lys Val Glu Ile Lys
            115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
            195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 240
<211> LENGTH: 1449
<212> TYPE: DNA
<213> ORGANISM: Unknown
<220> FEATURE:
<223> OTHER INFORMATION: Sequence of DCIB64 - Heavy variable

<400> SEQUENCE: 240

```
aagcttacca tgggatggag ctgtatcatc ctcttcttgg tagcaacagc taccggagtc      60
actcccaggt gcagctggtg gagactgggc ggaggcttaa tccagcctgg agggtccctg     120
agaatgtcct gcgggacagg cagggcaatg ctgggcacac acaccatgga agtgactgtc     180
taccattggg ttcggcaggc tccggggaag gggctggagt ggatcgcata cattggtagt     240
ggtggtagtt tttatgattt ttttgtgtgg ctccgattca ccatttccag agacaatagc     300
aagaacaccc tgtatttgca attgaacagt ctgagggctg aggacacagc cgtgtattac     360
tgtgcccgat ggaacaggca gctgtatcca gagtggacag aagcccagag acttgactgg     420
ggccaaggaa ccacggtcac cgtctccagc gctaaaacaa cagccccatc ggtctatcca     480
```

```
ctggcccctg tgtgtggaga tacaactggc tcctcggtga ctctaggatg cctggtcaag    540
ggttatttcc ctgagccagt gaccttgacc tggaactctg gttccctgtc agtggtgtg    600 cacaccttcc cagctgtcct gcagtctgac ctctacaccc tcagcagctc agtgactgta    660
acttcgagca cctggcccag ccagtccatc acctgcaatg tggcccaccc ggcaagcagc    720
accaaggtgg acaagaaaat tgagcccaga gggcccacaa tcaagccctg tcctccatgc    780
aaatgcccag cacctaacct cttgggtgga ccatccgtct tcatcttccc tccaaagatc    840
aaggatgtac tcatgatctc cctgagcccc atagtcacat gtgtggtggt ggatgtgagc    900
gaggatgacc cagatgtcca gatcagctgg tttgtgaaca cgtggaagt acacacagct    960 cagacacaaa cccatagaga ggattacaac agtactctcc gggtggtcag tgccctcccc   1020
atccagcacc aggactggat gagtggcaag gagttcaaat gcaaggtcaa caacaaagac   1080
ctcccagcgc ccatcgagag aaccatctca aacccaaag ggtcagtaag agctccacag   1140
gtatatgtct tgcctccacc agaagaagag atgactaaga acaggtcac tctgacctgc   1200 atggtcacag acttcatgcc tgaagacatt tacgtggagt ggaccaacaa cgggaaaaca   1260
gagctaaact acaagaacac tgaaccagtc ctggactctg atggttctta cttcatgtac   1320
agcaagctga gagtggaaaa gaagaactgg gtggaaagaa atagctactc ctgttcagtg   1380
gtccacgagg gtctgcacaa tcaccacacg actaagagct ctcccggac tccgggtaaa   1440 tgatctaga                                                             1449
```

<210> SEQ ID NO 241
<211> LENGTH: 476
<212> TYPE: PRT
<213> ORGANISM: Unknown
<220> FEATURE:
<223> OTHER INFORMATION: Sequence of DCIB64 - Heavy variable

<400> SEQUENCE: 241

```
Met Gly Trp Ser Cys Ile Ile Leu Phe Leu Val Ala Thr Ala Thr Gly
 1               5                  10                  15

Val His Ser Gln Val Gln Leu Val Glu Thr Gly Gly Gly Leu Ile Gln
            20                  25                  30

Pro Gly Gly Ser Leu Arg Met Ser Cys Gly Thr Gly Arg Ala Met Leu
        35                  40                  45

Gly Thr His Thr Met Glu Val Thr Val Tyr His Trp Val Arg Gln Ala
    50                  55                  60

Pro Gly Lys Gly Leu Glu Trp Ile Ala Tyr Ile Gly Ser Gly Gly Ser
65                  70                  75                  80

Val Tyr Asp Phe Phe Val Trp Leu Arg Phe Thr Ile Ser Arg Asp Asn
                85                  90                  95

Ser Lys Asn Thr Leu Tyr Leu Gln Leu Asn Ser Leu Arg Ala Glu Asp
            100                 105                 110

Thr Ala Val Tyr Tyr Cys Ala Arg Trp Asn Arg Gln Leu Tyr Pro Glu
        115                 120                 125

Trp Thr Glu Ala Gln Arg Leu Asp Trp Gly Gln Gly Thr Thr Val Thr
    130                 135                 140

Val Ser Ser Ala Lys Thr Thr Ala Pro Ser Val Tyr Pro Leu Ala Pro
145                 150                 155                 160

Val Cys Gly Asp Thr Thr Gly Ser Ser Val Thr Leu Gly Cys Leu Val
                165                 170                 175

Lys Gly Tyr Phe Pro Glu Pro Val Thr Leu Thr Trp Asn Ser Gly Ser
            180                 185                 190
```

```
Leu Ser Ser Gly Val His Thr Phe Pro Ala Val Leu Gln Ser Asp Leu
            195                 200                 205

Tyr Thr Leu Ser Ser Ser Val Thr Val Thr Ser Ser Thr Trp Pro Ser
    210                 215                 220

Gln Ser Ile Thr Cys Asn Val Ala His Pro Ala Ser Ser Thr Lys Val
225                 230                 235                 240

Asp Lys Lys Ile Glu Pro Arg Gly Pro Thr Ile Lys Pro Cys Pro Pro
                245                 250                 255

Cys Lys Cys Pro Ala Pro Asn Leu Leu Gly Pro Ser Val Phe Ile Phe
                260                 265                 270

Pro Pro Lys Ile Lys Asp Val Leu Met Ile Ser Leu Ser Pro Ile Val
            275                 280                 285

Thr Cys Val Val Val Asp Val Ser Glu Asp Asp Pro Asp Val Gln Ile
    290                 295                 300

Ser Trp Phe Val Asn Asn Val Glu Val His Thr Ala Gln Thr Gln Thr
305                 310                 315                 320

His Arg Glu Asp Tyr Asn Ser Thr Leu Arg Val Val Ser Ala Leu Pro
                325                 330                 335

Ile Gln His Gln Asp Trp Met Ser Gly Lys Glu Phe Lys Cys Lys Val
            340                 345                 350

Asn Asn Lys Asp Leu Pro Ala Pro Ile Glu Arg Thr Ile Ser Lys Pro
    355                 360                 365

Lys Gly Ser Val Arg Ala Pro Gln Val Tyr Val Leu Pro Pro Pro Glu
370                 375                 380

Glu Glu Met Thr Lys Lys Gln Val Thr Leu Thr Cys Met Val Thr Asp
385                 390                 395                 400

Phe Met Pro Glu Asp Ile Tyr Val Glu Trp Thr Asn Asn Gly Lys Thr
                405                 410                 415

Glu Leu Asn Tyr Lys Asn Thr Glu Pro Val Leu Asp Ser Asp Gly Ser
            420                 425                 430

Tyr Phe Met Tyr Ser Lys Leu Arg Val Glu Lys Lys Asn Trp Val Glu
    435                 440                 445

Arg Asn Ser Tyr Ser Cys Ser Val Val His Glu Gly Leu His Asn His
450                 455                 460

His Thr Thr Lys Ser Phe Ser Arg Thr Pro Gly Lys
465                 470                 475

<210> SEQ ID NO 242
<211> LENGTH: 738
<212> TYPE: DNA
<213> ORGANISM: Unknown
<220> FEATURE:
<223> OTHER INFORMATION: Sequence of DCIB64 - light variable

<400> SEQUENCE: 242
ggatccacca tgggatggag ctgtatcatc ctcttcttgg tagcaacagc taccggagtc      60
cactccgatg tgttgatgac ccaatctcca ctctccctgc ctgtcactcc tggggagcca     120
gcctccatct cttgcagatc tagtcagagc ctggtacata gtaatggaaa cacctattta     180
gaatggtacc tgcagaaacc aggccagtct ccacagctcc tgatctacaa agtttccaac     240
cgattttctg gggtcccaga cagattcagt ggcagtggat cagggacaga tttcacactc     300
aagatcagca gagtggaggc tgaggatacc ggagtgtatt actgctttca aggttcacat     360
gttccgtgga cgttcggtgg aggcaccaag gtggaaatca agcgtgcaga tgctgcacca     420
actgtatcga tcttcccacc atccagtgag cagttaacat ctggaggtgc ctcagtcgtg     480
```

```
tgcttcttga caacttctac ccccaaagac atcaatgtca gtggaagat tgatggcagt    540 gaacgacaaa atggcgtcct gaacagttgg actgatcagg acagcaaaga cagcaccctac  600 agcatgagca gcaccctcac gttgaccaag gacgagtatg aacgacataa cagctatacc   660
tgtgaggcca ctcacaagac atctacttca cccattgtca agagcttcaa caggaatgag   720
tgttagctcg agtctaga                                                 738
```

<210> SEQ ID NO 243
<211> LENGTH: 238
<212> TYPE: PRT
<213> ORGANISM: Unknown
<220> FEATURE:
<223> OTHER INFORMATION: Sequence of DCIB64 - light variable

<400> SEQUENCE: 243

```
Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
             20                  25                  30

Thr Pro Gly Glu Pro Ala Ser Ile Ser Cys Arg Ser Ser Gln Ser Leu
         35                  40                  45

Val His Ser Asn Gly Asn Thr Tyr Leu Glu Trp Tyr Leu Gln Lys Pro
     50                  55                  60

Gly Gln Ser Pro Gln Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Thr Gly Val Tyr Tyr Cys
            100                 105                 110

Phe Gln Gly Ser His Val Pro Trp Thr Phe Gly Gly Gly Thr Lys Val
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 244
<211> LENGTH: 453
<212> TYPE: DNA
<213> ORGANISM: Unknown
<220> FEATURE:
<223> OTHER INFORMATION: Sequence of DCIB68 - heavy variable

<400> SEQUENCE: 244

```
aagcttacca tgggatggag ctgtatcatc ctcttcttgg tagcaacagc taccggagtc    60
cactcccagg tgcagctggt ggagactggg ggaggcttaa tccagcctgg agggtccctg   120
agaatgtcct gcgggacagg caggcaatg ctgggcacac acaccatgga agtaactgtc    180
```

```
taccattggg ttcggcaggc tccggggaag gggctggagt ggatcgcata cattggtagt    240
ggtggtagtg tttatgattt ttttgtgtgg ctccgattca ccatttccag agacaatagc    300
aagaacaccc tgtatttgca attgaacagt ctgagggctg aggacacagc cgtgtattac    360
tgtgcccgat ggaacaggca gctgtatcca gagtggacag aagcccagag acttgactgg    420
ggccaaggta ccacggtcac cgtctccagc gct                                 453
```

<210> SEQ ID NO 245
<211> LENGTH: 147
<212> TYPE: PRT
<213> ORGANISM: Unknown
<220> FEATURE:
<223> OTHER INFORMATION: Sequence of DCIB68 - heavy variable

<400> SEQUENCE: 245

```
Met Gly Trp Ser Cys Ile Ile Leu Phe Leu Val Ala Thr Ala Thr Gly
  1               5                  10                  15

Val His Ser Gln Val Gln Leu Val Glu Thr Gly Gly Gly Leu Ile Gln
             20                  25                  30

Pro Gly Gly Ser Leu Arg Met Ser Cys Gly Thr Gly Arg Ala Met Leu
         35                  40                  45

Gly Thr His Thr Met Glu Val Thr Val Tyr His Trp Val Arg Gln Ala
     50                  55                  60

Pro Gly Lys Gly Leu Glu Trp Ile Ala Tyr Ile Gly Ser Gly Gly Ser
 65                  70                  75                  80

Val Tyr Asp Phe Phe Val Trp Leu Arg Phe Thr Ile Ser Arg Asp Asn
                 85                  90                  95

Ser Lys Asn Thr Leu Tyr Leu Gln Leu Asn Ser Leu Arg Ala Glu Asp
            100                 105                 110

Thr Ala Val Tyr Tyr Cys Ala Arg Trp Asn Arg Gln Leu Tyr Pro Glu
        115                 120                 125

Trp Thr Glu Ala Gln Arg Leu Asp Trp Gly Gln Gly Thr Thr Val Thr
    130                 135                 140

Val Ser Ser
145
```

<210> SEQ ID NO 246
<211> LENGTH: 435
<212> TYPE: DNA
<213> ORGANISM: Unknown
<220> FEATURE:
<223> OTHER INFORMATION: Sequence of DCIB68 - light variable

<400> SEQUENCE: 246

```
ggatccacca tgggatggag ctgtatcatc ctcttcttgg tagcaacagc taccggagtc     60
cactccgatg tgttgatgac ccaatctcca ctctccctgc ctgtcactcc tggggagcca    120
gcctcgatct cttgctggaa caggcagctg tatccagagt ggacagaagc ccagagactt    180
gactggtatc tgcagaaacc aggccagtct ccacagctcc tgatctacaa agtttccaac    240
cgattttctg ggtcccccaga cagattcagt ggcagtggat cagggacaga tttcacactc    300
aagatcagca gagtggaggc tgaggatacc ggagtgtatt actgcgggac aggcagggca    360
atgctgggca cacacaccat ggaagtgact gtctaccatt cggtggagg caccaaggtg    420 gaaatcaagc gtacg                                                      435
```

<210> SEQ ID NO 247
<211> LENGTH: 140

```
<212> TYPE: PRT
<213> ORGANISM: Unknown
<220> FEATURE:
<223> OTHER INFORMATION: Sequence of DCIB68 - light variable

<400> SEQUENCE: 247

Met Gly Trp Ser Cys Ile Ile Leu Phe Leu Val Ala Thr Ala Thr Gly
 1               5                  10                  15

Val His Ser Asp Val Leu Met Thr Gln Ser Pro Leu Ser Leu Pro Val
            20                  25                  30

Thr Pro Gly Glu Pro Ala Ser Ile Ser Cys Trp Asn Arg Gln Leu Tyr
        35                  40                  45

Pro Glu Trp Thr Glu Ala Gln Arg Leu Asp Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
            85                  90                  95

Leu Lys Ile Ser Arg Val Glu Ala Glu Asp Thr Gly Val Tyr Tyr Cys
            100                 105                 110

Gly Thr Gly Arg Ala Met Leu Gly Thr His Thr Met Glu Val Thr Val
        115                 120                 125

Tyr His Phe Gly Gly Gly Thr Lys Val Glu Ile Lys
        130                 135                 140

<210> SEQ ID NO 248
<211> LENGTH: 10
<212> TYPE: PRT
<213> ORGANISM: Unknown
<220> FEATURE:
<223> OTHER INFORMATION: Sequence of DCIB64 - Heavy variable

<400> SEQUENCE: 248

Thr Ile Met Asp Gln Val Pro Phe Ser Val
 1               5                  10
```

What is claimed is:

1. A nucleic acid which comprises a non-specific promoter and at least one sequence that encodes a recombinant heavy chain of an antibody, wherein the heavy chain has at least one heterologous T cell epitope therein such that the heavy chain does not fold correctly when the nucleic acid is expressed; wherein the heavy chain stimulates a T cell response against the at least one heterologous T cell epitope; wherein the T cell response is not mediated via CD64; and wherein the heavy chain cannot associate with a light chain to form an intact antibody or associates with a light chain to form decreased amounts of intact antibody as compared to a normal control antibody.

2. A nucleic acid as claimed in claim 1, further comprising at least one sequence that encodes a light chain of an antibody molecule.

3. A nucleic acid as claimed in claim 1, in combination with a nucleic acid comprising at least one sequence that encodes a light chain of an antibody molecule.

4. A nucleic acid as claimed in claim 2, wherein the light chain has at least one heterologous T cell epitope therein.

5. A nucleic acid as claimed in claim 4, wherein the heterologous T cell epitope of the light chain is such that the light chain does not fold correctly when the nucleic acid is expressed.

6. A nucleic acid as claimed in claim 4, wherein the at least one T cell epitope is in the variable region of the heavy chain and/or the light chain.

7. A nucleic acid as claimed in claim 6, wherein the at least one T cell epitope is in at least one of the CDRs of the heavy and/or light chain of the antibody.

8. A nucleic acid as claimed in claim 7, wherein the CDR is CDRL1, CDRH1 and/or CDRH2.

9. A nucleic acid as claimed in claim 1, wherein the sequence encoding the at least one T cell epitope is inserted into the sequence encoding the variable region of the heavy chain.

10. A nucleic acid as claimed in claim 1, wherein the antibody is a monoclonal antibody.

11. A nucleic acid as claimed in claim 1, wherein the at least one T cell epitope is a cytotoxic T cell epitope.

12. A nucleic acid as claimed in claim 1, wherein the at least one T cell epitope is a helper T cell epitope.

13. A nucleic acid as claimed in claim 4, wherein the heavy chain and/or light chain has at least one cytotoxic T cell epitope and at least one helper T cell epitope.

14. A vaccine comprising a nucleic acid as claimed in claim 1 and an adjuvant.

15. A pharmaceutical composition comprising a nucleic acid as claimed in claim 1 and a pharmaceutically acceptable carrier, excipient or diluent.

16. A nucleic acid as claimed in claim 4, wherein the heavy chain has at least one heterologous cytotoxic T cell epitope and the light chain has at least one heterologous helper T cell epitope.

17. A nucleic acid as claimed in claim 4, wherein the heterologous T cell epitopes are:
GTGRAMLGTHTMEVTVYH (SEQ ID NO: 3) in CDRH1 and CDRL3;
SVYDFFVWL (SEQ ID NO: 9) in CDRH2; and
WNRQLYPEWTEAQRLD (SEQ ID NO: 15) in CDRH3 and CDRL1.

18. A nucleic acid as claimed in claim 17, wherein the antibody comprises the sequences of SEQ ID NOS: 244, 245, 246 and 247.

19. A nucleic acid which comprises a promoter and at least one sequence that encodes a recombinant heavy chain of an antibody, wherein the heavy chain has at least one heterologous T cell epitope therein such that the heavy chain does not fold correctly when the nucleic acid is expressed, wherein the heavy chain stimulates a T cell response against the at least one heterologous T cell epitope, wherein the T cell response is not mediated via CD64; wherein the promoter causes expression of the nucleic acid in dendritic cells and/or keratinocytes; and wherein the heavy chain cannot associate with a light chain to form an intact antibody or associates with a light chain to form decreased amounts of intact antibody as compared to a normal control antibody.

20. A nucleic acid as claimed in claim 3, wherein the light chain has at least one heterologous T cell epitope therein.

21. A nucleic acid as claimed in claim 20, wherein the at least one heterologous T cell epitope of the light chain is such that the light chain does not fold correctly when the nucleic acid is expressed.

22. A nucleic acid as claimed in claim 20, wherein the at least one T cell epitope is in the variable region of the heavy chain and/or the light chain.

23. A nucleic acid as claimed in claim 22, wherein the at least one heterologous T cell epitope is in at least one of the CDRs of the heavy and/or light chain of the antibody.

24. A nucleic acid as claimed in claim 23, wherein the CDR is CDRL1, CDRH1 and/or CDRH2.

25. A nucleic acid as claimed in claim 20, wherein the heavy chain and/or light chain has at least one heterologous cytotoxic T cell epitope and at least one heterologous helper T cell epitope.

26. A nucleic acid as claimed in claim 20, wherein the heavy chain has at least one heterologous cytotoxic T cell epitope and the light chain has at least one heterologous helper T cell epitope.

27. A nucleic acid as claimed in claim 20, wherein the heterologous T cell epitopes are:
GTGRAMLGTHTMEVTVYH (SEQ ID NO: 3) in CDRH1 and CDRL3;
SVYDFFVWL (SEQ ID NO: 9) in CDRH2; and
WNRQLYPEWTEAQRLD (SEQ ID NO: 15) in CDRH3 and CDRL1.

28. A nucleic acid as claimed in claim 27, wherein the antibody comprises the sequences of SEQ ID NOS: 244, 245, 246 and 247.

29. A nucleic acid as claimed in claim 19, further comprising at least one sequence that encodes a light chain of an antibody molecule.

30. A nucleic acid as claimed in claim 19, in combination with a nucleic acid comprising at least one sequence that encodes a light chain of an antibody molecule.

31. A nucleic acid as claimed in claim 29, wherein the light chain has at least one heterologous T cell epitope therein.

32. A nucleic acid as claimed in claim 31, wherein the heterologous T cell epitope of the light chain is such that the light chain does not fold correctly when the nucleic acid is expressed.

33. A nucleic acid as claimed in claim 31, wherein the at least one T cell epitope is in the variable region of the heavy chain and/or the light chain.

34. A nucleic acid as claimed in claim 33, wherein the at least one T cell epitope is in at least one of the CDRs of the heavy and/or light chain of the antibody.

35. A nucleic acid as claimed in claim 34, wherein the CDR is CDRL1, CDRH1 and/or CDRH2.

36. A nucleic acid as claimed in claim 19, wherein the sequence encoding the at least one T cell epitope is inserted into the sequence encoding the variable region of the heavy chain.

37. A nucleic acid as claimed in claim 19, wherein the antibody is a monoclonal antibody.

38. A nucleic acid as claimed in claim 19, wherein the at least one T cell epitope is a cytotoxic T cell epitope.

39. A nucleic acid as claimed in claim 19, wherein the at least one T cell epitope is a helper T cell epitope.

40. A nucleic acid as claimed in claim 31, wherein the heavy chain and/or light chain has at least one cytotoxic T cell epitope and at least one helper T cell epitope.

41. A nucleic acid as claimed in claim 30, wherein the light chain has at least one heterologous T cell epitope therein.

42. A nucleic acid as claimed in claim 41, wherein the at least one heterologous T cell epitope of the light chain is such that the light chain does not fold correctly when the nucleic acid is expressed.

43. A nucleic acid as claimed in claim 41, wherein the at least one T cell epitope is in the variable region of the heavy chain and/or the light chain.

44. A nucleic acid as claimed in claim 43, wherein the at least one heterologous T cell epitope is in at least one of the CDRs of the heavy and/or light chain of the antibody.

45. A nucleic acid as claimed in claim 44, wherein the CDR is CDRL1, CDRH1 and/or CDRH2.

46. A nucleic acid as claimed in claim 41, wherein the heavy chain and/or light chain has at least one heterologous cytotoxic T cell epitope and at least one heterologous helper T cell epitope.

47. A nucleic acid as claimed in claim 41, wherein the heavy chain has at least one heterologous cytotoxic T cell epitope and the light chain has at least one heterologous helper T cell epitope.

48. A nucleic acid as claimed in claim 41, wherein the heterologous T cell epitopes are:
GTGRAMLGTHTMEVTVYH (SEQ ID NO: 3) in CDRH1 and CDRL3;
SVYDFFVWL (SEQ ID NO: 9) in CDRH2; and
WNRQLYPEWTEAQRLD (SEQ ID NO: 15) in CDRH3 and CDRL1.

49. A nucleic acid as claimed in claim 48, wherein the antibody comprises the sequences of SEQ ID NOS: 244, 245, 246 and 247.

50. A vaccine comprising a nucleic acid as claimed in claim 19 and an adjuvant.

51. A pharmaceutical composition comprising a nucleic acid as claimed in claim 19 and a pharmaceutically acceptable carrier, excipient or diluent.

* * * * *